United States Patent
Rodriguez et al.

(10) Patent No.: US 9,260,512 B2
(45) Date of Patent: Feb. 16, 2016

(54) HUMAN IGM ANTIBODIES, AND DIAGNOSTIC AND THERAPEUTIC USES THEREOF PARTICULARLY IN THE CENTRAL NERVOUS SYSTEM

(71) Applicants: Moses Rodriguez, Rochester, MN (US); David J. Miller, Ridgeway, WI (US); Larry R. Pease, Rochester, MN (US)

(72) Inventors: Moses Rodriguez, Rochester, MN (US); David J. Miller, Ridgeway, WI (US); Larry R. Pease, Rochester, MN (US)

(73) Assignee: Mayo Foundation for Medical Education & Research, Rochester, MN (US)

( * ) Notice: Subject to any disclaimer, the term of this patent is extended or adjusted under 35 U.S.C. 154(b) by 0 days.

(21) Appl. No.: 13/800,117

(22) Filed: Mar. 13, 2013

(65) Prior Publication Data

US 2014/0065167 A1 Mar. 6, 2014

Related U.S. Application Data

(60) Continuation of application No. 12/845,977, filed on Jul. 29, 2010, now Pat. No. 8,420,795, and a division of application No. 12/313,515, filed on Nov. 20, 2008, now Pat. No. 7,807,166, and a continuation of application No. 10/010,729, filed on Nov. 13, 2001, now Pat. No. 7,473,423, and a continuation-in-part of application No. 09/580,787, filed on May 30, 2000, now abandoned, and a continuation-in-part of application No. 09/322,862, filed on May 28, 1999, now abandoned.

(51) Int. Cl.
*A61K 38/00* (2006.01)
*C07K 16/18* (2006.01)

(52) U.S. Cl.
CPC ............... *C07K 16/18* (2013.01); *A61K 38/00* (2013.01); *C07K 2317/77* (2013.01)

(58) Field of Classification Search
CPC ..... A61K 38/00; C07K 16/18; C07K 2317/77
See application file for complete search history.

(56) References Cited

U.S. PATENT DOCUMENTS 5,591,629 A    1/1997 Rodriguez ............... 435/240.27

FOREIGN PATENT DOCUMENTS

WO    WO 92/04442    3/1992
WO    WO 95/30004   11/1995

OTHER PUBLICATIONS

Abo et al., J. Immunol., 127 (1981), 1024-1029.
Asakura et al., J. Neuroscience Res. (1996) 43, pp. 273-281.
Asakura, K. et al, Mol Brain Res (1996) 34:282-293.
Asakura, K., D.J. Miller, L.R. Pease, and M. Rodriguez *Journal of Neuroscience* (1998) 18:7700-7708.
Asakura, K. et al. Neurology 54(7): A126-A127 (Supp 3) (2000).
Bansal et al, Proc Natl Acad Sci (1989) 86:6181-6185.
Bansal, R. et al., J. Neurosci. Res. (1988) 21:260-267.
Benjamins, J.A. and Dyer, C.A., Ann. NY Acad. Sci., 605:90-100 (1990).
Diaz, M. et al., Brain Res., 154:231-239 (1978).
Dyer, C.A., Mol. Neurobiol., 7:1-22 (1993).
Eisenbarth et al., Proc. Natl. Acad. Sci. USA, 76 (1979), 4913-4917.
Fredman et al., Arch. Biochem. Biophys., 233 (1984), 661-666.
Gard et al., Neuron, 5 (1990), 615-625.
Kasai et al., Brain Res., 277 (1983), 155-158.
Kirschning, E. et al. J. Immun (1999) 99(1):122-130.
Lehrer, G.M. et al., Brain Res., 172:557-560 (1979).
Miller et al., J. Neurosci., 14 (1994), 6230-6238.
Miller, D.J. and M. Rodriguez, J Immunol (1995) 154:2460-2469.
Miller, D.J. and Rodriguez, M., Microscopy Res & Tech (1995) 32:230-245.
Miller, D.J. et al, J Neurosci Res (1995) 41:291-296.
Miller, D.J. et al, J Neurosci (1995)1545:8345-8352.
Miller et al., International Immunology, (1996) 8, pp. 131-141.
Miller, D.J. et al, J Neuroimmunol (1997) 75:204-209.
Raine, C.S. and Wu, E.J., lab Invest (1978) 38(4):397-403.
Rodriguez M. et al, J Neuropathol Exp Neurol (1987) 46:84-95.
Rodriguez, et al., Ann. Neurol (1990) 27:12-17.
Rodriguez, M., J Neuroimmunol (1992) 40:255-264.
Rodriguez, M. and Lindsley, M.D., Neurology (1992) 42(2):348-357.
Rodriguez, M. and Miller, D.J., Prog Brain Res (1994) 103:343-355.
Schachner, J. Neurochem., 39 (1982), 1-8.
Schuller-Petrovic et al., Nature, 306 (1983), 179-181.
Sommer et al., Dev. Biol., 83 (1981), 311-327.

*Primary Examiner* — John Ulm
(74) *Attorney, Agent, or Firm* — Klauber & Jackson LLC

(57) ABSTRACT

Antibodies, particularly human antibodies, are disclosed having activity in treatment of demyelinating diseases and diseases of the central nervous system. Neuromodulatory agents are provided comprising a material selected from the group consisting of an antibody capable of binding structures or cells in the central nervous system, a peptide analog, and active fragments, monomers and combinations thereof having one or more of the following characteristics: capable of inducing remyelination; binding to neural tissue; promoting $Ca^{++}$ signaling with oligodendrocytes; and promoting cellular proliferation of glial cells. Amino acid and DNA sequences of exemplary antibodies are disclosed. Methods are described for treating demyelinating diseases, and diseases of the central nervous system, using polyclonal IgM antibodies and human monoclonal antibodies sHIgm22 (LYM 22), sHIgm46(LYM46) ebvHIgM MSI19D10, CB2bG8, AKJR4, CB2iE12, CB2iE7, MSI19E5 and MSI10E10, and active fragments thereof. The invention extends to the use of antibodies and fragments in diagnostic and therapeutic applications, including screening assays.

23 Claims, 87 Drawing Sheets

FIG. 7
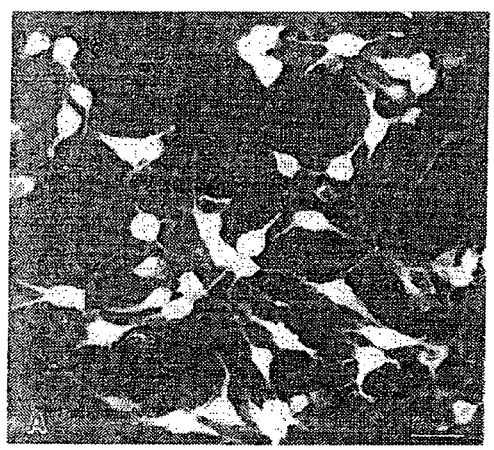
A
B
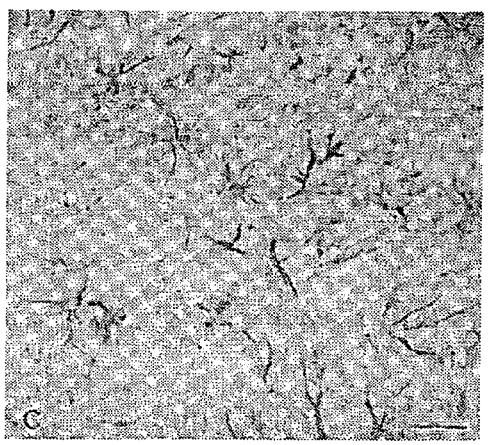
C
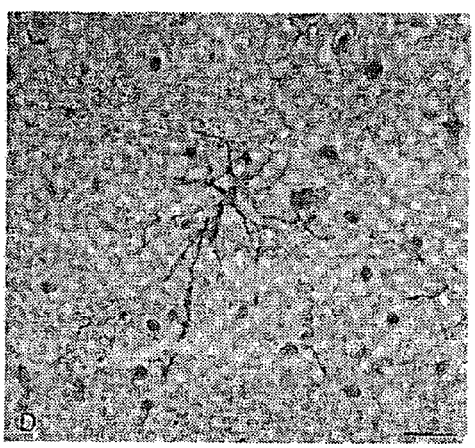
D

Leader Peptide

```
         M   E   S   Q   I   Q   V   F   V   F   L   W   L   S   G   V   D   G   +1
                                                                                 D   I   V   M   T   Q   S   H
A2B5    ATG GAG TCA CAG ATT CAG GTC TTT GTA TTC GTG CTC TGG TTG TCT GGT GTT GAC GGA GAC ATT GTG ATG ACC CAG TCT CAC
                                                                                          CDR1

K   F   M   S   T   S   V   G   D   R   V   S                          20                      30
                                                         I   T   C   K   A   S   Q   D   V   S   T   A   V   A   W   Y
A2B5    AAA TTC ATG TCC ACT TCA GTA GGA GAC AGG GTC AGC ATC ACC TGC AAG GCC AGT CAG GAT GTG AGT ACT GCT GTA GCC TGG TAT
                                                                                                   CDR2

Q   Q   K   P   G   Q   S   P   K   L   L   I   Y   S   A   S   Y   R   Y   T   G   V   P   D   R   F   T   G
                40                                          50                                  60
A2B5    CAA CAG AAA CCA GGA CAA TCT CCT AAA CTA CTG ATT TAC TCG GCA TCC TAC CGG TAC ACT GGA GTC CCT GAT CGC TTC ACT GGC

S   G   S   G   T   D   F   T   F   T   I   S   S   V   Q   A   E   D   L   A   V   Y   Y   C   Q   Q   H   Y
                    70                                      80                                              90
A2B5    AGT GGA TCT GGG ACG GAT TTC ACT TTC ACC ATC AGC AGT GTG CAG GCT GAA GAC CTG GCA GTT TAT TAC TGT CAG CAA CAT TAT
                                                                                                              CDR3

100                        106 106A
         T   T   P   L   T   F   G   A   G   T   K   L   E   L   K   R                               C region
A2B5    ACT ACT CCG CTC ACG TTC GGT GCT GGG ACC AAG CTG GAG CTG AAA CGG GCT GAT GCT TCA
germline rcs                                                         .G.                                ---   ---   ---
A2B5
```

FIG. 20
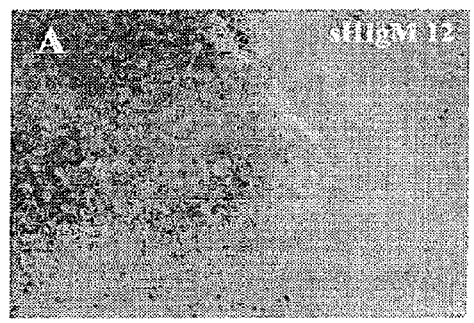
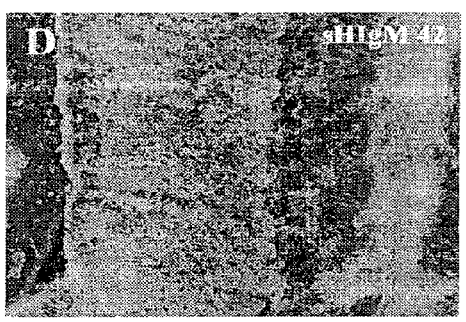
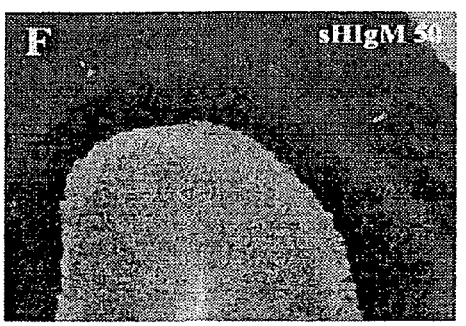

FIG. 22
A
B
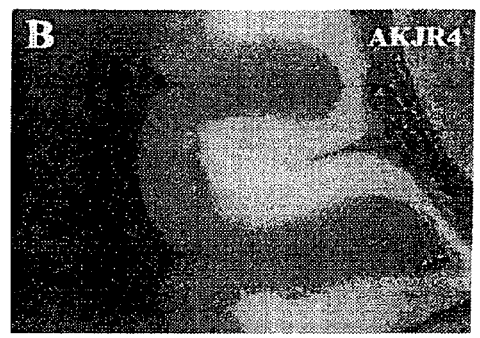
C
D
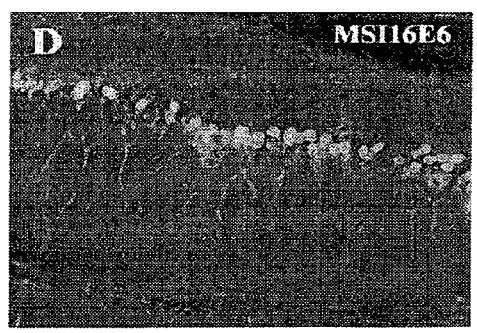
E
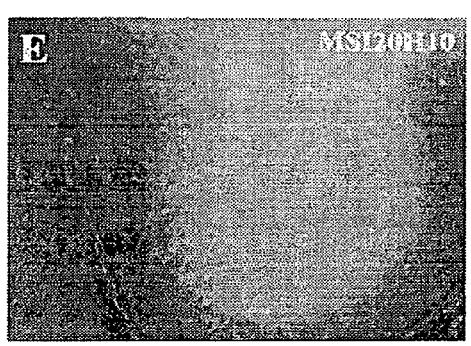
F
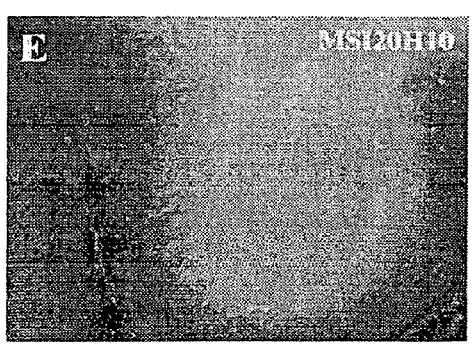

FIG. 25
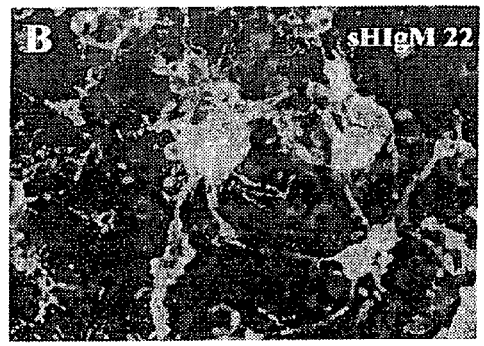
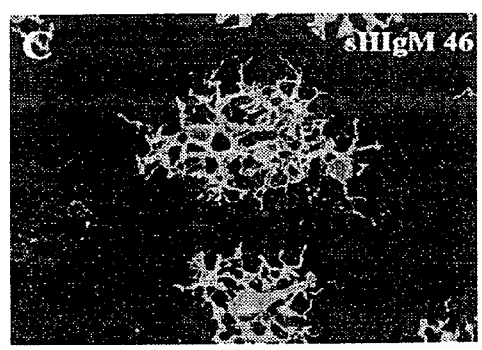
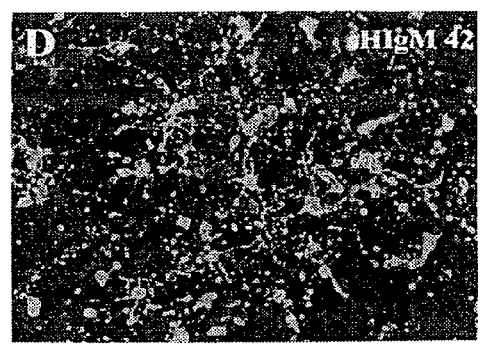
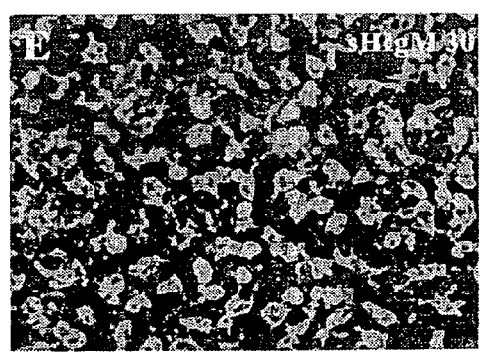
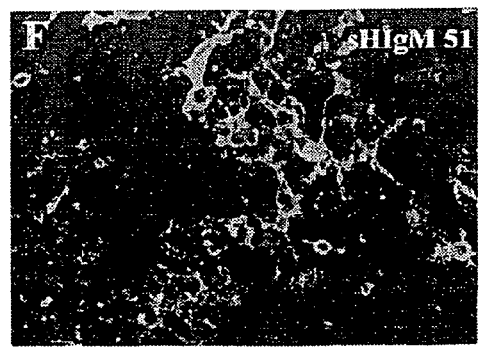

FIG. 26
A
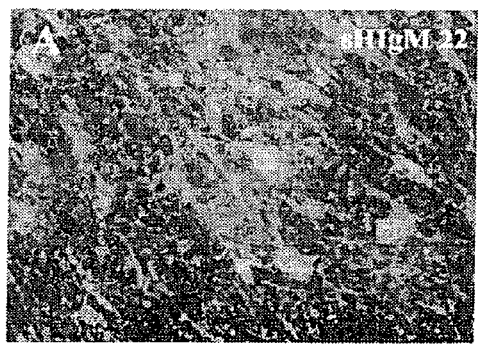
B
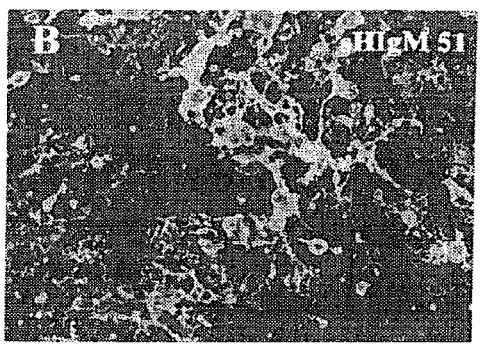
C
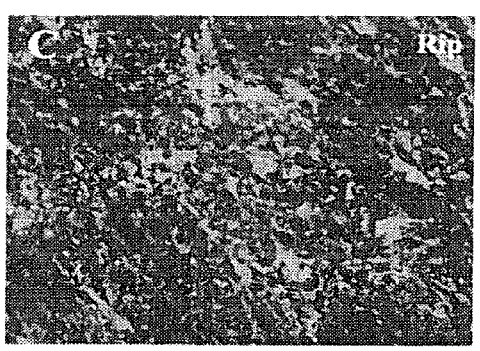
D
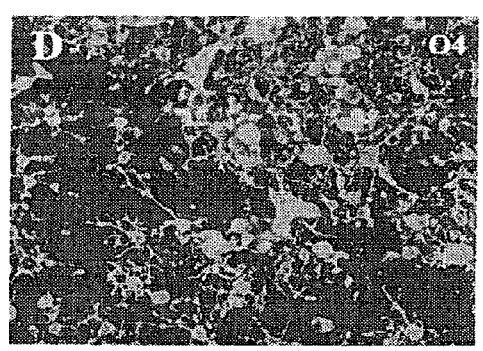
E
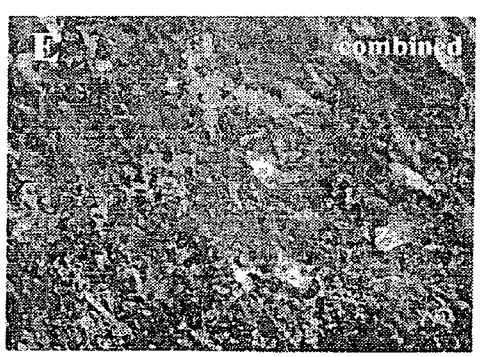
F
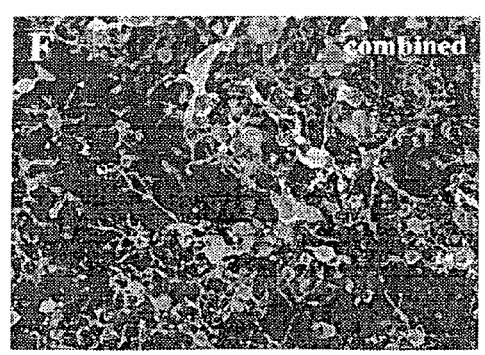

FIG. 27
A
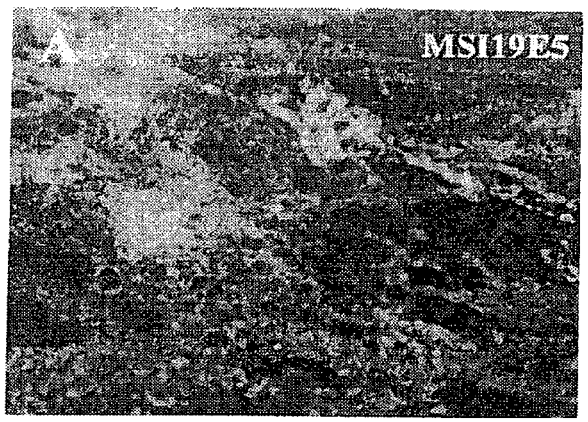
B
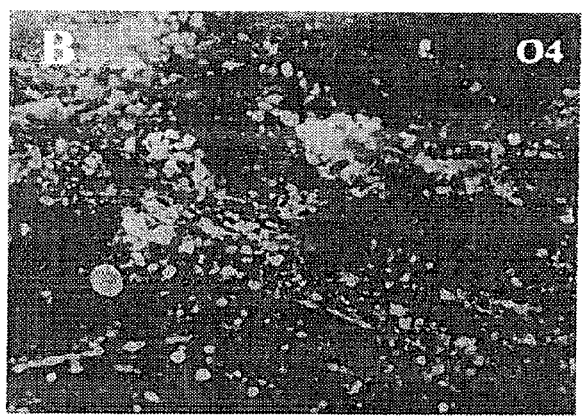
C
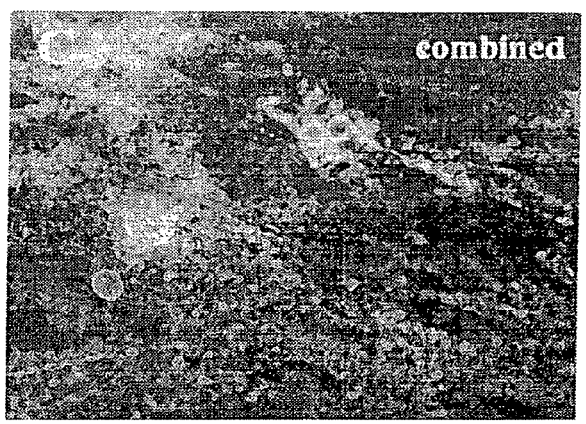

FIG. 31
A
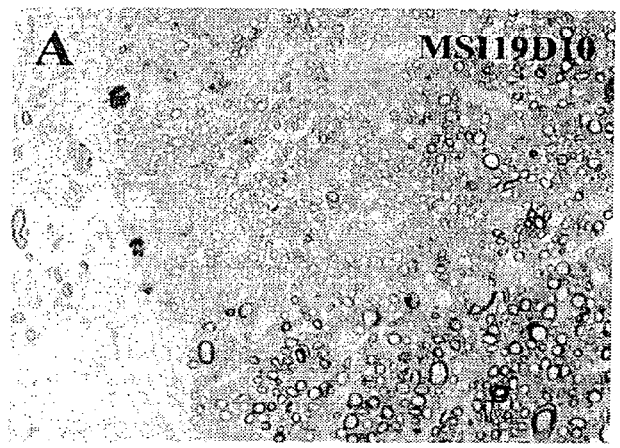
B
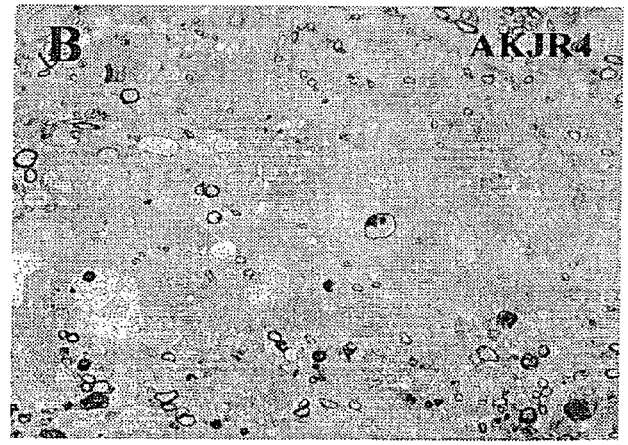

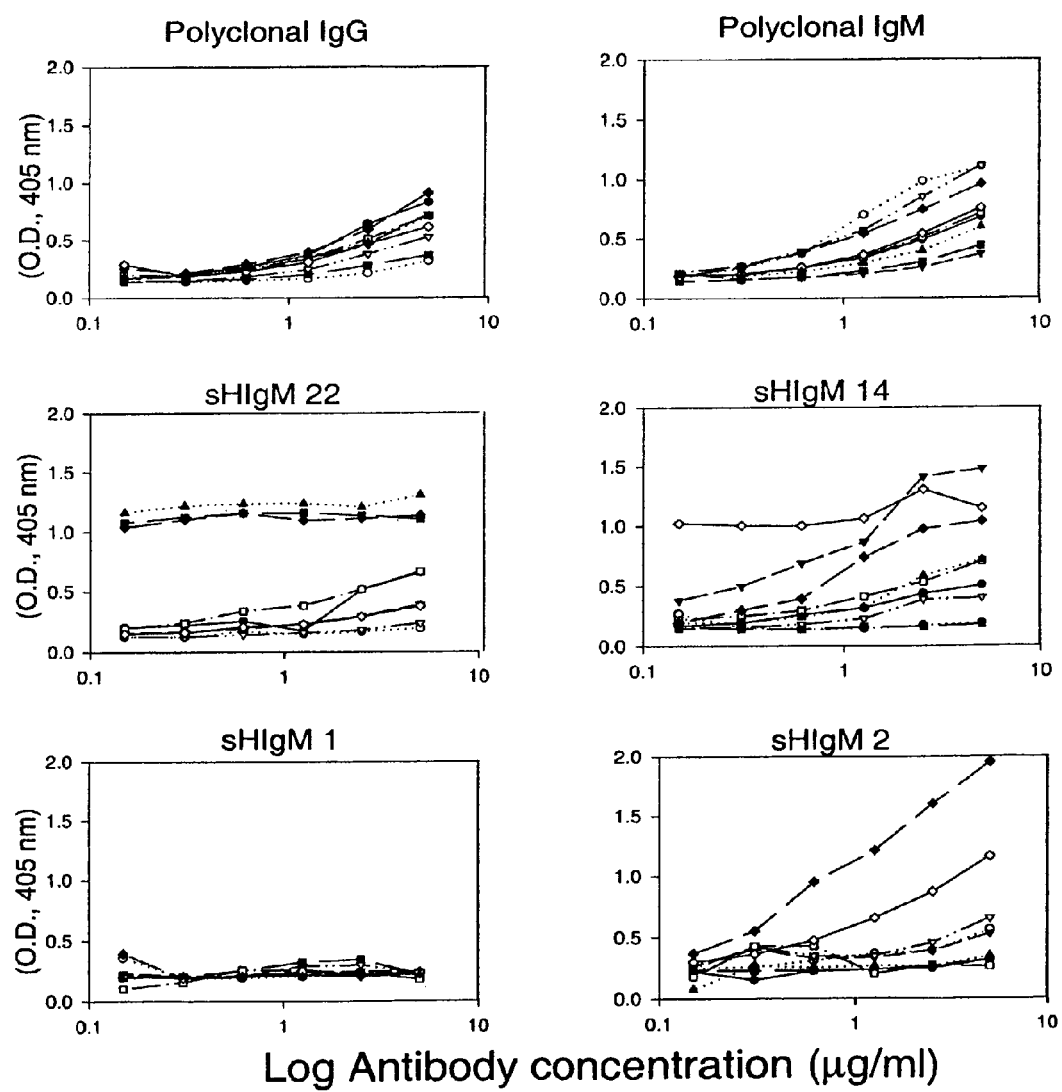

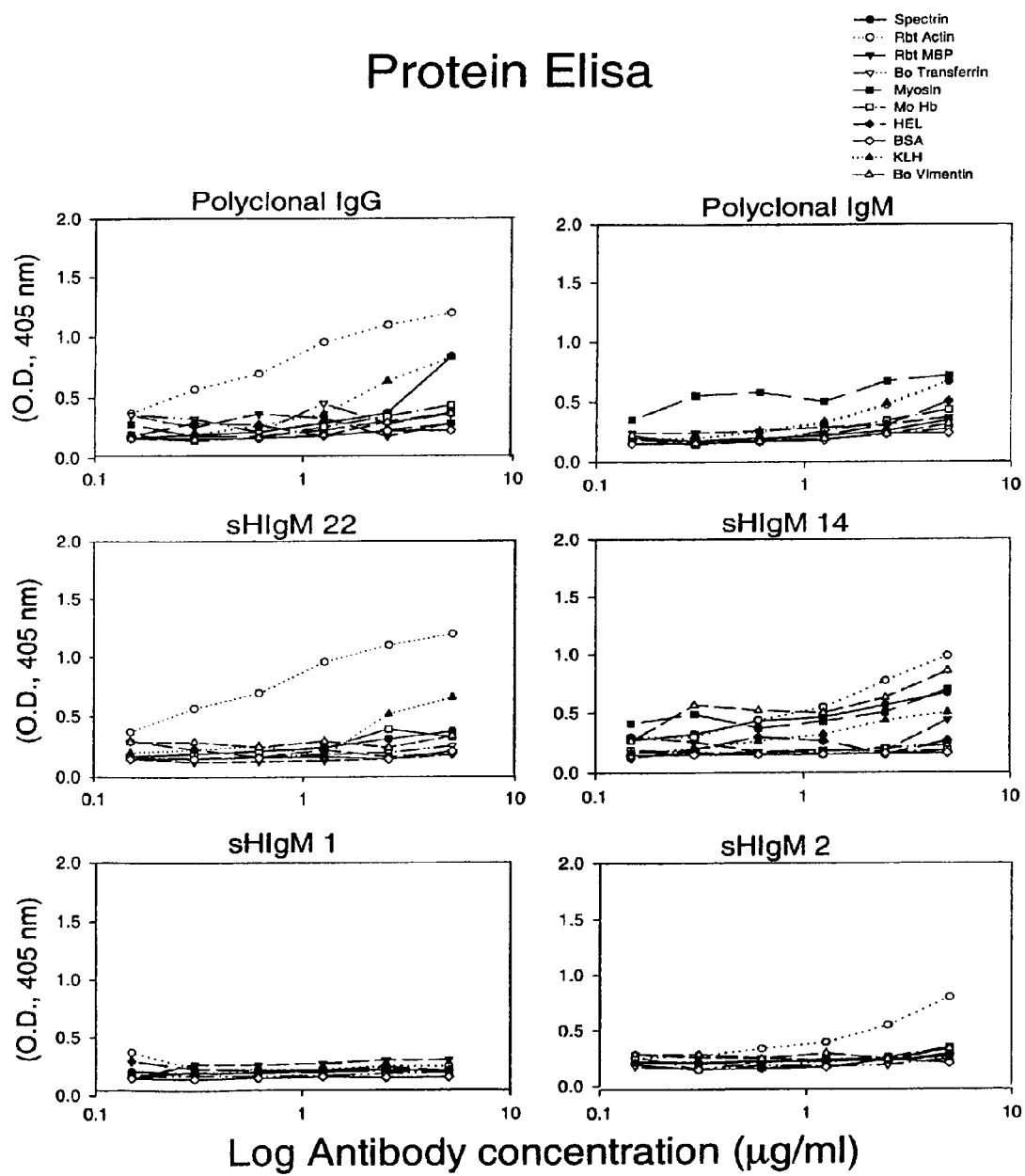

FIG. 35

```
/FR1-------------------------------------------------------------
   1    2    3    4    5    6    7    8    9   10   11   12   13   14   15
   Q    V    Q    L    V    E    S    G    G    G    V    V    Q    P    G
  CAG  GTG  CAG  CTG  GTG  GAG  TCT  GGG  GGA  GGC  GTG  GTC  CAG  CCT  GGG
Clone A sH-IgM.22 VH                          G
Clone B sH-IgM.22 VH
-----------------------------------------------------------------
  16   17   18   19   20   21   22   23   24   25   26   27   28   29   30
   R    S    L    R    L    S    C    A    A    S    G    F    T    F    S
  AGG  TCC  CTG  AGA  CTC  TCC  TGT  GCA  GCC  TCT  GGA  TTC  ACC  TTC  AGT /CDR1--------------/FR2------------------------------------------
  31   32   33   34   35   36   37   38   39   40   41   42   43   44   45
   S    S    G    M    H    W    V    R    Q    A    P    G    K    G    L
  AGC  TAT  GGC  ATG  CAC  TGG  GTC  CGC  CAG  GCT  CCA  GGC  AAG  GGG  CTG
       C                                      A
       C
-----------------/CDR2-------------------------------------------
  46   47   48   49   50   51   52  52A   53   54   55   56   57   58   59
   E    W    V    A   V(I)   I    S    Y    D    G    S    R    K    Y    Y
  GAG  TGG  GTG  GCA  GTT  ATA  TCA  TAT  GAT  GGA  AGT  AAT  AAA  TAC  TAT
                           T                                  GG
                      A C       T                             GG
------------------------------/FR3-------------------------------
  60   61   62   63   64   65   66   67   68   69   70   71   72   73   74
   A    D    S    V    K    G    R    F    T    I    S    R    D    N    S
  GCA  GAC  TCC  GTG  AAG  GGC  CGA  TTC  ACC  ATC  TCC  AGA  GAC  AAT  TCC
                                                                    C
                                                                    C
-----------------------------------------------------------------
  75   76   77   78   79   80   81   82  82A  82B  82C   83   84   85   86
   K    N    T    L    Y    L    Q    M    N    S    L    T    A   D(E)  D
  AAG  AAC  ACG  CTG  TAT  CTG  CAA  ATG  AAC  AGC  CTG  AGA  GCT  GAG  GAC
                 T                                            CG         C
            T    C                                            C
--------------------------------/CDR3----------------------------
  87   88   89   90   91   92   93   94   95   96   97   98   99  100 100A
   T    A    V    Y    Y    C    A    K    G    V    T    G    S    P    T
  ACG  GCT  GTG  TAT  TAC  TGT  GCG  AAA  GAG  GTG  ACT  GCT  ATT  CCC  TAC
                           T                   GA              G    G    G  ACG
                                               GA              G    G    G  ACG
-------------/FR4------------------------------------------------
 100B 101  102  103  104  105  106  107  108  109  110  111  112  113
   L    D    Y    W    G    Q    G    T    L    V    T    V    S    S
  TTT  GAC  TAC  TGG  GGC  CAG  GGA  ACC  CTG  GTC  ACC  GTC  TCC  TCA
   C                                                                 G
   C                                                                 G
```

FIG. 36

```
/FR1--------------------------------------------------------------
  1    2    3    4    5    6    7    8    9   11   12   13   14   15   16
  Q    S    V    L    T    Q    P    P    S    V    S    A    A    P    G
 CAG  TCT  GTG  TTG  ACG  CAG  CCG  CCC  TCA  GTG  TCT  GCG  GCC  CCA  GGA
Clone I sH-IgM.22 Vλ         G              T                   T
Clone II sH-IgM.22 Vλ        G              T                   T
--------------------------------/CDR1----------------------------
 17   18   19   20   21   22   23   24   25   26   27  27A  27B   28   29
  Q    K    V    T    I    S    C    S    G    S    S    S    N    I    G
 CAG  AAG  GTC  ACC  ATC  TCC  TGC  TCT  GGA  AGC  AGC  TCC  AAC  ATT  GGG
                                                                         C
                                                                         C
-------------------------/FR2-----------------------------------
 30   31   32   33   34   35   36   37   38   39   40   41   42   43   44
  N    N    F    V    S    W    Y    Q    Q    L    P    G    T    A    P
 AAT  AAT  TAT  GTA  TCC  TGG  TAC  CAG  CAG  CTC  CCA  GGA  ACA  GCC  CCC
                T                                  A
                T                                  A
---------------------/CDR2----------------------------/FR3-------
 45   46   47   48   49   50   51   52   53   54   55   56   57   58   59
 R(K)  L    L    I    Y    D    I    T    K    R    P    S    G    I    P
 AAA  CTC  CTC  ATT  TAT  GAC  AAT  AAT  AAG  CGA  CCC  TCA  GGG  ATT  CCT
  G                                 T    C
                                    T    C
-----------------------------------------------------------------
 60   61   62   63   64   65   66   67   68   69   70   71   72   73   74
  D    R    F    S    G    S    K    S    G    T    S    A    T    L    G
 GAC  CGA  TTC  TCT  GGC  TCC  AAG  TCT  GGC  ACG  TCA  GCC  ACC  CTG  GGC -------------------------------------------------------/CDR3-----
 75   76   77   78   79   80   81   82   83   84   85   86   87   88   89
  I    T    G    L    Q    T    G    D    E    A    D    Y    Y    C    G(E)
 ATC  ACC  GGA  CTC  CAG  ACT  GGG  GAC  GAG  GCC  GAT  TAT  TAC  TGC  GGA
                                                                         A
-----------------------------------------------/FR4-------------
 90   91   92   93   94   95  95A  95B   96   97   98   99  100  101  102
  T    W    D    S    S    L    S    A    V    V    F    G    G    G    T
 ACA  TGG  GAT  AGC  AGC  CTG  ...  ..T  GTG  GTA  TTC  GGC  GGA  GGG  ACC
                                AGT  GC                        G
                                AGT  GC                        G
----------------------------/Cλ----------
103  104  105  106 106A 107  108  109  110
  K    L    T    V    L    G    Q    P    K
 AAG  CTG  ACC  GTC  CTA  GGT  CAG  CCC  AAG
```

FIG. 37

Sequence of MSI 19-D10 V<sub>H</sub>

```
FR1----------------------------------------------------------------
  1   2   3   4   5   6   7   8   9  10  11  12  13  14  15  16
 CAG GTG CAG CTG CAG GAG TCG GGC CCA GGA CTG GTG AAG CCT TCG GAG
  Q   V   Q   L   Q   E   S   G   P   G   L   V   K   P   S   E

-------------------------------------------------------/CDR1
 17  18  19  20  21  22  23  24  25  26  27  28  29  30  31
 ACC CTG TCC CTC ACC TGC ACT GTC TCT GGT GGC TCC ATC AGT AGT
  T   L   S   L   T   C   T   V   S   G   G   S   I   S   S

----------------/FR2----------------------------------------
 32  33  34  35  36  37  38  39  40  41  42  43  44  45  46
 TAC TAC TGG AGC TGG ATC CGG CAG CCC CCA GGG AAG GGA CTG GAG
  Y   Y   W   S   W   I   R   Q   P   P   G   K   G   L   E

-----------/CDR2-------------------------------------------
 47  48  49  50  51  52  53  54  55  56  57  58  59  60  61
 TGG ATT GGG TAT ATC TAT TAC AGT GGG AGC ACC AAC TAC AAC CCC
  W   I   G   Y   I   Y   Y   S   G   S   T   N   Y   N   P

--------------/FR3-----------------------------------------
 62  63  64  65  66  67  68  69  70  71  72  73  74  75  76
 TCC CTC AAG AGT CGA GTC ACC ATA TCA GTA GAC ACG TCC AAG AAC
  S   L   K   S   R   V   T   I   S   V   D   T   S   K   N

-----------------------------------------------------------
 77  78  79  80  81  82  82A 82B 82C 83  84  85  86  87  88
 CAG TTC TCC CTG AAG CTG AGC TCT GTG ACC GCT GCG GAC ACG GCC
  Q   F   S   L   K   L   S   S   V   T   A   A   D   T   A

-------------------------/CDR3-----------------------------
 89  90  91  92  93  94  95  96  97  98  99  100 100A100B100C
 GTG TAT TAC TGT GCG AGG TCG GCA CAG CAG CAG CTG GTA TAC TAC
  V   Y   Y   C   A   R   S   A   Q   Q   Q   L   V   Y   Y

-----------/FR4-------------------------------------/Cµ-
 100D 101 102 103 104 105 106 107 108 109 110 111 112 113 114
 TTT GAC TAC TGG GGC CAG GGA ACC CTG GTC ACC GTC TCC TCA GGG
  F   D   Y   W   G   Q   G   T   L   V   T   V   S   S   G
```

FIG. 38

Sequence of MSI 19-D10 Vκ

*FR 1*-------------------------------------------------

| 1 | 2 | 3 | 4 | 5 | 6 | 7 | 8 | 9 | 10 | 11 | 12 | 13 | 14 | 15 |
|---|---|---|---|---|---|---|---|---|----|----|----|----|----|----|
| GAC | ATC | GTG | ATG | ACC | CAG | TCT | CCA | GAC | TCC | CTG | GCT | GTG | TCT | CTG |
| D | I | V | M | T | Q | S | P | D | S | L | A | V | S | L |

--------------------------------/CDR1--------------------

| 16 | 17 | 18 | 19 | 20 | 21 | 22 | 23 | 24 | 25 | 26 | 27 | 27A | 27B | 27C |
|---|---|---|---|---|---|---|---|---|---|---|---|---|---|---|
| GGC | GAG | AGG | GCC | ACC | ATC | AAC | TGC | AAG | TCC | AGC | CAG | AGT | GTT | TTA |
| G | E | R | A | T | I | N | C | K | S | S | Q | S | V | L |

-----------------------------------------/FR2-----------

| 27D | 27E | 27F | 28 | 29 | 30 | 31 | 32 | 33 | 34 | 35 | 36 | 37 | 38 |
|---|---|---|---|---|---|---|---|---|---|---|---|---|---|
| TAC | AGC | TCC | AAC | AAT | AAG | AAC | TAC | TTA | GCT | TGG | TAC | CAG | CAG |
| Y | S | S | N | N | K | N | Y | L | A | W | Y | Q | Q |

--------------------------------------/CDR2----------

| 39 | 40 | 41 | 42 | 43 | 44 | 45 | 46 | 47 | 48 | 49 | 50 | 51 | 52 | 53 |
|---|---|---|---|---|---|---|---|---|---|---|---|---|---|---|
| AAA | CCA | GGA | CAG | CCT | CCT | AAG | CTG | CTC | ATT | TAC | TGG | GCA | TCT | ACC |
| K | P | G | Q | P | P | K | L | L | I | Y | W | A | S | T |

-----------/FR3-------------------------------------

| 54 | 55 | 56 | 57 | 58 | 59 | 60 | 61 | 62 | 63 | 64 | 65 | 66 | 67 | 68 |
|---|---|---|---|---|---|---|---|---|---|---|---|---|---|---|
| CGG | GAA | TCC | GGG | GTC | CCT | GAC | CGA | TTC | AGT | GGC | AGC | GGG | TCT | GGG |
| R | E | S | G | V | P | D | R | F | S | G | S | G | S | G |

| 69 | 70 | 71 | 72 | 73 | 74 | 75 | 76 | 77 | 78 | 79 | 80 | 81 | 82 | 83 |
|---|---|---|---|---|---|---|---|---|---|---|---|---|---|---|
| ACA | GAT | TTC | ACT | CTC | ACC | ATC | AGC | AGC | CTG | CAG | GCT | GAA | GAT | GTG |
| T | D | F | T | L | T | I | S | S | L | Q | A | E | D | V |

-------------------/CDR3-----------------------------/FR4

| 84 | 85 | 86 | 87 | 88 | 89 | 90 | 91 | 92 | 93 | 94 | 95 | 96 | 97 | 98 |
|---|---|---|---|---|---|---|---|---|---|---|---|---|---|---|
| GCA | GTT | TAT | TAC | TGT | CAG | CAA | TAT | TAT | AGT | ACT | CCT | CTC | ACT | TTC |
| A | V | Y | Y | C | Q | Q | Y | Y | S | T | P | L | T | F |

----------------------------/Cκ--------------------

| 99 | 100 | 101 | 102 | 103 | 104 | 105 | 106 | 107 | 108 | 109 | 110 | 111 | 112 | 113 |
|---|---|---|---|---|---|---|---|---|---|---|---|---|---|---|
| GGC | CCT | GGG | ACC | AAA | GTG | GAT | ATC | AAA | CGA | ACT | GTG | GCT | GCA | CCA |
| G | P | G | T | K | V | D | I | K | R | T | V | A | A | P |

FIG. 40
A
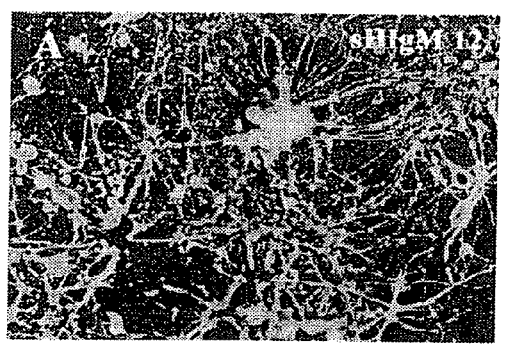
B

FIG. 42
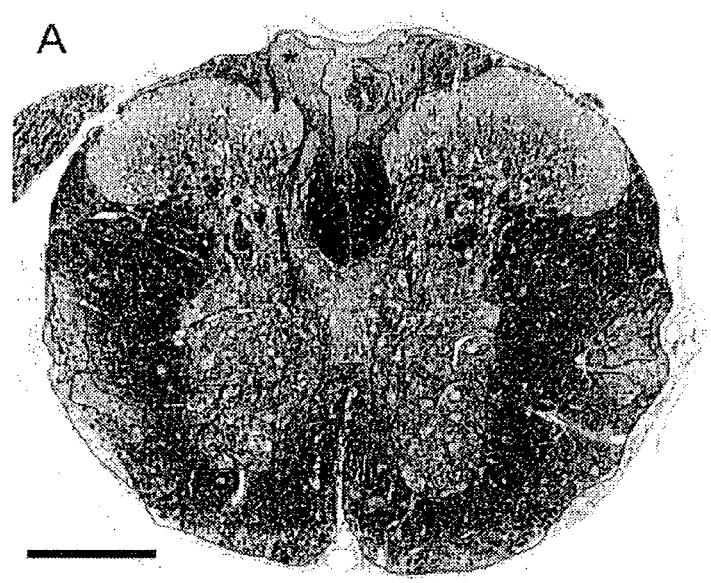
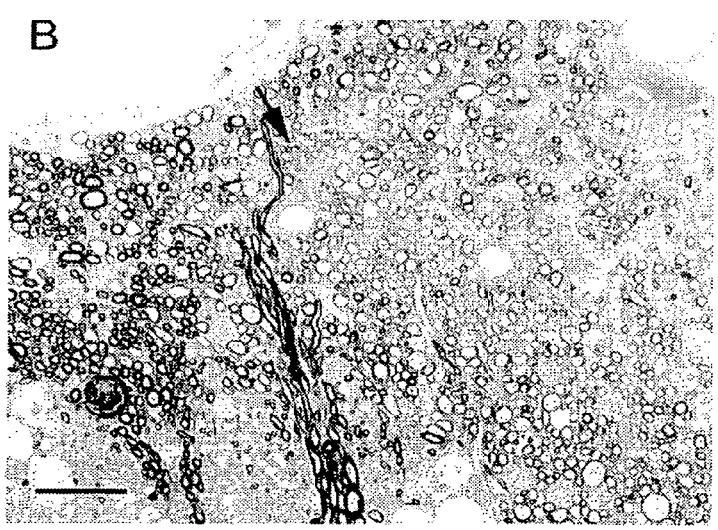

FIG. 45

Translation of CB2b-G8 V$_H$:

```
<--------------------- F  R  1  -  I  M  G  T ---------------------------------
1          5              10              15                  20
                           x     A   V   V   Q   P   G   R   S   L   R   L   S
... ... ... ... ... ... ... ... .AG ... GCC GTG GTC CAG CCT GGG AGG TCC CTG AGA CTC TCC

---------------->                                         <--------------------
                    _____ CDR1 - IMGT _____
         25                   30                  35              40
 C   A   A   S   G   F   I   F   S   S   Y   G                   M   H   W   V   R   Q
TGT GCA GCG TCT GGA TTC ATT TTC AGT AGC TAT GGC ... ... ... ... ATG CAC TGG GTC CGC CAG

F   R   2   -   I   M   G   T ----------->                                         <---
                                                    _____ CDR2 - IMGT _____
 45              50                  55                  60                  65
 V   P   G   K   G   L   E   W   V   A   V   I   W   Y   D   G   S   D   K           Y
GTT CCA GGC AAG GGG CTG GAG TGG GTG GCA GTT ATA TGG TAT GAT GGA AGT GAT AAA ... ... TAC

-----------------------------------------------         F   R   3   -   I   M   G   T ----
             70              75                  80                  85
 Y   V   D   S   V   K       G   R   F   T   I   S   R   D   N   S   K   N   T   L   Y
TAT GTA GAC TCC GTG AAG ... GGC CGA TTC ACC ATC TCC AGA GAC AAT TCT AAA AAC ACG CTC TAT

---------------------------------------------------------------->   _____
     90                  95                  100                 105                 110
 L   Q   M   N   S   L   R   A   E   D   T   A   V   Y   Y   C   A   R   D   R   S   S
CTG CAA ATG AAC AGC CTG AGA GCC GAG GAC ACG GCT GTG TAT TAC TGT GCG AGA GAT CGC AGC AGT

CDR3 - IMGT _____
                        115                 120                 125
 G   W   Y   W   S   C   D   S   W   G   Q   G   T   L   V   I   V   S   S
GGC TGG TAC TGG TCC TGC GAC TCC TGG GGC CAG GGA ACC CTG GTC ATT GTC TCC TCA
```

FIG. 46

Translation of CB2b-G8 V$_\lambda$

```
<-------------------- F  R  1  -  I  M  G  T --------------------------------
1              5                    10                  15                 20
                              x   x   L       L   S   G   S   P   G   Q   S   I   T   I   S
... ... ... ... ... ...    .TT XGC CTC ... CTG TCT GGG TCT CCT GGA CAG TCG ATC ACC ATC TCC

--------------->           _____ CDR1 - IMGT _____          <--------------------
              25                         30                       35                         40
  C   T   G   T   S   S   D   V   G   G   Y   N   Y                   V   S   W   Y   Q   Q
CTG ACT GGA ACC AGC AGT GAC GTT GGT GGT TAT AAC TAT ... ... ...  GTC TCC TGG TAC CAA CAG

F   R   2  -  I   M   G   T  ---------->                                                  <---
                                                            _____ CDR2 - IMGT _____
45                    50                    55                         60                         65
  H   P   G   K   A   P   K   L   M   I   Y   D   V   S                                                    D
CAC CCA GGC AAA GCC CCC AAA CTC ATG ATT TAT GAT GTC AGT ... ... ... ... ... ... ...  GAT

-------------------------------------------------------   F   R   3  -  I   M   G   T  ----
70                    75                    80                    85
  R   P   S   G   V   S       N   R   F   S   G   S   K               S   G   N   T   A   S
CGG CCC TCA GGG GTT TCT ... AAT CGC TTC TCT GGC TCC AAG ... ...  TCT GGC AAC ACG GCC TCC

------------------------------------------------------------------>
                                                                                   _____ CDR3 - IMGT
           90                    95                   100                   105                      110
  L   T   I   S   G   L   Q   A   E   D   E   A   D   Y   Y   C   S   S   Y   T   S   S
CTG ACC ATC TCT GGG CTC CAG GCT GAG GAC GAG GCT GAT TAT TAC TGC AGC TCA TAT ACA AGC AGC

_____ 115                   120                    125
130
  S   S   V   V   F   G   G   T   K   L   T   V   L   G   Q   P   K   A   A   P   S
AGC TCT GTG GTA TTC GGC GGA GGG ACC AAG CTG ACC GTC CTA GGT CAG CCC AAG GCT GCC CCC TCG

V   T   L   F   P   P   P   x
GTC ACT CTG TTC CCG CCT CCA AXG G
```

FIG. 49
A
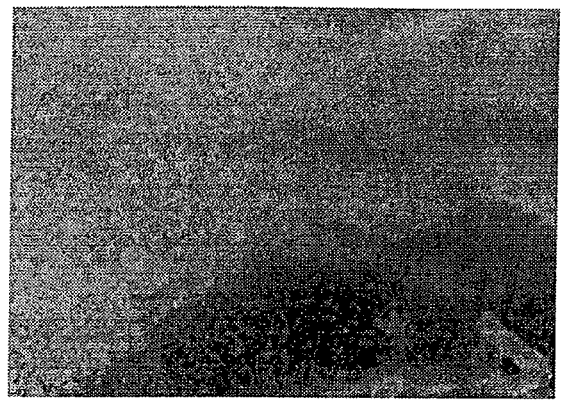
Mouse 94.03
B
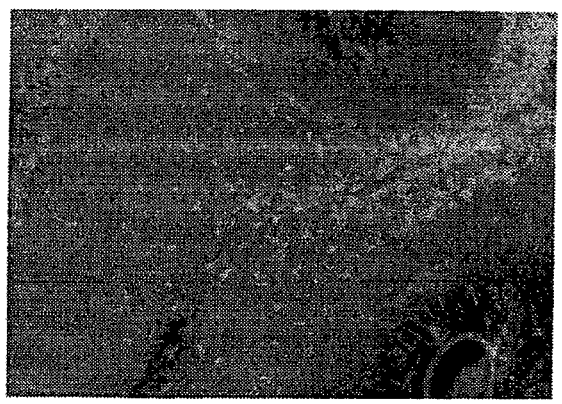
Humanized 94.03 clone 1
C
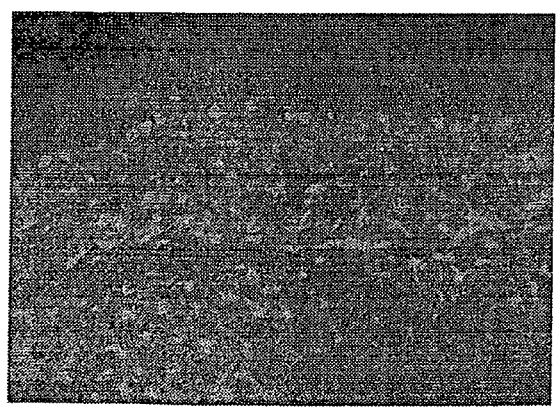
Humanized 94.03 clone 2

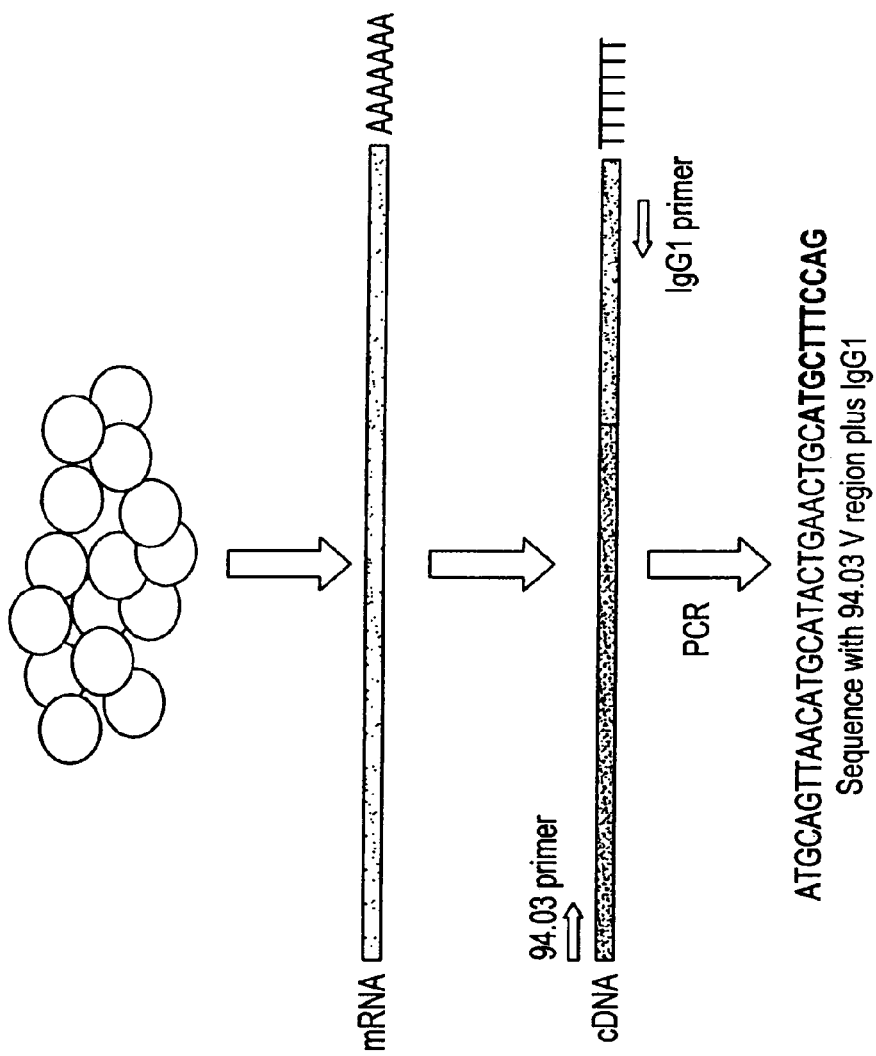

FIG. 52

09 V$_H$ Sequence with translation:

```
<------------------- F  R  1  -  I M G T ---------------------------------
   1              5                 10                15                  20
   Q  [ D   H   L   Q   Q   S   G   P      E   L   V ]  K   P   G   A   F   V   K   I   S
   CAG GAT CAC CTG CAG CAG TCT GGA CCT ...GAG CTG GTG AAG CCT GGG GCT TTT GTG AAG ATA TCC

--------------->                                          <--------------------
                                   CDR1 - IMGT
                      25                      30                 35              40
   C   K   A   S   G   Y   T   F   T   N   Y   D                   L   N   W   V   R   Q
   TGC AAG GCT TCT GGT TAC ACC TTC ACA AAC TAC GAT ... ... ... ...CTA AAC TGG GTG AGG CAG

F  R  2  -  I M G T ---------->                                                   <--
                                                        _____ CDR2 - IMGT _____
   45                 50                       55                60                 65
   R   P   G   Q   G   L   E   W   I   G   W   I   Y   P   G   N   D   N   T         K
   AGG CCT GGA CAG GGC CTT GAG TGG ATT GGA TGG ATT TAT CCT GGA AAT GAT AAT ACT ... ...AAG

----------------------------------------------------  F  R  3  -  I M G T --

70                 75                80                85
   Y   N   E   K   F   K       G   L   A   S   L   T   A   D   K   S   S   T   T   A   Y
   TAC AAT GAG AAG TTC AAG ...GGC CTG GCC TCA CTG ACT GCA GAC AAG TCC TCC ACC ACA GCC TAC

------------------------------------------------------------------->
      90                 95                100                 105                110
   L   H   L   S   S   L   T   S   E   S   S   A   V   Y   F   C   A   R   G   L   P   R
   TTG CAT CTC AGC AGC CTG ACT TCT GAG AGC TCT GCA GTC TAT TTC TGT GCA AGA GGG TTA CCT AGG

CDR3 - IMGT _____
                 115                 120
   G   W   Y   F   D   V   W   G   A   G   T   T   V   T   V   S   S   A
   GGC TGG TAC TTC GAT GTC TGG GGC GCA GGG ACC ACG GTC ACC GTC TCC TCA GCT
```

FIG. 53  Translation of 09 kappa light chain 1:

```
<----------------------- F R 1 - I M G T -----------------------
 1               5                10               15              20
[N  I  V  M  T  Q  S  P  K  S  M  S] M  S  V  G  E  R  V  T  L  T
AAC ATT GTA ATG ACC CAA TCT CCC AAA TCC ATG TCC ATG TCA GTA GGA GAG AGG GTC ACC TTG ACC

------------> <----------- CDR1 - IMGT -----------
         25                30                    35                   40
 C  K  A  S  E  N  V  V  T  Y           V  S  W  Y  Q  Q
TGC AAG GCC AGT GAG AAT GTG GTT ACT TAT ...     ... GTT TCC TGG TAT CAA CAG

<--- F R 2 - I M G T ---> <---------- CDR2 - IMGT ----------
 45                50                   55                   60                   65
 K  P  E  Q  S  Q  S  P  K  L  L  I  Y  G  A  S              N
AAA CCA GAG CAG TCA CAG TCT CCT AAA CTG CTG ATA TAC GGG GCA TCC ...           ... AAC

----------------------- F R 3 - I M G T -----------------------
         70                75                    80                   85
 R  Y  T  G  V  P  D  R  F  T  G  S  G           S  A  T  D  F  T
CGG TAC ACT GGG GTC CCC ... GAT CGC TTC ACA GGC AGT GGA ...     ... TCT GCA ACA GAT TTC ACT

-------> <---------- CDR3 - IMGT ----------
         90                95                    100                  105               110
 L  T  I  S  S  V  Q  A  E  D  L  A  D  Y  H  C  G  Q  G  Y  S  Y
CTG ACC ATC AGC AGT GTG CAG GCT GAA GAC CTT GCA GAT TAT CAC TGT GGA CAG GGT TAC AGC TAT

115
 P  Y  T  F  G  G  G
CCG TAC ACG TTC GGA GGG GGG
```

FIG. 54  Translation of 09 kappa light chain 2:

```
<------------------- FR 1 - IMGT -------------------
1                    5                    10                   15                   20
 D  V  Q  I  T  Q  S  P  S  Y  L  A  A  S  P  G  E  T  I  T  I  N
GAT GTC CAG ATA ACC CAG TCT CCA TCT TAT CTT GCT GCA TCT CCT GGA GAA ACC ATT ACT ATT AAT

-------|                   CDR1 - IMGT                   |<---
              25                   30                   35                   40
 C  R  A  S  K  S  I  S  K  Y        L  A  W  Y  Q  E
TGT AGG GCA AGT AAG AGC ATT AGT AAA TAT ... ... ...      TTA GCC TGG TAT CAA GAG

--- FR 2 - IMGT --->                              |--- CDR2 - IMGT ---|
45                   50                   55                   60                   65
 R  P  G  K  T  N  K  L  L  I  Y  S  G  S              T
AGA CCT GGA AAA ACT AAT AAG CTT CTT ATC TAC TCT GGA TCC ...           ACT

<---                      FR 3 - IMGT                       --->
              70                   75                   80                   85
 L  Q  S  G  I  P    S  R  F  S  G  S  G    S  G  T  D  F  T
TTG CAA TCT GGA ATT CCA ... TCA AGG TTC AGT GGC AGT GGA ... TCT GGT ACA GAT TTC ACT

|_____ CDR3 - IMGT
              90                   95                   100                  105                  110
 L  T  I  S  S  L  E  P  E  D  F  A  M  Y  Y  C  Q  Q  H  N  E  Y
CTC ACC ATC AGT AGC CTG GAG CCT GAA GAT TTT GCA ATG TAT TAC TGT CAA CAG CAT AAT GAA TAC

_____|
              115
 P  Y  T  F  G  G  G
CCG TAT ACG TTC GGA GGG GGG
```

FIG. 55    Translation of AKJR 4 Heavy Chain:

```
<---------------------------  FR 1 - IMGT  --------------------------->
1                         5                  10                      15                      20
E   V   Q   L   L   E   S   G   G   G   L   V   Q   P   G   G   S   L   R   L   S
GAG GTG CAA CTA TTG GAA TCT GGG GGA ... GGC TTG GTA CAG CCT GGG GGG TCC CTG AGA CTC TCC

|------- CDR1 - IMGT -------|
                25                      30                  Y   A       35
C   A   A   S   G   F   S   F       I   D   Y   A                           M   S   W   V   R   Q
TGT GCA GCC TCT GGA TTC AGC TTT ATC GAC TAT GCC ... ... ...                 ATG AGC TGG GTC CGC CAG

<--------  FR 2 - IMGT  -------->           |-------- CDR2 - IMGT --------|
            45              50                      55                      60                      65
A   P   G   K   G   L   E   W   V   S   S   L   S   G   D   S   G   S   S   S       Y
GCT CCA GGG AAG GGG CTG GAG TGG GTC TCA AGT CTT AGT GGT GAT AGT GGT AGT TCA ...     TAT

<------------  FR 3 - IMGT  ------------>
                70                      75                      80                      85
Y   A   D   S   V   K       G   R   F   T   I   S   R   D   N   S   K   S   T   V   F
TAT GCA GAC TCC GTG AAG ... GGC CGA TTC ACC ATC TCC AGA GAC AAT TCC AAG AGC ACG GTG TTT 90                      95                      100                     105                 |-- CDR3 - IMGT
                                                                                                                    110
L   Q   L   S   S   L   R   A   E   D   T   A   I   Y   Y   C   A   Q   E   T   G   P
CTG CAA CTG AGC AGC CTG AGA GCC GAG GAC ACG GCC ATA TAT TAC TGT GCG CAG GAG ACC GGT CCC 115                     120                     125                     130
Q   R   W   G   Q   G   T   L   V   T   V   S   S   G   S   A   S   A   P   T   L
CAG CGT CGC TGG GGC CAG GGA ACC CTG GTC ACC GTC TCC TCA GGG AGT GCA TCC GCC CCA ACC CTT
```

FIG. 56  Translation of AKJR 4 Kappa Light Chain:

```
<------------------------  F   R   1   -   I   M   G   T  ------------------------
 1                  5                   10                  15                  20
 D   I   Q   M   T   Q   S   P   S   T   L   S   A   S   V   G   D   R   V   T   I   T
GAC ATC CAG ATG ACC CAG TCT CCT TCC ACC CTG TCT GCA TCT GTA GGG GAC AGA GTC ACC ATC ACT
                                        -------------  CDR1 - IMGT  ------->
         25                  30                  35                  40
 C   R   A   S   Q   S   I   S   S   W                           L   A   W   Y   Q   Q
TGC CGG GCC AGT CAG AGT ATT AGT AGC TGG ... ... ... ... TTG GCC TGG TAT CAG CAG

------------  F   R   2   -   I   M   G   T  ------------>    <--- CDR2 - IMGT ---
 45                  50                  55                  60                  65
 K   P   G   K   A   P   K   L   L   I   Y   K   A   F                           N
AAA CCA GGG AAA GCC CCT AAA CTC CTG ATC TAT AAG GCG TTT ... ... ... ... ... ... AAT

----    ------------------  F   R   3   -   I   M   G   T  ------------------
                 70                  75                  80                  85
 L   E   S   G   V   P   S   R   F   R   G   S   G   S   G   T   E   F   T
TTA GAA AGT GGG GTC CCA ... TCA AGG TTC AGA GGC AGT GGC ... TCT GGG ACA GAA TTC ACT

-------------------------->    <---------- CDR3 - IMGT
             90                  95                 100                 105                 110
 L   T   I   S   S   L   Q   P   D   D   S   A   T   Y   Y   C   Q   Q   Y   S   S   Y
CTC ACC ATC AGC AGC CTG CAG CCT GAT GAT TCT GCA ACT TAT TAC TGC CAG CAG TAT AGT AGT TAC

----------    
             115                 120                 125                 130
 P   L   T   F   G   G   G   T   K   V   D   I   K   R   T   V   A   A   P   S   V   F
CCT CTC ACT TTC GGC GGA GGG ACC AAG GTG GAC ATT AAA CGA ACT GTG GCT GCA CCA TCT GTC TTC
```

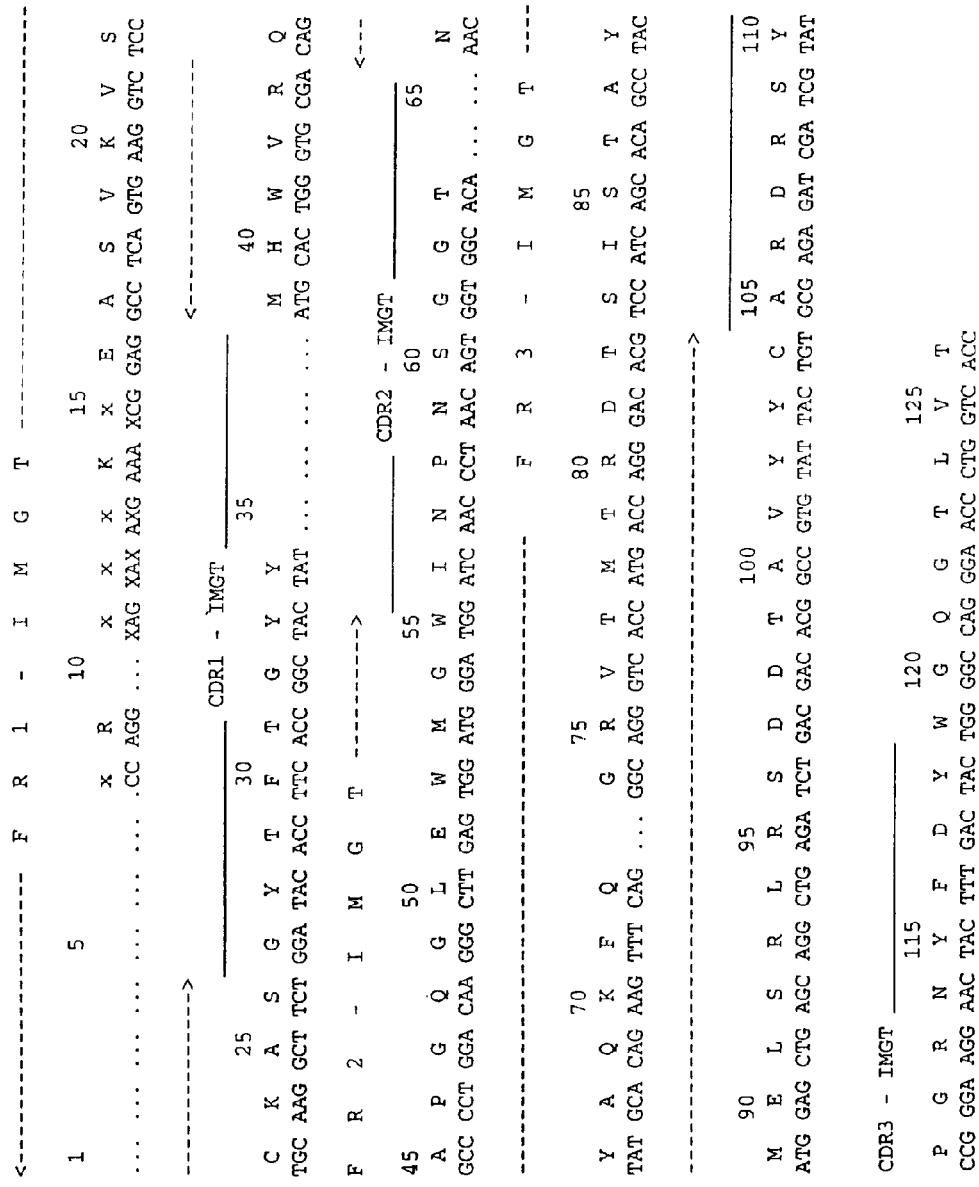
FIG. 57  Translation of CB2i-E12 Heavy Chain:

FIG. 58  Translation of CB2i-E12 kappa chain:

```
<--------------------- FR 1 - IMGT --------------------->
1               5                   10                  15                  20
E   I   V   L   T   Q   S   P   G   T   L   S   L   S   P   G   E   R   A   T   L   S
GAA ATT GTG TTG ACG CAG TCT CCA GGC ACC CTG TCT TTG TCT CCA GGG GAA AGA GCC ACC CTC TCC

<----- CDR1 - IMGT ----->
                25                  30                  35                          40
C   R   A   S   Q   S   V   S   S   Y           L   A   W   Y   Q   Q
TGC AGG GCC AGT CAG AGT GTT AGT AGC AGC TAC ... TTA GCC TGG TAC CAG CAG

<--------- FR 2 - IMGT --------->   <--- CDR2 - IMGT --->
45                  50                  55                      60                      65
K   P   G   Q   A   P   R   L   L   I   Y   G   A   S           S                       S
AAA CCT GGC CAG GCT CCC AGG CTC CTC ATC TAT GGT GCA TCC ... ... AGC

<----------------------- FR 3 - IMGT ----------------------->
                        70                  75                  80                  85
R   A   T   G   I   P   D   R   F   S   G   S   G           S   G   T   D   F   T
AGG GCC ACT GGC ATC CCA ... GAC AGG TTC AGT GGC AGT GGG ... ... TCT GGG ACA GAC TTC ACT

CDR3 - IMGT
            90                  95                  100                 105                 110
L   T   I   S   R   L   E   P   E   D   F   A   V   Y   Y   C   Q   Q   Y   G   S   S   T
CTC ACC ATC AGC AGA CTG GAG CCT GAA GAT TTT GCA GTG TAT TAC TGT CAG CAG TAT GGT AGC TCT

115
H   T   F   G   Q   G
CAC ACT TTT GGC CAG GGG
```

FIG. 59  Translation of CB2i-E7 Heavy Chain:

```
<----------------- FR1 - IMGT ------------------>
            1               5                  10                 15                  20
                            x       G   L   V   K   P   G   G   S   L   R   L   S
            ...     ...    .GA ... GGC TTG GTC AAG CCT GGA GGG TCC CTG AGA CTC TCC

<------- CDR1 - IMGT -------><------
                                25              30                  35                       40
            C   A   A   S   G   F   T   F   S   S   D   Y   Y               M   S   W   I   R   Q
            TGT GCA GCC TCT GGA TTC ACC TTC AGT GAC TAC TAC ... ...     ATG AGC TGG ATC CGC CAG

FR2 - IMGT ------------------><------------- CDR2 - IMGT ------------>
            45                  50                  55                  60                  65
            A   P   G   K   G   L   E   W   V   S   Y   I   S   S   S   S   S   Y   T       N
            GCT CCA GGG AAG GGG CTG GAG TGG GTT TCA GTT ATT AGT AGT AGT AGT TAC ACA ...  ... AAC

<------------------------- FR3 - IMGT ----------------
                                    70                  75                  80                   85
                        I   M   G   T       Y   A   D   S   V   K       G   R   F   T   I   S   R   D   N   A   K   N   S   L   Y
                                            TAC GCA GAC TCT GTG AAG ... GGC CGA TTC ACC ATC TCC AGA GAC AAC GCC AAG AAC TCA CTG TAT

---------------------------><-----
                                    90                  95                  100                 105                 110
            L   Q   M   N   S   L   R   A   E   D   T   A   V   Y   Y   C   A   R   D   R   S
            CTG CAA ATG AAC AGC CTG AGA GCC GAG GAC ACG GCT GTG TAT TAC TGT GCG AGA GAT CGG TCG AGC

CDR3 - IMGT --------------------------->
                            115                 120                 125
            S   S   W   Y   Y   Y   Y   Y   Y   G   M   D   V   W   G   Q   G
            AGC AGC TGG TAC TAC TAC TAC TAC TAC GGT ATG GAC GTC TGG GGC CAA GGG
```

FIG. 60  Translation of CB2i-E7 kappa Chain:

```
<------------------  FR 1 - IMGT  -------------------
1                 5                  10                 15                 20
D   I   Q   M   T   Q   S   P   S   S   L   S   A   S   V   G   D   R   V   T   I   T
GAC ATC CAG ATG ACC CAG TCT CCA TCC TCC CTG TCT GCA TCT GTA GGA GAC AGA GTC ACC ATC ACT

------->         ------------ CDR1 - IMGT -------         <----------------
         25                 30                 35                 40
C   R   A   S   Q   G   I   S   N   Y                   L   A   W   Y   Q   Q
TGC CGG GCG AGT CAG GGC ATT AGC AAT TAT ... ... ...     TTA GCC TGG TAT CAG CAG

FR 2 - IMGT  ----------->         ------------ CDR2 - IMGT -------         <---
         45                 50                 55                 60                 65
K   P   G   K   V   P   K   L   L   I   Y   A   A   S                               T
AAA CCA GGG AAA GTT CCT AAG CTC CTG ATC TAT GCT GCA TCC ... ... ... ... ... ...     ACT

--------         -------------------  FR 3 - IMGT  -------------------
                 70                 75                 80                 85
L   Q   S   G   V   P       S   R   F   N   G   S   G           S   G   T   D   F   T
TTG CAA TCA GGG GTC CCA ... TCT CGG TTC AAT GGC AGT GGA ... ... TCT GGG ACA GAT TTC ACT

--------         ----------->         ------------ CDR3 - IMGT ----
                 90                 95                 100                105                 110
L   T   I   S   S   L   Q   P   E   D   V   A   T   Y   Y   C   Q   K   Y   N   K   C
CTC ACC ATC AGC AGC CTG CAA CCT GAA GAT GTT GCA ACT TAT TAC TGT CAA AAG TAT AAC AAG TGC

------------
                115
P   S   H   F   R   G   R   D
CCC TCT CAC TTT CGG GGG AGG GAC
```

FIG. 61

Translation Of MSI 19-E5 Light Chain

```
<------------------  FR 1 - IMGT  ------------------
  1                  5                  10                 15                 20
  D   I   A   M   T   Q   S   P   D   S   L   A   V   S   L   G   E   R   A   T   I   N
 GAC ATC GCG ATG ACC CAG TCT CCA GAC TCC CTG GCA GTG TCT CTG GGC GAG AGG GCC ACC ATC AAC

------->|<------------  CDR1 - IMGT  ---------->
              25                 30                 35                 40
  C   K   S   S   R   S   V   L   F   S   S   N   N   N   N   Y   L   A   W   Y   Q   Q
 TGC AAG TCC AGC CGG AGT GTT TTA TTC AGC TCC AAC AAT AAC TAC TTA GCT TGG TAC CAG CAG

<-----------  FR 2 - IMGT  ------------>|<---- CDR2 - IMGT ---->|<---
          45                 50                 55                 60                 65
  K   P   G   Q   P   P   K   L   L   I   Y   W   A   S   .   .   .   .   .   T
 AAA CCA GGA CAG CCT CCT AAG CTA CTC ATT TAC TGG GCA TCT . . . . . . . . .  ACC

------------  FR 3 - IMGT  ------------------
                      70                 75                 80                 85
  R   E   S   G   V   P   .   D   R   F   S   G   S   G   .   S   G   T   D   F   T
 CGG GAA TCC GGG GTC CCT ... GAC CGA TTC AGT GGC AGC GGG ... ... TCT GGG ACA GAT TTC ACT

-------->|<------------------  CDR3 - I
               90                 95                 100                105                110
  L   T   I   S   S   L   Q   A   E   D   V   A   V   Y   Y   C   Q   Q   Y   Y   S   T
 CTC ACC ATC AGC AGC CTG CAG GCT GAA GAT GTG GCA GTT TAT TAC TGT CAG CAA TAT TAT AGT ACT

MGT  ----------|
  P   I   T   F   G
 CCA ATC ACC TTC GGC
```

FIG. 62   Translation of 04 kappa chain 2:

```
<------------------------  FR 1 - IMGT  ------------------------>
  1                           5                        10                       15                       20
  D   I   V   M   T   Q   S   H   K   F   M   S   T   S   V   G   D   R   V   S   I   T
 GAC ATC GTA ATG ACG CAG TCT CAC AAA TTC ATG TCC ACT TCA GTA GGA GAC AGG GTC AGC ATC ACC

|--------- CDR1 - IMGT ---------|
                                    25                          30
  C   K   A   S   Q   D   V   S   T   A                           V   A   W   Y   Q   Q
 TGC AAG GCC AGT CAG GAT GTG AGT ACT GCT ...    ...    ...    ... GTA GCC TGG TAT CAA CAG

|----- FR 2 - IMGT -----|                                                  <------
                                        35                              40
                                                                                        Y
                                                                                       TAC
                              |----- CDR2 - IMGT -----|   |------ FR 3 -------
  65                                          50                          55
  K   P   G   Q   S   P   K   L   L   I   Y   S   A   S                           I   M   G   T
 AAA CCA GGA CAA TCT CCT AAA CTA CTG ATT TAC TCG GCA TCC ...    ...    ...    ...

70                          75                          80                          85
  R   Y   T   G   V   P       D   R   F   T   G   S   G           S   G   T   D   F   T
 CGG TAC ACT GGA GTC CCT ... GAT CGC TTC ACT GGC AGT GGA ...    ... TCT GGG ACG GAT TTC ACT

|----- CDR3 - IMGT
                                        95                         100                         105                        110
  F   T   I   S   S   V   Q   A   E   D   L   A   V   Y   Y   C   Q   Q   H   Y   T   T
 TTC ACC ATC AGC AGT GTG CAG GCT GAA GAC CTG GCA GTT TAT TAC TGT CAG CAA CAT TAT ACT ACT

115
  P   L   T   F   G   A   G
 CCG CTC ACG TTC GGT GCT GGG
```

FIG. 63
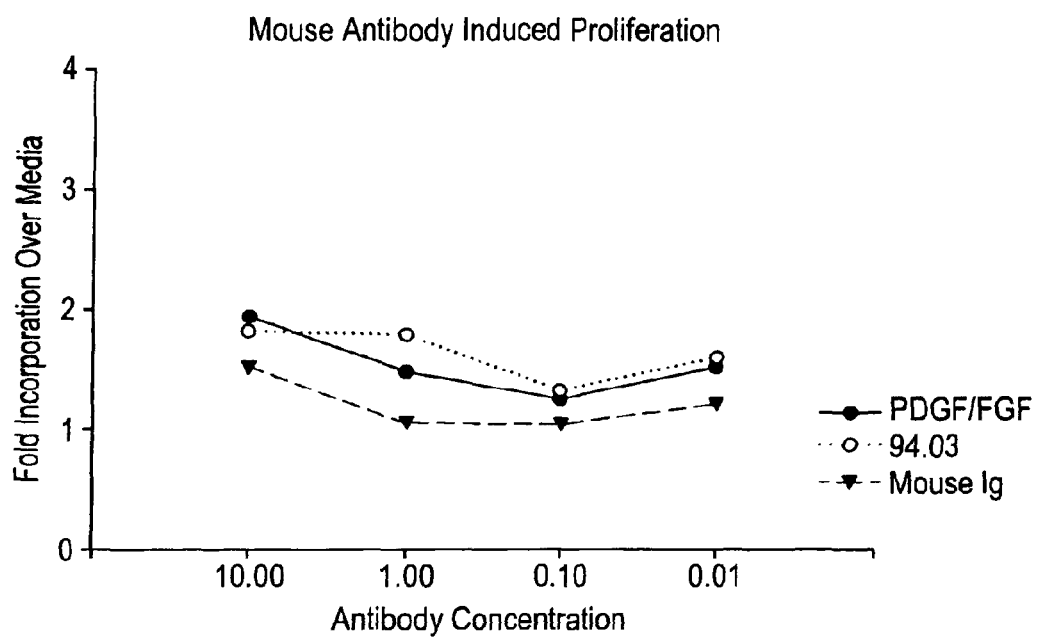
A
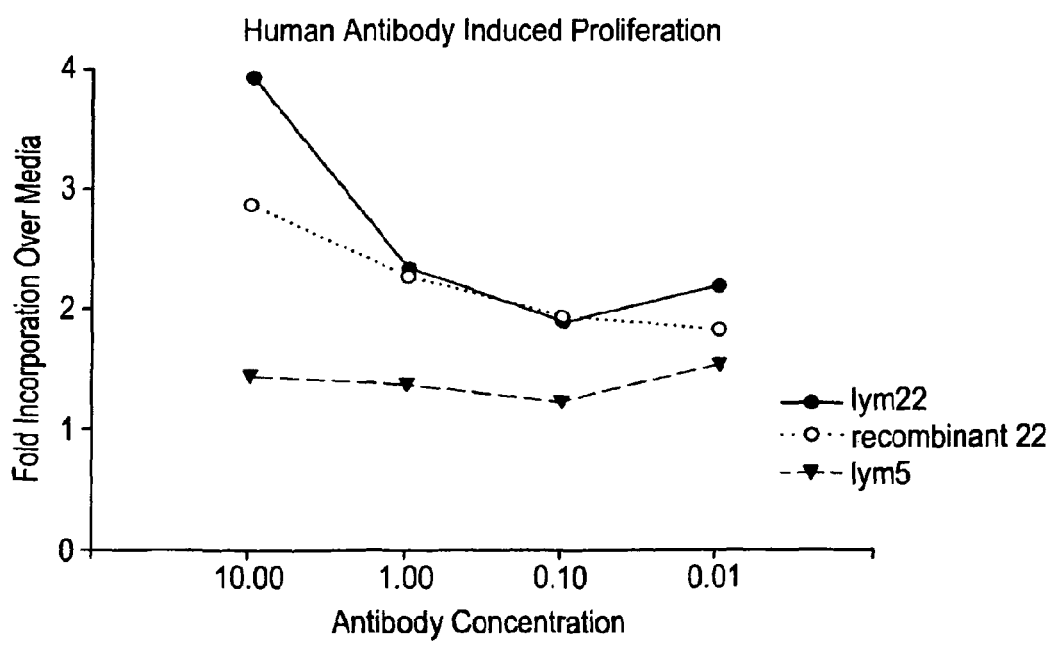
B

FIG. 67     TRANSLATION OF O4 KAPPA CHAIN

```
<----------------     F   R   1   -   I   M   G   T   ---------------
       1               5                          10                         15                         20
       D   I   V   M   T   Q   S   H   K   F   M   S   T   S   V   G   D   R   V   S   I   T
       GAC ATC GTA ATG ACG CAG TCT CAC AAA TTC ATG TCC ACT TCA GTA GGA GAC AGG GTC AGC ATC ACC
                                              ----------->  CDR1 - IMGT
                  25                          30                         35                                       40
       C   K   A   S   Q   D   V   S   T   A                               V   A   W   Y   Q   Q
       TGC AAG GCC AGT CAG GAT GTG AGT ACT GCT  ...  ...  ...  ...  ...  GTA GCC TGG TAT CAA CAG
                                                                                      <-----
       -----     F   R   2   -   I   M   G   T   ------------>                    <------ CDR2 - IMGT
       45                         50                         55                                          60                                65
       K   P   G   Q   S   P   K   L   L   I   Y   S   A   S                                             Y
       AAA CCA GGA CAA TCT CCT AAA CTA CTG ATT TAC TCG GCA TCC  ...  ...  ...  ...  ...  ...  ...  TAC
                                                              ---------     F   R   3   -   I   M   G   T   ---
                  70                         75                         80                         85
       R   Y   T   G   V   P   D   R   F   T   G   S   G   S   G   T   D   F   T
       CGG TAC ACT GGA GTC CCT  ... GAT CGC TTC ACT GGC AGT GGA  ... ... TCT GGG ACG GAT TTC ACT
                  90                         95                        100                        105                                     CDR3 - IMGT
       F   T   I   S   S   V   Q   A   E   D   L   A   V   Y   Y   C   Q   Q   H   Y   T   T        110
       TTC ACC ATC AGC AGT GTG CAG GCT GAA GAC CTG GCA GTT TAT TAC TGT CAG CAA CAT TAT ACT ACT
                 115                        120
       P   L   T   F   G   A   G   T   R   L   E   L   K   R
       CCG CTC ACG TTC GGT GCT GGG ACC AGG CTG GAG CTG AAA CGG
```

FIG. 68

TRANSLATION OF O1 KAPPA CHAIN

```
      1               5              10              15              20
      D   V   Q   I   T   Q   S   P   S   Y   L   A   A   S   P   G   E   T   I   T   I   N
     GAT GTC CAG ATA ACC CAG TCT CCA TCT TAT CTT GCT GCA TCT CCT GGA GAA ACC ATT ACT ATT AAT

|---------- CDR1 - IMGT ---------->
                      25              30              35                              40
      C   R   A   S   K   S   I   S   K   Y                           L   A   W   Y   Q   E
     TGC AGG GCA AGT AAG AGC ATT AGC AAA TAT ... ... ... ... ... ... TTA GCC TGG TAT CAA GAG

<---------|                                          |----- CDR2 - IMGT -----|
                      50              55              60              65
      F   R   2   -   I   M   G   T                       S                   T
      K   P   G   K   T   N   K   L   L   I   Y   S   G   S                   ACT
     AAA CCT GGG AAA ACT AAT AAG CTT CTT ATC TAC TCT GGA TCC ... ... ... ... ACT

|----- F   R   3   -   IMGT -----|
                      70              75              80              85
      L   Q   S   G   I   P       S   R   F   S   G   S   G       S   G   T   D   F   T
     TTG CAA TCT GGA ATT CCA ... TCA AGG TTC AGT GGC AGT GGA ... TCT GGT ACA GAT TTC ACT

|---------- CDR3 - IMGT ----------
                      90              95             100             105             110
      L   T   I   S   S   L   E   P   E   D   F   A   M   Y   Y   C   Q   Q   H   N   E   Y
     CTC ACC ATC AGT AGC CTG GAG CCT GAA GAT TTT GCA ATG TAT TAC TGT CAA CAG CAT AAT GAA TAC 115             120
      P   Y   T   F   G   G   G   T   K   L   E   I   K   R
     CCG TAC ACG TTC GGA GGG GGG ACC AAG CTG GAA ATA AAA CGG
```

FIG. 69   TRANSLATION OF HNK-1 KAPPA CHAIN

```
<------------------  F   R   1   -   I   M   G   T  ------------------
1               5                   10                  15                  20
D   I   Q   M   T   Q   T   P   S   S   L   S   A   S   L   G   E   R   V   S   L   T
GAC ATC CAG ATG ACC CAG TCT CCA TCC TCC TTA TCT GCC TCT CTG GGA GAA AGA GTC AGT CTC ACT

-------------------------->    CDR1 - IMGT    <--------
                25                  30                  35              40
C   R   A   S   Q   S   I   G   S   S   L   N   W   L   Q   Q
TGT CGG GCA AGT CAG AGT ATT GGT AGT AGC ... ... ... TTA AAC TGG CTT CAG CAG

F   R   2   -   I   M   G   T  ----------------->    CDR2 - IMGT    <---
                                    50                      55              60                  65
E   P   D   G   T   I   K   R   L   I   Y   A   T   S                       S
GAA CCA GAT GGA ACT ATT AAA CGC CTG ATC TAT GCC ACA TCC ... ... ... ... ... AGT

------       F   R   3   -   I   M   G   T  ----------------
        70                  75                  80                  85
L   D   S   G   V   P   K   R   F   S   G   S   R   S   G   S   D   Y   S
TTA GAT TCT GGT GTC CCC ... AAA AGG TTC AGT GGC AGT AGG TCT GGG TCA GAT TAT TCT

------------------------->    CDR3 - IMGT
        90                  95                  100                 105             110
L   T   I   S   S   L   E   S   E   D   F   V   D   Y   Y   C   L   Q   Y   A   S   F
CTC ACC ATC AGC AGC CTT GAG TCT GAA GAT TTT GTA GAC TAT TAC TGT CTA CAA TAT GCT AGT TTT 115                 120
P   Y   T   F   G   G   G   T   K   L   E   I   K   R
CCG TAC ACG TTC GGA GGG GGG ACC AAG CTG GAA ATA AAA CGG
```

FIG. 70  TRANSLATION OF A2B5 KAPPA CHAIN

```
<------------------------------ FR 1 - IMGT ------------------------------
  1              5                   10                  15                  20
  Q   I   V   L   T   Q   S   P   A   I   M   S   A   S   P   G   E   K   V   T   I   S
  CAA ATT GTT CTC ACC CAG TCT CCA GCA ATC ATG TCT GCA TCT CCA GGG GAG AAG GTC ACC ATA TCC

------------------------------>   <----------- CDR1 - IMGT ----------->
         25                  30                  35                  40
  C   S   S   A   S   S   S   V   S   Y                       M   Y   W   Y   Q   Q
  TGC AGT GCC AGC TCA AGT GTA AGT TAC ... ... ... ... ... ... ATG TAC TGG TAC CAG CAG

<---------- FR 2 - IMGT ---------->    <- CDR2 - IMGT ->
         45                  50                  55                  60                65
  K   P   G   S   S   P   K   P   W   I   Y   R   T   S                           N
  AAG CCA GGA TCC TCC CCC AAA CCC TGG ATT TAT CGC ACA TCC ... ... ... ... ... ... AAC

<------------------------------ FR 3 - IMGT ------------------------------
         70                  75                  80                  85
  L   A   S   G   V   P   A   R   F   S   G   S   G   S       I   M   G   T
  CTG GCT TCT GGA GTC CCT ... GCT CGC TTC AGT GGC AGT GGG ... ... ... ... ...

------------------------------>              <------ CDR3 - IMGT ----->
                  95                  100                 105                 110
  L   T   I   S   S   M   E   A   E   D   A   A   T   Y   Y   C   Q   Q   Y   H   S   Y
  CTC ACA ATC AGC AGC ATG GAG GCT GAA GAT GCT GCC ACT TAT TAC TGC CAG CAG TAT CAT AGT TAC

----------
         115                 120
  P   L   T   F   G   A   G   T   K   L   E   L   K   R
  CCA CTC ACG TTC GGT GCT GGG ACC AAG CTG GAG CTG AAA CGG
```

FIG. 71

LYM 46 Heavy Chain Sequence:

```
                  FR 1
 E   V   Q   L   V   E   S   G   G   G   L   V   Q   P   G
GAG GTG CAG CTG GTG GAG TCT GGG GGA GGC TTG GTC CAG CCT GGG

CDR1
 G   S   L   R   L   S   C   A   A   S   G   F   T   F   S
GGG TCC CTG AGA CTC TCC TGT GCA GCC TCT GGA TTC ACC TTT AGT

FR 2
 S   Y   W   M   T   W   V   R   Q   A   P   G   K   G   L
AGC TAT TGG ATG ACC TGG GTC CGC CAG GCT CCA GGG AAG GGG CTG

CDR2
 E   W   V   A   N   I   K   K   D   G   S   E   K   S   Y
GAG TGG GTG GCC AAC ATA AAG AAA GAT GGA AGT GAG AAA TCC TAT

FR3
 V   D   S   V   K   G   R   F   T   T   S   R   D   N   A
GTG GAC TCT GTG AAG GGC CGA TTC ACC ACC TCC AGA GAC AAC GCC

K   N   S   L   Y   L   Q   M   N   S   L   R   A   E   D
AAG AAC TCA CTG TAT CTG CAA ATG AAC AGC CTG AGA GCC GAG GAC

CDR3
 T   A   V   Y   Y   C   A   R   P   N   C   G   G   D   C
ACG GCT GTG TAT TAC TGT GCG AGA CCC AAT TGT GGT GGT GAC TGC

Y   L   P   W   Y   F   D   L   W   G   R   G   T   L   V
TAT TTA CCA TGG TAC TTC GAT CTC TGG GGC CGT GGC ACC CTG GTC

T   V   S   S
ACT GTC TCC TCA
```

FIG. 72

```
<---------------------------     FR1 - IMGT    -----------------------
1               5                  10                 15                 20
D   I   V   M   T   Q   S   P   D   S   L   A   V   S   L   G   E   R   A   T   I   N
GAC ATC GTG ATG ACC CAG TCT CCA GAC TCC CTG GCT GTG TCT CTG GGC GAG AGG GCC ACC ATC AAC
------------------------->                 <------ CDR1 - IMGT -------
                25                 30                 35                 40
C   K   S   S   Q   S   V   L   Y   S   S   N   N   K   N   Y   L   A   W   Y   Q   Q
TGC AAG TCC AGC CAG AGT GTT TTA TAC AGC TCC AAC AAT AAG AAC TAC TTA GCT TGG TAC CAG CAG
--- FR2 - IMGT --------->                          <--- CDR2 - IMGT ---
        45                 50                 55                 60                65
K   P   G   Q   P   P   K   L   L   I   Y   W   A   S   T                           T
AAA CCA GGA CAG CCT CCT AAA CTA CTC ATT TAC TGG GCA TCT ...                         ACC
-------->                          <----------    FR 3 - IMGT    --------------
                    70                 75                 80                 85
R   E   S   G   V   P   D   R   F   S   G   S   G                   S   G   T   D   F   T
CGG GAA TCC GGG GTC CCT ... GAC CGA TTC AGT GGC AGC GGG ...         TCT GGG ACA GAT TTC ACT
                                                     <------- CDR3 - IMGT --------
            90                 95                 100                105                110
L   T   I   S   S   L   Q   A   E   D   V   A   V   Y   Y   C   Q   Q   Y   Y   N   T
CTC ACC ATC AGC AGC CTG CAG GCT GAA GAT GTG GCA GTT TAT TAC TGT CAA CAA TAT TAT AAT ACT
------>
            115                120                125                130
P   Q   A   F   G   Q   G   T   K   V   E   I   K   R   T   V   A   A   P   S   V   F
CCT CAG GCG TTC GGC CAA GGG ACC AAG GTG GAA ATC AAA CGA ACT GTG GCT GCA CCA TCT GTC TTC
```

Chronically TMEV Infected SJL Mice
Treated with sHIgM46 or sHIgM22

FIG. 86
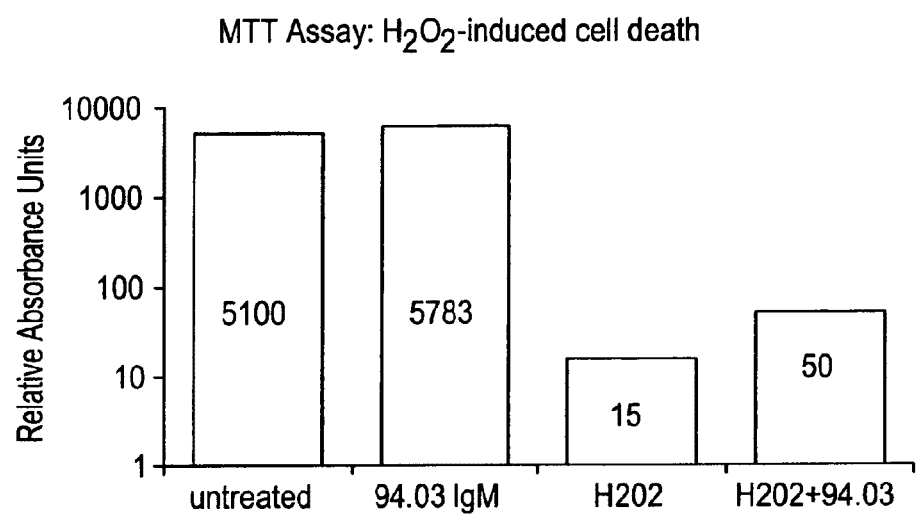
A
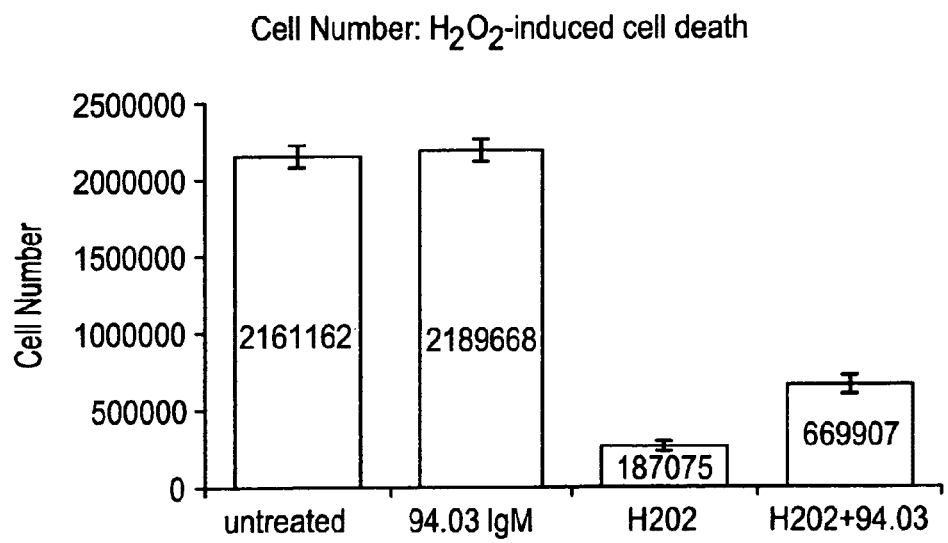
B

SEQUENCE LISTING

<160> NUMBER OF SEQ ID NOS: 82

<210> SEQ ID NO 1
<211> LENGTH: 420
<212> TYPE: DNA
<213> ORGANISM: Mus musculus

<400> SEQUENCE: 1

```
atgggatgga gatggatctt tcttttcctc ctgtcaggaa ctgcaggtgt ccattgccag      60
gttcagctgc agcagtctgg acctgagctg gtgaagcctg ggctttagt gaagatatcc     120 tgcaaggctt ctggttacac cttcacaagc tacgatataa actgggtgaa gcagaggcct    180
ggacagggac ttgagtggat tggatggatt tatcctggag atggtagtac taagtacaat    240
gagaaattca agggcaaggc cacactgact gcagacaaat cctccagcac agcctacatg    300
cagctcagca gcctgacttc tgagaactct gcagtctatt tctgtgcaag aggggccagg    360
ttctactggt acttcgatgt ctggggcgca gggaccacgg tcaccgtctc ctcagagagt    420
```

<210> SEQ ID NO 2
<211> LENGTH: 395
<212> TYPE: DNA
<213> ORGANISM: Mus musculus

<400> SEQUENCE: 2

```
atggctgtct tggggctgct cttctgcctg gtgacattcc caagctgtgt cctatcccag      60
gtgcagctga agcagtcagg acctggccta gtgcagccct cacagagcct gtccatcacc    120
tgcacagtct ctggtttctc attaactagc tatggtgtac actgggttcg ccagtctcca    180
ggaaagggtc tggagtggct gggagtgata tggagtggtg aagcacaga ctataatgca     240 gctttcatat ccagactgag catcagcaag gacgcttcca gagccaagt tttctttaaa     300 atgaacagtc tgcacgctac atatattatt gtgccagaga ctacggtagt aggggggact    360
actggggtca aggaacctca gtcaccgtct cctca                                395
```

<210> SEQ ID NO 3
<211> LENGTH: 423
<212> TYPE: DNA
<213> ORGANISM: Mus musculus

<400> SEQUENCE: 3

```
atgaagttgt ggttaaactg ggttttctt ttaacacttt tacatggtat ccagtgtgag       60
gtgaagctgg tggaatctgg tggaggcctg gtacagcctg ggggttctct gagactctcc    120
tgtgcaactt ctgggttcac cttcagtgat ttctacatgg agtgggtccg ccagcctcca    180
gggaagagac tggagtggat tgctgcaagt agaaagaaag ctaatgatta taaaacagag    240
tacagtgcat ctgtgaaggg gcggttcacc gtctccagag acacttccca agcatcctc     300 taccttcaga tgaatgccct gagagatgag gacactgcca tttattactg tgcaagagat    360
gcacggcagc tcgggctccc gtttgcttac tggggccaag gactctggt cactgtctct     420 gca                                                                    423
```

<210> SEQ ID NO 4
<211> LENGTH: 384
<212> TYPE: DNA
<213> ORGANISM: Mus musculus

<400> SEQUENCE: 4

```
atggaatcac agactctggt cttcatatcc atactgctct ggttatatgg agctgatggg      60
```

```
aacattgtaa tgacccaatc tcccaaatcc atgtccatgt cagtaggaga gagggtcacc    120
ttgacctgca aggccagtga aatgtggtt  acttatgttt cctggtatca acagaaacca    180
gagcagtctc ctaaactgct gatatacggg gcatccaacc ggtacactgg ggtccccgat    240
cgcttcacag gcagtggatc tgcaacagat ttcactctga ccatcagcag tgtgcaggct    300
gaagaccttg cagattatca ctgtggacag ggttacagct atccgtacac gttccgaggg    360
gggaccaagc tggaaataaa acgg                                           384

<210> SEQ ID NO 5
<211> LENGTH: 402
<212> TYPE: DNA
<213> ORGANISM: Mus musculus

<400> SEQUENCE: 5
atggacatga gggctcctgc acagattttt ggcttcttgt tgctcttgtt tcaaggtacc    60
agatgtgaca tccagatgac ccagtctcca tcctccttat ctgcctctct gggagaaaga    120
gtcagtctca cttgtcgggc aagtcaggac attggtagta gcttaaactg gcttcagcag    180
gaaccagatg gaactattaa acgcctgatc tacgccacat ccagtttaga ttctggtgtg    240
cccaaaaggt tcagtggcag taggtctggg tcagattatt ctctcaccat cagcagcctt    300
gagtctgaag attttgtaga ctattactgt ctacaatatg ctagttctcc gtacacgttc    360 ggaggggga ccaagctgga aataaaacgg gctgatgctt ca                        402

<210> SEQ ID NO 6
<211> LENGTH: 396
<212> TYPE: DNA
<213> ORGANISM: Mus musculus

<400> SEQUENCE: 6
atggagtcac agattcaggt cttttgtattc gtgtttctct ggttgtctgg tgttgacgga    60
gacattgtga tgacccagtc tcacaaattc atgtccactt cagtaggaga cagggtcagc    120
atcacctgca aggccagtca ggatgtgagt actgctgtag cctggtatca acagaaacca    180
ggacaatctc ctaaactact gatttactcg gcatcctacc ggtacactgg agtccctgat    240
cgcttcactg gcagtggatc tgggacggat ttcactttca ccatcagcag tgtgcaggct    300
gaagacctgg cagtttatta ctgtcagcaa cattatacta ctccgctcac gttcggtgct    360
gggaccaggc tggagctgaa acgggctgat gcttca                              396

<210> SEQ ID NO 7
<211> LENGTH: 119
<212> TYPE: PRT
<213> ORGANISM: Homo sapiens
<220> FEATURE:
<221> NAME/KEY: VARIANT
<222> LOCATION: (50)...(50)
<223> OTHER INFORMATION: Xaa can be Val or Ile
<221> NAME/KEY: VARIANT
<222> LOCATION: (89)...(89)
<223> OTHER INFORMATION: Xaa can be Asp or Glu

<400> SEQUENCE: 7

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Ser
            20                  25                  30

Gly Met His Trp Val Arg Gln Ala Pro Gly Lys Gly Leu Glu Trp Val
```

```
                35                  40                  45
Ala Xaa Ile Ser Tyr Asp Gly Ser Arg Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Thr Ala Xaa Asp Thr Ala Val Tyr Tyr Cys
                 85                  90                  95

Ala Lys Gly Val Thr Gly Ser Pro Thr Leu Asp Tyr Trp Gly Gln Gly
            100                 105                 110

Thr Leu Val Thr Val Ser Ser
        115

<210> SEQ ID NO 8
<211> LENGTH: 357
<212> TYPE: DNA
<213> ORGANISM: Homo sapiens
<220> FEATURE:
<221> NAME/KEY: variation
<222> LOCATION: (27)...(27)
<223> OTHER INFORMATION: n is a or g
<221> NAME/KEY: variation
<222> LOCATION: (117)...(117)
<223> OTHER INFORMATION: n is g or a
<221> NAME/KEY: variation
<222> LOCATION: (148)...(148)
<223> OTHER INFORMATION: n is g or a
<221> NAME/KEY: variation
<222> LOCATION: (150)...(150)
<223> OTHER INFORMATION: n is t or c
<221> NAME/KEY: variation
<222> LOCATION: (237)...(237)
<223> OTHER INFORMATION: n is g or c
<221> NAME/KEY: variation
<222> LOCATION: (261)...(261)
<223> OTHER INFORMATION: n is g or a
<221> NAME/KEY: variation
<222> LOCATION: (267)...(267)
<223> OTHER INFORMATION: n is g or c
<221> NAME/KEY: variation
<222> LOCATION: (285)...(285)
<223> OTHER INFORMATION: n is c or t

<400> SEQUENCE: 8
caggtgcagc tggtggagtc tgggggnggc gtggtccagc ctggagggtc cctgagactc     60
tcctgtgcag cctctggatt caccttcagt agctctggca tgcactgggt ccgccangct    120
ccaggcaagg ggctggagtg ggtggcantn atttcatatg atggaagtag gaaatactat    180
gcagactccg tgaagggccg attcaccatc tccagagaca actccaagaa cactctntat    240
ctgcaaatga acagcctgac ngctgangac acggctgtgt attantgtgc gaaaggagtg    300
actggtagtc cgacgcttga ctactggggc caggaaccc tggtcaccgt ctcctcg       357

<210> SEQ ID NO 9
<211> LENGTH: 114
<212> TYPE: PRT
<213> ORGANISM: Homo sapiens
<220> FEATURE:
<221> NAME/KEY: VARIANT
<222> LOCATION: (46)...(46)
<223> OTHER INFORMATION: Xaa is Arg or Lys
<221> NAME/KEY: VARIANT
<222> LOCATION: (90)...(90)
<223> OTHER INFORMATION: Xaa is Gly or Glu

<400> SEQUENCE: 9

Gln Ser Val Leu Thr Gln Pro Pro Ser Val Ser Ala Ala Pro Gly Gln
  1               5                  10                  15
```

```
Lys Val Thr Ile Ser Cys Ser Gly Ser Ser Asn Ile Gly Asn Asn
            20                  25                  30

Phe Val Ser Trp Tyr Gln Gln Leu Pro Gly Thr Ala Pro Xaa Leu Leu
        35                  40                  45

Ile Tyr Asp Ile Thr Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Xaa Thr Trp Asp Ser Ser Leu
                85                  90                  95

Ser Ala Val Val Phe Gly Gly Gly Thr Lys Leu Thr Val Leu Gly Gln
            100                 105                 110

Pro Lys
```

```
<210> SEQ ID NO 10
<211> LENGTH: 342
<212> TYPE: DNA
<213> ORGANISM: Homo sapiens
<220> FEATURE:
<221> NAME/KEY: variation
<222> LOCATION: (137)...(137)
<223> OTHER INFORMATION: n is g or a
<221> NAME/KEY: variation
<222> LOCATION: (269)...(269)
<223> OTHER INFORMATION: n is g or a

<400> SEQUENCE: 10
cagtctgtgt tgacggagcc gccttcagtg tctgctgccc caggacagaa ggtcaccatc      60
tcctgctctg gaagcagctc aacattggc aataattttg tatcctggta ccagcaactc     120
ccaggaacag cccccanact cctcatttat gacattacta gcgaccctc agggattcct     180 gaccgattct ctggctccaa gtctggcacg tcagccaccc tgggcatcac cggactccag     240 actgggacg aggccgatta ttactgcgna acatgggata gcagcctgag tgctgtggta     300
ttcggcgggg ggaccaagct gaccgtccta ggtcagccca ag                        342
```

```
<210> SEQ ID NO 11
<211> LENGTH: 121
<212> TYPE: PRT
<213> ORGANISM: Homo sapiens

<400> SEQUENCE: 11

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ser Ala Gln Gln Gln Leu Val Tyr Tyr Phe Asp Tyr Trp Gly Gln
            100                 105                 110

Gly Thr Leu Val Thr Val Ser Ser Gly
        115                 120
```

<210> SEQ ID NO 12
<211> LENGTH: 370
<212> TYPE: DNA
<213> ORGANISM: Homo sapiens

<400> SEQUENCE: 12

```
caggtgcagc tgcaggagtc gggcccagga ctggtgaagc cttcggagac cctgtccctc    60
acctgcactg tctctggtgg ctccatcagt agttactact ggagctggat ccggcagccc   120
ccagggaagg gactggagtg gattgggtat atctattaca gtgggagcac caactacaac   180
ccctccctca gagtcgagt caccatatca gtagacacgt ccaagaacab ccagttctcc   240
ctgaagctga gctctgtgac cgctgcggac acggccabcg tgtattactg tgcgaggtcg   300
gcacagcagc agctggtata ctacdtttga ctactggggc cagggaaccc tggtcaccgt   360
ctcctcaggg                                                          370
```

<210> SEQ ID NO 13
<211> LENGTH: 119
<212> TYPE: PRT
<213> ORGANISM: Homo sapiens

<400> SEQUENCE: 13

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
             20                  25                  30

Ser Asn Asn Lys Asn Tyr Leu Ala Trp Tyr Gln Gln Lys Pro Gly Gln
         35                  40                  45

Pro Pro Lys Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Thr Pro Leu Thr Phe Gly Pro Gly Thr Lys Val Asp Ile
            100                 105                 110

Lys Arg Thr Val Ala Ala Pro
        115
```

<210> SEQ ID NO 14
<211> LENGTH: 357
<212> TYPE: DNA
<213> ORGANISM: Homo sapiens

<400> SEQUENCE: 14

```
gacatcgtga tgacccagtc tccagactcc ctggctgtgt ctctgggcga gagggccacc    60
atcaactgca gtccagcca gagtgtttta tacagctcca acaataagaa ctacttagct   120
tggtaccagc agaaaccagg acagcctcct aagctgctca tttactgggc atctacccgg   180
gaatccgggg tccctgaccg attcagtggc agcgggtctg ggacagattt cactctcacc   240
atcagcagcc tgcaggctga agatgtgca gtttattact gtcagcaata ttatagtact   300
cctctcactt tcggccctgg gaccaaagtg gatatcaaac gaactgtggc tgcacca     357
```

<210> SEQ ID NO 15
<211> LENGTH: 112
<212> TYPE: PRT

<213> ORGANISM: Homo sapiens

<400> SEQUENCE: 15

Ala Val Val Gln Pro Gly Arg Ser Leu Arg Leu Ser Cys Ala Ala Ser
1               5                   10                  15

Gly Phe Ile Phe Ser Ser Tyr Gly Met His Trp Val Arg Gln Val Pro
            20                  25                  30

Gly Lys Gly Leu Glu Trp Val Ala Val Ile Trp Tyr Asp Gly Ser Asp
        35                  40                  45

Lys Tyr Tyr Val Asp Ser Val Lys Gly Arg Phe Thr Ile Ser Arg Asp
50                  55                  60

Asn Ser Lys Asn Thr Leu Tyr Leu Gln Met Asn Ser Leu Arg Ala Glu
65                  70                  75                  80

Asp Thr Ala Val Tyr Tyr Cys Ala Arg Asp Arg Ser Ser Gly Trp Tyr
                85                  90                  95

Trp Ser Cys Asp Ser Trp Gly Gln Gly Thr Leu Val Ile Val Ser Ser
            100                 105                 110

<210> SEQ ID NO 16
<211> LENGTH: 338
<212> TYPE: DNA
<213> ORGANISM: Homo sapiens

<400> SEQUENCE: 16
aggccgtggt ccagcctggg aggtccctga gactctcctg tgcagcgtct ggattcattt      60
tcagtagcta tggcatgcac tgggtccgcc aggttccagg caaggggctg gagtgggtgg     120
cagttatatg gtatgatgga agtgataaat actatgtaga ctccgtgaag ggccgattca     180
ccatctccag agacaattct aaaaacacgc tctatctgca aatgaacagc ctgagagccg     240
aggacacggc tgtgtattac tgtgcgagag atcgcagcag tggctggtac tggtcctgcg     300
actcctgggg ccagggaacc ctggtcattg tctcctca                             338

<210> SEQ ID NO 17
<211> LENGTH: 117
<212> TYPE: PRT
<213> ORGANISM: Homo sapiens

<400> SEQUENCE: 17

Leu Leu Ser Gly Ser Pro Gly Gln Ser Ile Thr Ile Ser Cys Thr Gly
1               5                   10                  15

Thr Ser Ser Asp Val Gly Gly Tyr Asn Tyr Val Ser Trp Tyr Gln Gln
            20                  25                  30

His Pro Gly Lys Ala Pro Lys Leu Met Ile Tyr Asp Val Ser Asp Arg
        35                  40                  45

Pro Ser Gly Val Ser Asn Arg Phe Ser Gly Ser Lys Ser Gly Asn Thr
50                  55                  60

Ala Ser Leu Thr Ile Ser Gly Leu Gln Ala Glu Asp Glu Ala Asp Tyr
65                  70                  75                  80

Tyr Cys Ser Ser Tyr Thr Ser Ser Ser Val Val Phe Gly Gly Gly Thr
                85                  90                  95

Lys Leu Thr Val Leu Gly Gln Pro Lys Ala Ala Pro Ser Val Thr
            100                 105                 110

Leu Phe Pro Pro Pro
        115

<210> SEQ ID NO 18

<211> LENGTH: 358
<212> TYPE: DNA
<213> ORGANISM: Homo sapiens

<400> SEQUENCE: 18

```
ttgcctcctg tctgggtctc ctggacagtc gatcaccatc tccctgactg gaaccagcag      60
tgacgttggt ggttataact atgtctcctg gtaccaacag cacccaggca aagcccccaa     120
actcatgatt tatgatgtca gtgatcggcc ctcaggggtt tctaatcgct tctctggctc     180
caagtctggc aacacggcct ccctgaccat ctctgggctc aggctgagg acgaggctga     240
ttattactgc agctcatata caagcagcag ctctgtggta ttcggcggag ggaccaagct     300
gaccgtccta ggtcagccca aggctgcccc ctcggtcact ctgttcccgc ctccaagg      358
```

<210> SEQ ID NO 19
<211> LENGTH: 120
<212> TYPE: PRT
<213> ORGANISM: Mus musculus

<400> SEQUENCE: 19

```
Gln Asp His Leu Gln Gln Ser Gly Pro Glu Leu Val Lys Pro Gly Ala
  1               5                  10                  15
Phe Val Lys Ile Ser Cys Lys Ala Ser Gly Tyr Thr Phe Thr Asn Tyr
             20                  25                  30
Asp Leu Asn Trp Val Arg Gln Arg Pro Gly Gln Gly Leu Glu Trp Ile
         35                  40                  45
Gly Trp Ile Tyr Pro Gly Asn Asp Asn Thr Lys Tyr Asn Glu Lys Phe
     50                  55                  60
Lys Gly Leu Ala Ser Leu Thr Ala Asp Lys Ser Ser Thr Thr Ala Tyr
 65                  70                  75                  80
Leu His Leu Ser Ser Leu Thr Ser Glu Ser Ser Ala Val Tyr Phe Cys
                 85                  90                  95
Ala Arg Gly Leu Pro Arg Gly Trp Tyr Phe Asp Val Trp Gly Ala Gly
            100                 105                 110
Thr Thr Val Thr Val Ser Ser Ala
            115                 120
```

<210> SEQ ID NO 20
<211> LENGTH: 360
<212> TYPE: DNA
<213> ORGANISM: Mus musculus

<400> SEQUENCE: 20

```
caggatcacc tgcagcagtc tggacctgag ctggtgaagc ctggggcttt tgtgaagata      60
tcctgcaagg cttctggtta caccttcaca aactacgatc taaactgggt gaggcagagg     120
cctggacagg gccttgagtg gattggatgg atttatcctg gaaatgataa tactaagtac     180
aatgagaagt tcaagggcct ggcctcactg actgcagaca gtcctccac cacagcctac     240
ttgcatctca gcagcctgac ttctgagagc tctgcagtct atttctgtgc aagagggtta     300
cctaggggct ggtacttcga tgtctggggc gcagggacca cggtcaccgt ctcctcagct     360
```

<210> SEQ ID NO 21
<211> LENGTH: 101
<212> TYPE: PRT
<213> ORGANISM: Mus musculus

<400> SEQUENCE: 21

Asn Ile Val Met Thr Gln Ser Pro Lys Ser Met Ser Met Ser Val Gly

```
                1               5                   10                  15
            Glu Arg Val Thr Leu Thr Cys Lys Ala Ser Glu Asn Val Val Thr Tyr
                            20                  25                  30

Val Ser Trp Tyr Gln Gln Lys Pro Glu Gln Ser Pro Lys Leu Leu Ile
                        35                  40                  45

Tyr Gly Ala Ser Asn Arg Tyr Thr Gly Val Pro Asp Arg Phe Thr Gly
                        50                  55                  60

Ser Gly Ser Ala Thr Asp Phe Thr Leu Thr Ile Ser Ser Val Gln Ala
            65                  70                  75                  80

Glu Asp Leu Ala Asp Tyr His Cys Gly Gln Gly Tyr Ser Tyr Pro Tyr
                            85                  90                  95

Thr Phe Gly Gly Gly
                        100

<210> SEQ ID NO 22
<211> LENGTH: 303
<212> TYPE: DNA
<213> ORGANISM: Mus musculus

<400> SEQUENCE: 22
aacattgtaa tgacccaatc tcccaaatcc atgtccatgt cagtaggaga gagggtcacc      60
ttgacctgca aggccagtga gaatgtggtt acttatgttt cctggtatca acagaaacca    120
gagcagtctc ctaaactgct gatatacggg gcatccaacc ggtacactgg ggtccccgat    180
cgcttcacag gcagtggatc tgcaacagat ttcactctga ccatcagcag tgtgcaggct    240
gaagaccttg cagattatca ctgtggacag ggttacagct atccgtacac gttcggaggg    300
ggg                                                                  303

<210> SEQ ID NO 23
<211> LENGTH: 101
<212> TYPE: PRT
<213> ORGANISM: Mus musculus

<400> SEQUENCE: 23

Asp Val Gln Ile Thr Gln Ser Pro Ser Tyr Leu Ala Ala Phe Pro Gly
            1               5                   10                  15

Glu Thr Ile Thr Ile Asn Cys Arg Ala Ser Lys Ser Ile Ser Lys Tyr
                            20                  25                  30

Leu Ala Trp Tyr Gln Glu Arg Pro Gly Lys Thr Asn Lys Leu Leu Ile
                        35                  40                  45

Tyr Ser Gly Ser Thr Leu Gln Ser Gly Ile Pro Ser Arg Phe Ser Gly
                        50                  55                  60

Ser Gly Ser Gly Thr Asp Phe Thr Leu Thr Ile Ser Ser Leu Glu Pro
            65                  70                  75                  80

Glu Asp Phe Ala Met Tyr Tyr Cys Gln Gln His Asn Glu Tyr Pro Tyr
                            85                  90                  95

Thr Phe Gly Gly Gly
                        100

<210> SEQ ID NO 24
<211> LENGTH: 303
<212> TYPE: DNA
<213> ORGANISM: Mus musculus

<400> SEQUENCE: 24
gatgtccaga taacccagtc tccatcttat cttgctgcat ttcctggaga aaccattact      60
```

```
attaattgta gggcaagtaa gagcattagt aaatatttag cctggtatca agagagacct    120
ggaaaaacta ataagcttct tatctactct ggatccactt tgcaatctgg aattccatca    180
aggttcagtg gcagtggatc tgtacagat ttcactctca ccatcagtag cctggagcct     240
gaagattttg caatgtatta ctgtcaacag cataatgaat acccgtatac gttcggaggg    300
ggg                                                                  303
```

<210> SEQ ID NO 25
<211> LENGTH: 124
<212> TYPE: PRT
<213> ORGANISM: Homo sapiens
<400> SEQUENCE: 25

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Ser Phe Ile Asp Tyr
            20                  25                  30

Ala Met Ser Trp Val Arg Gln Ala Pro Gly Lys Gly Leu Glu Trp Val
        35                  40                  45

Ser Ser Leu Ser Gly Asp Ser Gly Ser Ser Tyr Tyr Ala Asp Ser Val
    50                  55                  60

Lys Gly Arg Phe Thr Ile Ser Arg Asp Asn Ser Lys Ser Thr Val Phe
65                  70                  75                  80

Leu Gln Leu Ser Ser Leu Arg Ala Glu Asp Thr Ala Ile Tyr Tyr Cys
                85                  90                  95

Ala Gln Glu Thr Gly Pro Gln Arg Arg Trp Gly Gln Gly Thr Leu Val
            100                 105                 110

Thr Val Ser Ser Gly Ser Ala Ser Ala Pro Thr Leu
        115                 120
```

<210> SEQ ID NO 26
<211> LENGTH: 372
<212> TYPE: DNA
<213> ORGANISM: Homo sapiens
<400> SEQUENCE: 26

```
gaggtgcaac tattggaatc tggggaggc ttggtacagc ctggggggtc cctgagactc     60
tcctgtgcag cctctggatt cagctttatc gactatgcca tgagctgggt ccgccaggct    120
ccagggaagg gactggagtg gtctcaagt cttagtggtg atagtggtag ttcatatat     180 gcagactccg tgaagggccg attcaccatc tccagagaca attccaagag cacggtgttt    240
ctgcaactga gcagcctgag agccgaggac acggccatat attactgtgc gcaggagacc    300
ggtccccagc gtcgctgggg ccagggaacc ctggtcaccg tctcctcagg gagtgcatcc    360
gccccaaccc tt                                                        372
```

<210> SEQ ID NO 27
<211> LENGTH: 116
<212> TYPE: PRT
<213> ORGANISM: Homo sapiens
<400> SEQUENCE: 27

```
Asp Ile Gln Met Thr Gln Ser Pro Ser Thr Leu Ser Ala Ser Val Gly
 1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
```

```
            35                  40                  45
Tyr Lys Ala Phe Asn Leu Glu Ser Gly Val Pro Ser Arg Phe Arg Gly
 50                  55                  60

Ser Gly Ser Gly Thr Glu Phe Thr Leu Thr Ile Ser Ser Leu Gln Pro
 65                  70                  75                  80

Asp Asp Ser Ala Thr Tyr Tyr Cys Gln Gln Tyr Ser Ser Tyr Pro Leu
                 85                  90                  95

Thr Phe Gly Gly Gly Thr Lys Val Asp Ile Lys Arg Thr Val Ala Ala
            100                 105                 110

Pro Ser Val Phe
        115

<210> SEQ ID NO 28
<211> LENGTH: 348
<212> TYPE: DNA
<213> ORGANISM: Homo sapiens

<400> SEQUENCE: 28
gacatccaga tgacccagtc tccttccacc ctgtctgcat ctgtagggga cagagtcacc      60
atcacttgcc gggccagtca gagtattagt agctggttgg cctggtatca gcagaaacca     120
gggaaagccc ctaaactcct gatctataag gcgtttaatt tagaaagtgg ggtcccatca     180
aggttcagag gcagtggctc tgggacagaa ttcactctca ccatcagcag cctgcagcct     240
gatgattctg caacttatta ctgccagcag tatagtagtt accccctcac tttcggcgga     300
gggaccaagg tggacattaa acgaactgtg gctgcaccat ctgtcttc                  348

<210> SEQ ID NO 29
<211> LENGTH: 106
<212> TYPE: PRT
<213> ORGANISM: Homo sapiens

<400> SEQUENCE: 29

Arg Lys Glu Ala Ser Val Lys Val Ser Cys Lys Ala Ser Gly Tyr Thr
 1               5                  10                  15

Phe Thr Gly Tyr Tyr Met His Trp Val Arg Gln Ala Pro Gly Gln Gly
             20                  25                  30

Leu Glu Trp Met Gly Trp Ile Asn Pro Asn Ser Gly Gly Thr Asn Tyr
         35                  40                  45

Ala Gln Lys Phe Gln Gly Arg Val Thr Met Thr Arg Asp Thr Ser Ile
 50                  55                  60

Ser Thr Ala Tyr Met Glu Leu Ser Arg Leu Arg Ser Asp Asp Thr Ala
 65                  70                  75                  80

Val Tyr Tyr Cys Ala Arg Asp Arg Ser Tyr Pro Gly Arg Asn Tyr Phe
                 85                  90                  95

Asp Tyr Trp Gly Gln Gly Thr Leu Val Thr
            100                 105

<210> SEQ ID NO 30
<211> LENGTH: 327
<212> TYPE: DNA
<213> ORGANISM: Homo sapiens

<400> SEQUENCE: 30
ccaggagaag aaacggaggc ctcagtgaag gtctcctgca aggcttctgg atacaccttc      60
accggctact atatgcactg ggtgcgacag gcccctggac aagggcttga gtggatggga     120
tggatcaacc ctaacagtgg tggcacaaac tatgcacaga gtttcagggc agggtcacc     180
```

```
atgaccaggg acacgtccat cagcacagcc tacatggagc tgagcaggct gagatctgac      240
gacacggccg tgtattactg tgcgagagat cgatcgtatc cgggaaggaa ctactttgac      300
tactggggcc agggaaccct ggtcacc                                          327
```

<210> SEQ ID NO 31
<211> LENGTH: 101
<212> TYPE: PRT
<213> ORGANISM: Homo sapiens

<400> SEQUENCE: 31

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser His
             85                  90                  95

Thr Phe Gly Gln Gly
            100
```

<210> SEQ ID NO 32
<211> LENGTH: 303
<212> TYPE: DNA
<213> ORGANISM: Homo sapiens

<400> SEQUENCE: 32

```
gaaattgtgt tgacgcagtc tccaggcacc ctgtctttgt ctccagggga aagagccacc       60
ctctcctgca gggccagtca gagtgttagc agcagctact tagcctggta ccagcagaaa      120
cctggccagg ctcccaggct cctcatctat ggtgcatcca gcagggccac tggcatccca      180
gacaggttca gtggcagtgg gtctgggaca gacttcactc tcaccatcag cagactggag      240
cctgaagatt ttgcagtgta ttactgtcag cagtatggta gctctcacac ttttggccag      300
ggg                                                                    303
```

<210> SEQ ID NO 33
<211> LENGTH: 109
<212> TYPE: PRT
<213> ORGANISM: Homo sapiens

<400> SEQUENCE: 33

```
Gly Leu Val Lys Pro Gly Gly Ser Leu Arg Leu Ser Cys Ala Ala Ser
 1               5                  10                  15

Gly Phe Thr Phe Ser Asp Tyr Tyr Met Ser Trp Ile Arg Gln Ala Pro
             20                  25                  30

Gly Lys Gly Leu Glu Trp Val Ser Tyr Ile Ser Ser Ser Ser Ser Tyr
         35                  40                  45

Thr Asn Tyr Ala Asp Ser Val Lys Gly Arg Phe Thr Ile Ser Arg Asp
 50                  55                  60

Asn Ala Lys Asn Ser Leu Tyr Leu Gln Met Asn Ser Leu Arg Ala Glu
65                  70                  75                  80
```

Asp Thr Ala Val Tyr Tyr Cys Ala Arg Asp Arg Ser Ser Ser Trp
            85                  90                  95

Tyr Tyr Tyr Tyr Tyr Gly Met Asp Val Trp Gly Gln Gly
            100                 105

<210> SEQ ID NO 34
<211> LENGTH: 329
<212> TYPE: DNA
<213> ORGANISM: Homo sapiens

<400> SEQUENCE: 34
gaggcttggt caagcctgga gggtccctga gactctcctg tgcagcctct ggattcacct    60
tcagtgacta ctacatgagc tggatccgcc aggctccagg aaggggctg gagtgggttt    120 catacattag tagtagtagt agttacacaa actacgcaga ctctgtgaag gccgattca    180 ccatctccag agacaacgcc aagaactcac tgtatctgca aatgaacagc ctgagagccg    240
aggacacggc tgtgtattac tgtgcgagag atcggtcgag cagcagctgg tactactact    300
actacggtat ggacgtctgg ggccaaggg                                      329

<210> SEQ ID NO 35
<211> LENGTH: 102
<212> TYPE: PRT
<213> ORGANISM: Homo sapiens

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Asn Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Lys Cys Pro Ser
            85                  90                  95

His Phe Arg Gly Arg Asp
            100

<210> SEQ ID NO 36
<211> LENGTH: 306
<212> TYPE: DNA
<213> ORGANISM: Homo sapiens

<400> SEQUENCE: 36
gacatccaga tgacccagtc tccatcctcc ctgtctgcat ctgtaggaga cagagtcacc    60
atcacttgcc gggcgagtca gggcattagc aattatttag cctggtatca gcagaaacca    120
gggaaagttc ctaagctcct gatctatgct gcatccactt tgcaatcagg ggtcccatct    180
cggttcaatg gcagtggatc tgggacagat ttcactctca ccatcagcag cctgcaacct    240
gaagatgttg caacttatta ctgtcaaaag tataacaagt gccctctca ctttcggggg    300 agggac                                                               306

<210> SEQ ID NO 37
<211> LENGTH: 105
<212> TYPE: PRT

<213> ORGANISM: Homo sapiens

<400> SEQUENCE: 37

Asp Ile Ala Met Thr Gln Ser Pro Asp Ser Leu Ala Val Ser Leu Gly
1               5                   10                  15
Glu Arg Ala Thr Ile Asn Cys Lys Ser Ser Arg Ser Val Leu Phe Ser
            20                  25                  30
Ser Asn Asn Asn Asn Tyr Leu Ala Trp Tyr Gln Gln Lys Pro Gly Gln
        35                  40                  45
Pro Pro Lys Leu Leu Ile Tyr Trp Ala Ser Thr Arg Glu Ser Gly Val
50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Tyr Tyr Ser Thr Pro Ile Thr Phe Gly
            100                 105

<210> SEQ ID NO 38
<211> LENGTH: 315
<212> TYPE: DNA
<213> ORGANISM: Homo sapiens

<400> SEQUENCE: 38
gacatcgcga tgacccagtc tccagactcc ctggcagtgt ctctgggcga gagggccacc     60
atcaactgca gtccagccg gagtgtttta ttcagctcca acaataacaa ctacttagct    120
tggtaccagc agaaaccagg acagcctcct aagctactca tttactgggc atctacccgg    180
gaatccgggg tccctgaccg attcagtggc agcgggtctg ggacagattt cactctcacc    240
atcagcagcc tgcaggctga agatgtggca gtttattact gtcagcaata ttatagtact    300
ccaatcacct tcggc                                                     315

<210> SEQ ID NO 39
<211> LENGTH: 101
<212> TYPE: PRT
<213> ORGANISM: Mus musculus

<400> SEQUENCE: 39

Asp Ile Val Met Thr Gln Ser His Lys Phe Met Ser Thr Ser Val Gly
1               5                   10                  15
Asp Arg Val Ser Ile Thr Cys Lys Ala Ser Gln Asp Val Ser Thr Ala
            20                  25                  30
Val Ala Trp Tyr Gln Gln Lys Pro Gly Gln Ser Pro Lys Leu Leu Ile
        35                  40                  45
Tyr Ser Ala Ser Tyr Arg Tyr Thr Gly Val Pro Asp Arg Phe Thr Gly
50                  55                  60
Ser Gly Ser Gly Thr Asp Phe Thr Phe Thr Ile Ser Ser Val Gln Ala
65                  70                  75                  80
Glu Asp Leu Ala Val Tyr Tyr Cys Gln Gln His Tyr Thr Thr Pro Leu
                85                  90                  95
Thr Phe Gly Ala Gly
            100

<210> SEQ ID NO 40
<211> LENGTH: 303
<212> TYPE: DNA
<213> ORGANISM: Mus musculus

<400> SEQUENCE: 40

```
gacatcgtaa tgacgcagtc tcacaaattc atgtccactt cagtaggaga cagggtcagc    60
atcacctgca aggccagtca ggatgtgagt actgctgtag cctggtatca acagaaacca   120
gcacaatctc ctaaactact gatttactcg gcatcctacc ggtacactgg agtccctgat   180
cgcttcactg gcagtggatc tgggacggat ttcactttca ccatcagcag tgtgcaggct   240
gaagacctgg cagtttatta ctgtcagcaa cattatacta ctccgctcac gttcggtgct   300
ggg                                                                 303
```

<210> SEQ ID NO 41
<211> LENGTH: 101
<212> TYPE: PRT
<213> ORGANISM: Mus musculus

<400> SEQUENCE: 41

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Leu
                85                  90                  95

Thr Phe Gly Ala Gly
            100

<210> SEQ ID NO 42
<211> LENGTH: 303
<212> TYPE: DNA
<213> ORGANISM: Mus musculus

<400> SEQUENCE: 42

```
gacatcgtaa tgacgcagtc tcacaaattc atgtccactt cagtaggaga cagggtcagc    60
atcacctgca aggccagtca ggatgtgagt actgctgtag cctggtatca acagaaacca   120
ggacaatctc ctaaactact gatttactcg gcatcctacc ggtacactgg agtccctgat   180
cgcttcactg gcagtggatc tgggacggat ttcactttca ccatcagcag tgtgcaggct   240
gaagacctgg cagtttatta ctgtcagcaa cattatacta ctccgctcac gttcggtgct   300
ggg                                                                 303
```

<210> SEQ ID NO 43
<211> LENGTH: 108
<212> TYPE: PRT
<213> ORGANISM: Mus musculus

<400> SEQUENCE: 43

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile

```
                 35                  40                  45
Tyr Ser Gly Ser Thr Leu Gln Ser Gly Ile Pro Ser Arg Phe Ser Gly
         50                  55                  60
Ser Gly Ser Gly Thr Asp Phe Thr Leu Thr Ile Ser Ser Leu Glu Pro
 65                  70                  75                  80
Glu Asp Phe Ala Met Tyr Tyr Cys Gln Gln His Asn Glu Tyr Pro Tyr
                 85                  90                  95
Thr Phe Gly Gly Gly Thr Lys Leu Glu Ile Lys Arg
                100                 105

<210> SEQ ID NO 44
<211> LENGTH: 324
<212> TYPE: DNA
<213> ORGANISM: Mus musculus

<400> SEQUENCE: 44
gatgtccaga taacccagtc tccatcttat cttgctgcat ctcctggaga aaccattact    60
attaattgca gggcaagtaa gagcattagc aaatatttag cctggtatca agagaaacct   120
gggaaaacta taagcttcta tctactctct ggatccactt tgcaatctgg aattccatca   180
aggttcagtg gcagtggatc tggtacagat ttcactctca ccatcagtag cctggagcct   240
gaagattttg caatgtatta ctgtcaacag cataatgaat acccgtacac gttcggaggg   300
gggaccaagc tggaaataaa acgg                                         324

<210> SEQ ID NO 45
<211> LENGTH: 108
<212> TYPE: PRT
<213> ORGANISM: Mus musculus

<400> SEQUENCE: 45

Asp Ile Gln Met Thr Gln Ser Pro Ser Ser Leu Ser Ala Ser Leu Gly
 1               5                  10                  15
Glu Arg Val Ser Leu Thr Cys Arg Ala Ser Gln Asp Ile Gly Ser Ser
                 20                  25                  30
Leu Asn Trp Leu Gln Gln Glu Pro Asp Gly Thr Ile Lys Arg Leu Ile
         35                  40                  45
Tyr Ala Thr Ser Ser Leu Asp Ser Gly Val Pro Lys Arg Phe Ser Gly
         50                  55                  60
Ser Arg Ser Gly Ser Asp Tyr Ser Leu Thr Ile Ser Ser Leu Glu Ser
 65                  70                  75                  80
Glu Asp Phe Val Asp Tyr Tyr Cys Leu Gln Tyr Ala Ser Phe Pro Tyr
                 85                  90                  95
Thr Phe Gly Gly Gly Thr Lys Leu Glu Ile Lys Arg
                100                 105

<210> SEQ ID NO 46
<211> LENGTH: 324
<212> TYPE: DNA
<213> ORGANISM: Mus musculus

<400> SEQUENCE: 46
gacatccaga tgacccagtc tccatcctcc ttatctgcct ctctgggaga aagagtcagt    60
ctcacttgtc gggcaagtca ggacattggt agtagcttaa actggcttca gcaggaacca   120
gatggaacta ttaaacgcct gatctacgcc acatccagtt tagattctgg tgtccccaaa   180
aggttcagtg gcagtaggtc tgggtcagat tattctctca ccatcagcag ccttgagtct   240
```

```
gaagattttg tagactatta ctgtctacaa tatgctagtt ttccgtacac gttcggaggg      300
gggaccaagc tggaaataaa acgg                                            324
```

<210> SEQ ID NO 47
<211> LENGTH: 107
<212> TYPE: PRT
<213> ORGANISM: Mus musculus

<400> SEQUENCE: 47

```
Gln Ile Val Leu Thr Gln Ser Pro Ala Ile Met Ser Ala Ser Pro Gly
  1               5                  10                  15

Glu Lys Val Thr Ile Ser Cys Ser Ala Ser Ser Val Ser Tyr Met
             20                  25                  30

Tyr Trp Tyr Gln Gln Lys Pro Gly Ser Ser Pro Lys Pro Trp Ile Tyr
         35                  40                  45

Arg Thr Ser Asn Leu Ala Ser Gly Val Pro Ala Arg Phe Ser Gly Ser
     50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Tyr His Ser Tyr Pro Leu Thr
                 85                  90                  95

Phe Gly Ala Gly Thr Lys Leu Glu Leu Lys Arg
            100                 105
```

<210> SEQ ID NO 48
<211> LENGTH: 321
<212> TYPE: DNA
<213> ORGANISM: Mus musculus

<400> SEQUENCE: 48

```
caaattgttc tcacccagtc tccagcaatc atgtctgcat ctccagggga gaaggtcacc       60
atatcctgca gtgccagctc aagtgtaagt tacatgtact ggtaccagca gaagccagga     120
tcctccccca aaccctggat ttatcgcaca tccaacctgg cttctggagt ccctgctcgc     180
ttcagtggca gtgggtctgg gacctcttac tctctcacaa tcagcagcat ggaggctgaa     240
gatgctgcca cttattactg ccagcagtat catagttacc cactcacgtt cggtgctggg     300
accaagctgg agctgaaacg g                                              321
```

<210> SEQ ID NO 49
<211> LENGTH: 124
<212> TYPE: PRT
<213> ORGANISM: Homo sapiens

<400> SEQUENCE: 49

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Trp Met Thr Trp Val Arg Gln Ala Pro Gly Lys Gly Leu Glu Met Val
         35                  40                  45

Ala Asn Ile Lys Lys Asp Gly Ser Glu Lys Ser Tyr Val Asp Ser Val
     50                  55                  60

Lys Gly Arg Phe Thr Thr Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95
```

Ala Arg Pro Asn Cys Gly Gly Asp Cys Tyr Leu Pro Trp Tyr Phe Asp
            100                 105                 110
Leu Trp Gly Arg Gly Thr Leu Val Thr Val Ser Ser
        115                 120

<210> SEQ ID NO 50
<211> LENGTH: 372
<212> TYPE: DNA
<213> ORGANISM: Homo sapiens

<400> SEQUENCE: 50
gaggtgcagc tggtggagtc tgggggaggc ttggtccagc ctgggggtc cctgagactc        60 tcctgtgcag cctctggatt cacctttagt agctattgga tgacctgggt ccgccaggct      120
ccagggaagg gctggagtg gtggccaac ataaagaaag atggaagtga aaatcctat         180 gtggactctg tgaagggccg attcaccacc tccagagaca cgccaagaa ctcactgtat       240 ctgcaaatga acagcctgag agccgaggac acggctgtgt attactgtgc gagacccaat     300
tgtggtggtg actgctattt accatggtac ttcgatctct ggggccgtgg caccctggtc      360
actgtctcct ca                                                           372

<210> SEQ ID NO 51
<211> LENGTH: 122
<212> TYPE: PRT
<213> ORGANISM: Homo sapiens

<400> SEQUENCE: 51

Asp Ile Val Met Thr Gln Ser Pro Asp Ser Leu Ala Val Ser Leu Gly
 1               5                  10                  15
Glu Arg Ala Thr Ile Asn Cys Lys Ser Ser Gln Ser Val Leu Tyr Ser
            20                  25                  30
Ser Asn Asn Lys Asn Tyr Leu Ala Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Tyr Tyr Asn Thr Pro Gln Ala Phe Gly Gln Gly Thr Lys Val Glu Ile
            100                 105                 110
Lys Arg Thr Val Ala Ala Pro Ser Val Phe
        115                 120

<210> SEQ ID NO 52
<211> LENGTH: 366
<212> TYPE: DNA
<213> ORGANISM: Homo sapiens

<400> SEQUENCE: 52
gacatcgtga tgacccagtc tccagactcc ctggctgtgt ctctgggcga gagggccacc     60
atcaactgca agtccagcca gagtgtttta tacagctcca acaataagaa ctacttagct    120
tggtaccagc agaaaccagg acagcctcct aaactactca tttactgggc atctacccgg    180
gaatccgggg tccctgaccg attcagtggc agcgggtctg ggacagattt cactctcacc    240
atcagcagcc tgcaggctga agatgtgca gtttattact gtcagcaata ttataatact    300
cctcaggcgt tcggccaagg gaccaaggtg gaaatcaaac gaactgtggc tgcaccatct   360

```
gtcttc                                                                  366

<210> SEQ ID NO 53
<211> LENGTH: 78
<212> TYPE: DNA
<213> ORGANISM: Artificial Sequence
<220> FEATURE:
<223> OTHER INFORMATION: primer

<400> SEQUENCE: 53
actcccaagt cggctcgctt tctcttcagt gacaaacaca gacatagaac attcaccatg       60
ggatggagct gtatcact                                                    78

<210> SEQ ID NO 54
<211> LENGTH: 47
<212> TYPE: DNA
<213> ORGANISM: Artificial Sequence
<220> FEATURE:
<223> OTHER INFORMATION: primer

<400> SEQUENCE: 54
actgactctc ttaattaaga ctcacctgag gagactgtga gagtggt                    47

<210> SEQ ID NO 55
<211> LENGTH: 48
<212> TYPE: DNA
<213> ORGANISM: Artificial Sequence
<220> FEATURE:
<223> OTHER INFORMATION: primer

<400> SEQUENCE: 55
ttggcgcgcc aaagactcag cctggacatg atgtcctctg ctcagttc                   48

<210> SEQ ID NO 56
<211> LENGTH: 43
<212> TYPE: DNA
<213> ORGANISM: Artificial Sequence
<220> FEATURE:
<223> OTHER INFORMATION: primer

<400> SEQUENCE: 56
atagtttagc ggccgcattc ttatctaaca ctctcccctg ttg                        43

<210> SEQ ID NO 57
<211> LENGTH: 155
<212> TYPE: DNA
<213> ORGANISM: Artificial Sequence
<220> FEATURE:
<223> OTHER INFORMATION: synthetic

<400> SEQUENCE: 57
gactcggtcc gcccagccac tggaagtcgc cggtgtttcc attcggtgat catcactgaa      60
cacagaggac tcaccatgga gtttgggctg agctgggttt cctcgttgc tcttttaaga      120 ggtgtccagt gtcaggtgca gctggtggag tctgg                                155

<210> SEQ ID NO 58
<211> LENGTH: 56
<212> TYPE: DNA
<213> ORGANISM: Artificial Sequence
<220> FEATURE:
<223> OTHER INFORMATION: synthetic

<400> SEQUENCE: 58
```
ccttaattaa gacctggaga ggccattctt acctgaggag acggtgacca gggttc    56

<210> SEQ ID NO 59
<211> LENGTH: 36
<212> TYPE: DNA
<213> ORGANISM: Artificial Sequence
<220> FEATURE:
<223> OTHER INFORMATION: synthetic

<400> SEQUENCE: 59
ctagctagcg tcctaggtca gcccaaggct gccccc    36

<210> SEQ ID NO 60
<211> LENGTH: 36
<212> TYPE: DNA
<213> ORGANISM: Artificial Sequence
<220> FEATURE:
<223> OTHER INFORMATION: synthetic

<400> SEQUENCE: 60
atagtttagc ggccgcacct atgaacattc tgtagg    36

<210> SEQ ID NO 61
<211> LENGTH: 111
<212> TYPE: DNA
<213> ORGANISM: Artificial Sequence
<220> FEATURE:
<223> OTHER INFORMATION: primer

<400> SEQUENCE: 61
ctagctagcc cgaatttcgg gacaatcttc atcatgacct gctccctct cctcctcacc    60 cttctcattc actgcacagg gtcctgggcc cagtctgtgt tgacgcagcc g    111

<210> SEQ ID NO 62
<211> LENGTH: 32
<212> TYPE: DNA
<213> ORGANISM: Artificial Sequence
<220> FEATURE:
<223> OTHER INFORMATION: primer

<400> SEQUENCE: 62
gggcagcctt gggctgagct aggacggtca gc    32

<210> SEQ ID NO 63
<211> LENGTH: 393
<212> TYPE: DNA
<213> ORGANISM: Mus musculus

<400> SEQUENCE: 63
atgatgtcct ctgctcagtt ccttggtctc ctgttgctct gttttcaagg taccagatgt    60
gatatccaga tgacacagac tacatcctcc ctgtctgcct ctctgggaga cagagtcacc    120
atcagttgca gggcaagtca ggacattagc aattatttaa actggtatca gcagaaacca    180
gatggaactg ttaaactcct gatctactac acatcaagat tacactcagg agtcccatca    240
aggttcagtg gcagtgggtc tggaacagat tattctctca ccattagcaa cctggagcaa    300
gaagatattg ccacttactt ttgccaacag ggtaatacgc ttccgtggac gttcggtgga    360
ggcaccaagc tggaaatcaa acgggctgat gct    393

<210> SEQ ID NO 64
<211> LENGTH: 131
<212> TYPE: PRT
<213> ORGANISM: Mus musculus -continued

<400> SEQUENCE: 64

Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Asn Tyr Leu Asn Trp Tyr Gln Gln Lys Pro Asp Gly Thr Val
    50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn
            100                 105                 110

Thr Leu Pro Trp Thr Phe Gly Gly Gly Thr Lys Leu Glu Ile Lys Arg
        115                 120                 125

Ala Asp Ala
    130

<210> SEQ ID NO 65
<211> LENGTH: 429
<212> TYPE: DNA
<213> ORGANISM: Mus musculus

<400> SEQUENCE: 65
atgggatgga gctgtatcat cctcttttg gtagcagcag ctacaggtgt ccactcccag      60
gtccaactgc agcagcctgg gactgaactg gtgaagcctg ggcttcagt gaagctgtcc     120 tgcaaggctt ctggctacac cttcaccagc tactggatgc actgggtgaa gcagaggcct    180
ggacaaggcc ttgagtggat tggaaatatt aatcctagca atggtggtac taactacaat    240
gagaagttca gagcaaggc cacactgact gtagacaaat cctccagcac agcctacatg     300
cagctcagca gcctgacatc tgaggactct gcggtctatt attgtgcaag acgggccccc    360
tactacggta gtaggaactt tgactactgg ggccaaggca ccactctcac agtctcctca    420
gagagtcag                                                            429

<210> SEQ ID NO 66
<211> LENGTH: 143
<212> TYPE: PRT
<213> ORGANISM: Mus musculus

<400> SEQUENCE: 66

Met Gly Trp Ser Cys Ile Ile Leu Phe Leu Val Ala Ala Ala Thr Gly
1               5                   10                  15

Val His Ser Gln Val Gln Leu Gln Gln Pro Gly Thr Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Trp Met His Trp Val Lys Gln Arg Pro Gly Gln Gly Leu
    50                  55                  60

Glu Trp Ile Gly Asn Ile Asn Pro Ser Asn Gly Gly Thr Asn Tyr Asn
65                  70                  75                  80

Glu Lys Phe Lys Ser Lys Ala Thr Leu Thr Val Asp Lys Ser Ser Ser
                85                  90                  95

```
Thr Ala Tyr Met Gln Leu Ser Ser Leu Thr Ser Glu Asp Ser Ala Val
            100                 105                 110

Tyr Tyr Cys Ala Arg Arg Ala Pro Tyr Tyr Gly Ser Arg Asn Phe Asp
            115                 120                 125

Tyr Trp Gly Gln Gly Thr Thr Leu Thr Val Ser Glu Ser Gln
130                 135                 140

<210> SEQ ID NO 67
<211> LENGTH: 138
<212> TYPE: PRT
<213> ORGANISM: Mus musculus

<400> SEQUENCE: 67

Met Gly Trp Arg Trp Ile Phe Leu Phe Leu Leu Ser Gly Thr Ala Gly
1               5                   10                  15

Val His Cys Gln Val Gln Leu Gln Gln Ser Gly Pro Glu Leu Val Lys
            20                  25                  30

Pro Gly Ala Leu Val Lys Ile Ser Cys Lys Ala Ser Gly Tyr Thr Phe
        35                  40                  45

Thr Ser Tyr Asp Ile Asn Trp Val Lys Gln Arg Pro Gly Gln Gly Leu
    50                  55                  60

Glu Trp Ile Gly Trp Ile Tyr Pro Gly Asp Gly Ser Thr Lys Tyr Asn
65                  70                  75                  80

Glu Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asn Ser Ala Val
            100                 105                 110

Tyr Phe Cys Ala Arg Gly Ala Arg Phe Tyr Trp Tyr Phe Asp Val Trp
            115                 120                 125

Gly Ala Gly Thr Thr Val Thr Val Ser Ser
        130                 135

<210> SEQ ID NO 68
<211> LENGTH: 135
<212> TYPE: PRT
<213> ORGANISM: Mus musculus

<400> SEQUENCE: 68

Met Ala Val Leu Gly Leu Leu Phe Cys Leu Val Thr Phe Pro Ser Cys
1               5                   10                  15

Val Leu Ser Gln Val Gln Leu Lys Gln Ser Gly Pro Gly Leu Val Gln
            20                  25                  30

Pro Ser Gln Ser Leu Ser Ile Thr Cys Thr Val Ser Gly Phe Ser Leu
        35                  40                  45

Thr Ser Tyr Gly Val His Trp Val Arg Gln Ser Pro Lys Gly Leu
    50                  55                  60

Glu Trp Leu Gly Val Ile Trp Ser Gly Gly Ser Thr Asp Tyr Asn Ala
65                  70                  75                  80

Ala Phe Ile Ser Arg Leu Ser Ile Ser Lys Asp Asn Ser Lys Ser Gln
                85                  90                  95

Val Phe Phe Lys Met Asn Ser Leu Gln Ser Asn Asp Thr Ala Ile Tyr
            100                 105                 110

Tyr Cys Ala Arg Asp Cys Gly Ser Arg Gly Asp Tyr Trp Gly Gln Gly
            115                 120                 125

Thr Ser Val Thr Val Ser Ser
        130                 135
```

<210> SEQ ID NO 69
<211> LENGTH: 143
<212> TYPE: PRT
<213> ORGANISM: Mus musculus

<400> SEQUENCE: 69

Met Lys Leu Trp Leu Asn Trp Val Phe Leu Thr Leu Leu His Gly
1               5                   10                  15

Ile Gln Cys Glu Val Lys Leu Val Glu Ser Gly Gly Gly Leu Val Gln
            20                  25                  30

Pro Gly Gly Ser Leu Arg Leu Ser Cys Ala Thr Ser Gly Phe Thr Phe
        35                  40                  45

Ser Asp Phe Tyr Met Glu Trp Val Arg Gln Pro Pro Gly Lys Arg Leu
    50                  55                  60

Glu Trp Ile Ala Ala Ser Arg Asn Lys Ala Asn Asp Tyr Thr Thr Glu
65                  70                  75                  80

Tyr Ser Ala Ser Val Lys Gly Arg Phe Ile Val Ser Arg Asp Thr Ser
                85                  90                  95

Gln Ser Ile Leu Tyr Leu Gln Met Asn Ala Leu Arg Ala Glu Asp Thr
            100                 105                 110

Ala Ile Tyr Tyr Cys Ala Arg Asp Ala Arg Gln Leu Gly Leu Pro Ala
        115                 120                 125

Trp Phe Ala Tyr Trp Gly Gln Gly Thr Leu Val Thr Val Ser Ala
    130                 135                 140

<210> SEQ ID NO 70
<211> LENGTH: 128
<212> TYPE: PRT
<213> ORGANISM: Mus musculus

<400> SEQUENCE: 70

Met Glu Ser Gln Thr Leu Val Phe Ile Ser Ile Leu Leu Trp Leu Tyr
1               5                   10                  15

Gly Ala Asp Gly Asn Ile Val Met Thr Gln Ser Pro Lys Ser Met Ser
            20                  25                  30

Met Ser Val Gly Glu Arg Val Thr Leu Thr Cys Lys Ala Ser Glu Asn
        35                  40                  45

Val Val Thr Tyr Val Ser Trp Tyr Gln Gln Lys Pro Glu Gln Ser Pro
    50                  55                  60

Lys Leu Leu Ile Tyr Gly Ala Ser Asn Arg Tyr Thr Gly Val Pro Asp
65                  70                  75                  80

Arg Phe Thr Gly Ser Gly Ser Ala Thr Asp Phe Thr Leu Thr Ile Ser
                85                  90                  95

Ser Val Gln Ala Glu Asp Leu Ala Asp Tyr His Cys Gly Gln Gly Tyr
            100                 105                 110

Ser Tyr Pro Tyr Thr Phe Gly Gly Thr Lys Leu Glu Ile Lys Arg
        115                 120                 125

<210> SEQ ID NO 71
<211> LENGTH: 130
<212> TYPE: PRT
<213> ORGANISM: Mus musculus

<400> SEQUENCE: 71

Met Asp Met Arg Ala Pro Ala Gln Ile Phe Gly Phe Leu Leu Leu Leu
1               5                   10                  15

Phe Gln Gly Thr Arg Cys Asp Ile Gln Met Thr Gln Ser Pro Ser Ser
            20                  25                  30

Leu Ser Ala Ser Leu Gly Glu Arg Val Ser Leu Thr Cys Arg Ala Ser
        35                  40                  45

Gln Asp Ile Gly Ser Ser Leu Asn Trp Leu Gln Gln Glu Pro Asp Gly
    50                  55                  60

Thr Ile Lys Arg Leu Ile Tyr Ala Thr Ser Ser Leu Asp Ser Gly Val
65                  70                  75                  80

Pro Lys Arg Phe Ser Gly Ser Arg Ser Gly Ser Asp Tyr Ser Leu Thr
                85                  90                  95

Ile Ser Ser Leu Glu Ser Glu Asp Phe Val Asp Tyr Tyr Cys Leu Gln
            100                 105                 110

Tyr Ala Ser Ser Pro Tyr Thr Phe Gly Gly Gly Thr Lys Leu Glu Ile
        115                 120                 125

Lys Arg
    130

<210> SEQ ID NO 72
<211> LENGTH: 128
<212> TYPE: PRT
<213> ORGANISM: Mus musculus

<400> SEQUENCE: 72

Met Glu Ser Gln Ile Gln Val Phe Val Phe Val Phe Leu Trp Leu Ser
1               5                   10                  15

Gly Val Asp Gly Asp Ile Val Met Thr Gln Ser His Lys Phe Met Ser
            20                  25                  30

Thr Ser Val Gly Asp Arg Val Ser Ile Thr Cys Lys Ala Ser Gln Asp
        35                  40                  45

Val Ser Thr Ala Val Ala Trp Tyr Gln Gln Lys Pro Gly Gln Ser Pro
    50                  55                  60

Lys Leu Leu Ile Tyr Ser Ala Ser Tyr Arg Tyr Thr Gly Val Pro Asp
65                  70                  75                  80

Arg Phe Thr Gly Ser Gly Ser Gly Thr Asp Phe Thr Phe Thr Ile Ser
                85                  90                  95

Ser Val Gln Ala Glu Asp Leu Ala Val Tyr Tyr Cys Gln Gln His Tyr
            100                 105                 110

Thr Thr Pro Leu Thr Phe Gly Ala Gly Thr Lys Leu Glu Leu Lys Arg
        115                 120                 125

<210> SEQ ID NO 73
<211> LENGTH: 21
<212> TYPE: DNA
<213> ORGANISM: Artificial Sequence
<220> FEATURE:
<223> OTHER INFORMATION: synthetic

<400> SEQUENCE: 73
actcccaagt cggtccgctt t                                            21

<210> SEQ ID NO 74
<211> LENGTH: 270
<212> TYPE: DNA
<213> ORGANISM: Artificial Sequence
<220> FEATURE:
<223> OTHER INFORMATION: template

<400> SEQUENCE: 74
actcccaagt cggtccgctt tctcttcagt gacaaacaca gacatagaac attcaccatg    60

```
gagtttgggc tgacctggct ttctcttgtt gctattttag aaggtgtcca gtgtgaggtg    120
cagctggtgg agtctggggg aggcttggtc cagcctgggg ggtccctgag actctcctgt    180
gcagcctctg gattcacctt tagtagctat tggatgacct gggtccgcca ggctccaggg    240
aaggggctgg agtgggtggc aacataaag                                      270

<210> SEQ ID NO 75
<211> LENGTH: 266
<212> TYPE: DNA
<213> ORGANISM: Artificial Sequence
<220> FEATURE:
<223> OTHER INFORMATION: template

<400> SEQUENCE: 75
ctggagtggg tggccaacat aaagaaagat ggaagtgaga atcctatgt ggactctgtg      60 aagggccgat tcaccacctc cagagacaac gccaagaact cactgtatct gcaaatgaac    120
agcctgagag ccgaggacac ggctgtgtat tactgtgcga gacccaattg tggtggtgac    180
tgctatttac catggtactt cgatctctgg ggccgtggca ccctggtcac tgtctcctca    240
ggtgagtctt aattaagaga gtcagt                                         266

<210> SEQ ID NO 76
<211> LENGTH: 18
<212> TYPE: DNA
<213> ORGANISM: Artificial Sequence
<220> FEATURE:
<223> OTHER INFORMATION: primer

<400> SEQUENCE: 76
actgactctc ttaattag                                                   18

<210> SEQ ID NO 77
<211> LENGTH: 105
<212> TYPE: DNA
<213> ORGANISM: Artificial Sequence
<220> FEATURE:
<223> OTHER INFORMATION: 5' primer with leader sequence

<400> SEQUENCE: 77
ctagctagct caagactcag cctggacatg gtgttgcaga cccaggtctt catttctctg     60
ttgctctgga tctctggtgc ctacggggac atcgtgatga cccag                    105

<210> SEQ ID NO 78
<211> LENGTH: 105
<212> TYPE: DNA
<213> ORGANISM: Artificial Sequence
<220> FEATURE:
<223> OTHER INFORMATION: 3' primer

<400> SEQUENCE: 78
ctagctagct caagactcag cctggacatg gtgttgcaga cccaggtctt catttctctg     60
ttgctctgga tctctggtgc ctacggggac atcgtgatga cccag                    105

<210> SEQ ID NO 79
<211> LENGTH: 39
<212> TYPE: DNA
<213> ORGANISM: Artificial Sequence
<220> FEATURE:
<223> OTHER INFORMATION: 5' primer

<400> SEQUENCE: 79
```

```
ctgatgctac gatggatccg cctccaccaa gggcccatc                           39

<210> SEQ ID NO 80
<211> LENGTH: 42
<212> TYPE: DNA
<213> ORGANISM: Artificial Sequence
<220> FEATURE:
<223> OTHER INFORMATION: 5' primer

<400> SEQUENCE: 80
gcatgagtct gacagctgtt tacccggaga cagggagagg ct                       42

<210> SEQ ID NO 81
<211> LENGTH: 357
<212> TYPE: DNA
<213> ORGANISM: Homo sapiens

<400> SEQUENCE: 81
caggtgcagc tggtggagtc tgggggaggc gtggtccagc ctgggaggtc cctgagactc    60
tcctgtgcag cctctggatt caccttcagt agctatggca tgcactgggt ccgccaggct   120
ccaggcaagg ggctggagtg ggtggcagtt atatcatatg atggaagtaa taaatactat   180
gcagactccg tgaagggccg attcaccatc tccagagaca attccaagaa cacgctgtat   240
ctgcaaatga acagcctgag agctgaggac acggctgtgt attactgtgc gaaagaggtg   300
actgctattc cctactttga ctactggggc cagggaaccc tggtcaccgt ctcctca     357

<210> SEQ ID NO 82
<211> LENGTH: 337
<212> TYPE: DNA
<213> ORGANISM: Homo sapiens

<400> SEQUENCE: 82
cagtctgtgt tgacgcagcc gccctcagtg tctgcggccc caggacagaa ggtcaccatc    60
tcctgctctg gaagcagctc caacattggg aataattatg tatcctggta ccagcagctc   120
ccaggaacag cccccaaact cctcatttat gacaataata gcgaccctc agggattcct    180 gaccgattct ctggctccaa gtctggcacg tcagccaccc tgggcatcac cggactccag   240
actggggacg aggccgatta ttactgcgga acatgggata gcagcctgtg tggtattcgg   300
cggagggacc aagctgaccg tcctaggtca gcccaag                            337
```

HUMAN IGM ANTIBODIES, AND DIAGNOSTIC AND THERAPEUTIC USES THEREOF PARTICULARLY IN THE CENTRAL NERVOUS SYSTEM

CROSS REFERENCE TO RELATED APPLICATIONS

The present Application is a Continuation of co-pending application Ser. No. 12/845,977, filed Jul. 29, 2010, which is a Divisional of application Ser. No. 12/313,515, filed Nov. 20, 2008, and now U.S. Pat. No. 7,807,166, issued Oct. 5, 2010, which is a continuation of application Ser. No. 10/010,729, filed Nov. 13, 2001, and now U.S. Pat. No. 7,473,432, issued Jan. 6, 2009, which is, in turn, a continuation-in-part of copending application Ser. No. 09/730,473, which is a continuation-in-part of copending application Ser. No. 09/568,531, filed May 10, 2000, copending application Ser. No. 09/580,787, filed May 30, 2000, which is a continuation-in-part of copending application Ser. No. 09/322,862, filed May 28, 1999, which is a continuation-in-part of copending application Ser. No. 08/779,784, filed Jan. 7, 1997, which is a continuation of copending application Ser. No. 08/692,084, filed Aug. 8, 1996, which is a continuation-in-part of application Ser. No. 08/236,520, filed Apr. 29, 1994, and now U.S. Pat. No. 5,519,629, issued Jan. 7, 1997. Applicants claim the benefit of these applications under 35 U.S.C. §120, all of which are incorporated herein by reference in their entireties.

GOVERNMENT SUPPORT

This invention was made with government support under NS024180 awarded by the National Institutes of Health. The government has certain rights in the invention.

FIELD OF THE INVENTION

The present invention relates generally to the field of neurobiology, and more particularly to the identification of autoantibodies that play a role in central nervous system function and therapy. The invention also relates to diagnostic and therapeutic materials and methods, including by way of example, pharmaceutical compositions, methods of treatment of diseases associated with neurological impairment, methods of regeneration and restoration of neural function, screening assays and vaccines.

BACKGROUND OF THE INVENTION

Multiple sclerosis (MS) is a chronic, frequently progressive, inflammatory central nervous system (CNS) disease characterized pathologically by primary demyelination, usually without initial axonal injury. The etiology and pathogenesis of MS are unknown. Several immunological features of MS, and its moderate association with certain major histocompatibility complex alleles, has prompted the speculation that MS is an immune-mediated disease.

An autoimmune hypothesis is supported by the experimental autoimmune (allergic) encephalomyelitis (EAE) model, where injection of certain myelin components into genetically susceptible animals leads to T cell-mediated CNS demyelination. However, specific autoantigens and pathogenic myelin-reactive T cells have not been definitively identified in the CNS of MS patients, nor is MS associated with other autoimmune diseases. An alternative hypothesis, based upon epidemiological data, is that an environmental factor, perhaps an unidentified virus, precipitates an inflammatory response in the CNS, which leads to either direct or indirect ("bystander") myelin destruction, potentially with an induced autoimmune component. This hypothesis is supported by evidence that several naturally occurring viral infections, both in humans and animals, can cause demyelination. One commonly utilized experimental viral model is induced by Theiler's murine encephalomyelitis virus (TMEV) (Dal Canto, M. C., and Lipton, H. L., *Am. J. Path.,* 88:497-500 (1977)).

The limited efficacy of current therapies for MS and other demyelinating diseases, has stimulated interest in novel therapies to ameliorate these diseases. However, due to the apparently complex etiopathogenesis of these diseases, potentially involving both environmental and autoimmune factors, the need still exists for an effective treatment of these demyelinating disorders.

In earlier related patent applications referred to hereinabove, a group of autoantibodies were identified that were found to exhibit activity in the central nervous system, and that were particularly associated with the stimulation of remyelination. One of the objectives of the applicants has been to investigate the full range of activities of the antibodies and concomitantly, to identify other members of the class that demonstrate such activities. Accordingly, it is toward the fulfillment of the foregoing and other objectives that the present invention is directed.

The citation of any reference herein should not be construed as an admission that such reference is available as "Prior Art" to the instant application.

SUMMARY OF THE INVENTION

In a first aspect of the present invention, human autoantibodies, including both polyclonal antibodies and monoclonal antibodies, have been identified and isolated, that demonstrate activity in the promotion, stimulation, regeneration and/or remyelination of neurons in the central nervous system, and/or in the blocking or reduction of demyelination in the central nervous system. Polyclonal IgM immunoglobulin antibodies have been tested and utilized herein and the invention extends to polyclonal IgM immunoglobulin, particularly human polyclonal IgM immunoglobulin, and its use in the promotion, stimulation, regeneration and/or remyelination of neurons in the central nervous system, and/or in the blocking or reduction of demyelination in the central nervous system. Particular antibodies have been identified and tested herein, and the invention accordingly extends to human autoantibodies, which human autoantibodies are exemplified by sHIgM22 (LYM 22), sHIgM46 (LYM46), ebvHIgM MSI19D10, CB2bG8, AKJR4, CB2iE12, CB2iE7, MSI19E5 and MSI10E10. The invention further provides fragments, monomers, and recombinant antibodies derived from or related to the human antibodies of the present invention. Thus, the invention particularly extends to fragments, monomers or recombinant antibodies derived from or based on any of sHIgM22 (LYM 22), sHIgM46 (LYM46), ebvHIgM MSI19D10, CB2bG8, AKJR4, CB2iE12, CB2iE7, MSI19E5 and MSI10E10. The invention also provides in another aspect, an assay for screening other antibodies and related binding partners, including haptens and peptide analogs, that may exhibit a like therapeutic activity. Such activities would include the treatment or prevention of neurological injuries or dysfunctions such as multiple sclerosis, ALS, stroke, Parkinsons disease and Alzheimers disease.

The present invention relates in another aspect to the promotion or stimulation of regeneration or remyelination of central nervous system axons in a mammal. Specifically, the present invention relates to methods of stimulating the remyelination of central nervous system (CNS) axons using autoantibodies, and particularly human autoantibodies, including antibodies of the IgM subtype and monomers thereof, or mixtures and/or active fragments thereof, characterized by their ability to bind to structures and cells in the central nervous system, particularly including oligodendrocytes. Certain of these monoclonals (mAbs) are referred to herein as SCH94.03, SCH 79.08, O1, O4, A2B5, and O9. Of these monoclonal antibodies, O1, O4, O9, A2B5 and HNK-1 are well-known oligodendrocyte-reactive (OL-reactive) monoclonal antibodies. See, for instance, Eisenbarth et al., *Proc. Natl. Acad. Sci. USA,* 76 (1979), 4913-4917, and Abo et al. *J. Immunol.,* 127 (1981), 1024-1029). The monoclonal antibodies referred to as SCH94.03 and SCH 79.08, and the corresponding hybridomas producing them, have been deposited on Apr. 28, 1994, and Feb. 27, 1996, respectively, under the terms of the Budapest Treaty, with the American Type Culture Collection (ATCC) and given ATCC Accession Nos. CRL 11627 and HB12057, respectively. The present invention also extends to the preparation and use of human autoantibodies, which human autoantibodies are exemplified by sHIgM22 (LYM 22), sHIgM46 (LYM46), ebvHIgM MSI19D10, CB2bG8, AKJR4, CB2iE12, CB2iE7, MSI19E5 and MSI10E10. The heavy and light chain variable region sequences of these antibodies are provided herein as follows:

LYM 22 are set forth in FIGS. 35 and 36; the corresponding sequences for ebvHIgM MSI19D10 are set forth in FIGS. 37 and 38; the corresponding sequences for CB2bG8 are set forth in FIGS. 45 and 46; the corresponding sequences for AKJR4 are set forth in FIGS. 55 and 56; the corresponding sequences for CB2iE12 are set forth in FIGS. 57 and 58; the corresponding sequences for CB2iE7 are set forth in FIGS. 59 and 60; the corresponding light chain sequences for MSI19E5 are set forth in FIG. 61; the corresponding heavy and light chain sequences for sHIgM46 (LYM46) are set forth in FIGS. 71 and 72; and accordingly, the invention extends to antibodies and corresponding antibody proteins, and small molecules such as haptens, that have or correspond at least in part to the sequences set forth in the noted Figures.

This work provides confirmation of the generic utility of the group of natural autoantibodies as effective in producing remyelination of the central nervous system. In accordance with a further embodiment of the invention, and as stated above, a broader class of antibodies has been defined and is disclosed herein. Specifically, human polyclonal and monoclonal autoantibodies are disclosed and prepared in accordance herewith, that provide affinity for neural tissue and both diagnostic and therapeutic capability. The invention extends further in that the newly identified antibodies may be employed for a variety of purposes such as the promotion of remyelination, regeneration of damaged nerve cells, neuronal protection, neuronal outgrowth and the like.

A significant feature and advantage of the present invention resides in the source of the antibodies, as they may be obtained directly from the host or patient, and then used to promote safer self-therapies. More broadly, the development of peptides, small molecules and the like, based on these endogenous materials reduces, if not eliminates, possible pathologies or dysfunctions such as autoimmune reactions, that may result from the in vivo introduction and use of exogenous materials. Also, the endogenous origin of the antibodies offers a further advantage in that it may be possible to study the repair process in the patient or host, and potentially identify an underlying mechanism of action in the treatment of the condition, that itself may yield further therapeutic insights and strategies.

Moreover, the identification of the relationship between agents that promote calcium signaling, as by the induction of $Ca^{++}$ peaks, on oligodendrocytes, and the initiation and/or promotion of the noted therapeutic activities, is contemplated to provide a method of identifying therapeutic agents by the demonstration of calcium signaling on glial cells, e.g. oligodendrocytes and astrocytes. Accordingly, the invention extends to this use and activity as well.

The antibodies described herein may be used to screen peptide libraries or haptens whereby the reactive peptides or haptens can then be isolated and tested for their ability to remyelinate, block or reduce demyelination, induce cellular proliferation, differentiation, neural outgrowth, neurite sprouting, $Ca^{++}$ signaling and/or block cell death, e.g. hydrogen-peroxide induced cell death. Once isolated and purified, such peptides can then be used to screen for other polyclonal or monoclonal antibodies or other molecules that may induce remyelination, cellular proliferation or differentiation, neuronal outgrowth, neurite sprouting and/or $Ca^{++}$ signaling, the last mentioned noted herein to be relevant to the proliferation and the corresponding activity of glial cells. Particularly, peptides, haptens, and other molecules corresponding to the antibodies of the invention may be identified by their ability to bind to oligodendrocytes and thereby inducing neural rehabilitation, such as remyelination, regeneration and neuroprotection.

The invention is also broadly directed to peptides which bind to the autoantibodies described herein, whereby these peptides by virtue of their sequence, three-dimensional structure, or conformational changes arising from antibody binding, can be used in and of themselves as peptide vaccines. In a further aspect of the invention, these peptides may have neuromodulatory and/or immunomodulatory properties and may provide a method of inducing a neural cell proliferative response and/or neuroprotective, neuroregenerative and/or remyelinating role in mammals in need of such therapy.

Likewise, the invention includes haptens that may bind to the peptides, the antibodies and/or other relevant substrates and that may possess immunogenicity, so that they may also function as active components in therapeutic formulations, also including vaccines. In a particular embodiment, one or more haptens may be combined with other of the peptides of the present invention, in a vaccine formulation.

In yet a further aspect of the invention these peptides can be formulated as pharmaceutical compositions with stabilizers to prevent proteolytic degradation, thus extending their half-life to be given orally, subcutaneously, intravenously, intranasally, intrathecally or as liposome preparations to mammals in need of such therapy.

The present invention also relates to methods of treating demyelinating diseases in mammals, such as multiple sclerosis in humans, and viral diseases of the central nervous system of humans and domestic animals, such as post-infectious encephalomyelitis, or prophylactically inhibiting the initiation or progression of demyelination in these disease states, using the monoclonal antibodies, or active fragments thereof, of this invention. This invention further relates to in vitro methods of producing and stimulating the proliferation of glial cells, such as oligodendrocytes, and the use of these glial cells to treat demyelinating diseases.

In a further aspect, the invention extends to a group of molecules that will be referred to herein as neuromodulatory agents, and that are notable in their therapeutic activity in the CNS. Accordingly, the invention relates to neuromodulatory agents with particular effectiveness in the CNS, which agents comprise a material selected from the group consisting of an antibody of the IgM subtype, a peptide analog, a hapten, active fragments thereof, monomers thereof, agonists thereof, mimics thereof, and combinations thereof. Related antibodies of different subtypes, including those that have undergone a class switch (naturally or as generated by recombinant or synthetic means), are also contemplated, wherein the class switch antibodies have characteristice as neuromodulatory agents useful in the methods of the present invention. The neuromodulatory agents have one or more of the following characteristics: they induce remyelination and/or cellular proliferation of glial cells; and/or evoke CC signaling with oligodendrocytes; and/or block cell death, e.g. hydrogen-peroxide induced cell death.

The antibodies of and for use in the present invention include polyclonal antibodies, and the invention particularly provides polyclonal IgM antibodies, particularly polyclonal IgM immunoglobulin and preparation thereof, more particularly pooled polyclonal IgM immunoglobulin, particularly preferred pooled polyclonal human IgM immunoglobulin.

More particularly, the antibodies comprehended within the scope of neuromodulatory agents of the invention may be selected from the group consisting of mAb SCH94.03, SCH79.08, O1, O4, O9, A2B5, HNK-1, sHIgM22 (LYM 22), ebvHIgM MSI19D10, sHIgM46 (LYM46), CB2bG8, AKJR4, CB2iE12, CB2iE7, MSI19E5, MSI10E10, mixtures thereof, monomers thereof, active fragments thereof, and natural or synthetic autoantibodies having the characteristics of the particular mAb SCH94.03, SCH79.08, O1, O4, O9, A2B5, sHIgM22 (LYM 22), ebvHIgM MSI19D10, sHIgM46 (LYM46), CB2bG8, AKJR4, CB2iE12, CB2iE7, MSI19E5 and MSI10E10. Antibodies further comprehended within the scope of the neuromodulatory agents of the invention are recombinant antibodies derived from mAb SCH94.03, SCH79.08, O1, O4, O9, A2B5, HNK-1, sHIgM22 (LYM 22), ebvHIgM MSI19D10, sHIgM46 (LYM46), CB2bG8, AKJR4, CB2iE12, CB2iE7, and MSI10E10. The present neuromodulatory agents may be derived from mammalian cells and specifically, may be derived from human cells. Further, the neuromodulatory agents may comprise a polypeptide having an amino acid sequence corresponding at least in part, to a sequence selected from the group consisting of FIG. 35 (SEQ ID NO: 8, 7), FIG. 36 (SEQ ID NO: 10, 9), FIG. 37 (SEQ ID NO: 11, 12), FIG. 38 (SEQ ID NO: 13, 14), FIG. 45 (SEQ ID NO: 15, 16), FIG. 46 (SEQ ID NO: 17, 18), FIG. 55 (SEQ ID NO: 25, 26), FIG. 56 (SEQ ID NO: 27, 28), FIG. 57 (SEQ ID NO: 29, 30), FIG. 58 (SEQ ID NO: 31, 32), FIG. 59 (SEQ ID NO: 33, 34), FIG. 60 (SEQ ID NO: 35, 36), FIG. 61 (SEQ ID NO: 37, 38), FIG. 71 (SEQ ID NO: 49), FIG. 72 (SEQ ID NO: 51) and active fragments thereof. Recombinant or synthetic antibodies derived or based therefrom and corresponding at least in part to a sequence selected from the above group are further included in the present invention.

The present invention thus relates to the monoclonal antibody sHIgM22 (LYM22), monomers thereof, active fragments thereof, and natural or synthetic antibodies having the characteristics of sHIgM22. Recombinant antibodies derived from sHIgM22 are further contemplated and are provided herein. An sHIgM22(LYM22) antibody myeloma has been deposited as ATTC Accession No. PTA-8671. The invention provides antibodies comprising a polypeptide having an amino acid sequence corresponding at least in part to a sequence selected from FIG. 35 (SEQ ID NO: 8, 7) and FIG. 36 (SEQ ID NO: 10, 9), and active fragments thereof. Recombinant or synthetic antibodies derived or based therefrom and corresponding at least in part to a sequence selected from SEQ ID NO: 8, 7, 10 and 9 are further included in the present invention.

The present invention further relates to the monoclonal antibody sHIgM46 (LYM46), monomers thereof, active fragments thereof, and natural or synthetic antibodies having the characteristics of sHIgM46. Recombinant antibodies derived from sHIgM46 are further contemplated and are provided herein. The invention provides antibodies comprising a polypeptide having an amino acid sequence corresponding at least in part to a sequence selected from FIG. 71 (SEQ ID NO: 49) and FIG. 72 (SEQ ID NO: 51), and active fragments thereof. Recombinant or synthetic antibodies derived or based therefrom and corresponding at least in part to a sequence selected from SEQ ID NO: 49 and 51 are further included in the present invention.

The present invention further relates to sequences identified for mouse antibodies suitable and useful in the present invention as neuromodulatory agents having one or more of the following characteristics: they induce remyelination and/or cellular proliferation of glial cells; and/or evoke $Ca^{++}$ signaling with oligodendrocytes. In particular, antibody sequences are provided in FIGS. 67-70. Thus, the neuromodulatory agents of the present invention may comprise a polypeptide having an amino acid sequence corresponding at least in part, to a sequence selected from the group consisting of FIG. 67 (SEQ ID NO: 41, 42), FIG. 68 (SEQ ID NO: 43, 44), FIG. 69 (SEQ ID NO: 45, 46), FIG. 70 (SEQ ID NO: 47, 48), and active fragments thereof. Recombinant or synthetic antibodies derived or based therefrom and corresponding at least in part to a sequence selected from the above group are further included in the present invention.

The present invention also relates to a recombinant DNA molecule or cloned gene, or a degenerate variant thereof, which encodes a class of molecules that will also be referred to herein as neuromodulatory agents, and that include and may be selected from the antibodies of the invention, and particularly antibodies having sequences corresponding at least in part, to the sequences presented in FIGS. 35-38, 45, 46 and 55-61 and FIGS. 67-72; peptides that may correspond at least in part to the antibodies of the present invention, that will also be referred to herein as antibody peptides, and for example, peptides having one or more sequences corresponding at least in part to FIGS. 35-38, 45, 46 and 55-61 and FIGS. 67-72; and small molecules such as haptens; including recombinant DNA molecules or cloned genes having the same or complementary sequences.

More particularly, the recombinant DNA molecule comprises a DNA sequence or degenerate variant thereof, which encodes an antibody, a peptide analog thereof, a hapten corresponding thereto, or an active fragment thereof, and which may be selected from the group consisting of:

(A) the DNA sequence encoding a protein having a sequence corresponding to at least a portion of FIG. 35 (SEQ ID NO: 8, 7);

(B) the DNA sequence encoding a protein having a sequence corresponding to at least a portion of FIG. 36 (SEQ ID NO: 10, 9);

(C) the DNA sequence encoding a protein having a sequence corresponding to at least a portion of FIG. 37 (SEQ ID NO: 11, 12);

(D) the DNA sequence encoding a protein having a sequence corresponding to at least a portion of FIG. 38 (SEQ ID NO: 13, 14);

(E) the DNA sequence encoding a protein having a sequence corresponding to at least a portion of FIG. 45 (SEQ ID NO: 15, 16);

(F) the DNA sequence encoding a protein having a sequence corresponding to at least a portion of FIG. 46 (SEQ ID NO: 17, 18);

(G) the DNA sequence encoding a protein having a sequence corresponding to at least a portion of FIG. 55 (SEQ ID NO: 25, 26);

(H) the DNA sequence encoding a protein having a sequence corresponding to at least a portion of FIG. 56 (SEQ ID NO: 27, 28);

(I) the DNA sequence encoding a protein having a sequence corresponding to at least a portion of FIG. 57 (SEQ ID NO: 29, 30);

(J) the DNA sequence encoding a protein having a sequence corresponding to at least a portion of FIG. 58 (SEQ ID NO: 31, 32);

(K) the DNA sequence encoding a protein having a sequence corresponding to at least a portion of FIG. 59 (SEQ ID NO: 33, 34);

(L) the DNA sequence encoding a protein having a sequence corresponding to at least a portion of FIG. 60 (SEQ ID NO: 35, 36);

(M) the DNA sequence encoding a protein having a sequence corresponding to at least a portion of FIG. 61 (SEQ ID NO: 37, 38);

(N) the DNA sequence encoding a protein having a sequence corresponding to at least a portion of FIG. 67 (SEQ ID NO: 41, 42);

(O) the DNA sequence encoding a protein having a sequence corresponding to at least a portion of FIG. 68 (SEQ ID NO: 43, 44);

(P) the DNA sequence encoding a protein having a sequence corresponding to at least a portion of FIG. 69 (SEQ ID NO: 45, 46);

(Q) the DNA sequence encoding a protein having a sequence corresponding to at least a portion of FIG. 70 (SEQ ID NO: 47, 48);

(R) the DNA sequence encoding a protein having a sequence corresponding to at least a portion of FIG. 71 (SEQ ID NO: 49, 50);

(S) the DNA sequence encoding a protein having a sequence corresponding to at least a portion of FIG. 72 (SEQ ID NO: 51, 52);

(T) DNA sequences that hybridize to any of the foregoing DNA sequences under standard hybridization conditions; and (U) DNA sequences that code on expression for an amino acid sequence encoded by any of the foregoing DNA sequences.

The present invention also includes proteins derived from or corresponding to said antibodies, or fragments or derivatives thereof, having the activities noted herein, and that display the amino acid sequences set forth and described above and selected at least in part, from the group consisting of FIGS. 35-38, 45, 46 and 55-61 and FIGS. 67-72. The present invention likewise extends to haptens that demonstrate the same activities as the proteins or antibody peptides, and that may be administered for therapeutic purposes in like fashion, as by formulation in a vaccine. In one embodiment, a vaccine including both peptides and haptens may be prepared.

In a further embodiment of the invention, the full DNA sequence of the recombinant DNA molecule or cloned gene so determined may be operatively linked to an expression control sequence which may be introduced into an appropriate host. The invention accordingly extends to unicellular hosts transformed with the cloned gene or recombinant DNA molecule comprising a DNA sequence encoding the present antibody peptides.

In a particular embodiment, the variable region DNA sequence of an antibody of the present invention may be utilized in generating synthetic antibody(ies). In particular, variable region sequence may be combined with its natural or a genetically provided constant region sequence to provide a synthetic antibody. The present invention provides vectors for generating synthetic antibodies derived from and comprising the DNA sequences, particularly variable region sequences, of the antibodies of the present invention.

According to other preferred features of certain preferred embodiments of the present invention, a recombinant expression system is provided to produce biologically active animal or particularly human antibody peptides.

The present invention includes several means for the preparation of clones of the autoantibodies, peptides, corresponding haptens, or other small molecule analogs thereof, including as illustrated herein known recombinant techniques, and the invention is accordingly intended to cover such synthetic preparations within its scope. The isolation of the cDNA and amino acid sequences disclosed herein facilitates the reproduction of the present antibodies or their analogs by such recombinant techniques, and accordingly, the invention extends to expression vectors prepared from the disclosed DNA sequences for expression in host systems by recombinant DNA techniques, and to the resulting transformed hosts.

The invention includes an assay system for screening of potential drugs effective to modulate the neurological activity of target mammalian neural cells by, for example, potentiating the activity of the present autoantibodies or their analogs. In one instance, the test drug could be administered to a cellular sample with the ligand that suppresses or inhibits the activity of the autoantibodies, or an extract containing the suppressed antibodies, to determine its effect upon the binding activity of the autoantibodies to any chemical sample (including DNA), or to the test drug, by comparison with a control.

The assay system could more importantly be adapted to identify drugs or other entities that are capable of binding to the autoantibodies and/or their targets, including peptides, haptens, other factors or proteins, whether found in the cytoplasm, the nucleus or elsewhere, thereby potentiating antibody activity, including e.g. immune response, neural growth, neuroprotection and remyelination, and the corresponding therapeutic activities noted herein. Such assay would be useful in the identification of drug candidates from among peptide and other small molecule libraries, sera, and other relevant body fluids, and in the development of drugs that would be specific either in the promotion or the inhibition of particular cellular activity, or that would potentiate such activity, in time or in level of activity. For example, such drugs might be used to promote remyelination, or to treat other pathologies or injuries, as for example, in making CNS neurons able or better able to engage in regrowth or regeneration.

The present invention likewise extends to the development of antibodies corresponding to the neuromodulatory agents of the invention, including naturally raised and recombinantly prepared antibodies. For example, the antibodies could be used to screen expression libraries to obtain the gene or genes that encode the peptides that may function as neuromodulatory agents, and that could function e.g. in a vaccine. Such antibodies could include both polyclonal and monoclonal antibodies prepared by known genetic techniques, as well as bi-specific (chimeric) antibodies, and antibodies including other functionalities suiting them for additional diagnostic use conjunctive with their capability of emulating or modulating the activity of the human autoantibodies that are a part of the neuromodulatory agents of the present invention.

Thus, the neuromodulatory agents, their analogs and/or analogs, and any antagonists or antibodies that may be raised thereto, are capable of use in connection with various diagnostic techniques, including immunoassays, such as a radioimmunoassay, using for example, an antibody to the neuromodulatory agents that has been labeled by either radioactive addition, or radioiodination.

In an immunoassay, a control quantity of the antagonists or antibodies thereto, or the like may be prepared and labeled with an enzyme, a specific binding partner and/or a radioactive element, and may then be introduced into a cellular sample. After the labeled material or its binding partner(s) has had an opportunity to react with sites within the sample, the resulting mass may be examined by known techniques, which may vary with the nature of the label attached.

In the instance where a radioactive label, such as the isotopes $^{3}$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re are used, known currently available counting procedures may be utilized. In the instance where the label is an enzyme, detection may be accomplished by any of the presently utilized colorimetric, spectrophotometric, fluoro spectrophotometric, amperometric or gasometric techniques known in the art.

The present invention includes an assay system which may be prepared in the form of a test kit for the quantitative analysis of the extent of the presence of the neuromodulatory agents, or to identify drugs or other agents that may mimic or block their activity. The system or test kit may comprise a labeled component prepared by one of the radioactive and/or enzymatic techniques discussed herein, coupling a label to the neuromodulatory agents, their agonists and/or antagonists, and one or more additional immunochemical reagents, at least one of which is a free or immobilized ligand, capable either of binding with the labeled component, its binding partner, one of the components to be determined or their binding partner(s).

In a particular and further aspect, the present invention extends to the use and application of the antibodies of the present invention, particularly autoantibodies, including antibodies of the IgM subtype and monomers thereof, or mixtures and/or active fragments thereof, characterized by their ability to bind to structures and cells in the central nervous system, particularly including oligodendrocytes, in imaging and in vivo diagnostic applications. Thus, the antibodies, by virtue of their ability to bind to structures and cells in the central nervous system, particularly including oligodendrocytes, can be utilized via immunofluorescent, radioactive and other diagnostically suitable tags as imaging agents or imaging molecules for the characterization of the nervous system, including the central nervous system and the diagnosis, monitoring and assessment of nervous disease, particularly including multiple sclerosis. The antibodies may further be utilized as imaging agents or imaging molecules in the diagnosis, monitoring and assessment of stroke, spinal cord injury and various dementias including Alzheimer's disease.

In a further embodiment, the present invention relates to certain therapeutic methods which would be based upon the activity of the neuromodulatory agents, their subunits, or active fragments thereof, peptide equivalents thereof, analogs thereof, or upon agents or other drugs determined to possess the same activity. A first therapeutic method is associated with the prevention of the manifestations of conditions causally related to or following from the binding activity of the antibodies or their subunits, and comprises administering an agent capable of stimulating the production and/or activity of the neuromodulatory agents, the corresponding autoantibodies, antibody peptides, active fragments or subunits thereof, either individually or in mixture with each other in an amount effective to prevent or treat the development of those conditions in the host. For example, drugs or other binding partners to the antibodies or their fragments, or the like, may be administered to potentiate neuroregenerative and/or neuroprotective activity, or to stimulate remyelination as in the treatment of multiple sclerosis.

More specifically, the therapeutic method generally referred to herein could include the method for the treatment of various pathologies or other cellular dysfunctions and derangements by the administration of pharmaceutical compositions that may comprise effective inhibitors or enhancers of activation of the neuromodulatory agents, or other equally effective drugs developed for instance by a drug screening assay prepared and used in accordance with an aspect of the present invention discussed above. For example, drugs or other binding partners to the neuromodulatory agents or like proteins, having sequences corresponding at least in part to the sequences as represented by FIG. 35 (SEQ ID NO: 8, 7), FIG. 36 (SEQ ID NO: 10, 9), FIG. 37 (SEQ ID NO: 11, 12), FIG. 38 (SEQ ID NO: 13, 14), FIG. 45 (SEQ ID NO: 15, 16), FIG. 46 (SEQ ID NO: 17, 18), FIG. 55 (SEQ ID NO: 25, 26), FIG. 56 (SEQ ID NO: 27, 28), FIG. 57 (SEQ ID NO: 29, 30), FIG. 58 (SEQ ID NO: 31, 32), FIG. 59 (SEQ ID NO: 33, 34), FIG. 60 (SEQ ID NO: 35, 36), FIG. 61 (SEQ ID NO: 37, 38), FIG. 71 (SEQ ID NO: 49, 50), FIG. 72 (SEQ ID NO: 51, 52) may be administered to inhibit or potentiate neuroregeneration, neuroprotection, or remyelination, as in the treatment of Parkinsons disease or multiple sclerosis. In particular, the proteins of one or more antibodies selected from the group of sHIgM22 (LYM22), ebvHIgM MSI19D10, sHIgM46 (LYM46), CB2bG8, AKJR4, CB2iE12, CB2iE7 and MSI19E5, whose sequences are presented in FIGS. 35-38, 45, 46, 55-61, and 71-72, their antibodies, agonists, antagonists, monomers or active fragments thereof, including mixtures and combinations thereof, could be prepared in pharmaceutical formulations including vaccines, for administration in instances wherein neuroregenerative and/or neuroprotective therapy or remyelination is appropriate, such as to treat Alzheimers disease, ALS, Parkinsons disease, or spinal cord injury. The present invention includes combinations or mixtures of the antibodies provided herein, wherein more than one of the antibodies, particularly human antibodies, most particularly selected from the group of sHIgM22, sHIgM46, MSI19E10, CB2bG8, AKJR4, CB2iE12, CB2iE7, MSI19E5, and MSI10E10 can be prepared in pharmaceutical and therapeutic compositions or formulations. Combinations or mixtures of various human antibodies, mouse antibodies, or monomers, fragments, recombinant or synthetic antibodies derived therefrom or based thereon are also provided by and included in the present invention. The human antibodies (extending to monomers, fragments, recombinant or synthetic antibodies derived therefrom) are particularly selected from the group of sHIgM22, sHIgM46, MSI19E10, CB2bG8, AKJR4, CB2iE12, CB2iE7, MSI19E5, and MSI10E10. The mouse antibodies (extending to monomers, fragments, recombinant or synthetic antibodies and humanized antibodies derived therefrom) are particularly selected from the group of SCH 94.03, SCH79.08, O1, O4, O9, A2B5 and FINK-1. In addition, the invention provides further combinations of the antibody(ies) with therapeutic compounds, drugs or agents useful in any such neuroregenerative and/or neuroprotective therapy or remyelination. For instance, the antibody formulation or composition of the present invention may be combined with therapeutic compounds for the treatment of multiple sclerosis, including but not limited to beta interferon formulations (Betaseron, etc.) and copolymer 1 (Copaxone).

Accordingly, it is a principal object of the present invention to provide neuromodulatory agents, including the human autoantibodies and corresponding antibody peptides, haptens, analogs and active fragments thereof in purified form that exhibits certain characteristics and activities associated with the promotion of neuroregenerative and/or neuroprotective activity.

It is a further object of the present invention to provide a method for detecting the presence, amount and activity of the autoantibodies in mammals in which invasive, spontaneous, or idiopathic pathological states are suspected to be present.

It is a further object of the present invention to provide a method and associated assay system for screening substances such as drugs, agents and the like, potentially effective in either mimicking the activity or combating any adverse effects of the autoantibodies and/or their fragments, subunits or the like, in mammals.

It is thus an object of the present invention to provide methods for treating demyelinating diseases in mammals, such as multiple sclerosis in humans, and viral diseases of the central nervous system of humans and domestic animals, such as post-infectious encephalomyelitis, or prophylactically inhibiting the initiation or progression of demyelination in these disease states, using the described monoclonal autoantibodies, active fragments thereof, or other natural or synthetic autoantibodies having the characteristics of mAb SCH94.03, SCH 79.08, O1, O4, O9, A2B5, HNK-1, and the human autoantibodies exemplified by sHIgM22 (LYM 22), ebvHIgM MSI19D10, sHIgM46 (LYM46), CB2bG8, AKJR4, CB2iE12, CB2iE7, MSI19E5 and MSI10E10.

It is further an object of the present invention to provide in vitro methods of producing, and stimulating the proliferation of, glial cells, such as oligodendrocytes, and the use of these glial cells to treat demyelinating diseases.

It is a still further object of the present invention to provide the present neuromodulatory agents, and pharmaceutical compositions, including vaccines comprising the same, for use in therapeutic methods which comprise or are based upon the present neuromodulatory agents, and particularly the human autoantibodies, fragments, including peptide fragments, haptens, subunits, agonists, binding partner(s), or upon agents or drugs that control the production, or that mimic or antagonize the activities of the neuromodulatory agents.

It is a still further object of the present invention to provide assay methods including screening assays, for the identification of drugs and other molecules that mimic or antagonize the neuromodulatory agents of the invention, and that can consequently be considered for use as therapeutic agents.

Other objects and advantages will become apparent to those skilled in the art from a review of the following description which proceeds with reference to the following illustrative drawings.

DESCRIPTION OF THE FIGURES

FIGS. 7A-7D shows the immunostaining of cultured glial cells and frozen CNS tissue sections with mAb SCH94.03. Scale bars represent 15 µm.

FIGS. 11A and 11B shows the alignment of the immunoglobulin light (FIG. 11A, SEQ ID NO: 63, 64) and heavy (FIG. 11B, SEQ ID NO: 65, 66) chain variable region sequences of SCH94.03 and control IgM, CH12, and germline Ig gene segments.

FIG. 14 shows the nucleotide and deduced amino acid sequences of $V_H$, D and $J_H$ regions encoding A2B5 (SEQ. ID NO: 3, 69), compared with those reported for germline gene V1 and $J_H3$ germline gene. Dashed lines indicate identity with germline gene V1 and $J_H3$. Underline indicates identity with germline DFL16.2. Amino acids are represented by the single-letter code. CDR represents the complementarity determining region. This sequence has been assigned the GenBank TM/EMBL Data Bank Accession Number L41874.

FIG. 15 shows the nucleotide and deduced amino acid sequences of $V_H$ and $J_H$ regions encoding O1 and O4 (SEQ. ID NO: 4, 70), compared with those reported for myeloma MOPC21, for natural autoantibody E7 and for $3_x2$ germline gene. Dashed lines indicate identity with MOPC21 and germline gene $J_H2$ (N, undetermined nucleotide). Amino acids are represented by the single-letter code. CDR represents the complementarity determining region. These sequence have been assigned the GenBank TM/EMBL Data Bank Accession Numbers L41879 (O1) and L41881 (O4).

Figure 16:
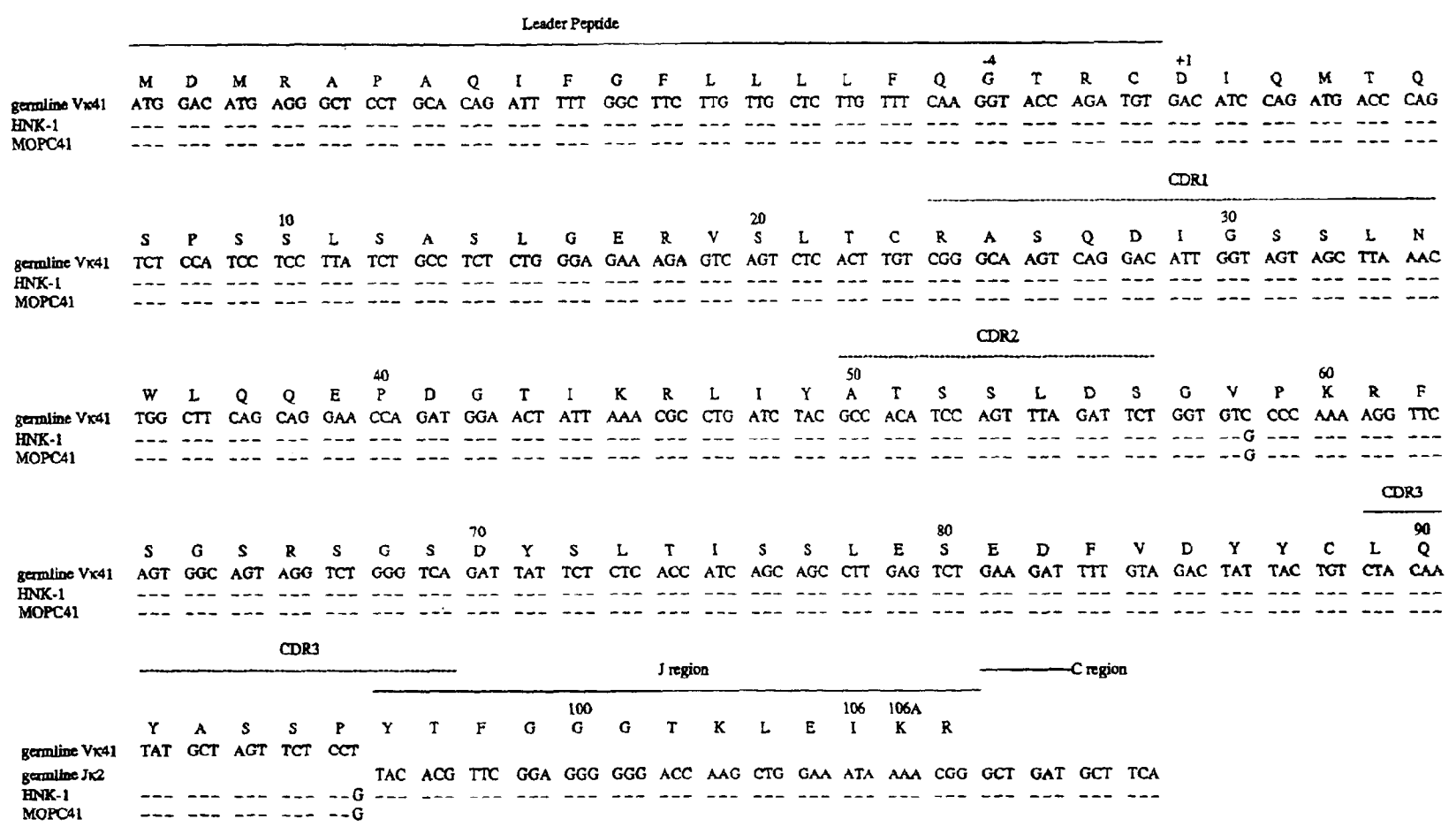

FIG. 16 shows the nucleotide and deduced amino acid sequences of $V_H$ and $J_H$ regions encoding HNK-1 (SEQ. ID NO: 5, 71), compared with those reported for germline $V_H41$, myeloma MOPC21, and $J_H2$. Dashed lines indicate identity with germline genes. Amino acids are represented by the single-letter code. CDR represents the complementarity determining region. This sequence has been assigned the GenBank TM/EMBL Data Bank Accession Number L41880.

FIG. 17 shows the nucleotide and deduced amino acid sequences of $V_H$ and $J_H$ regions encoding A2B5 (SEQ ID NO: 6, 72). Dashed lines indicate identity with germline $J_H$. Amino acids are represented by the single-letter code. CDR represents the complementarity determining region. This sequence has been assigned the GenBank TM/EMBL Data Bank Accession Number L41875.

FIG. 20A-20F comprises photographs showing that additional sHIgMs bind with high specificity to cells in slices of cerebellum. Indirect immunofluorescent labeling of unfixed slices of postnatal rat cerebellum. sHIgM demonstrate a variety of specificities to cell populations and structures within an unfixed brain slice. sHIgM 12 (A) binds to lend a spongy appearance to the central white matter of the folia, and a uniform label over the molecular layer, reminiscent of an extracellular matrix molecule. Overlying astrocytes are also well defined. sHIgM 29 (B) binds weakly to many structures in the cerebellum with an intensity just above background, except for a small population of neurons in the granular and molecular layer. Axon extensions over 100 (m long are clearly delineated. sHIgM 31 (C) and sHIgM 50 (F) each bind predominately to the granular layer, with little binding to the white matter, Purkinje cells or astrocytes. The binding pattern of sHIgM 50 is also reminiscent of an extracellular matrix molecule. sHIgM 42 (D) binds in a fibrous pattern to the entire folia, molecular and granular layers and white matter. sHIgM 46 (E) binds in a fibrous pattern to the granular layer and white matter. The Purkinje cell bodies are well defined.

FIG. 22A-22F comprise photographs that show that EBV-immortalized human B-cell clone-derived monoclonal IgM antibodies (ebvHIgMs) bind with high specificity to surface antigens on cells in the cerebellum. Indirect immunofluorescent labeling of unfixed slices of postnatal rat cerebellum. ebvHIgMs demonstrate a variety of specificities to cell populations and structures within an unfixed rat brain slice. ebvHIgM MSI19E15 (A) binds to fibrous structures within the white matter and to the granular and molecular layer in a pattern of near confluency. ebvHIgM AKJR4 (B) binds almost exclusively to the granular layer. Small cells within the molecular layer are also identified. ebvHIgMs MSI17A2 (C) and MSI20H10 (E) bind to the central white matter, the granular and molecular layer and Purkinje cells with varying degrees of intensity. ebvHIgM MSI16E6 (D) demonstrates a very strong affinity for Purkinje cells and their dendrictic arbors, while the granular layer is far less distinctly labeled. ebvHIgM MSI7E11 (F) binds in a punctate manner to only a few glial-appearing cells at the surface of the brain slice. Magnification x.

FIG. 25A-25F shows that sHIgMs bind with high specificity to surface antigens on glial cells in culture. Indirect immunofluorescent labeling of live rat primary mixed glial cell cultures at nine days post seeding. sHIgMs demonstrate a variety of specificities as to the cell types bound as well as the cell differentiation-stage identified in mixed glial cultures. sHIgM 12 binds to clusters of presumptive oligodendrocyte progenitors (A, green label) in the midst of more mature O4+ oligodendrocytes (A, red label). sHIgM22 binds to mature stages of oligodendrocytes (B) adherent to the surface of the glial culture. sHIgM 46 strongly binds to both mature stages of oligodendrocyte (C, center of figure) and immature stages of oligodendrocyte with a fainter, punctate label (C, left side of figure). sHIgM 42 (D) and sHIgM 51 (F) both bind to mature stages of the oligodendrocyte and faintly, the underlying astrocytes. sHIgM 30 binds to the cell bodies of most cells in the culture, while no process extensions are delineated (E). Magnification x.

FIG. 26A-26F shows that sHIgMs bind to cells of the oligodendrocyte lineage in slices of cerebellum and cultures of mixed primary glial cells. Cells identified by sHIgMs co-label with markers for the oligodendrocyte lineage. Cells that bind sHIgM22 in an unfixed slice of neonatal rat cerebellum co-label the Rip antibody, a cytoplasmic marker for mature stages of the oligodendrocyte. Double label confocal images demonstrate sHIgM22 positive cells (A) that are also Rip positive (C). Images (A) and (C) are merged in (E). Cells that bind sHIgM 51 in mixed primary rat glial cell cultures (B) are also O4 positive (D). O4, an anti-sulfatide, is a well established marker for the oligodendrocyte lineage that appears prior the cessation of proliferation and is maintained on into the adult myelin sheath. Images (B) and (D) are merged in (F). Magnification x.

FIG. 27A-27C shows that ebvHIgMs bind to cells of the oligodendrocyte lineage in slices of cerebellum. Cells identified by ebvHIgM MSI19E5 in a an unfixed slice of neonatal rat cerebellum co-label with the O4 antibody, an anti-sulfatide and cell-surface marker for oligodendrocytes. Double label confocal images of cells within the white matter of the folia demonstrate ebvHIgM MSI19E5 positive cells (A) that are also O4 positive (B). Images (A) and (B) are merged in (C).

FIG. 31A-31B shows that an ebvHIgM can promote remyelination in TMEV infected mice. Light photomicrographs of regions of myelin pathology in the spinal cords of SJL/J mice chronically infected with TMEV. Extensive CNS remyelination, characterized by thin myelin sheaths in relation to axon diameter, is observed in mice after treatment with ebvHIgM MSI19D10 (A). Demyelination without significant remyelination was observed in mice treated with ebvHIgM AKJR4 (B). Araldite embedded sections were stained with 1% p-phenylenediamine. Again, strong CNS specificity appears to be one of the requirements for an antibody to promote remyelination in vivo, but alone is not sufficient to predict an antibody's capacity to promote remyelination.

FIG. 33 demonstrates that human antibodies are polyreactive to chemical haptens via ELISA. Antigen binding specificities of immunoglobulins assessed by direct ELISA. Chemical hapten reactivities of polyclonal human IgM, polyclonal human IgG. Abbreviations used in these figures: NP, (4-hydroxy-3-nitrophenyl)acetyl; PhOX, phenyloxazolone; TMA, azophenyltrimethylammonium; FITC, fluorescein; PC, azophenylphosphoryl-choline; ARS, azophenylarsonate; TNP, trinytrophenyl acetyl.

FIG. 34 shows that human antibodies are polyreactive to self protein via ELISA. Protein antigen binding specificities of immunoglobulins assessed by direct ELISA. Abbreviations used in these figures: MBP, myelin basic protein; KLH, keyhole limpet hemocyanin; HEL, hen egg lysozyme; BSA, bovine serum albumin; Rbt, rabbit; Bo, bovine; Mo Hb, mouse hemoglobin.

FIG. 35 presents the sHIgM22 heavy chain variable region sequences (SEQ. ID NO: 7, 8). The sequence is aligned according to the numbering system of human $V_H$ sequences in the publication: *Sequences of Proteins of Immunological Interest*, Vol I, Fifth Edition (1991), Kabat E. A., Wu, T. T., Perry, H. M. Gottesman, K. S. and Foeller, C., NIH Publication. The sHIgM22 $V_H$ is a member of the $V_H$ subgroup III. Underlined amino acids have been confirmed by protein sequencing. Amino acid sequence corresponds to sHIgM22 nucleotide sequence. SHIgM22 $V_H$ type A and B sequences are represented only with nucleotides that differ from the IGHV3-30/3-30-05*01, IGHJ4*02 and IGHD2-21*02 germline sequences. Two amino acid replacements in the protein sequence of sHIgM22 $V_H$ type B are printed in bold. The sequences of both SHIgM22 $V_H$ type A and B most closely matched the IGHV3-30/3-30-5*01 germline sequence (96% homology). References for germline sequences: IMGT, the international ImMunoGeneTics database [http://imgt.cnusc.fr:8104]. (Initiator and coordinator: Marie-Paule Lefranc, Montpellier, France)

FIG. 36 presents the sHIgM22 light chain variable region sequences (SEQ. ID NO: 9, 10). The sequence is aligned according to the numbering system of human $V_H$ sequences in the publication: *Sequences of Proteins of Immunological Interest*, Vol I, Fifth Edition (1991), Kabat E. A., Wu, T. T., Perry, H. M. Gottesman, K. S. and Foeller, C., NIH Publication. $V_\lambda$ sHIgM22 is a member of the lambda subgroup I. Underlined amino acids have been confirmed by protein sequencing. Amino acid sequence corresponds to sHIgM22 nucleotide sequence. SHIgM22 $V_\lambda$ type I and II sequences are represented only with nucleotides that differ from the IGLV1-51*01 and IGLJ3*01 germline sequences. Two amino acid replacements in the protein sequence of sHIgM22 $V_\lambda$ type II are printed in bold. The $V_\lambda$ sequences from SHIgM22 most closely matched the IGLV-51*01 germline sequence (97% homology). The two genes differ from their common ancestor by a single nucleotide change. References for germline sequences: IMGT, the international ImMunoGeneTics database [http://imgt.cnusc.fr:8104]. (Initiator and coordinator: Marie-Paule Lefranc, Montpellier, France).

FIG. 37 presents the ebvHIgM MSI19D10 heavy chain variable region sequence (SEQ. ID NO: 11, 12).

FIG. 38 presents the ebvHIgM MSI19D10 light chain variable region sequence (SEQ. ID NO: 13, 14).

FIG. 40A-40B demonstrates that sHIgMs and ebvHIgMs bind to primary neurons in culture. Indirect immunofluorescent labeling of live primary rat granule cells at six days in culture. sHIgM 12 binds to virtually all axon and dendritic extensions of cerebellar granule cells in culture (A). The binding pattern is similar to that observed with anti-ganglioside antibodies, such as mouse antibody A2B5. A2B5 has been shown to promote remyelination in vivo (Asakara et al, 1998). ebvHIgM CB2iE12 binds only to granule cell bodies and their proximal axon extensions (B). The antigen recognized by CB2iE12 is developmentally regulated, for granule cells in culture are negative for CB2iE12 staining until 4-5 days after plating. Magnification x.

FIG. 42A-42B presents the methodology used to quantify white matter, white matter pathology and remyelination in the spinal cords of TMEV-infected mice. Light photomicrograph of a thorasic level spinal cord section from an SJL/J mouse chronically infected with TMEV and treated with polyclonal human IgM (A). White matter at the periphery stains darker than the lighter central gray matter. The area of total white matter is traced (indicated by the red outlines), at a magnification of 40×. Then at a magnification of 100× the areas of white matter pathology are traced (indicated by the green outlines). In this example, the areas of white matter pathology appear as lighter areas at the periphery of the section. Finally, at a magnification of 250× the areas of OL remyelination (indicated by the blues outlines) and SC remyelination (indicated by the yellow outline) are traced. OL remyelination is characterized by thin myelin sheaths in relation to axon diameter. The percent area of white matter pathology is calculated by dividing the area in green by the area in red×100. The percent area of OL remyelination is calculated by dividing the area in blue by the area in green×100. Ten spinal cord cross sections are traced for each animal considered and the areas combined to calculate a score for that animal. Generally, 7-8 animals are treated in each experimental group to allow for deaths and animals that do not contain at least 5% total white matter pathology. Usually 4-5 treated animals meet the criteria for inclusion into the final data set. A high magnification field of the dorsal column white matter (B, from the area indicated by the asterisk in A) demonstrates significant OL remyelination (arrow). Scale bars are 250 µm in A and 20 µm in B.

Figure 1:
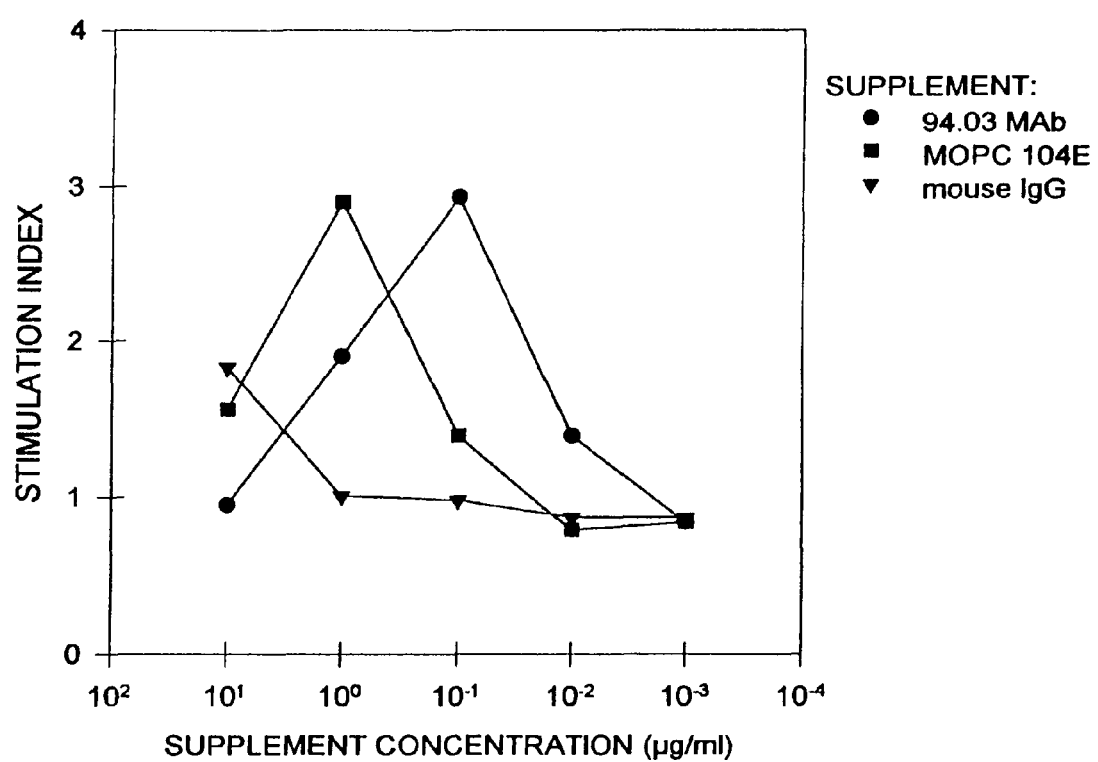
FIG. 1 is a graph depicting the dose-response characteristics of antibody-mediated proliferation of cells in mixed rat brain culture.

mice demonstrated white matter pathology without significant OL remyelination. Infiltrating inflammatory cells and macrophages ingesting myelin debris (A, arrowhead), signs of active myelin destruction were also evident. Spinal cord cross sections in four of eight animals treated with sHIgM22 and five of five animals treated with sHIgM46 contained at least one area of nearly confluent OL remyelination, a rare event indicating significant tissue repair. In contrast, the 10 spinal cord cross sections from each mouse treated with sHIgM1, sHIgM2, sHIgM14, or PBS contained none. Scale bar is 20 mm.

FIG. 44A-44D Human mAbs isolated for their ability to bind to rat OLs also bind to the surface of human OLs in culture. sHIgM14 (A), which did not promote remyelination, and sHIgM22 (B) and sHIgM46 (C), which did promote remyelination, bound to the perikaryon and elaborate process and membrane extensions of sulfatide positive human OLs maintained in culture for 3 weeks. sHIgM2 (D, green channel) is an example of a human mAb that did not bind to sulfatide positive (D, red channel) human OLs. Nuclei are labeled blue. IVIg, polyclonal human IgM, and human mAbs sHIgM 1 and sHIgM2 did not bind to the surface of human OLs at any time point examined. Scale bar is 25 mm.

FIG. 45 presents the heavy chain variable region sequence of EBV transformant antibody CB2b-G8 (SEQ. ID NO: 15, 16).

FIG. 46 presents the light chain variable region sequence of EBV transformant antibody CB2b-G8 (SEQ. ID NO: 17, 18).

FIG. 47A-47C Amplification of light chain RNA and protein expression in transfected hybridoma cells by methotrexate amplification of a dHfR-containing expression plasmid. Expression plasmid containing the coding sequence for humanized 94.03 kappa light chain under control of the CMV promoter along with a linked dHfR gene under control of the SV40 promoter was introduced by electroporation into the immunoglobulin negative F3B6 human/mouse hybridoma cell line. Cell under minimal methotrexate selection (0.5 μg/ml) and those that had undergone more stringent selection (51.2 μg/ml) were cultured to harvest supernatant to assess light chain secretion and RNA to assess light chain gene expression. Northern blot analysis indicates substantial amplification of RNA expression in one clone (#5). Protein expression was increased following methotrexate selection in clone 4, but not in clone 5. These findings indicate that methotrexate amplification sometimes results in the amplification of mRNA and protein expression by closely linked genes, but in other cases no amplification of transcription and protein synthesis is seen.

Figure 48:
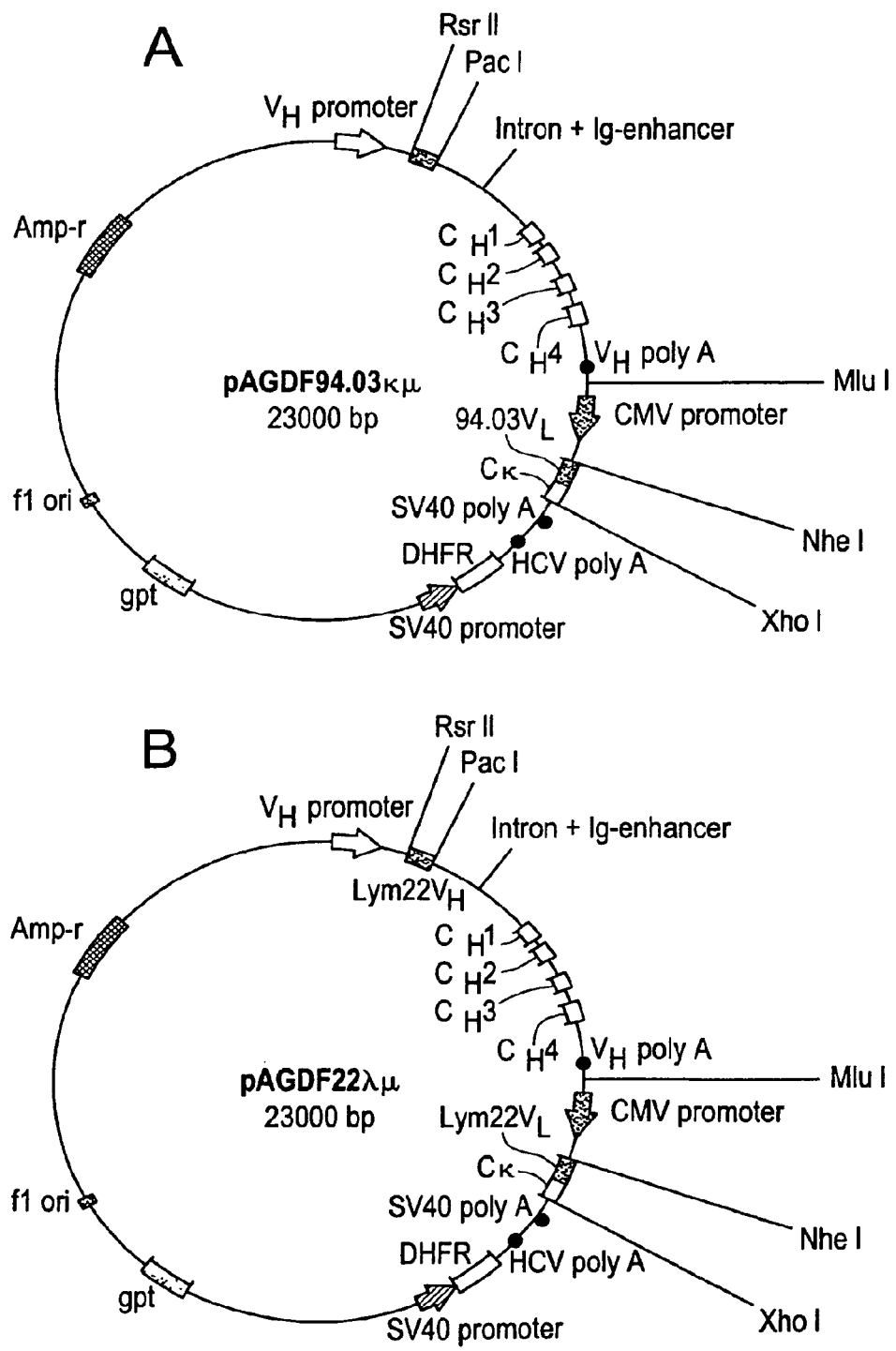

FIG. 48A-48B Amplifiable vectors encoding humanized 94.03 and sHIgM22. Top panel (A) is the prototype vector containing the coding sequence for humanized 94.03 light chain (κ) and a hybrid genomic construct encoding humanized 94.03 heavy chain (μ). Bottom panel (B) is a similar construct that contains the coding sequences derived from the sHIgM22 sequence. Both of these constructs have been expressed in F3B6 hybridoma cells under minimal methotrexate selection conditions and are now being selected under more stringent conditions to isolate clones expressing amplified amount of immunoglobulin.

FIG. 49A-49C Postnatal Rat cerebellum stained with murine and humanized 94.03. Cerebellum sections were stained with mouse and humanized 94.03. Bound antibody was localized using fluorescent secondary antibody reagent specific for mouse or human IgM, respectively. Both antibodies showed similar staining patterns to white matter tracks and astrocytes in the cerebellum.

FIG. 50A-50B Isolation of an IgG variant of 94.03. A natural switch variant of 94.03 was isolated from culture by sorting for cells expressing IgG on their surface. Pre-sort and post-sort profiles of the cell cultures are shown. IgG cells were isolated from the post-sort population by limiting dilution cloning. The antibody produced was identified as IgG1 using IgG isotype specific antibodies.

FIG. 51 Demonstration that the IgG1 producing cells were in fact a variant of 94.03. RNA was isolated from the clonal IgG1 expressing cells. cDNA was generated using RTPCR with primers specific for the variable region of 94.03 and the constant region of the γ1 isotype. The resulting DNA was sequenced to demonstrate the precise splicing junction expected for a spontaneous switch variant.

FIG. 52 presents the heavy chain variable region sequence of mouse O9 antibody (SEQ. ID NO: 19, 20).

FIG. 53 presents the kappa light chain 1 variable region sequence of mouse O9 variable region sequence of mouse O9 antibody_(SEQ. ID NO: 21, 22).

FIG. 54 presents the kappa light chain 2 variable region sequence of mouse O9 antibody (SEQ. ID NO: 23, 24).

FIG. 55 presents the AKJR4 heavy chain variable region sequence (SEQ. ID NO: 25, 26).

FIG. 56 presents the AKJR4 kappa light chain variable region sequence (SEQ. ID NO: 27, 28).

FIG. 57 presents the CB2iE12 heavy chain variable region sequence (SEQ. ID NO: 29, 30).

FIG. 58 presents the CB2iE12 kappa light chain variable region sequence (SEQ. ID NO: 31, 32).

FIG. 59 presents the CB2iE7 heavy chain variable region sequence (SEQ. ID NO: 33, 34).

FIG. 60 presents the CB2iE7 kappa light chain variable region sequence (SEQ. ID NO: 35, 36).

FIG. 61 presents the MSI 19E5 light chain variable region sequence (SEQ. ID NO: 37, 38).

FIG. 62 presents the kappa light chain 2 of the mouse O4 antibody (SEQ. ID NO: 39, 40).

FIG. 63A depicts assessment of glial cell proliferation by mouse antibody 94.03.

FIG. 63B depicts assessment of glial cell proliferation by human antibodies lym22, recombinant 22 and lym5.

Figure 64:
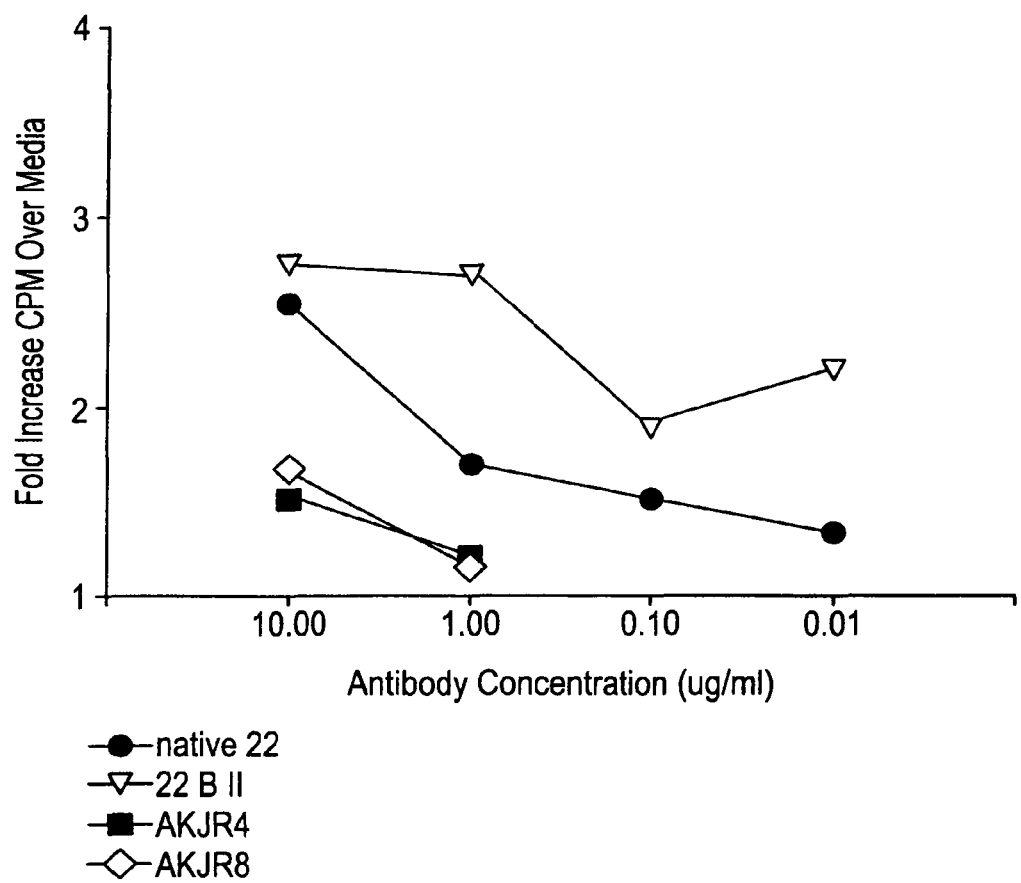

FIG. 64 depicts assessment of glial cell proliferation by human antibodies native 22, 22BII, AKJR4 and AKJR8.

Figure 65:
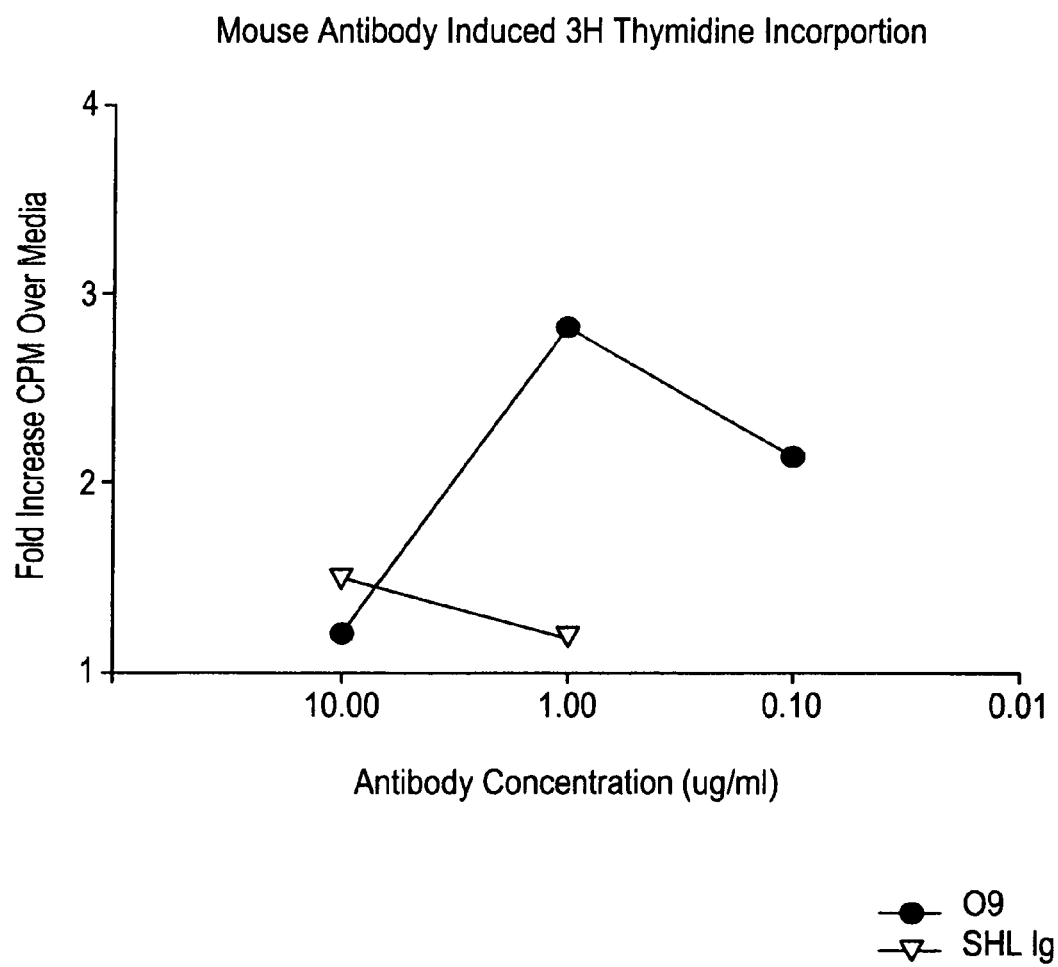

FIG. 65 depicts assessment of glial cell proliferation by mouse antibody O9 versus serum Ig of SJL mice.

FIG. 66A-66B depicts immunofluorescence assessment of white matter binding by sHIgM22 (A) and RsHIgM22 (B).

FIG. 67 depicts the kappa light chain sequence of antibody 04 (SEQ. ID NO: 41, 42).

FIG. 68 depicts the kappa light chain sequence of antibody 01 (SEQ. ID NO: 43, 44).

FIG. 69 depicts the kappa light chain sequence of antibody HNK-1 (SEQ. ID NO: 45, 46).

FIG. 70 depicts the kappa light chain sequence of antibody A2B5 (SEQ. ID NO: 47, 48).

FIG. 71 depicts the Lym 46 heavy chain sequence (SEQ. ID NO: 49, 50).

FIG. 72 depicts the Lym 46 kappa light chain sequence (SEQ. ID NO: 51, 52).

Figure 73:
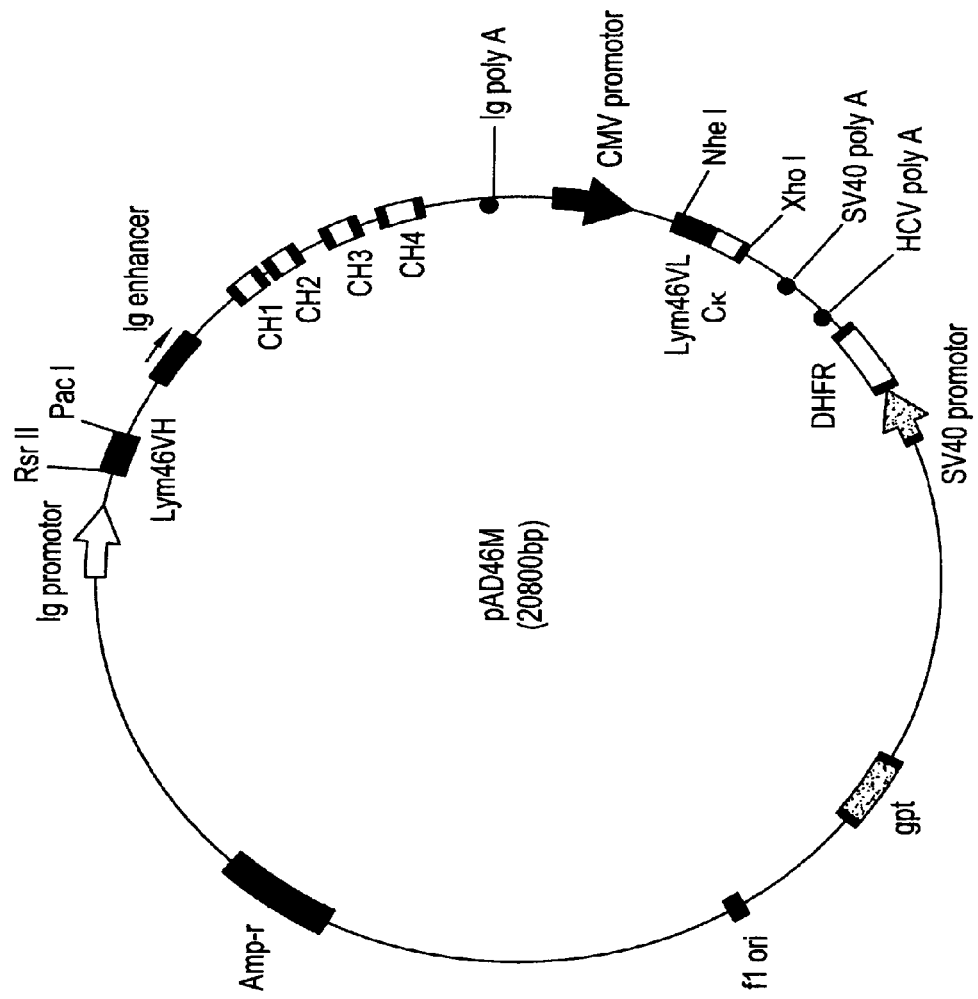

FIG. 73 depicts vector pAD46M for expression of recombinant Lym 46.

Figure 74:
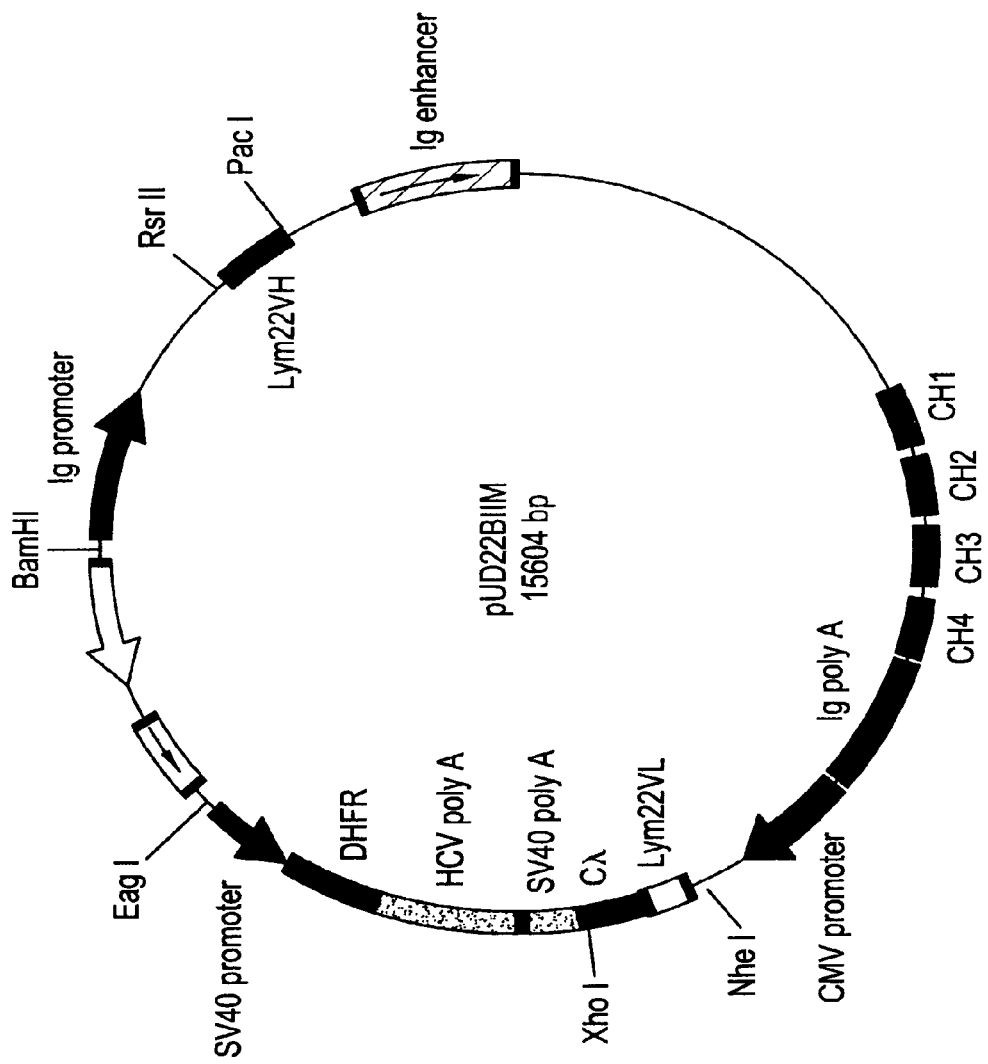

FIG. 74 depicts vector pUD22BIIM for expression of recombinant Lym22, containing the DHFR gene for amplification of the vector with methotrexate.

Figure 75:
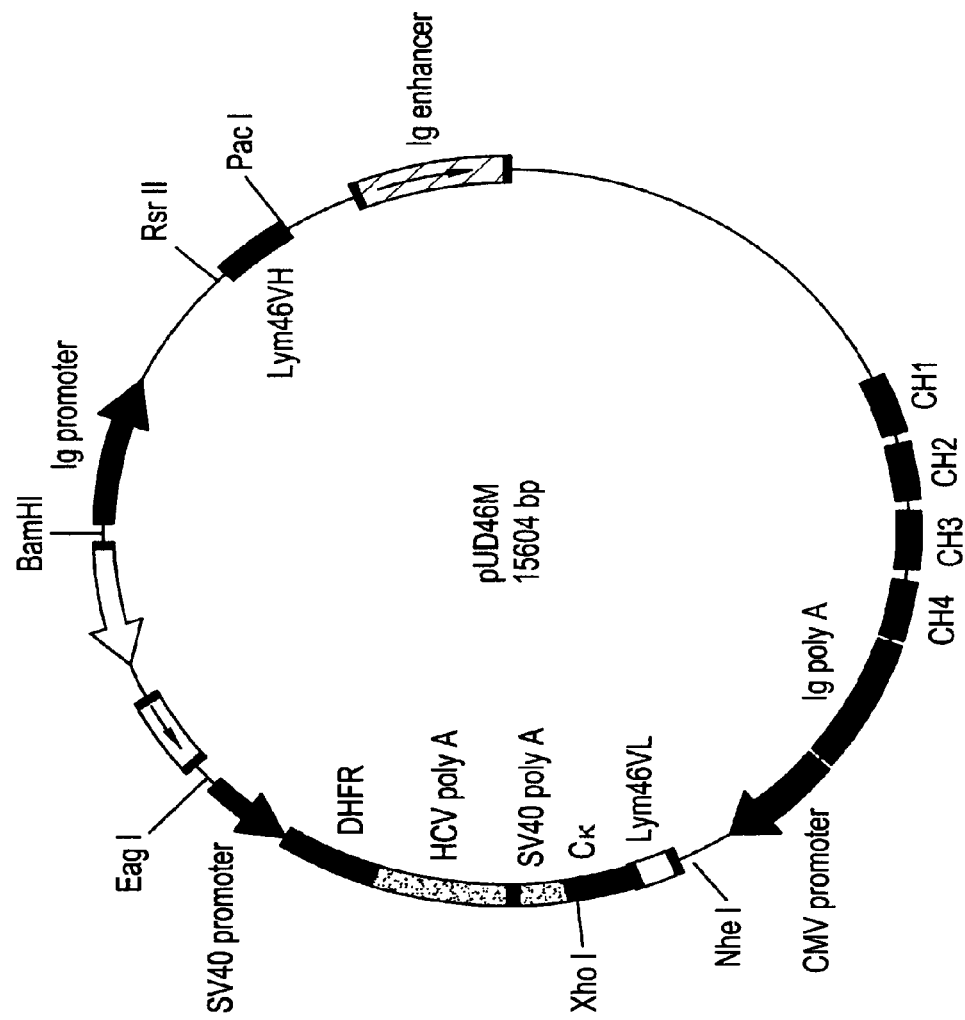

FIG. 75 depicts vector pUD46M for expression of recombinant Lym46, containing the DHFR gene for amplification of the vector with methotrexate.

Figure 76:
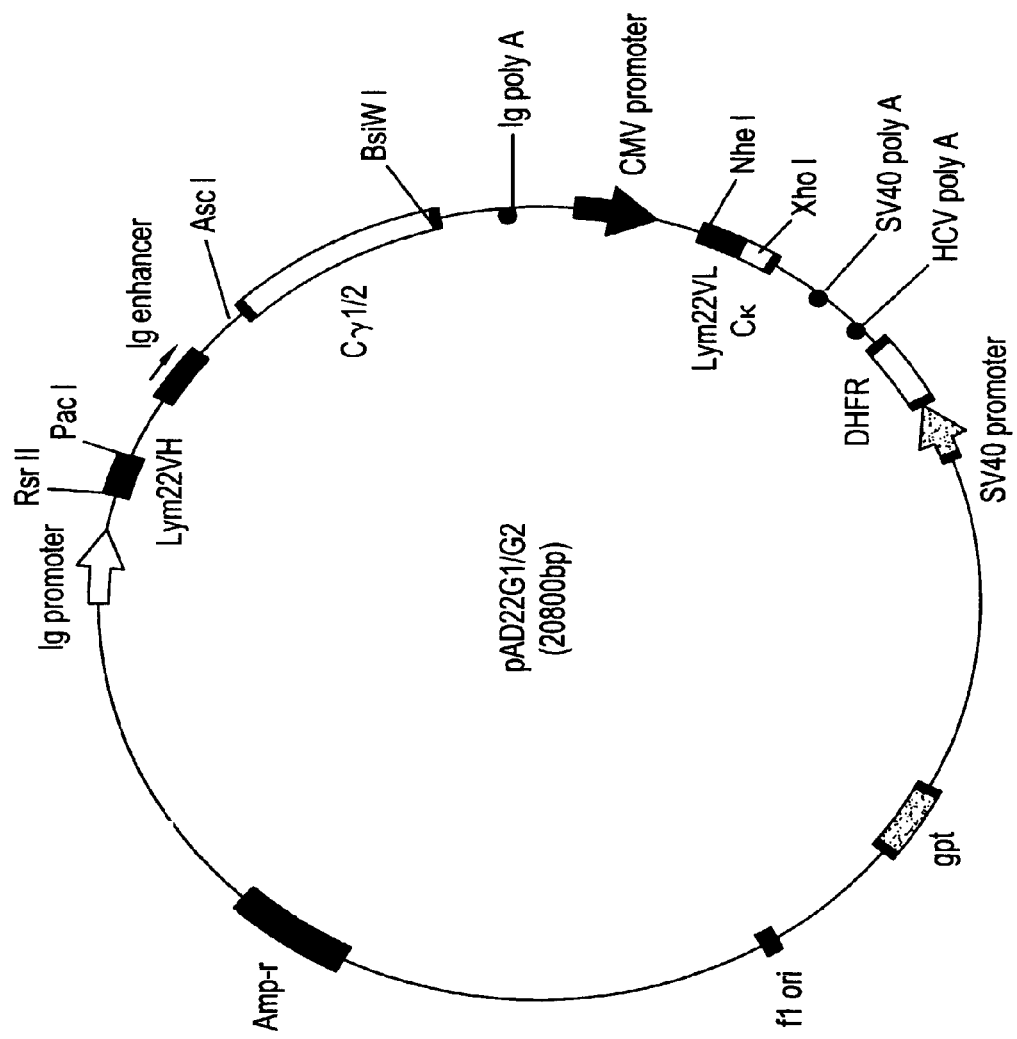

FIG. 76 depicts vector pAD22G1/G2 for generation of and recombinant expression of IgG subclass G1 and G2 of Lym 22.

Figure 77:
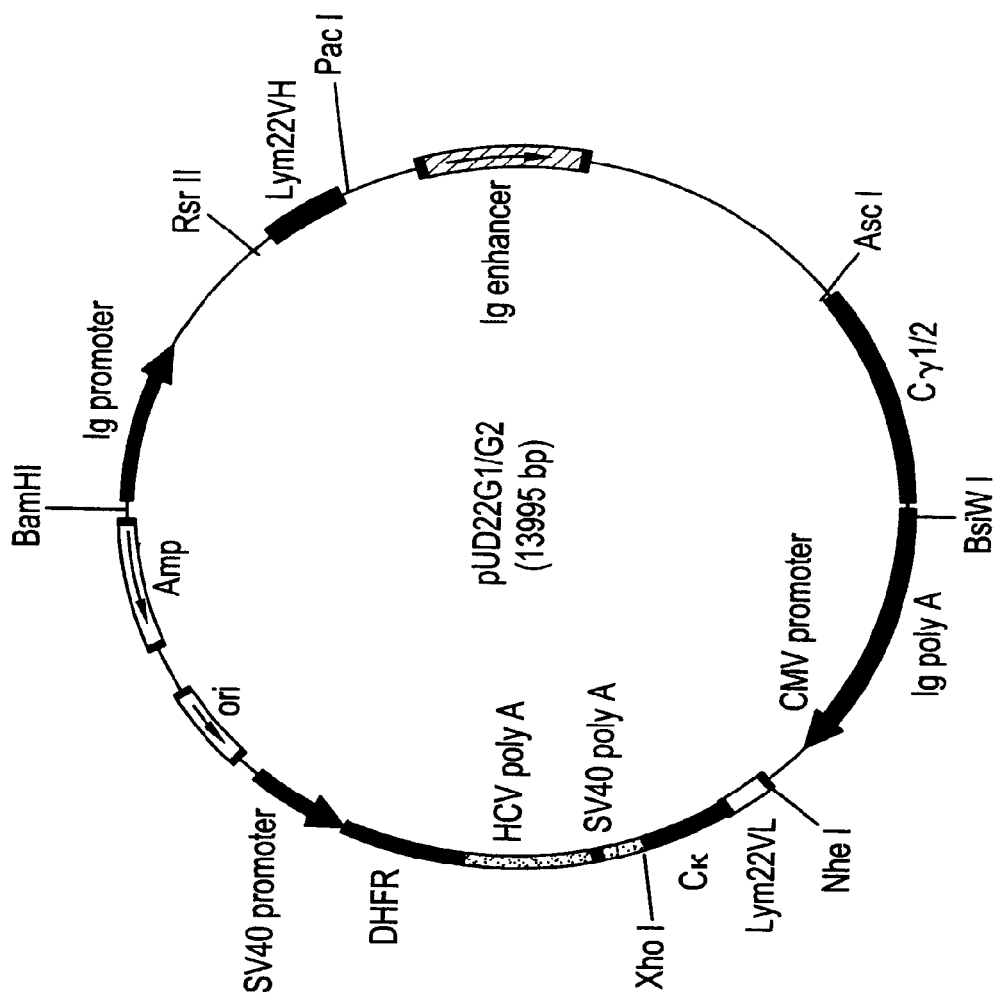

FIG. 77 depicts vector pUD22G1/G2 for generation of and recombinant expression of IgG subclass G1 and G2 of Lym 22, also containing the DHFR gene for amplification of the vector with methotrexate.

Figure 78:
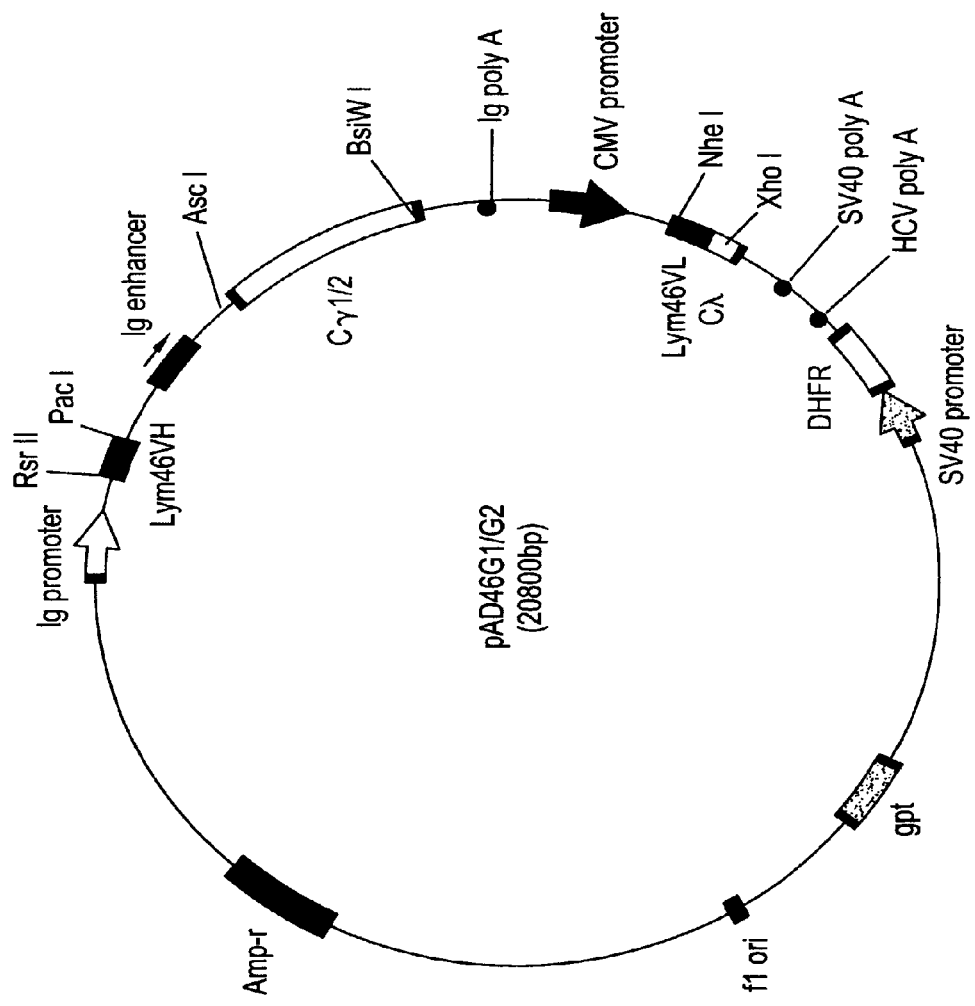

FIG. 78 depicts vector pAD46G1/G2 for generation of and recombinant expression of IgG subclass G1 and G2 of Lym 46.

Figure 79:
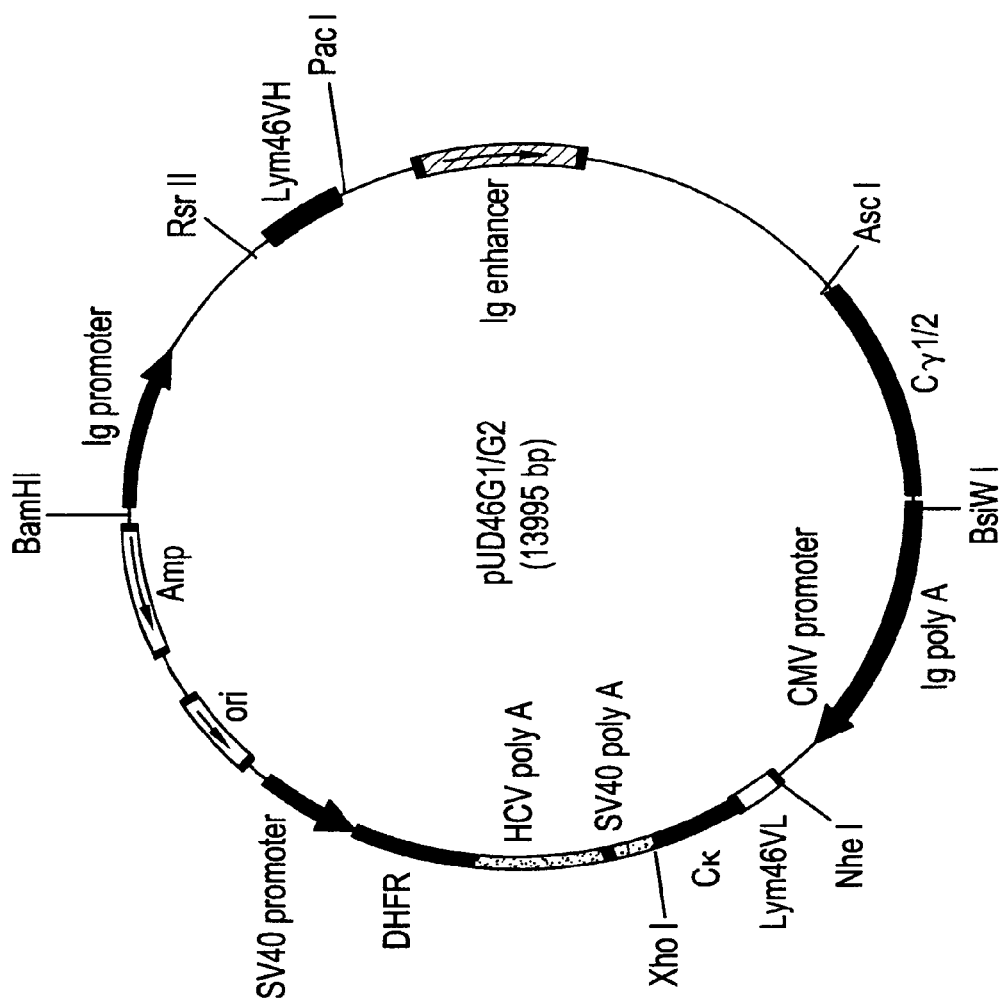

FIG. 79 depicts vector pUD46G1/G2 for generation of and recombinant expression of IgG subclass G1 and G2 of Lym 46, also containing the DHFR gene for amplification of the vector with methotrexate.

FIG. 80A-80B depicts assessment of percent demyelination (A) and inflammation (B) in TMEV infected SJL mice treated with ●PBS, ■□SHIgM22, and ▲SHIgM46 21 days post infection.

Figure 81:
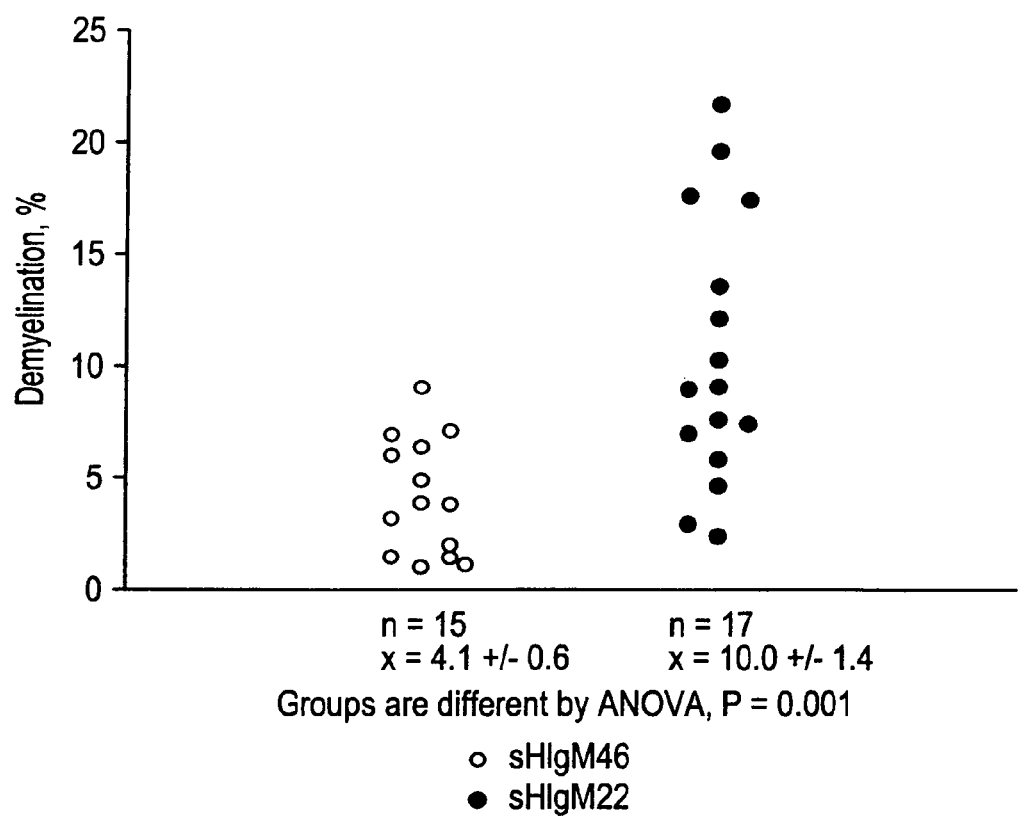

FIG. 81 depicts assessment of percent demyelination in TMEV infected SJL mice treated with SHIgM46 or SHIgM22.

Figure 82:
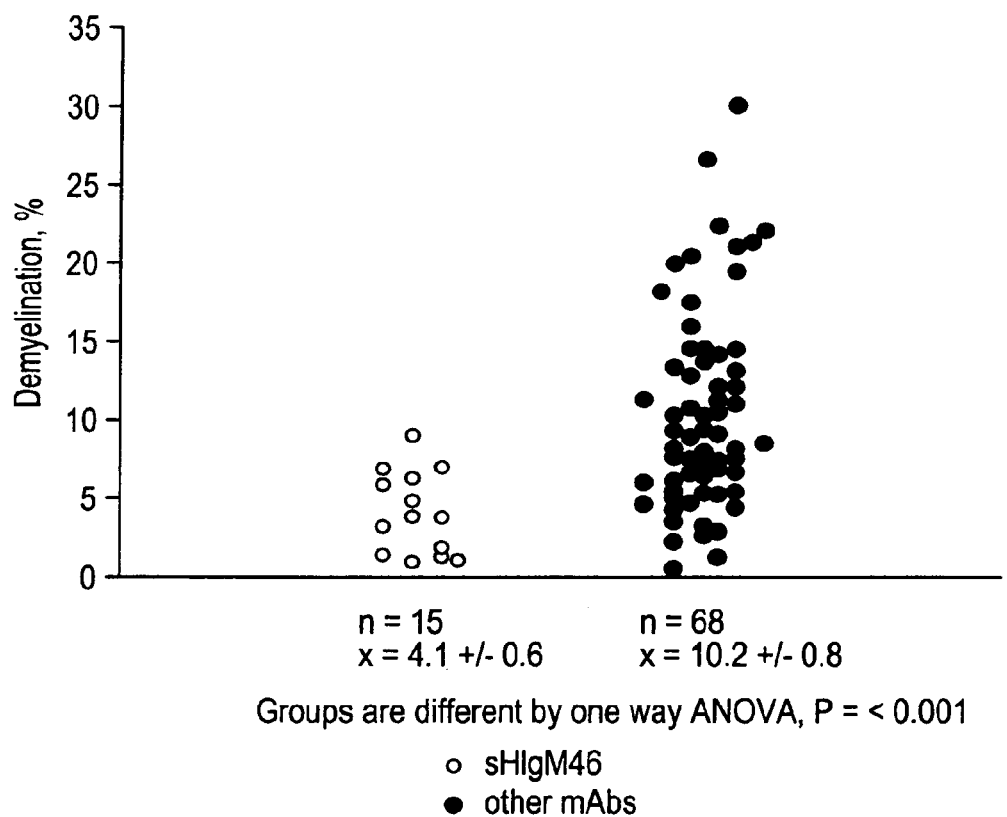

FIG. 82 depicts assessment of percent demyelination in TMEV infected SJL mice treated with SHIgM46 versus all other remyelination promoting monoclonal antibodies.

Figure 83:
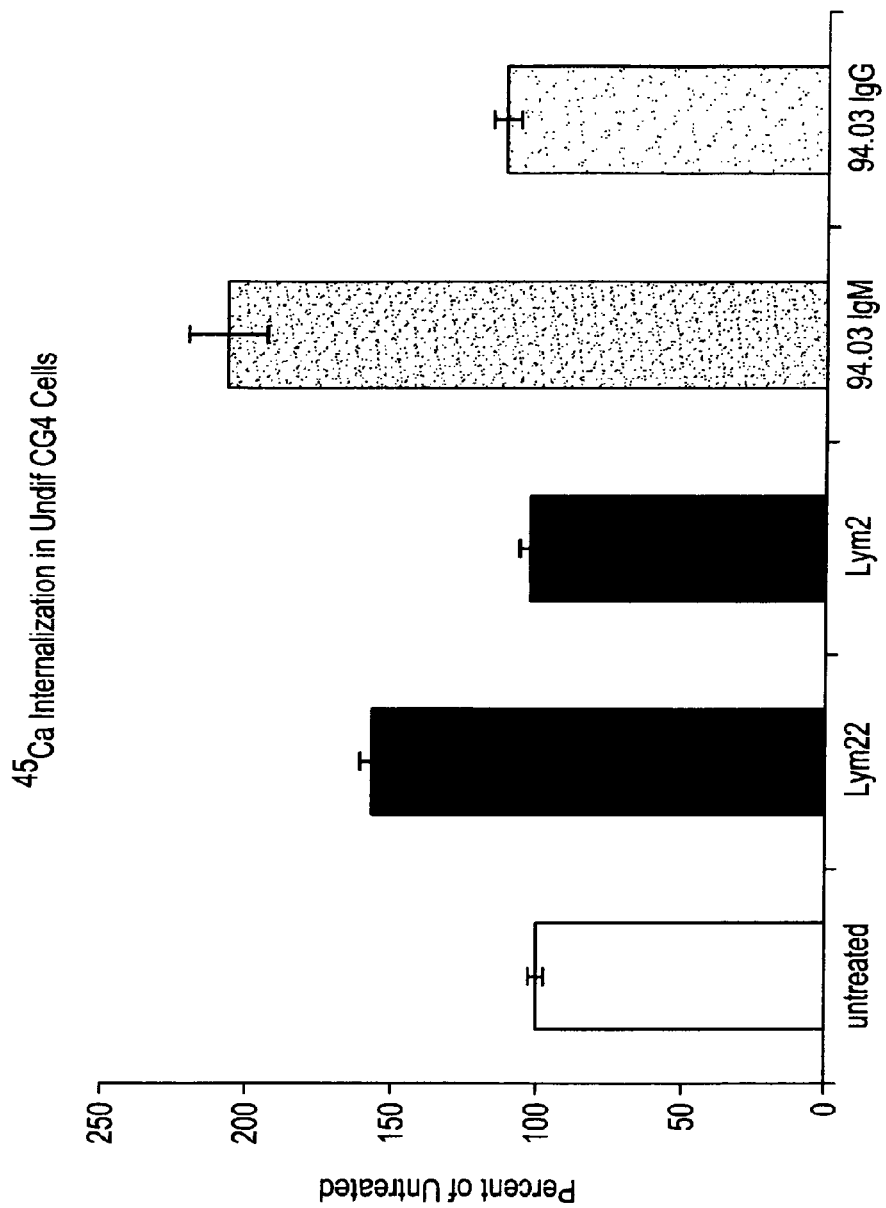

FIG. 83 presents internalization of labeled $^{45}$Ca in undifferentiated CG4 oligodendrocyte cells. $^{45}$Ca internalization is presented for untreated cells and cells treated with Lym22, Lym2, 94.03 IgM and 94.03 IgG, respectively.

Figure 84:
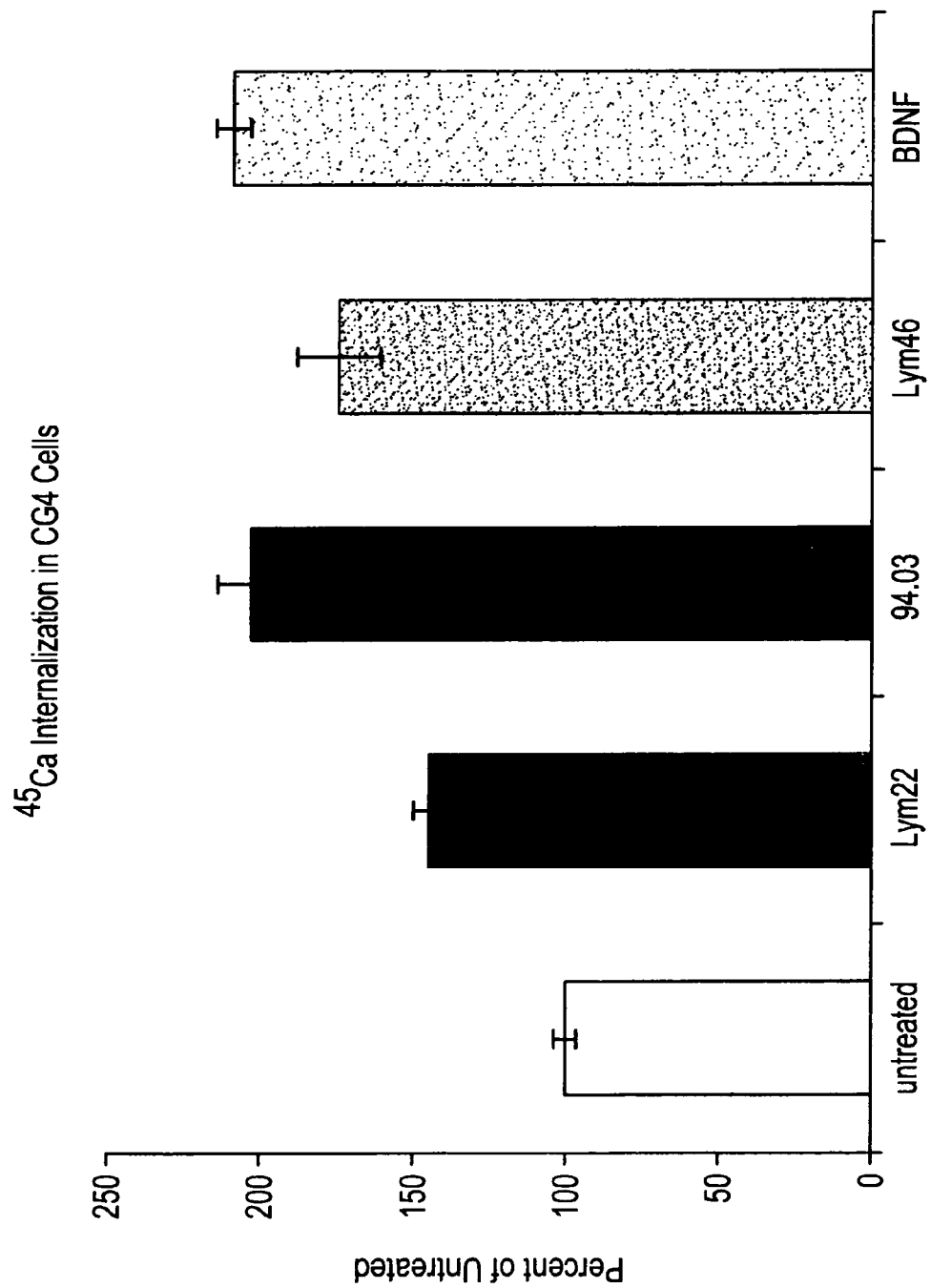

FIG. 84 presents internalization of labeled $^{45}$Ca in CG4 oligodendrocyte cells for untreated cells and cells treated with Lym22, 94.03, Lym46, and BDNF, respectively.

Figure 85:
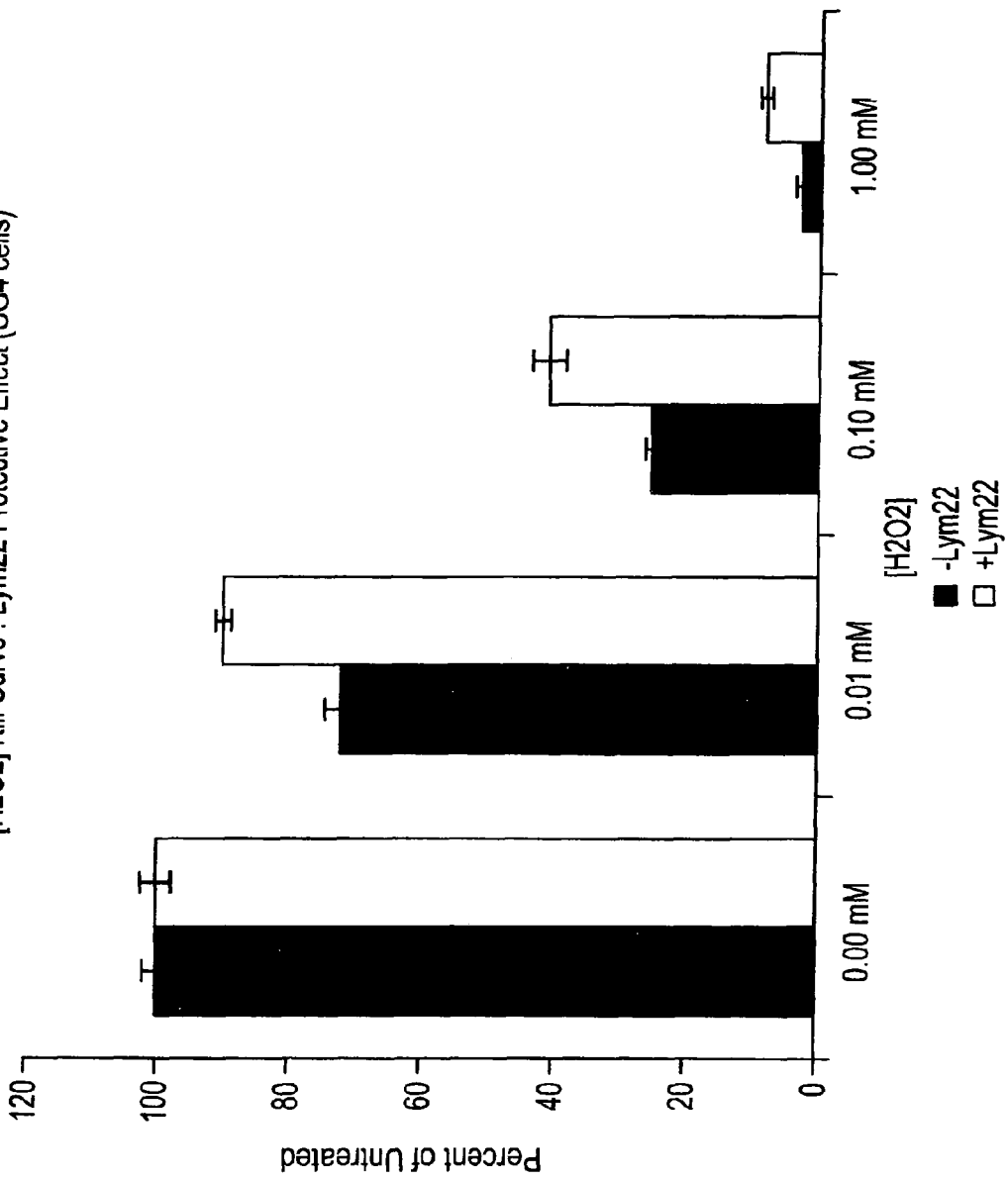

FIG. 85 presents a hydrogen peroxide ($H_2O_2$) kill curve—the percentage of GC4 cells surviving—on exposure to 0.00 mM, 0.01 mM, 0.10 mM and 1.0 mM $H_2O_2$, in the absence and presence of Lym22 antibody.

FIG. 86A-86B presents assessment and comparison of $H_2O_2$-induced cell death by MTT (A) assay or cell number (B) in untreated, 94.03 IgM treated, $H_2O_2$ treated and $H_2O_2$+94.03 IgM treated GC4 cells.

DETAILED DESCRIPTION

The present invention relates to the promotion, stimulation, regeneration, protection, and/or remyelination of central nervous system axons in a mammal. Specifically, the present invention relates to methods of stimulating the remyelination of central nervous system (CNS) axons using a monoclonal autoantibody, including of the IgM subtype and monomers thereof, particularly including human antibodies, or an active fragment thereof, characterized by its ability to bind to structures and cells of the central nervous system, particularly oligodendrocytes, or a natural or synthetic analog thereof. The pres using a monoclonal autoantibody, including of the IgM subtype and monomers thereof, particularly including human antibodies, or an active fragment thereof, characterized by its ability to bind to structures and cells of the central nervous system, particularly oligodendrocytes, or a natural or synthetic analog thereof.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The term "neuromodulatory agent(s)" as used herein singularly throughout the present application and claims, is intended to refer to a broad class of materials that function to promote neurite outgrowth, regeneration and remyelination with particular benefit and effect in the CNS, and therefore includes the antibodies of the IgM sub-type, and particularly, human antibodies such as those referred to specifically herein as sHIgM22 (LYM 22), ebvHIgM MSI19D10, sHIgM46 (LYM46), CB2bG8, AKJR4, CB2iE12, CB2iE7 and MSI19E5, peptide analogs, haptens, active fragments thereof, monomers thereof, agonists, mimics and the like, including such materials as may have at least partial sequence similarity to the peptide sequences set forth in FIGS. 35-38, 45, 46, 55-61 and 71-72. An sHIgM22(LYM22) antibody myeloma has been deposited as ATTC Accession No. PTA-8671. Neuromodulatory agent(s) also includes and encompasses combinations or mixtures of more than one of the antibodies provided herein, including monomers or active fragments thereof Also, the terms "neuromodulatory agent," "autoantibody," "antibody peptide," "peptide," "hapten" and any variants not specifically listed, may be used herein interchangeably, to the extent that they may all refer to and include proteinaceous material including single or multiple proteins, and extends to those proteins having the amino acid sequence data described herein and presented in FIGS. 35-38, 45, 46, 55-61 and 71-72 (SEQ ID NOS: 7, 8, 10, 9, 11, 12, 13, 14, 15, 16, 17, 18, 25, 26, 27, 28, 29, 30, 31, 32, 33, 34, 35, 36, 37, 38, 49 and 51), and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "neuromodulatory agent," "autoantibody," "antibody peptide," "peptide," "hapten" are intended where appropriate, to include within their scope proteins specifically recited herein as well as all substantially homologous analogs and allelic variations.

The amino acid residues described herein are preferred to be in the "L" isomeric form. However, residues in the "D" isomeric form can be substituted for any L-amino acid residue, as long as the desired fuctional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, J. Biol. Chem., 243:3552-59 (1969), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Gln | glutamic acid |
| W | Trp | tryptophan |
| R | Arg | arginine |
| D | Asp | aspartic acid |
| N | Asn | aspargine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alio, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to probes of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra. In particular, the heavy chain and light chain variable region sequences of the antibodies of the present invention are substantially homologous to a corresponding germline gene sequence, having at least about 90% homology to a corresponding germline gene sequence.

It should be appreciated that also within the scope of the present invention are DNA sequences encoding an antibody of the invention, or a peptide analog, hapten, or active fragment thereof, which code for a peptide that defines in at least a portion thereof, or has the same amino acid sequence as set forth in FIGS. 35-38, 45, 46, 55-61 and 71-72 (SEQ ID NOS: 7, 8, 10, 9, 11, 12, 13, 14, 15, 16, 17, 18, 25, 26, 27, 28, 29, 30, 31, 32, 33, 34, 35, 36, 37, 38, 49 and 51), but which are degenerate to the same SEQ ID NOS. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Mutations can be made in a particular DNA sequence or molecule such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:
Amino Acids with Nonpolar R Groups
Alanine
Valine
Leucine
Isoleucine
Proline
Phenylalanine
Tryptophan
Methionine Amino Acids with Uncharged Polar R Groups
Glycine
Serine
Threonine
Cysteine
Tyrosine
Asparagine
Glutamine
Amino Acids with Charged Polar R Groups (Negatively Charged at pH 6.0)
Aspartic acid
Glutamic acid
Basic Amino Acids (Positively Charged at pH 6.0)
Lysine
Arginine
Histidine (at pH 6.0)
Another Grouping May be Those Amino Acids with Phenyl Groups:
Phenylalanine
Tryptophan
Tyrosine
Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:
Lys for Arg and vice versa such that a positive charge may be maintained;
Glu for Asp and vice versa such that a negative charge may be maintained;
Ser for Thr such that a free —OH can be maintained; and
Gln for Asn such that a free NW can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Two amino acid sequences are "substantially homologous" when at least about 70% of the amino acid residues (preferably at least about 80%, and most preferably at least about 90 or 95%) are identical, or represent conservative substitutions. In particular, the heavy chain and light chain variable region sequences of the antibodies of the present invention are substantially homologous to a corresponding germline gene amino acid sequence, having at least about 90%, and preferably at least about 95% homology to a corresponding germline gene amino acid sequence.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

As used herein, the term "antibody" is any immunoglobulin, including antibodies and fragments thereof, that binds a specific epitope. The term is intended to encompass polyclonal, monoclonal, and chimeric antibodies, the last mentioned described in further detail in U.S. Pat. Nos. 4,816,397 and 4,816,567. Such antibodies include both polyclonal and monoclonal antibodies prepared by known generic techniques, as well as bi-specific or chimeric antibodies, and antibodies including other functionalities suiting them for additional diagnostic use conjunctive with their capability of modulating activity, e.g. that stimulates the remyelenation and/or regeneration of CNS axons, or that provides neuroprotection. An "antibody combining site" is that structural portion of an antibody molecule comprised of heavy and light chain variable and hypervariable regions that specifically binds antigen. The phrase "antibody molecule" in its various grammatical forms as used herein contemplates both an intact immunoglobulin molecule and an immunologically active portion of an immunoglobulin molecule. Exemplary antibody molecules are intact immunoglobulin molecules, substantially intact immunoglobulin molecules and those portions of an immunoglobulin molecule that contains the paratope, including those portions know in the art as Fab, Fab', F(ab')$_2$ and F(v).

Fab and F(ab')$_2$ portions of antibody molecules, or antibody fragments, may be prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chains portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bi-specific (chimeric) monoclonal antibody.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies useful in the present invention methods or produced against neuromodulatory agent peptides or autoantibody peptides can be screened for various properties; i.e., isotype, epitope, affinity, etc. Of particular interest are monoclonal antibodies that exhibit the same activity as the neuromodulatory agents, and particularly the present autoantibodies. Such monoclonals can be readily identified in activity assays such as the Theilers virus, EAE and lysolecithin models presented and illustrated herein. High affinity antibodies are also useful when immunoaffinity purification of native or recombinant autoantibodies is possible.

Preferably, the antibody used in the diagnostic methods and therapeutic methods of this invention is an affinity purified polyclonal antibody. More preferably, the antibody is a monoclonal antibody (mAb). In addition, it is contemplated for the antibody molecules used herein be in the form of Fab, Fab', $F(ab')_2$ or F(v) portions of whole antibody molecules.

As suggested earlier, the diagnostic method of the present invention comprises examining a cellular sample or medium by means of an assay including an effective amount of an antagonist to an antibody peptide/protein, such as an anti-peptide antibody, preferably an affinity-purified polyclonal antibody, and more preferably a mAb. In addition, it is preferable for the anti-peptide antibody molecules used herein be in the form of Fab, Fab', $F(ab')_2$ or F(v) portions or whole antibody molecules. As previously discussed, patients capable of benefiting from this method include those suffering from a neurological condition such as multiple sclerosis, Alzheimers disease, Parkinsons disease, a viral infection or other like neuropathological derangement, including damage resulting from physical trauma. Methods for isolating the peptides and inducing anti-peptide antibodies and for determining and optimizing the ability of anti-peptide antibodies to assist in the examination of the target cells are all well-known in the art.

Methods for producing polyclonal anti-polypeptide antibodies are well-known in the art. See U.S. Pat. No. 4,493,795 to Nestor et al. A monoclonal antibody, typically containing Fab and/or $F(ab')_2$ portions of useful antibody molecules, can be prepared using the hybridoma technology described in *Antibodies—A Laboratory Manual*, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with an antibody peptide-binding portion thereof, or the antibody peptide or fragment, or an origin-specific DNA-binding portion thereof.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact in the same fashion as the present autoantibodies and their ability to inhibit or promote specified activity in target cells and tissues.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., *Virol*. 8:396 (1959)) supplemented with 4.5 gm/l glucose, 20 mm glutamine, and 20% fetal calf serum. An exemplary inbred mouse strain is the Balb/c.

Methods for producing monoclonal anti-peptide antibodies are also well-known in the art. See Niman et al., *Proc. Natl. Acad. Sci. USA*, 80:4949-4953 (1983). Typically, the present antibody peptides, or a peptide analog or fragment, is used either alone or conjugated to an immunogenic carrier, as the immunogen in the before described procedure for producing anti-peptide monoclonal antibodies. The hybridomas are screened for the ability to produce an antibody that immunoreacts with the antibody peptide analog and thereby reacts similarly to the antibodies of the present invention.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

Antibodies can be labeled for detection in vitro, e.g., with labels such as enzymes, fluorophores, chromophores, radioisotopes, dyes, colloidal gold, latex particles, and chemiluminescent agents. Alternatively, the antibodies can be labeled for detection in vivo, e.g., with radioisotopes (preferably technetium or iodine); magnetic resonance shift reagents (such as gadolinium and manganese); or radio-opaque reagents.

The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. The polypeptide can also be labeled with a radioactive element or with an enzyme. The radioactive label can be detected by any of the currently available counting procedures. The preferred isotope may be selected from $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654, 090; 3,850,752; and 4,016,043 are referred to by way of example for their disclosure of alternate labeling material and methods.

Polyclonal immunoglobulin preparations have been shown to exert a beneficial clinical effect in various clinical situations that are characterized or accompanied by a dysfunction or dysregulation of the immune system. Immunoglobulin is also used to prevent or treat some illnesses that can occur when an individual does not produce enough of its own immunity to prevent these illnesses. Nearly all immunoglobulin preparations in use today are comprised of highly purified IgG, derived from large pools of human plasma by fractionation. These preparations are commonly administered intravenously (WIG), although intramuscular administration (IGIM) and oral administration is also used.

Commonly used IgG preparations include Gamimune (5% and 10%) (Bayer Corporation), Gammagard (Baxter Healthcare Corporation), Polygam (American Red Cross), Sandoglobin (Sandoz Pharmaceuticals), Venoglobin (Alpha Therapeutic) and Intraglobin (Biotest Pharma GmbH). An intramuscular immunoglobulin (IGIM), BayGam, is available from Bayer Corporation. IVIG preparations in clinical use contain predominantly IgG, smaller amounts of IgA, and yet smaller amounts of IgM, IgE and IgD, and generally comprise 95% or greater IgG, 2-5% IgA and trace amounts of IgM.

Pentaglobin (Biotest Pharma GmbH) is an IgM-enriched polyvalent immunoglobulin preparation and each ml of solution comprises: IgM 6 mg; IgA 6 mg; IgG 38 mg and glucose monohydrate for injection 27.5 mg; or 12% IgM, generally 10-15% IgM. Immunoglobulin preparations which have been further enriched for IgM can be readily generated and have been reported as effective in animal models for treatment or alleviation of certain conditions. Riebert et al. report the use of IgM enriched human intravenous immunoglobulin in a rat model of acute inflammation, particularly use of Pentaglobin and a laboratory preparation of IVIgM (35 gl/IgM, 12 g/l IgA, 3 g/l IgG). (Riebert, R. et al (1999) Blood 93(3):942-951). Hurez et al report use of an intravenous IgM preparation of greater than 90% in experimental autoimmune ueveitis (EAU) (Hurez, V. et al (1997) Blood 90(10):4004-4013). IgM antibody immunoglobulin preparations of at least 20% by weight IgM are described in U.S. Pat. Nos. 5,256,771, 5,510, 465 and 5,612,033, incorporated herein by reference in their entity. Intravenously administerable polyclonal immunoglobulin preparations containing at least 50% by weight of IgM in terms of the total content of immunoglobulin are described by Moller et al in U.S. Pat. No. 5,190,752, incorporated herein by reference in its entirety.

Immunoglobulin preparations are generated by methods and processes generally well known to those of skill in the art. Immunoglobulins are prepared from blood of healthy volunteers, where the number of blood donors is at least about 5 or 10; preferably at least about 100; more preferably at least about 1,000; still more preferably at least about 10,000. In one common method, human plasma derived from pools of thousands of donors is fractionated by cold ethanol fractionation (the Cohn process or Cohn-Oncley process) (Cohn, et al (1946) J. Am. Chem. Soc. 68:459-475; Oncley, et al (1949) J. Am. Chem. Soc. 71:541-550) followed by enzymatic treatment at low pH, fractionation and chromatography. Cold ethanol fractionation may also be followed by ultrafiltration and ion exchange chromatography. Further steps are incorporated to render immunoglobulin preparations safe from viral transmission, including but not limited to enzymatic modification, chemical modification, treatment with beta-propiolactone, treatment at low pH, treatment at high heat and treatment with solvent/detergent. Treatment with an organic solvent/detergent (S/D) mixture eliminates viral transmission by enveloped viruses (HIV, hepatitis B, hepatitis C) (Gao, F. et al (1993) Vox Sang 64(4):204-9; U.S. Pat. Nos. 4,481,189 and 4,540,573, incorporated herein by reference). Particular processes and methods for preparation of IgM enriched immunoglobulin solutions are described in U.S. Pat. Nos. 4,318,902 and 6,136,132, which are incorporated herein by reference in their entirety.

Polyclonal IgM-enriched immunoglobulin preparations contemplated herein and suitable for use in the methods of the present invention can be made by any of the well-known methods used for preparing immunoglobulin preparations. Suitable immunoglobulin preparations can also be obtained commercially. The immunoglobulin preparation can be a human immunoglobulin preparation. Suitable immunoglobulin preparations include at least about 10% IgM, at least about 15% IgM, at least about 20% IgM, at least about 25% IgM, at least about 30% IgM, at least about 40% IgM, at least about 50% IgM, at least about 60% IgM, at least about 70% IgM, at least about 80% IgM, at least about 90% IgM and at least about 95% IgM. Polyclonal IgM immunoglobulin preparations suitable for use in the present invention include greater 10% IgM, greater than 20% IgM, and greater than 50% IgM. Polyclonal IgM immunoglobulin preparations suitable for use in the present invention include an amount of IgM which is greater than the amount if IgG and greater than the amount of IgA.

Preparations of fragments of IgM enriched immunoglobulins, particularly human immunoglobulins can also be used in accordance with the present invention. Fragments of immunoglobulins refer to portions of intact immunoglobulins such as Fc, Fab, Fab', F(ab)'$_2$ and single chain immunoglobulins or monomers.

The IgM-enriched immunoglobulin preparation in preferably provided in a pharmaceutically acceptable carrier, vehicle or diluent and is administered intravenously, intramuscularly or orally. IgM immunoglobulin is administered in doses and amounts similar to the administration recognized and utilized by the skilled artisan for the administration of clinically adopted immunoglobulins, including IVIG or IGIM or Pentaglobin, or as instructed or advised clinically or by the manufacturer. IgM preparations for use in the present invention are administered in doses of about 0.5 mg/kg to about 1-2 g/kg body weight and can be administered as a single dose or in multiple separated doses daily or over the course of days or months. Suitable dosages include 10 mg/kg body weight, 20 mg/kg body weight, 30 mg/kg body weight, 40 mg/kg body weight, 50 mg/kg body weight, 75 mg/kg body weight, 100 mg/kg body weight, 200 mg/kg body weight, 300 mg/kg body weight, 400 mg/kg body weight, 500 mg/kg body weight, 1 g/kg body weight, and 2 g/kg body weight The polyclonal IgM immunoglobulin preparations may be administered alone or in combination with other treatments, including but not limited to other compounds or agents for treatment or alleviation of the condition. In the instance of treatment or alleviation of a demyelinating disease, multiple sclerosis in particular, the IgM immunoglobulin may be administered with anti-inflammatories, steroids, Betaseron, Copaxone, etc.

Accordingly, in one aspect of the diagnostic application of the present invention, a method is disclosed for detecting the presence or activity of a neuromodulatory agent, the neuromodulatory agent comprising a material selected from the group consisting of an antibody, a peptide analog, a hapten, monomers thereof, active fragments thereof, agonists thereof, mimics thereof, and combinations thereof, said neuromodulatory agent having one or more of the following characteristics: inducing remyelination; binding to neural tissue; promoting $Ca^{++}$ signaling with oligodendrocytes; and, optionally, promoting cellular proliferation of glial cells; wherein said neuromodulatory agent is measured by:

A) contacting a biological sample from a mammal in which the presence or activity of said neuromodulatory agent is suspected with a binding partner of said neuromodulatory agent under conditions that allow binding of said neuromodulatory agent to said binding partner to occur; and B) detecting whether binding has occurred between said neuromodulatory agent from said sample and the binding partner;

wherein the detection of binding indicates that presence or activity of the neuromodulatory agent in the sample.

In a variant aspect, the invention extends to a method for detecting the presence and activity of a polypeptide ligand associated with a given invasive stimulus in mammals comprising detecting the presence or activity of the neuromodulatory agent as set forth above, where detection of the presence or activity of the neuromodulatory agent indicates the presence and activity of a polypeptide ligand associated with a given invasive stimulus in mammals. In a particular aspect, the invasive stimulus is an infection, and may be selected from viral infection, protozoan infection, bacterial infection, tumorous mammalian cells, and toxins.

In a further aspect, the invention extends to a method for detecting the binding sites for a neuromodulatory agent, said neuromodulatory agent comprising a material selected from the group consisting of an antibody, including antibodies of the IgM subtype and monomers thereof, a peptide analog, a hapten, active fragments thereof, agonists thereof, mimics thereof, and combinations thereof, said neuromodulatory agent having one or more of the following characteristics: inducing remyelination; binding to neural tissue; promoting $Ca^{++}$ signaling with oligodendrocytes; and, optionally, promoting cellular proliferation of glial cells; said method comprising:

A. placing a labeled neuromodulatory agent sample in contact with a biological sample from a mammal in which binding sites for said neuromodulatory agent are suspected;

B. examining said biological sample in binding studies for the presence of said labeled neuromodulatory agent;

wherein the presence of said labeled neuromodulatory agent indicates a binding site for a neuromodulatory agent.

Yet further, the invention includes a method of testing the ability of a drug or other entity to modulate the activity of a neuromodulatory agent, said agent comprising a material selected from the group consisting of an antibody, including antibodies of the IgM subtype, a peptide analog, a hapten, monomers thereof, active fragments thereof, agonists thereof, mimics thereof, and combinations thereof, which method comprises:

A. culturing a colony of test cells which has a receptor for the neuromodulatory agent in a growth medium containing the neuromodulatory agent;

B. adding the drug under test; and

C. measuring the reactivity of said neuromodulatory agent with the receptor on said colony of test cells;

wherein said neuromodulatory agent has one or more of the following characteristics:

a) inducing remyelination;
b) binding to neural tissue, particularly oligodendrocytes;
b) promoting $Ca^{++}$ signaling with oligodendrocytes; and
c) promoting cellular proliferation of glial cells.

Correspondingly, the invention covers an assay method for screening drugs and other agents for ability to modulate the production or mimic the activities of a neuromodulatory agent, said neuromodulatory agent comprising a material selected from the group consisting of an antibody, a peptide analog, a hapten, monomers thereof, active fragments thereof, agonists thereof, mimics thereof, and combinations thereof, said method comprising:

A. culturing an observable cellular test colony inoculated with a drug or agent;

B. harvesting a supernatant from said cellular test colony; and

C. examining said supernatant for the presence of said neuromodulatory agent wherein an increase or a decrease in a level of said neuromodulatory agent indicates the ability of a drug to modulate the activity of said neuromodulatory agent, said neuromodulatory agent having one or more of the following characteristics:

i) inducing remyelination;
ii) binding to neural tissue, particularly oligodendrocytes;
iii) promoting $Ca^{++}$ signaling with oligodendrocytes; and
iv) promoting cellular proliferation of glial cells.

Lastly, a test kit is contemplated for the demonstration of a neuromodulatory agent in a eukaryotic cellular sample, said neuromodulatory agent comprising a material selected from the group consisting of an antibody, including antibodies of the IgM subtype and monomers thereof, a peptide analog, a hapten, active fragments thereof, agonists thereof, mimics thereof, and combinations thereof, which kit comprises:

A. a predetermined amount of a detectably labeled specific binding partner of a neuromodulatory agent, said neuromodulatory agent having one or more of the following characteristics: inducing remyelination; binding to neural tissue; promoting $Ca^{++}$ signaling with oligodendrocytes; and promoting cellular proliferation of glial cells;

B. other reagents; and

C. directions for use of said kit.

A variant test kit is disclosed for demonstrating the presence of a neuromodulatory agent in a eukaryotic cellular sample, said agent comprising a material selected from the group consisting of an antibody, a peptide analog, a hapten, monomers thereof, active fragments thereof, agonists thereof, mimics thereof, and combinations thereof. The kit comprises:

A. a predetermined amount of a neuromodulatory agent, said neuromodulatory agent having one or more of the following characteristics: inducing remyelination; binding to neural tissue; promoting $Ca^{++}$ signaling with oligodendrocytes; and promoting cellular proliferation of glial cells;

B. a predetermined amount of a specific binding partner of said neuromodulatory agent;

C. other reagents; and

D. directions for use of said kit;

wherein either said neuromodulatory agent or said specific binding partner are detectably labeled. Both of the above kits may utilize a labeled immunochemically reactive component selected from the group consisting of polyclonal antibodies to the neuromodulatory agent, monoclonal antibodies to the neuromodulatory agent, fragments thereof, and mixtures thereof.

The present invention extends to the use and application of the antibodies of the present invention, particularly autoantibodies, including antibodies of the IgM subtype and monomers thereof, or mixtures and/or active fragments thereof, characterized by their ability to bind to structures and cells in the central nervous system. particularly including oligodendrocytes, in imaging and in vivo diagnostic applications. Thus, the antibodies, by virtue of their ability to bind to structures and cells in the central nervous system, particularly including oligodendrocytes, can be utilized via immunofluorescent, radioactive and other diagnostically suitable tags as imaging agents or imaging molecules for the characterization of the nervous system, including the central nervous system and the diagnosis, monitoring and assessment of nervous disease, particularly including multiple sclerosis. The antibodies may further be utilized as imaging agents or imaging molecules in the diagnosis, monitoring and assessment of stroke, spinal cord injury and various dementias including Alzheimer's disease. The appropriate and suitable immunofluorescent, radioactive, or other tagging molecules or agents for coupling or attachment to the antibodies for use in in vivo imaging will be well known to and within the skill of the skilled artisan. The present invention also relates to methods of treating demyelinating diseases in mammals, such as multiple sclerosis in humans, and viral diseases of the central nervous system of humans and domestic animals, such as post-infectious encephalomyelitis, using the SCH 94.03, SCH 79.08, O1, O4, A2B5 and HNK-1 monoclonal antibodies, and the human autoantibodies sHIgM22, ebvHIgM MSI19D10, sHIgM46, analogs thereof including haptens, active fragments thereof, or a natural or synthetic autoantibody having the characteristics thereof. Methods of prophylactic treatment using these mAb, active fragments thereof, or other natural or synthetic autoantibodies having the same characteristics, to inhibit the initiation or progression demyelinating diseases are also encompassed by this invention.

Oligodendrocytes (OLs), the myelin-forming cells of the central nervous system (CNS), originate as neuroectodermal cells of the subventricular zones, and then migrate and mature to produce myelin. The sequential development of OLs is identified by well-characterized differentiation stage-specific markers. Proliferative and migratory bipolar precursors, designated oligodendrocyte/type-3 astrocyte (O-2A) progenitors, are identified by monoclonal antibodies (mAbs) anti-$GD_3$ and A2B5 [Eisenbarth et al., Proc. Natl. Acad. Sci. USA, 76 (1979), 4913-4917]. The next developmental stage, characterized by multipolar, postmigratory, and proliferative cells, is recognized by mAb O4 [Gard et al., Neuron, 5 (1990), 615-625; Sommer et al., Dev. Biol., 83 (1981), 311-327]. Further development is defined by the cell surface expression of galactocerebroside, recognized by mAb O1 [Schachner, J. Neurochem., 39 (1982), 1-8; Sommer et al., supra], and by the expression of 2',3'-cyclic nucleotide 3'-phosphohydrolase. The most mature cells express terminal differentiation markers such as myelin basic protein and proteolipid protein.

The mAbs (A2B5, O1, and O4) used to characterize the stages of OL development were made by immunizing BALB/c mice with chicken embryo retina cells or homogenate of bovine corpus callosum [Eisenbarth et al., supra; Sommer et al., supra]. A2B5 recognizes not only O-2A progenitors but also neurons and reacts with cell surface ganglioside GQ1c [Kasai et al., Brain Res., 277 (1983), 155-158] and other gangliosides [Fredman et al., Arch. Biochem. Biophys., 233 (1984), 661-666]. O4 reacts with sulfatide, seminolipid and cholesterol [Bansal et al., J. Neurosci. Res., 24 (1989), 548-557], whereas O1 reacts with galactocerebroside, monogalactosyl-diglyceride and psychosine [Bansal et al., supra]. These mAbs belong to the IgM immunoglobulin (Ig) subclass and recognize cytoplasmic structures as well as the surface antigens of OLs [Eisenbarth et al., supra; Sommer et al., supra]. Mouse mAb HNK-1 (anti-Leu-7), made by immunizing BALB/c mice with the membrane suspension of HSB-2 T lymphoblastoid cells, was first reported as a marker for natural killer cells [Abo et al., J. Immunol., 127 (1981), 1024-1029]. Later, HNK-1 was shown to share antigenic determinants with the nervous system [Schuller-Petrovic et al., Nature, 306 (1983), 179-181]. The carbohydrate epitope on myelin-associated glycoprotein, found in both central and peripheral myelin sheaths, was shown to be a principal antigen of nervous tissue the reacted with HNK-1 [McGarry et al., Nature, 306 (1983), 376-378]. However, other glycoproteins in nervous tissue react with this mAb, some of which are important in embryogenesis, differentiation, and myelination [Keilhauer et al., Nature, 316 (1985), 728-730; Kruse et al., Nature, 311 (1984), 153-155; Kruse et al., Nature, 316 (1985), 146-148; McGarry et al., J. Neuroimmunol., 10 (1985), 101-114]. Of interest, HNK-1 also reacts with cytoplasmic structures and belongs to the IgM Ig subclass.

A monoclonal antibody, disclosed and claimed in copending parent application U.S. Ser. No. 08/236,520, filed Apr. 29, 1994, and designated SCH94.03, was found to promotes CNS remyelination in mice infected chronically with Theiler's murine encephalomyelitis virus (TMEV) [Miller et al., J. Neurosci., 14 (1994), 6230-6238]. SCH94.03 belongs to the IgM(x) Ig subclass and recognizes an unknown surface antigen on OLs, but cytoplasmic antigens in all cells (Asakura et al., Molecular Brain Research, in press). The polyreactivity of SCH94.03 by ELISA, and the unmutated Ig variable region germline sequences indicated that SCH94.03 is a natural autoantibody [Miller et al., J. Neurosci., 14 (1994), 6230-6238]. A close study of SCH94.03, and comparison thereof with well-known OL-reactive mAbs A2B5, O1, O4, and HNK-1 raised the possibility that these are natural autoantibodies. A subsequent analysis of the Ig variable region cDNA sequences and the polyreactivity of these mAbs by ELISA confirmed that this is a generic group of natural autoantibodies having similar utilities.

The antigen reactivity of the monoclonal antibody, IgM monoclonal antibody referred to herein as SCH 94.03 (also referred to herein as SCH94.32) and SCH 79.08 (both prepared from a mammal immunized with spinal cord homogenate from a normal mammal (i.e., uninfected with any demyelinating disease)), have been characterized and described in the aforesaid parent Application U.S. Ser. No. 08/236,520, filed Apr. 29, 1994, whose teachings are incorporated herein by reference, using several biochemical and molecular assays, including immunohistochemistry, immunocytochemistry, Western blotting, solid-phase enzyme-linked immunosorbant assays (ELISA), and Ig variable region sequencing. The hybridomas producing monoclonal antibody SCH 94.03 and SCH 79.08 have been deposited on Apr. 28, 1994, and Feb. 27, 1996, respectively, under the terms of the Budapest Treaty, with the American Type Culture Collection (ATCC) and have been given ATCC Accession Nos. CRL 11627 and HB12057, respectively. All restrictions upon the availability of the deposit material will be irrevocably removed upon granting of a patent.

Natural or physiologic autoantibodies are present normally in serum, are characterized by being reactive or capable of binding to self structures, antigens or cells. They are often polyreactive, are frequently of the IgM subtype, and are encoded by unmutated germline genes or are substantially homologous to germline genes with few or several sequence differences. By sequencing immunoglobulin (Ig) cDNAs of the oligodendrocyte-reactive O1, O4, A2B5, and HNK-1 IgM×monoclonal antibodies and comparing these with published germline sequences, it was determined that these were natural autoantibodies. O1 $V_H$ was identical with unrearranged $V_H$ segment transcript A1 and A4, O4 $V_H$ had three and HNK-1 $V_H$ had six nucleotide differences from $V_H$101 in the $V_H$ coding region. The D segment of O1 was derived from germline SP2 gene family, $J_H$4, whereas O1 $J_H$ was encoded by germline $J_H$1 with one silent nucleotide change. O1 and O4 light chains were identical with myeloma MOPC21 except for one silent nucleotide change. HNK-1 $V_x$ was identical with germline $V_x$41 except for two silent nucleotide changes. O1 $J_x$, O4$J_x$ and HNK $J_x$ were encoded by unmutated germline $J_x$2. In contrast, A2B5 $V_H$ showed seven nucleotide differences from germline V1, whereas no germline sequence encoding A2B5 $V_x$ was identified. O1 and O4, but not A2B5 were polyreactive against multiple antigens by direct ELISA. Therefore, O1, O4 and HNK-1 Igs are encoded by germline genes, and have the genotype and phenotype of natural autoantibodies.

Selection of SCH mAbs to Promote CNS Remyelination

A panel of monoclonal antibodies (mAbs) derived from splenocytes of uninfected SJL/J mice injected with SCH was constructed as described in detail in Example 1. After the initial fusion and cloning, 2 of the 95 wells with viable Ig-secreting hybridomas contained mAb with significant binding to SCH as demonstrated by ELISA. Hybridoma cells from these two wells, called the 79 and 94 series, were subcloned by limiting dilution and screened again for binding to SCH by ELISA. For the 79 series hybridomas, 14 out of 49 clones were positive by SCH ELISA, while for the 94 series, 17 out of 32 were positive for binding to SCH. Based upon the ELISA data, two 79 series hybridomas (SCH79.08 and SCH79.27), both of which also reacted with myelin basic protein (MBP) by ELISA, and three 94 series hybridomas (SCH94.03, SCH94.11, and SCH94.32), none of which reacted with MBP, were chosen for ascites production and in vivo transfer experiments.

mAbs Promote Proliferation of Glial Cells

As described in Example 2, the mAbs were tested for their ability to promote proliferation of glial cells in vitro.

The dose-response characteristic of antibody-mediated proliferation were then examined. As shown in FIG. 1, maximal stimulation with 94.03 was seen at 100 ng/ml. Control myeloma IgMs MOPC 104E and TEPC183 (data not shown) also stimulated the mixed rat brain cultures to proliferate. However, the maximal effect was seen at a 10-fold higher concentration than that seen with the mAbs.

Figure 2:
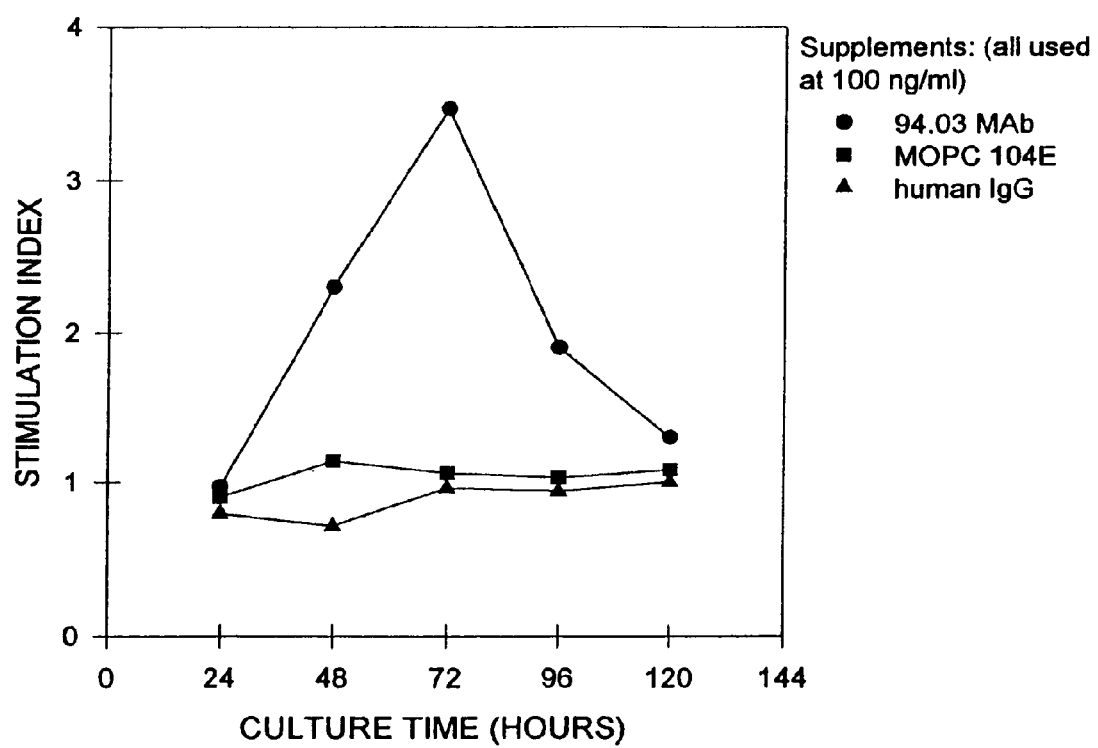
FIG. 2 is a graph depicting the temporal profile of antibody-mediated proliferation of cells in mixed rat brain culture.

The temporal profile of antibody-mediated proliferation was also examined as shown in FIG. 2. On day 8, after culture initiation, 100 ng/ml antibody was added to the cultures (time 0). Cells were harvested at 24 hour intervals; [$^3$H]thymidine was present for the final 24 hours of culture to measure the total proliferation during the interval. The maximal stimulation with 94.03 was seen at 72 hours after antibody addition. Similar results were obtained with 94.32. None of the isotype control antibodies showed any significant proliferation throughout the 120 hours of culture. These data demonstrates that both mAbs 94.32 and 94.03 induce proliferation of glial cells of mixed rat brain culture. This proliferation is maximal at an antibody concentration of 100 ng/ml and a culture period of 72 hours after antibody addition.

CNS Remyelination Promoted by mAbs SCH94.033 and SCH94.32

As described in Example 3, SJL/J mice chronically infected with TMEV were treated with a total mAb dose of 0.5 mg iv or 5.0 mg ip divided into twice weekly doses for 4-5 weeks. CNS remyelination was measured by a quantitative morphological assessment on ten spinal cord cross-sections from each mouse. The criterion for CNS remyelination was abnormally thin myelin sheaths relative to axonal diameter. The data are composite of six experiments and are presented as the ±SEM, where n indicates the number of mice. Statistical comparisons for remyelination data were made with the cumulative values from both IgM and buffer only controls using a modified rank sum test. The number of demyelinated lesions and the area of demyelination were not significantly different between treatment groups assessed by a one-way ANOVA. For control IgMs, myelomas MOPC 104E and ABPC 22 (both from Sigma), and TB5-1, an anti-mycobacteria mAb, were used.

SJL/J mice chronically infected with TMEV and treated with either mAb SCH94.03 or SCH94.32 showed significantly greater CNS remyelination than animals treated with either isotype-matched control mAb or buffer onl+(Table 1).

TABLE 1

Monoclonal antibodies SCH94.03 and SCH94.32 promote CNS remyelination

| Treatment | n | Number of Demylination (lesions) | Number of Remyelinated Lesions | p-value | Area of Remyelination (mm$^2$) | Area of Lesion (mm$^2$) | Area Remyelination/ area Lesion (%) |
|---|---|---|---|---|---|---|---|
| SCH94.03 | 12 | 25.6 ± 2.6 | 12.8 ± 2.6 | <0.0025 | 0.35 ± 0.09 | 1.09 ± 0.19 | 28.9 ± 3.8 |
| SCH94.32 | 12 | 24.9 P ± 2.8 | 12.3 ± 2.3 | <0.0001 | 0.42 ± 0.11 | 1.46 ± 0.21 | 26.7 ± 4.2 |
| IgM control | 13 | 29.9 ± 2.0 | 6.7 ± 1.2 | — | 0.11 ± 0.02 | 1.70 ± 0.28 | 7.7 ± 1.8 |
| Buffer only | 11 | 27.7 ± 2.7 | 5.1 ± 1.1 | — | 0.06 ± 0.01 | 1.11 ± 0.29 | 6.5 ± 1.2 |

Remyelination was seen with either iv or ip injections. SCH94.03- or SCH94.32-treated animals had approximately 2-3-fold more remyelinated lesions, and a 3-4-fold larger total area of CNS remyelination than control animals. When a cumulative statistical comparison was made using these two parameters of therapeutic effectiveness, the CNS remyelination induced by mAbs SCH94.03 and SCH94.32 was highly significant (p<0.005; Table 2). In a chronic progressive disease like TMEV infection, the extent of CNS repair is a direct function of the extent of CNS damage. Both the number and area of CNS lesions were not different between treatment groups, indicating similar disease severity (Table 1). When CNS remyelination was expressed as the percentage of lesion area showing remyelination, approximately one-third of the cumulative demyelinated lesion area shown CNS remyelination in mice treated with either mAb SCH94.03 or SCH94.32 (Table 1).

Similar results were obtained using Schh 79.08 (Results shown in Table 2) and for O1, O4, A2B5 and HNK-1 (Results shown in Table 3).

TABLE 2

Enhancement of CNS remyelination by SCH79.08

| Treatment | No. of Mice | Area of white matter (mm$^2$) | Area of CNS-type remyelination (mm$^2$) | Area of demyelinated lesion (mm$^2$) | Area of CNS-type remyelination/ area of lesions (%) |
|---|---|---|---|---|---|
| SCH79.08 | 15 | 8.42 ± 0.33 | 0.20 ± 0.05 | 1.01 ± 0.16 | 20.2 ± 4.7 |
| PBS | 6 | 8.89 ± 0.26 | 0.03 ± 0.01 | 1.01 ± 0.21 | 2.4 ± 0.8 |

Values represent the mean ± SEM.
Statistics by student t-test comparing area of CNS-type remyelination/area of lesions revealed p < 0.05.
PBS: phosphate buffered saline.

TABLE 3

Enhancement of CNS remyelination by oligodendrocyte-reactive monoclonal antibodies

| Treatment | No. of mice | Area of White matter (mm$^2$) | Area of CNS-type remyelination (mm$^2$) | Area of demyelinated lesion (mm$^2$) | Area of CNS-type remyelination/ area of lesions (%) |
|---|---|---|---|---|---|
| O1 | 6 | 7.57 ± 0.52 | 0.14 ± 0.04 | 0.53 ± 0.10 | 24.8 ± 6.2* |
| O4 | 7 | 8.01 ± 0.15 | 0.17 ± 0.04 | 0.84 ± 0.10 | 20.4 ± 4.2* |
| A2B5 | 7 | 7.28 ± 0.38 | 0.18 ± 0.05 | 0.70 ± 0.17 | 24.6 ± 4.6* |
| HNK-1 | 7 | 7.16 ± 0.38 | 0.15 ± 0.03 | 0.78 ± 0.10 | 20.6 ± 2.8* |
| PBS | 6 | 7.46 ± 0.70 | 0.05 ± 0.02 | 0.51 ± 0.14 | 8.0 ± 2.2 |

Values represent the mean ± SEM.
Statistics by student t-test comparing area of CNS-type remyelination/area of lesions revealed *p < 0.05, **p < 0.01.
PBS: phosphate buffered saline Morphology of CNS Remyelination CNS remyelination was readily identified morphologically both by light and electron microscopy (FIG. 3A-3D). FIG. 3A shows a remyelinated lesion from an animal treated with SCH94.03. The majority of axons in the lesion show morphologic evidence of repair, with abnormally thin myelin sheaths relative to axonal diameter (Ludwin, S. K. "Remyelination in the central nervous system of the mouse," In: THE PATHOLOGY OF THE MYELINATED AXON (Adachi M, Hirano A, Aronson S M eds), pp 49-79, Tokyo: Igaku-Shoin Ltd. (1985)). For comparison, FIG. 3B shows a demyelinated lesion, with minimal remyelination, whereas FIG. 3C is an area of normal myelin, with thickly myelinated axons. Within remyelinated lesions (FIG. 3A), there were 15.3±1.0 (mean±SEM) myelinated axons per 100 µm$^2$, compared to only 1.1±0.2 myelinated axons per 100 µm$^2$ in demyelinated lesions (FIG. 3B). FIG. 3C shows a light micrograph of spinal cord section with normal myelin. By electron microscopy, CNS remyelination was especially evident (FIG. 3D). Almost every axon in the field has evidence of new myelin formation, although the degree of remyelination (i.e., myelin thickness) is variable between individual axons, suggesting different stages of the repair process. The ratio of myelin thickness to axonal diameter was 0.08±0.01 (mean±SEM; n=25 axons) for remyelinated axons compared to 0.21±0.01 (n=34 axons) for normally myelinated axons.

Correlation Between Clinical Disease and Morphological Remyelination

Figure 4:
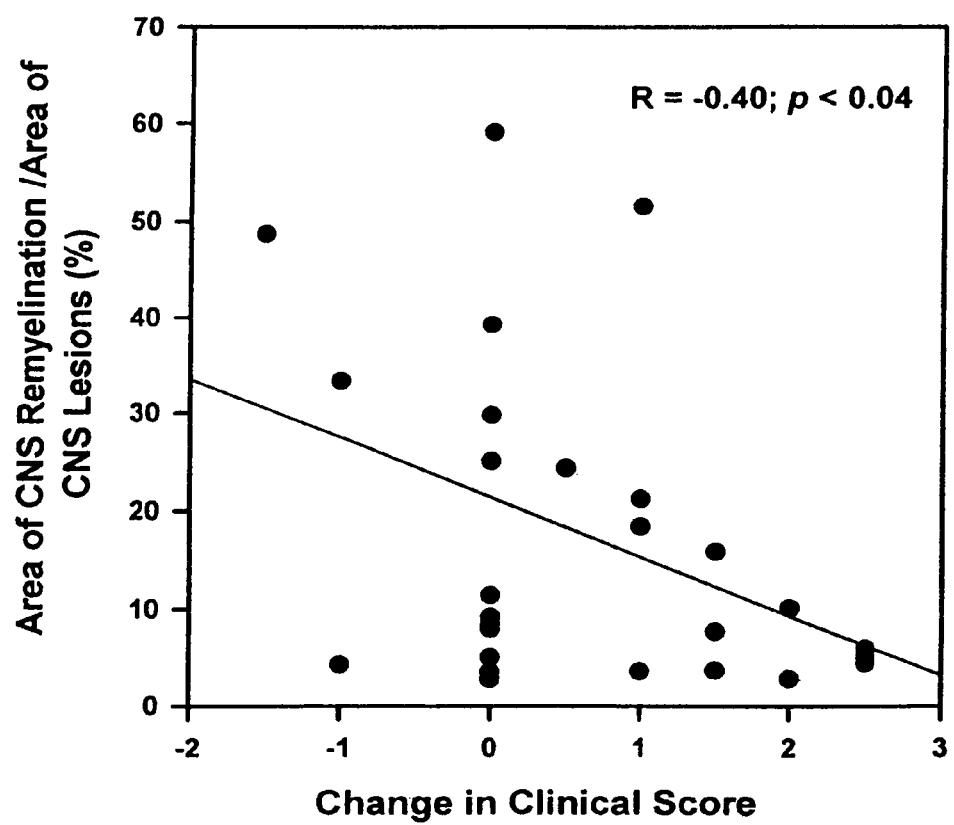
FIG. 4 is a graph depicting the correlation between the change in clinical disease and morphological remyelination.

The correlation of morphological remyelination with clinical signs of disease improvement was assessed as described in Example 3. At each treatment injection, mice were assessed clinically as described in Example 3. The change in clinical score was correlated with the percentage of lesion area showing remyelination (FIG. 4). Morphological remyelination is represented as the percentage of lesion area showing CNS remyelination. A change in clinical score of 0 represent stable disease over the treatment period (4-5 weeks), whereas a positive change indicates worsening of clinical disease, and a negative change indicates improvement. Data represent individual animals from all treatment groups. A positive change in clinical score indicates worsening of disease. Using data from all treatment groups, the change in clinical score showed a moderate but significant negative correlation (R=−0.40; p<0.04) with the percentage of lesion area showing remyelination. Although few animals actually improved clinically (Δ clinical score<0), animals with an increase in disease severity (Δ clinical score>0) tended to have less morphological remyelination, while animals that remained stable clinically (Δ clinical score=0) showed the most remyelination. A similar negative correlation was obtained when the other quantitative measures of remyelination were used (the number of remyelinated lesions and the area of remyelination) as shown in Table 1. These data demonstrate that remyelination quantitated by morphology is associated with slowing of clinical disease progression.

Titration of mAb SCH94.03 Dose and CNS Remyelination

Figure 5:
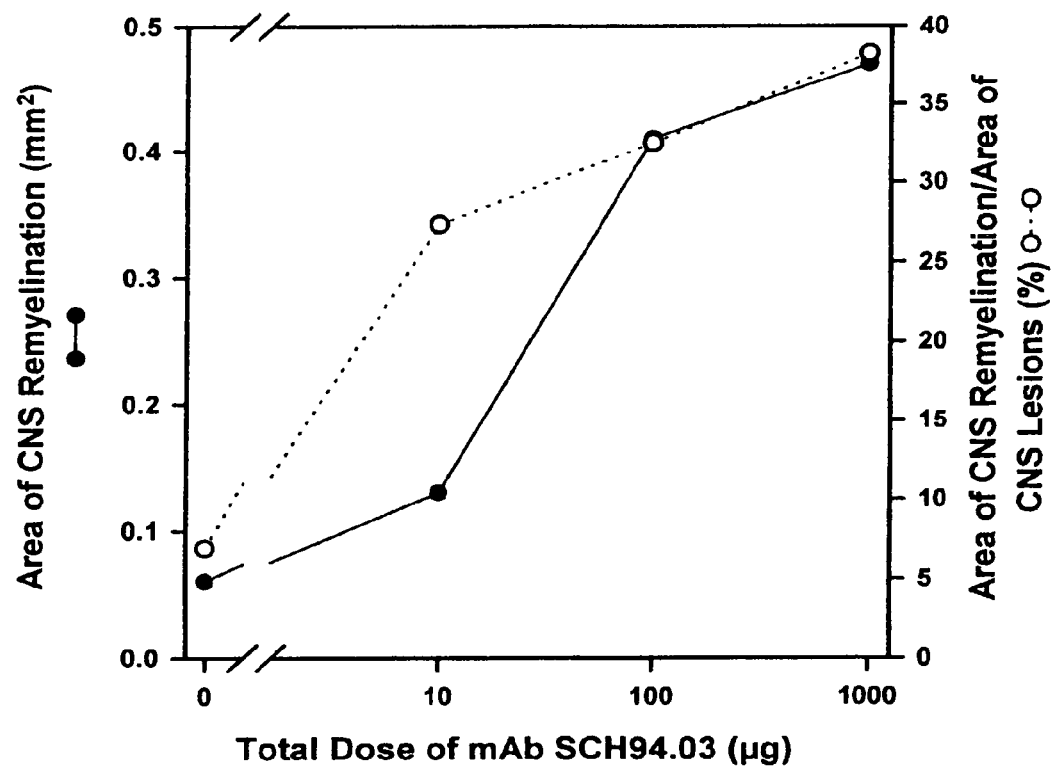
FIG. 5 is a graph depicting the dose-response relationship between treatment with mAb SCH94.03 and CNS remyelination. Area of CNA remyelination (●) and percentage of lesion area with remyelination (○) in animals treated with various doses of mAb SCH94.03.

For the initial treatment experiments, a total mAb dose of 25 mg/kg for intravenous (iv) injections and 250 mg/kg for intraperitoneal (ip) injection was empirically chosen. To assess the dose-response characteristics, and to determine the minimal amount of mAb needed to promote remyelination, chronically-infected mice were treated with various ip doses of SCH94.03. Remyelination was quantitated as described for Table 1. Data are the mean values of 4-5 animals per mAb dose, with the final cumulative dose indicated on the graph. SEM averaged 35% of the mean. There was no statistical difference assessed by one-way ANOVA in the number of demyelinated lesions or the area of demyelination between treatment groups, indicated similar extent of disease in all animals. The number of demyelinated lesions and area of lesions were 33.2±7.5 and 1.25±0.43 for the 1000 µg group, 31.8±8 and 1.11±0.31 for the 100 µg group, 23.8±3.4 and 0.54±0.14 for the 10 µg group, and 20.0±6.5 and 0.74±0 . . . 20 for the buffer only group (represented as the 0 dose point on the graph). Animals treated with 100 µg control IgM (MOPC 104E) had remyelination scores similar to control animals treated with buffer only. The positive correlation between the dose of mAb SCH94.03 and CNS remyelination was especially striking when the severity of CNS disease was taken into account. When CNS repair was expressed as the percentage of lesion area showing remyelination, mice treated with a total dose of 1000, 100, or 10 µg of SCH94.03 had 6-, 5-, and 4-fold more remyelination than control animals, respectively (FIG. 5). Mice given as little as 10 µg of SCH94.03 ip (0.5 mg/kg) showed evidence of enhanced CNS remyelination. These data indicated that mAb SCH94.03 and CNS remyelination had a positive does-response relationship, and that very small quantities of mAb were needed to promote myelin repair.

Antigen Specificity of SCH94.03 and SCH94.32

Figure 6:
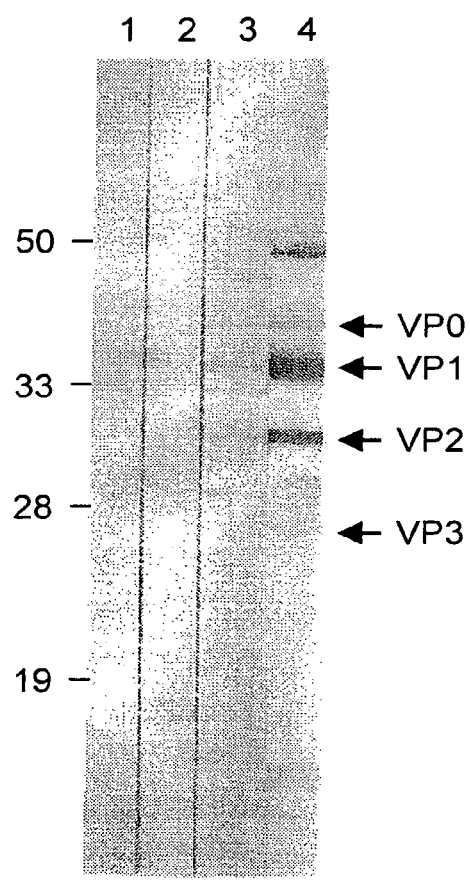
FIG. 6 shows a Western blot of TMEV proteins. Lysates from infected L2 fibroblast cells were separated by SDS-PAGE, transferred to nitrocellulose, and blotted with SCH94.03 (lane 1), SCH93.32 (lane 2), serum from susceptible mice chronically infected with TMEV (lane 3), and polyclonal rabbit anti-TMEV IgG (lane 4). Molecular weights are indicated on the left in kilodaltons (kDa). The position and identification of the major TMEV capsid proteins are indicated on the right.

Although mAbs SCH94.03 and SCH94.32 were generated from splenocytes of uninfected mice, and screened against SCH from uninfected mice, it was directly assessed whether either mAb could react with TMEV capsid proteins or inhibit viral infectivity in vitro. By Western blotting (FIG. 6), SCH94.03 and SCH94.32 did not react with any TMEV proteins recognized by either serum from chronically infected mice or polyclonal IgG from rabbits injected with purified TMEV (Rodriguez, et al., Ann. Neurol., 13:426-433 (1983)). Western blot of lysates from control mock infected L2 cells showed single bands with the serum from chronically infected animals and the polyclonal rabbit anti-TMEV IgG at 32 and 43 kDa, respectively, but no reactivity with SCH94.03 or SCH94.32.

In addition, no significant inhibition of TMEV infectivity in vitro with up to 5 µg/ml of either SCH94.03 or SCH94.32, was observed under assay conditions where 50% neutralization was observed with a 1:34,000 dilution of serum from chronically infected animals. These results indicated that the therapeutic effect of SCH94.03 and SCH94.32 was not due to direct inhibition of the virus.

To initially characterize the antigens recognized by mAbs SCH94.03 and SCH94.32, various cell lines derived from glial (rat C6, mouse G26-20, human U373MG and U87MG), neural (human neuroblastoma), fibroblast (mouse L and 3T3), epithelial (human SCC-9 carcinoma), and lymphocytic (mouse CTLL2) origin were stained. Both mAbs stained internal antigens of all cell lines tested, which indicated that certain antigens recognized by these mAbs were not restricted to unique cell types in vitro. Based on the hypothesis that the therapeutic effect of SCH94.03 and SCH94.32 was due to a CNS-specific interaction, the immunostaining of cultured cells by SCH94.03 and SCH94.32 using the rat glial cell line 5.5B8 was further investigated. This immortalized glial cell line has phenotypic characteristics of both oligodendrocytes and astrocytes, with expression of MBP and 2',3'-cyclic nucleotide 3'-phosphodiesterase (CNP), and low, but detectable, expression of glial fibrillary acidic protein (GFAP) and the lipids or proteins recognized by the mAbs A2B5 and 04 (Bozyczko, et al., Ann. NY Acad. Sci., 605:350-353 (1990)). SCH94.03 and SCH94.32 recognized both a surface and cytoplasmic determinant on 5.5B8 cells. The surface staining was most prominent on small cells which lay on top of a layer of flat, morphologically differentiated cells (FIG. 7A). Surface staining was confirmed by flow cytometry on live cells. When the cell membrane was permeabilized by dehydration or brief treatment with a non-ionic detergent to expose internal antigens, the staining pattern was altered considerably (FIG. 7B). The cytoplasmic staining was filamentous, with a dense perinuclear network that extended out into the cell processes. This pattern closely resembled the staining pattern of the intermediate filament cytoskeletal protein vimentin. These data indicated that SCH94.03 and SCH94.32 recognized antigens that were not restricted to cells derived from the nervous system, but that they did recognize both surface and cytoplasmic determinants on glial cells.

Immunohistochemical staining of frozen mouse, rat, and human tissue confirmed that SCH94.03 and SCH94.32 were not CNS-specific mAbs, but rather showed multi-organ reactivity. Both mAbs immunostained all major organs examined, including the brain, spinal cord, optic nerve, heart, liver, kidney, stomach, and small intestine and skeletal muscle. However, not all cells within an organ stained, suggesting in situ cytological specificity. Within the CNS, SCH94.03 and SCH94.32 stained predominately blood vessels, ependymal cells, and stellate-shaped cells with the morphological features of glial cells, which were enriched in neonatal cerebellar, periventricular, and brain stem white matter (FIG. 7C), and both neonatal and adult optic nerve. Similar glial cells positive for SCH94.03 and SCH94.32 were found in autopsied human brain tissue, especially at the gray-white matter junction (FIG. 7D). Identical immunostaining results were obtained with mAb SCH94.32. Immunostaining with a control IgM (MOPC 104E) was negative for all samples and tissue structures which immunostained with SCH94.03 and SCH94.32.

The identification and characterization of an entire family of autoantibodies, referred to as "natural" or "physiological" autoantibodies, has influenced traditional view of autoimmunity and self-reactivity. The autoantibodies that have been studied extensively are typically IgMs, although other isotypes have been identified, are reactive toward a wide range of self structures or antigens, including cytoskeletal proteins, surface proteins, nucleic acids, phospholipids, bacterial antigens such as lipopolysaccharides, and various chemical haptens (reviewed by Avrameas and Ternynck, Mol. Immunol., 30:1133-1142 (1993)). Natural autoantibodies share extensive idiotypic cross-reactivity or "connectivity", which includes expression of similar idiotypes, some of which are expressed by pathogenic autoantibodies, as well as reactivity toward common idiotypes expressed on other antibodies. Molecular analysis has shown that natural autoantibodies are typically encoded by unmutated germline immunoglobulin (Ig) genes, or substantially homologous thereto, with few or several somatic mutations, and therefore represent a substantial fraction of the Ig repertoire, especially in neonatal animals which have not had extensive exogenous antigen exposure.

The function of natural autoantibodies remains enigmatic. Several hypotheses have been proposed based upon their biochemical and molecular characteristics. These include: (1) clearance of senescent or damage tissue, (2) providing a first line of immunological defense in the lag period between pathogen exposure and an Ag-specific immune response, (3) masking autoantigens from a potentially pathogenic autoimmune response, (4) immunomodulation, including shaping of the neonatal immune repertoire via an idiotypic network, and (5) participation in the positive selection of B cells in the bone marrow, similar to the process proposed for T cells in the thymus.

The hypothesis that antibodies SCH94.03 and SCH94.32 were natural autoantibodies was tested. To characterize the antigen reactivities of SCH94.03 and SCH94.32, several biochemical and molecular assays, including immunohistochemistry and immunocytochemistry, Western blotting, solid-phase enzyme-linked immunosorbant assays (ELISA), and Ig variable region sequencing, were used. As described below, for all biochemical assays, SCH94.03 and SCH94.32 were indistinguishable. In addition, SCH94.03 and SCH94.32 had identical Ig variable region sequences, which confirmed that they were the same mAb. Further details of these characterizing studies are reported in Asakura et al., J. Neuroscience Res. (1996) 43, pp 273-281, which disclosure is incorporated herein by reference.

A potential mechanism whereby SCH94.03 could stimulate remyelination in the central nervous system would be to stimulate the proliferation and/or differentiation of cells involved in myelinogenesis, primarily oligodendrocytes or their immature precursors. Thus, it was tested whether SCH94.03 stained the surface of various cells. Using immortalized cells, it was determined that SCH94.03 stained two glial cells lines, 5.5B8 (FIG. 7A) and 20.2E11, but did not stain the surface of several other glial cells lines (10.IA3, 20.2A40, C6, G26-20), a neuroblastoma cell line (B104), two fibroblast lines (L2, Cos-1), or two myoblastomas (G8, L6). Similar results were obtained with cells isolated from animal tissues and grown in culture. SCH94.03 stained the surface of oligodendrocytes, but not astrocytes, microglia, Schwann cells, myoblasts, or fibroblasts.

The reactivity of SCH94.03 with proteins from glial and lymphoid cell lines, and tissue lysates from brain, liver, and intestine by Western blotting was also assessed. SCH94.03 reacted with multiple bands from all cells and tissues examined, with prominent reactivity towards bands at 50, 95, 120, and >200 kDa. The exact identity of these protein bands has not been determined.

Figure 8:
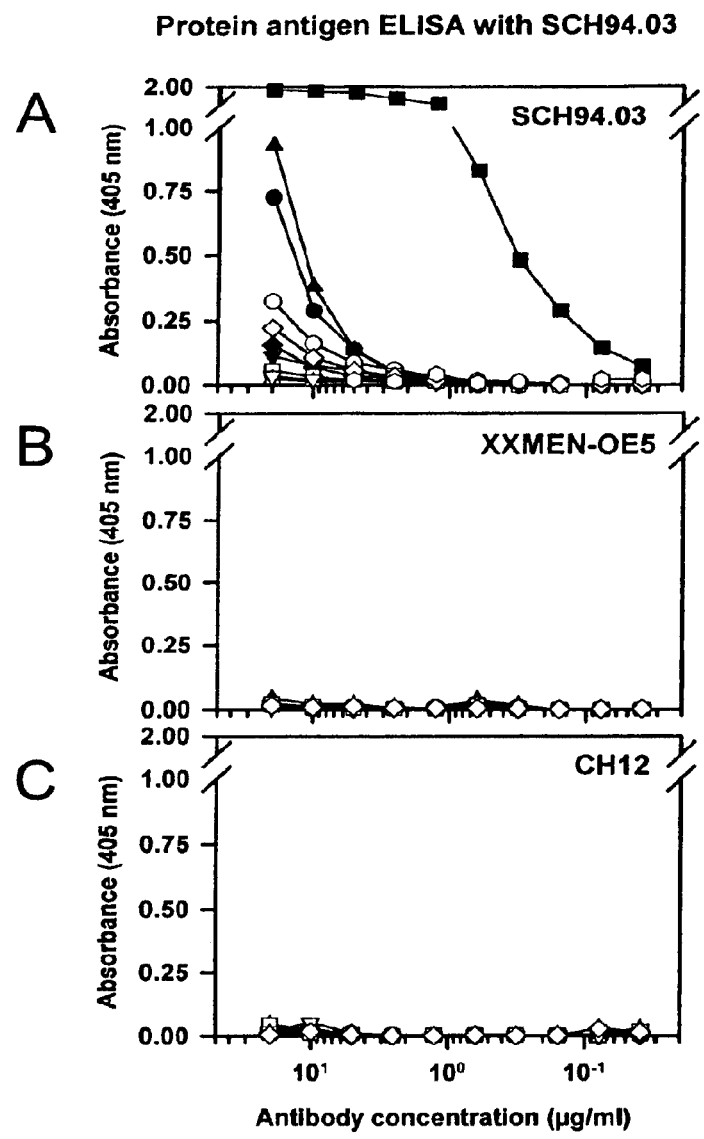
FIGS. 8A-8C shows the results of SCH94.03 (FIG. 8A) and control IgMs (FIGS. 8B and 8C) binding to protein antigens as determined by ELISA.

The activity of SCH94.03 with several purified protein self-antigens by solid-phase ELISA was determined. (FIG. 8A-8C). SCH94.03 showed strong reactivity toward the RBC antigen spectrin, but also showed consistent reactivity toward hemoglobin, actin, tublin, and vimentin, and thyroglobulin, although to a lesser qualitative degree than toward spectrin. No reactivity was observed with myosin, transferrin, albumin, lysozyme, or myelin basic protein under our assay conditions. Six other monoclonal or myeloma IgM controls XXMEN-OE5 (FIG. 8B), A2B5, MOPC104E, TEPC183, 01, and CH12 (FIG. 8C), were also tested, and no reactivity with any of the antigens tested was observed.

Figure 9:
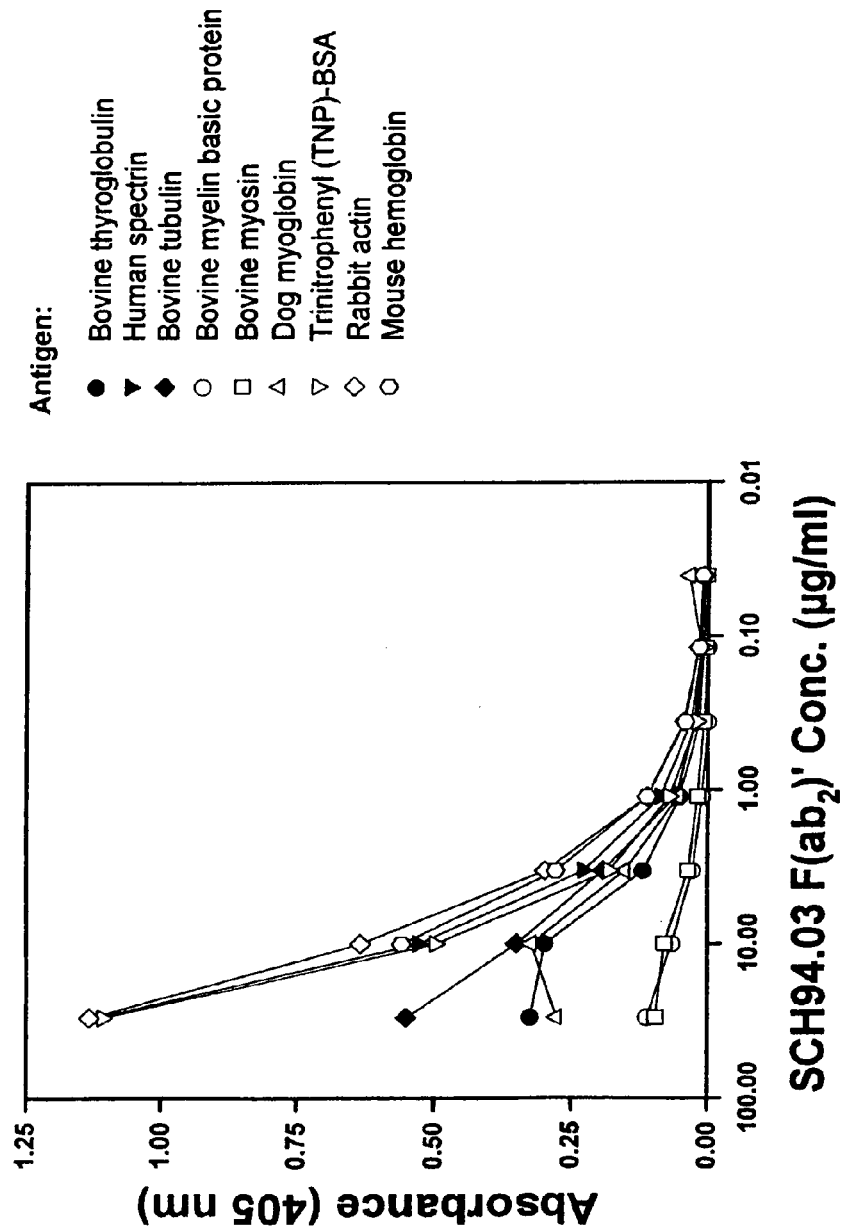
FIG. 9 shows the results of SCH94.03 F(ab2)' binding to protein antigens as determined by ELISA.

To confirm the monoclonality of SCH94.03, 18 subclones of SCH94.03 (9 each from SCH94.03 and SCH94.32 parents) were tested for polyreactivity by solid-phase ELISA. All 18 subclones showed identical reactivity patterns with the panel of protein antigens as the parent SCH94.03. To further support the conclusion that the polyreactivity of SCH94.03 was via its Fab region, we generated F(ab)$_2$' fragments and assessed their reactivity with the protein antigens by ELISA (FIG. 9). SCH94.03 F(ab)$_2$' fragments showed similar polyreactivity as the whole IgM molecule.

Figure 10:
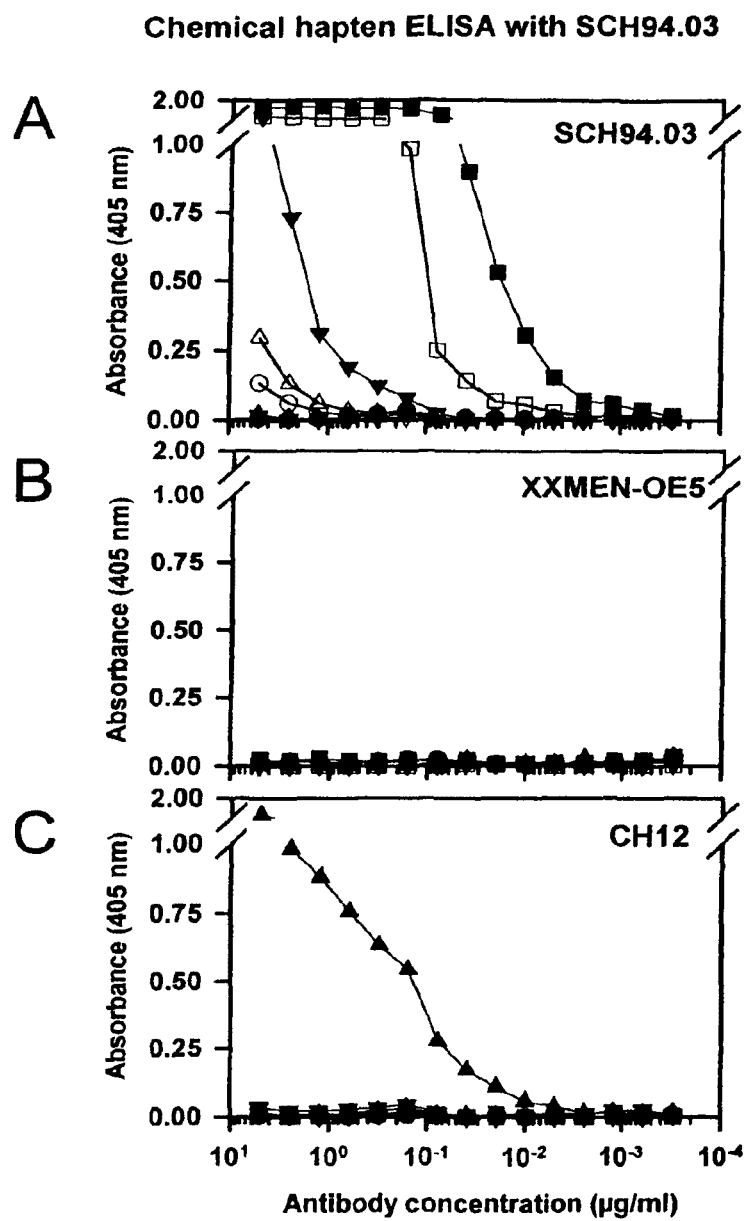
FIG. 10A-10C show the results of SCH94.03 (FIG. 10A) and control IgMs (FIGS. 10B and 10C) binding to chemical haptens as determined by ELISA.

A panel of chemical haptens coupled to bovine serum albumin (BSA) was constructed and used to assess SCH94.03 reactivity by solid-phase ELISA (FIG. 10A-10C). SCH94.03 showed strong reactivity toward fluorescein (FL) and 4-hydroxy-3-nitrophenyl acetic acid (NP), moderate reactivity toward phenyloxazolone (PhOx), and weak reactivity toward 2, 4, 6-trinitrophenyl (TNP) and p-azophenylarsonic acid (Ars). No reactivity with p-azophenyltrimethylammonium (TMA), p-azophenylphosphorylcholine (PC), or the carrier protein BSA was detected. Control IgMs (FIGS. 10B and 10C) showed no significant binding to any of the haptens tested, with the exceptions of CH12 reactivity with TMA, which has been previously reported, and A2B5 reactivity with NP.

Figure 11A:
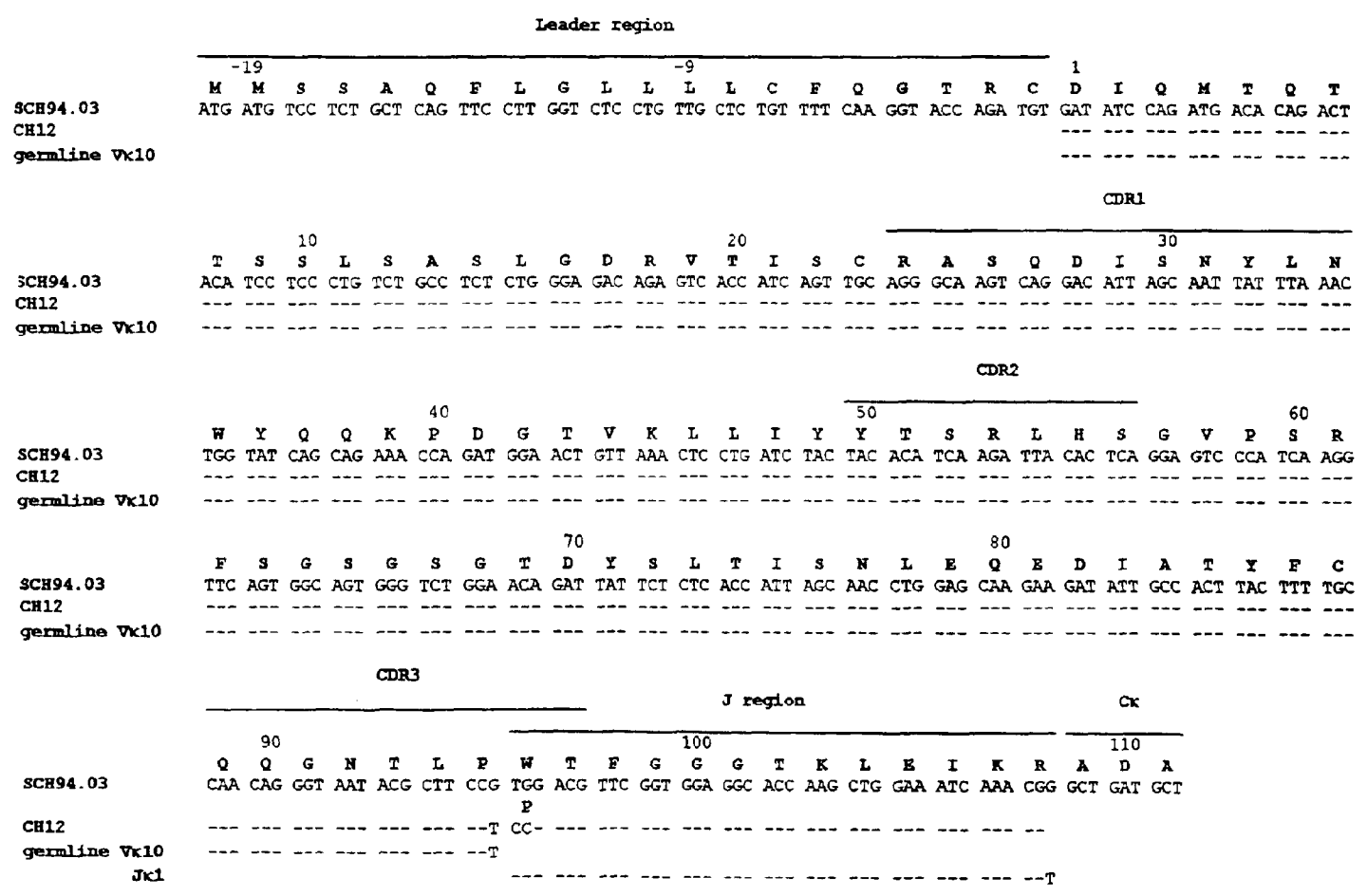
Figure 11B:
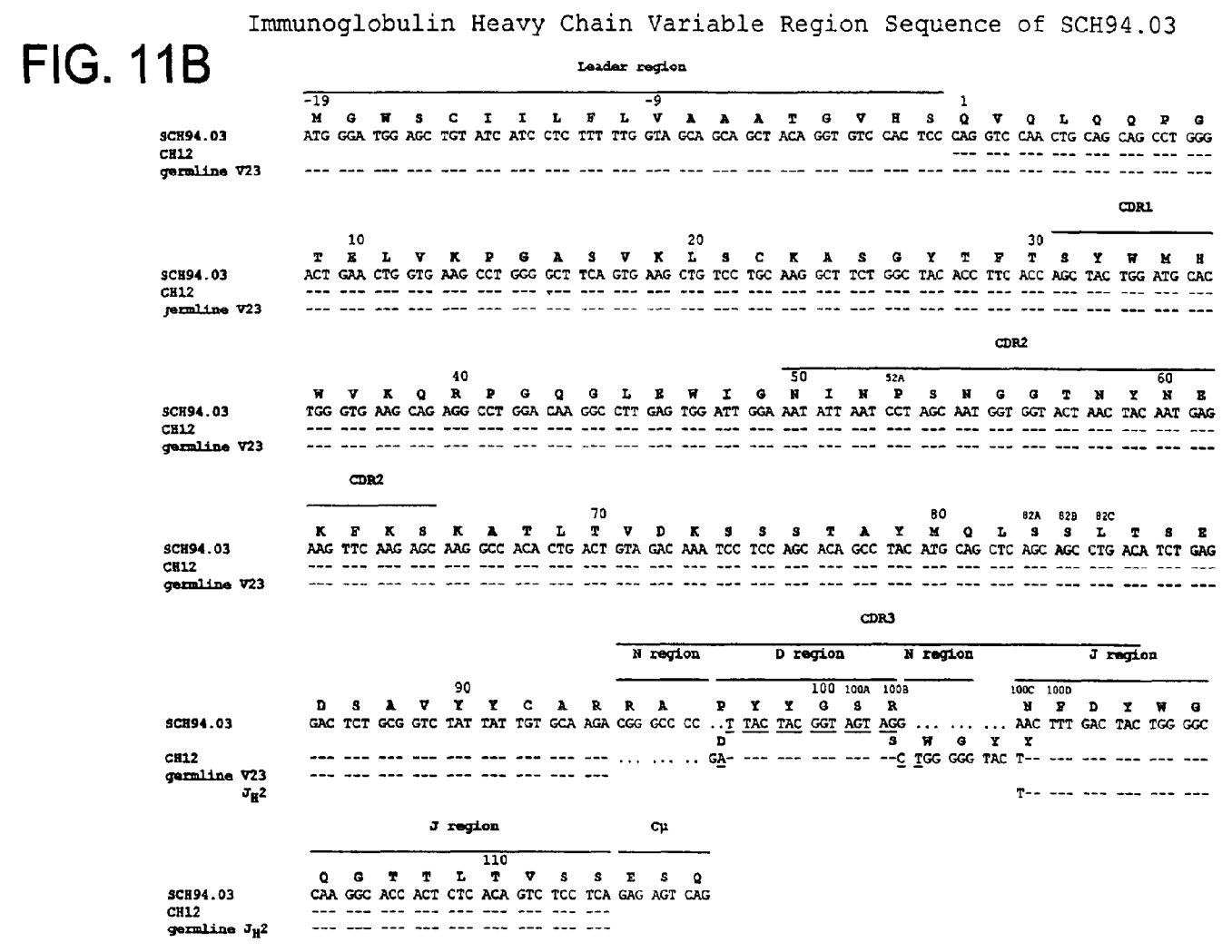

It was further investigated whether the Ig light (L) and heavy (H) chains of SCH94.03 were encoded by germline Ig genes (FIG. 11). The light chain variable ($V_L$) and joining ($J_L$) region nucleotide sequences from SCH94.03 had 99.4% identity with the previously published sequences of the germline Vκ10 and Jκ1 genes, with only two silent changes at the 3' end of both the $V_L$ and $J_L$ regions. The SCH94.03 $V_H$ region nucleotide sequence was identical to the previously published germline $V_H$23 sequence, the $J_H$ region sequence differed from the published germline $J_H$2 sequence by one nucleotide, at the 5' end of the J region, and the diversity (D) region contained 15 contiguous nucleotides derived from the germline DFL16.1 gene. There were 8 nucleotides in the V-D junction, and 1 in the D-J junction, which did not correspond to any known germline V or D region genes, and probably represent noncoded (N) nucleotides inserted by the enzyme terminal deoxynucleotide transferase during V-D-J recombination. The only changes from the germline genes in the heavy chain of SCH94.03 occurred at either the V-D or D-J junction, and therefore could represent either N nucleotides or the result of imprecise joining, rather than somatic mutations. In addition, both the light and heavy chain variable regions of SCH94.03 showed extensive sequence similarity with the IgM produced by the B-cell lymphoma CH12 (FIG. 11).

These antigen reactivity results suggest that SCH94.03 is a natural autoantibody. Although this conclusion does not readily present a mechanism as to how SCH94.03 stimulates remyelination in the central nervous system, it does suggest an important physiological function of natural autoantibodies. Autoantibodies that are produced either during normal physiology, or in response to tissue damage and the subsequent release of previously sequestered antigens, might actively participate to promote repair in the damaged tissue. In line with previously proposed functions of natural autoantibodies, this active participation might be to facilitate removal of damaged tissue, mask autoantigens thereby preventing vigorous pathogenic autoimmune response, modulate the immune response which actually resulted in the tissue destruction, thereby allowing normal endogenous tissue repair to occur, or directly stimulate cells involved in the repair process.

Thus, as a result of the work described herein, it is now demonstrated that an autoantibody generated and screened for its autoantigen-binding capability, also promotes CNS remyelination. Mice chronically infected with TMEV and treated either intravenously (iv) or intraperitoneally (ip) with IgM mAbs from hybridomas SCH94-03 or SCH94.32 had significantly more CNS repair than control animals, measured by a detailed quantitative morphological assessment of CNS remyelination. Moreover, preliminary data suggest that the autoantibody, SCH94.03 is also effective in preventing clinical relapses in mammals afflicted with experimental autoimmune encephalomyelitis (EAE).

Clinical Disease in SJL/J Mice with Established R-EAE after Treatment with SCH94.03.

R-EAE was induced in SJL/J mice through adoptive transfer of MBP peptide (91-103)-specific T cells and treatment was initiated with monoclonal autoantibody SCH94.03, control IgM, or PBS after recovery from the initial episode of clinical disease. Both the initial clinical disease peak and severity were similar between treatment groups (Table 4).

However, treatment with SCH94.03 reduced the percentage of mice with a first clinical relapse by half compared to mice treated with control IgM or PBS, and prolonged relapse onset by 6 days in those mice that did have a clinical relapse. When only mice with severe initial clinical disease (score 3) were analyzed, 10 of 12 mice (83%) treated with control IgM or PBS had a first relapse compared to only 3 of 9 mice (33%) treated with SCH94.03 (P<0.04 using a Fisher exact test), indicating that SCH94.03 was effective regardless of initial disease severity. In addition, 4 mice treated with control IgM or PBSD had a second clinical relapse, whereas no mouse treated with SCH94.03 had more than one relapse, although this difference was not statistically significant because of the few mice with a second relapse prior to sacrifice.

Spinal Cord Pathology in SJL/J Mice with Established R-EAE after Treatment with SCH94.03.

Treatment with SCH94.03 also improved pathological disease in established R-EAE. Consistent with the reduction in clinical disease, treatment with SCH94.03d reduced by 40% both demyelination and meningeal inflammation in the spinal cords of SJL/J mice with R-EAE (Table 5). Demyelinated lesions in mice treated with SCH94.03 were typically smaller in size with fewer inflammatory cells than mice treated with control IgM or PBS. The majority of demyelinated lesions were located in the dorsal columns in mice treated with SCH94.03 (57.0±5.4%; mean±SEM) and control IgM or PBS (51.5±4.8%; P>0.4 using a Student's t test). The remainder of the demyelinated lesions in mice treated with SH94.03 or control IgM or PBS were distributed between posterolateral (12.0±2.9% and 11.0±2.0%, respectively), anterolateral (14.3±3.0% and 20.3±2.5%), and ventral (14.9±17.1±1.6%) columns (P>0.1 for all).

To evaluate the relationship between clinical and pathological disease in R-EAE, we correlated pathology scores (Table 5) with the severity of the initial clinical attack and any subsequent relapse (Table 4) in individual mice. Regression analyses indicated a moderate but statistically significant correlation between relapse severity and both demyelination ©=0.64; P>0.6). These results suggest that in addition to preventing demyelination and meningeal inflammation, the overall clinical benefits of SCH94.03 were secondary to inhibition of disease processes not readily identifiable by standard pathological analysis.

TABLE 4

Clinical Disease in SJL/L Mice With R-EAE After Treatment With SCH94.03 TREATMENT

|  | SCH94.03 | Control* |
|---|---|---|
| Number of Mice | 14 | 19 |
| Initial attack | | |
| Peak (day) | 13 ± 1‡ | 14 ± 1 |
| Maximal clinical severity | 2.8 ± 0.2‡ | 2.8 ± 0.2 |
| First relapse | | |
| No. mice relapsed (%) | 5/14 (35.7)§ | 15/19 (78.9) |
| Onset¶ | 2.4 ± 2** | 18 ± 2 |
| Maximal clinical severity | 2.4 ± 2‡ | 2.1 ± 0.2 |
| Second Relapse | | |
| No. mice relapsed (%) | 0/14(0.0)‡‡ | 4/19 (21.1) |
| Onset¶ | — | 29 ± 2 |
| Maximal clinical severity | — | 2.3 ± 0.4 |

TABLE 4-continued

Clinical Disease in SJL/L Mice With R-EAE After Treatment With SCH94.03 TREATMENT

|  | SCH94.03 | Control* |
|---|---|---|
| Cumulative relapses | 4 | 19 |
| Length of follow-up (days) | 56 ± 1‡ | 58 ± 1 |

SJL/J mice with R-EAE were injected with 50 μg SCH94.03, IgM, or an equivalent volume of PBS twice weekly after spontaneous recovery from the initial episode of clinical disease. Subsequent relapses were assessed and graded for severity. the data are a composite of 4 independent experiments and are presented as the means ± SEM where appropriate.
*Combined data from mice treated with control IgM (n = 10) or PBS (n = 9). No differences were observed with any disease parameter between the two control groups.
‡Not significant (P > 0.05) when compared to control data using a Mann-Whitney rank sum test.
§P < 0.03 when compared to control data using a Fisher exact test.
¶Number of days from the peak of the initial attack.
**P < 0.05 when compared to control data using a Mann-Whitney rank sum test.
‡‡P = 0.12 when compared to control data using a Fisher exact test.

TABLE 5

Pathological Disease in SJL/J Mice with R-EAE After Treatment with SCH 94.03 Pathological Score

| Treatment | n | Demyelination | Meningeal inflammation |
|---|---|---|---|
| SCH94.03 | 14 | 24.6 ± 3.6* | 18.7 ± 3.6* |
| Control‡ | 19 | 39.3 ± 6.0 | 31.8 ± 5.3 |

SJL/J mice with R-EAE were treated as described in the Table 1 legend. The pathological scores were determined by a semi-quantitative morphological analysis and represent the percentage of spinal cord quadrants with the indicated pathological abnormality. One mouse treated with control IgM had minimal gray matter inflammation, whereas all other animals shoed no inflammation in spinal cord gray matter. The data are from 4 independent experimented and are presented as the mean ± SEM where nd indicates the number of mice.
*P < 0.05 when compared to control data.
‡Combined data from mice treated with control IgM or PBS as described in the Table 4 legend.

Thus, it is reasonable to predict that autoantibodies, such as SCH94.03, play a critical role in stopping an immune-mediated process of demyelination in CNS diseases.

Two potential mechanisms can be proposed by which Abs promote remyelination. First, Abs might inhibit some pathogenic component of the disease process, such as virus activity, an immune response which directly suppresses remyelination. If the disease outcome is based upon a balance between tissue destruction and repair, inhibition of pathogenic components would allow a physiological repair response to predominate. Experimental and clinical evidence support this hypothesis. Spontaneous CNS remyelination is seen in MS patients and several experimental models of CNS demyelination as well as described herein, demonstrating spontaneous remyelination in control mice. This indicates that remyelination is a normal physiological response to myelin damage. In addition, treatment of mice chronically infected with TMEV with various immunosuppressive regiments promotes remyelination, but does not decrease demyelination, indicating that there is an immunological component which inhibits remyelination. Immunological function studies reported in Miller et al., *International Immunology*, (1996) 8, pp 131-141, the disclosure of which is incorporated herein by reference, indicate that animals treated with SCH94.03 had similar numbers of B and T (both CD4+ and CD8+) cells in their spleens compared to control animals, had similar in vitro splenocyte proliferative responses to mitogens and antigens, and mounted comparable Ab responses to both T cell-dependent and T cell-independent antigens. See Table 6, below. However, there was a 2 to 3 fold reduction in the number of CD4 and CD8 T cells infiltrating the CNS of mice treated with the mAb 94.03. Treatment with 94.03 also suppresses the humoral immune response to a T cell-dependent antigen in chronically infected mice. Immuhistochemical staining showed that 94.03 labeled MHC Class II positive dendrite cells in peripheral lymphoid organs. These results thus suggest that one of the mechanisms by which Mab SCH94.03 may be promoting remyelination is by inhibiting a pathogenic immune response.

TABLE 6

FCM analysis of mononuclear cells infiltrating the CNS of chronically infected SJL/J mice.

| Treatment | N | Total No. of surface marker positive CNS-infiltrating mononuclear cells (×10$^{-5}$)$^a$ | | | |
|---|---|---|---|---|---|
| | | CD5$^+$ | CD4$^+$ | CD8$^+$ | CD45R(B220)$^+$ |
| PBS | 10 | 6.2 ± 0.8 | 3.0 ± 0.4 | 2.4 ± 0.3 | 0.4 ± 0.1 |
| Control IgM | 12 | 5.0 ± 0.6 | 3.0 ± 0.4 | 1.7 ± 0.2 | 0.2 ± 0.0 |
| SCH94.03 | 12 | 2.3 ± 0.4$^b$ | 1.4 ± 0.2$^c$ | 0.8 ± 0.2$^b$ | 0.1 ± 0.0$^d$ |

SJL/J mice chronically infected with TMEV were injected i.p. with a total dose of 0.5 mg SCH94.03, control IfgM or an equivalent volume PBS, divided into twice weekly doses for 5 weeks. For control IgM, MOPC104E and XXMEN-OE5 were used. The data are a composite of independent experiments and are presented as the mean ± SEM, where N indicates the number of mice.
$^a$Cell numbers were calculated by multiplying the percentage of positive cells assessed by FCM with the total number of mononuclear cells isolated from brain and spinal homogenates of individual mice by Percoll gradient separation.
$^b$P < 0.00001 when compared with combined control IgM and PBS data.
$^c$P < 0.00005 when compared with combined control IgM and PBS data.
$^d$P < 0.007 when compared with combined control IgM and PBS data.

The second hypothesis is that certain Abs can actively stimulate CNS remyelination, perhaps via stimulation of oligodendrocyte proliferation and/or differentiation in vivo, as has been demonstrated in vitro (Diaz, M. et al., Brain Res., 154:231-239 (1978); Raine, C. S., et al., Lab. Invest., 38:397-403 (1979); Lehrer, G. M. et al., Brain Res., 172:557-560 (1979); Bansal, R. et al., J. Neurosci. Res., 21:260-267 (1988); Benjamins. J. A. and Dyer, C. A., Ann. NY Acad. Sci., 605:90-100 (1990); Dyer, C. A., Mol. Neurobiol., 7:1-22 (1993)). MAb SCH94.03 may directly stimulate precursor glial cells which are known to be present at the edges of both human and experimental CNS lesions which show active remyelination. Alternatively, SCH94.03 may work indirectly, via activation of astrocytes or other accessory cells, which could release factors important for the survival or proliferation of cells in the oligodendroglial lineage. The formation of Ab-antigen complexes in situ with tissue components released upon myelin destruction may also participate in Ab-mediated CNS remyelination. Although SCH94.03 is not CNS-specific, the recognition of both surface and cytoplasmic antigens on glial cells by the mAb supports an active mechanism hypothesis. In contrast to the immunomodulatory hypothesis, which would not necessarily require that Abs has direct access to the CNS, the hypothesis that Abs actively stimulate CNS remyelination implies the prerequisite of direct access to the CNS. This is contrary to the view of the selective permeability of the blood-brain barrier, especially toward large molecules such as pentameric IgM. However, during chronic inflammatory conditions such as TMEV infection or MS, peripheral leukocytes migrate into the CNS, indicating an alteration in the blood-brain barrier permeability. Therefore, large proteins such as serum Ig might also enter, via either passive diffusion through "open" endothelium, or perhaps via an unidentified active transport mechanism.

Treatment of Demyelinating Diseases

The results of the experiments described herein have practical applications to multiple sclerosis (MS), EAE, and other related central nervous system demyelinating disorders. Rare examples of spontaneous CNS-type remyelination ("shadow plaques") are found in MS and occasional peripheral nervous system (PNS)-type remyelination is found in demyelinated spinal cord plaques near the root entry zone. Oligodendrocytes are infrequent at the center of the chronic plaques in MS but they appear to proliferate at the periphery of plaques, where they are associated with abortive remyelination. The process of remyelination may correlate with the spontaneous remission and improvements observed clinically in MS. These clinical observations indicate that new myelin formation is possible in MS. The remyelination that has been stimulated in mice with TMEV-induced demyelination by using a mAb holds promise for therapeutic applications in multiple sclerosis.

Of importance clinically is the question of whether morphologic regeneration of thin myelin sheaths contributes to functional recovery. Computer simulations indicate that new myelin formation even by inappropriately thin sheaths improves impulse conduction. Since the axon membrane of normally myelinated fibers is highly differentiated, it is necessary for sodium channels to be present at high density at the node of Ranvier to propagate salutatory conduction. Experimental evidence suggests that newly formed nodes do develop the required high sodium channel density as demonstrated by saxitoxin binding. Data to date suggest that remyelination even by inappropriately thin myelin improves conduction in a previously demyelinated axon. Therefore, any strategy to promote this morphologic phenomenon has the potential of producing functional recovery.

The data presented herein demonstrates, for the first time, that administration of a monoclonal antibody to a mammal is capable of stimulating remyelination of central nervous system axons in vivo. Specifically, treatment of chronically infected TMEV-infected mice with as little as 10 µg of SCH94.03 resulted in a 4- to 5-fold increase in the total area of CNS myelination compared to mice treated with a control mAb.

In addition, the isolation and testing of human autoantibodies, specifically polyclonal IgM antibodies and monoclonal antibodies, as set forth herein and particularly with reference to Examples 5-25 infra. supplements and enhances the advantages and capabilities of the present invention. Importantly, the use of human antibodies avoids the potential for human immune response against the therapeutic antibody. Therapeutic antibodies derived from non-human animals have been shown to generate an immune response, which can be significant and detrimental to the individual. Accordingly, polyclonal human IgM and polyclonal human IgG have been tested in two models of in vivo spinal cord demyelination; a chronic viral infection model, and an acute toxicity model. In both models polyclonal human IgM treated animals had a significantly higher density of newly myelinated axons than animals treated with polyclonal human IgG. A panel of human monoclonal IgM antibodies have also been identified, based on their reactivity with surface antigens specific to the central nervous system. These human antibodies promote significantly more central nervous system remyelination than polyclonal human IgG when given to mammals with demyelinating disease. The human monoclonal antibodies are antigenically polyreactive and recognize determinants on the surface of oligodendrocytes and specific populations of neurons. The light and heavy chain variable regions of several human antibodies that promote remyelination have been sequenced. In particular, these antibodies can induce calcium fluxes in glial cells (oligodendrocytes and astrocytes) in culture, suggestive of direct binding and signaling through glial cells. These human antibodies bind to human white matter and may be effective in promoting remyelination in humans. The benefits of a monoclonal antibody for use as a therapeutic agent are 1) the antibody can be grown free of possible host infection and, 2) the antibody can be genetically altered in vitro to change its effectiveness.

Thus, as a result of the experiments described herein, the method of the present invention can be used to treat mammals, including humans and domestic animals, afflicted with demyelinating disorders, and to stimulate remyelination and regeneration of the CNS axons, as well as to offer neuroprotection. As described herein, an effective amount of the monoclonal antibody or a peptide fragment, hapten, or equivalent, can be administered by conventional routes of administration, and particularly by, intravenous (iv) or intraperitoneal (ip) injection. As described herein, therapeutic compositions and vaccines are contemplated and may be prepared and administered. An effective amount of the antibody can vary depending on the size of the mammal being treated, the severity of the disease, the route of administration, and the course of treatment. For example, each dose of antibody administered can range from approximately 0.5 mg/kg to approximately 400 mg/kg, with the preferred range from approximately 0.5 mg/kg to approximately 250 mg/kg. It is important to note that a dose of mAb as low as 10 µs (0.5 mg/kg) was effective in promoting remyelination of CNS axons in mice. The dose of antibody will also depend on the route of administration. For example, an iv dose administered to mice was 0.5 mg/kg, and an ip dose was 5.0 mg/kg. The course of treatment includes the frequency of administration of the antibody (e.g., daily, weekly, or bi-weekly) and the duration of the treatment (e.g., four weeks to four months). Thus, for example, a larger amount of mAb can be given daily for four to five weeks, as opposed to a smaller amount of mAb given for four months.

The effectiveness of the amount of the monoclonal antibody being administered can be assessed using any number of clinical criteria, for example, as described in the Examples herein, including overall appearance of the mammal, the activity of the mammal and the extent of paralysis of the mammal. The effectiveness of the amount of monoclonal antibody necessary to induce remyelination in humans can also be assessed in a double blinded controlled trial. Patients with fixed neurological deficits from demyelinating disease can be treated with monoclonal antibody or controls. Improvement in isometric muscle strength as detected by quantitative biomechanics muscle testing could be used as the primary therapeutic end-po int.

Additionally, the monoclonal antibody may be genetically altered, e.g. "humanized" by the substitution of human antibody nucleotide sequences in non-variable regions of the murine mAb to reduce immunogenicity.

In addition to in vivo methods of promoting remyelination, ex vivo methods of stimulating remyelination in CNS axons are also encompassed by the present invention. For example, the monoclonal antibody may be used in vitro to stimulate the proliferation and/or differentiation of glial cells, such as oligodendrocytes, as described e.g. in Example 2 and Example 17. These exogenous glial cells can then be introduced into the CNS of mammals using known techniques. Remyelination of CNS axons would be increased by increasing the number of endogenous glial cells present (glial cells, such as oligodendrocytes play a critical role in the production of myelin).

In vitro methods of producing glial cells, or stimulating the proliferation of glial cells from mixed culture (e.g., rat optic nerve cell, or rat brain cell cultures) are also encompassed by this invention. For example, cells obtained from rat optic nerve, or rat brain, containing glial cells, are cultured as a mixed culture under conditions sufficient to promote growth of the cells. An effective amount of mAb capable of promoting remyelination of CNS axons, such as SCH94.03, sHIgM22 or sHIgM46, or a combination thereof, is then added to the mixed culture of cells and maintained under conditions sufficient for growth and proliferation of cells. The mAb stimulates the proliferation of glial cells cultured in the presence of the mAb is increased, relative to the proliferation of glial cells grown in the absence of the mAb.

As stated above, the antibodies for use in the methods of the present invention can be, and are preferably, administered as medicaments, i.e., pharmaceutical compositions. An effective amount of the polyclonal IgM antibody can thus be combined with, or diluted with, an appropriate pharmaceutically acceptable carrier, diluent or vehicle, such as a physiological buffer or saline solution. An effective amount of the monoclonal antibody can thus be combined with, or diluted with, an appropriate pharmaceutically acceptable carrier, diluent or vehicle, such as a physiological buffer, or saline solution. An effective amount of a combination of one or more monoclonal antibody may be similarly combined with or diluted with an appropriate pharmaceutically acceptable carrier, diluent or vehicle. In the instance where a vaccine is to be prepared, the monoclonal antibody or equivalent active of the invention may be prepared with a pharmaceutically effective and suitable carrier or adjuvant, and the protocol for administration may proceed in accordance with standard procedures for immunization known to the skilled practitioner.

The pharmaceutical compositions used in the methods of this invention for administration to animals and humans comprise the polyclonal IgM antibodies or monoclonal antibodies in combination with a pharmaceutical carrier or excipient. In a preferred embodiment, the pharmaceutical composition may contain more than one, preferably two, monoclonal autoantibodies of the present invention. Thus, pharmaceutical compositions comprising, for example, an effective amount in combination of sHIgM22 and sHIgM46 are contemplated herein. Such compositions are advantageous in that the presence of more than one monoclonal autoantibody will potentiate the activity of others in the same therapeutic composition or method.

The medicament can be in the form of tablets (including lozenges and granules), dragees, capsules, pills, ampoules or suppositories comprising the compound of the invention.

Advantageously, the compositions are formulated as dosage units, each unit being adapted to supply a fixed dose of active ingredients. Tablets, coated tablets, capsules, ampoules and suppositories are examples of preferred dosage forms according to the invention. It is only necessary that the active ingredient constitute an effective amount, i.e., such that a suitable effective dosage will be consistent with the dosage form employed in single or multiple unit doses. The exact individual dosages, as well as daily dosages, will, of course, be determined according to standard medical principles under the direction of a physician or veterinarian.

The monoclonal antibodies can also be administered as suspensions, solutions and emulsions of the active compound in aqueous or non-aqueous diluents, syrups, granulates or powders.

Diluents that can be used in pharmaceutical compositions (e.g., granulates) containing the active compound adapted to be formed into tablets, dragees, capsules and pills include the following: (a) fillers and extenders, e.g., starch, sugars, mannitol and silicic acid; (b) binding agents, e.g., carboxymethyl cellulose and other cellulose derivatives, alginates, gelatine and polyvinyl pyrrolidone; (c) moisturizing agents, e.g., glycerol; (d) disintegrating agents, e.g., agar-agar, calcium carbonate and sodium bicarbonate; (e) agents for retarding dissolution, e.g., paraffin; (f) resorption accelerators, e.g., quaternary ammonium compounds; (g) surface active agents, e.g., cetyl alcohol, glycerol monostearate; (g) adsorptive carriers, e.g., kaolin and bentonite; (i) lubricants, e.g., talc, calcium and magnesium stearate and solid polyethylene glycols.

The tablets, dragees, capsules and pills comprising the active compound can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, from polymeric substances or waxes.

The diluents to be used in pharmaceutical compositions adapted to be formed into suppositories can, for example, be the usual water-soluble diluents, such as polyethylene glycols and fats (e.g., cocoa oil and high esters, [e.g., $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200, except in the presence of a surface-active agent), such as solvents, dissolving agents and emulsifiers. Specific non-limiting examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example, ground nut oil, glycerol, tetrahydrofurfuryl alcohol, polyethylene glycols and fatty acid esters of sorbitol or mixtures thereof For parental administration, solutions and suspensions should be sterile, e.g., water or arachis oil contained in ampoules and, if appropriate, blood-isotonic.

The pharmaceutical compositions which are suspensions can contain the usual diluents, such as liquid diluents, e.g., water, ethyl alcohol, propylene glycol, surface active agents (e.g., ethoxylated isostearyl alcohols, polyoxyethylene sorbitols and sorbitan esters), microcrystalline cellulose, aluminum methahydroxide, bentonite, agar-agar and tragacanth, or mixtures thereof The pharmaceutical compositions can also contain coloring agents and preservatives, as well as perfumes and flavoring additions (e.g., peppermint oil and eucalyptus oil), and sweetening agents, (e.g., saccharin and aspartame).

The pharmaceutical compositions will generally contain from 0.5 to 90% of the active ingredient by weight of the total composition.

In addition to the monoclonal antibodies, the pharmaceutical compositions and medicaments can also contain other pharmaceutically active compounds, e.g. steroids, anti-inflammatory agents or the like.

Any diluent in the medicaments of the present invention may be any of those mentioned above in relation to the pharmaceutical compositions. Such medicaments may include solvents of molecular weight less than 200 as the sole diluent.

It is envisaged that the polyclonal IgM antibodies and monoclonal antibodies will be administered perorally, parenterally (for example, intramuscularly, intraperitoneally, subcutaneously, transdermally or intravenously), rectally or locally, preferably orally or parenterally, especially perlingually, or intravenously.

The administered dosage rate will be a function of the nature and body weight of the human or animal subject to be treated, the individual reaction of this subject to the treatment, type of formulation in which the active ingredient is administered, the mode in which the administration is carried out and the point in the progress of the disease or interval at which it is to be administered. Thus, it may in some case suffice to use less than a minimum dosage rate, while other cases an upper limit must be exceeded to achieve the desired results. Where larger amounts are administered, it may be advisable to divide these into several individual administrations over the course of the day.

According to the invention, the component or components of a therapeutic composition of the invention may be introduced parenterally, intrathecally, transmucosally, e.g., orally, nasally, pulmonarally, or rectally, or transdermally. Preferably, administration is parenteral, e.g., via intravenous injection, and also including, but is not limited to, intra-arterial, intramuscular, intradermal, subcutaneous, intraperitoneal, intraventricular, and intracranial administration. Oral or pulmonary delivery may be preferred to activate mucosal immunity; since the bacteria responsible for the conditions under treatment generally colonize the nasopharyngeal and pulmonary mucosa, mucosal administration may be particularly effective as a treatment. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

In another embodiment, the active compound can be delivered in a vesicle, in particular a liposome (see Langer, Science 249:1527-1533 (1990); Treat et al., in *Liposomes in the Therapy of Infectious Disease and Cancer*, Lopez-Berestein and Fidler (eds.), Liss, New York, pp. 353-365 (1989); Lopez-Berestein, ibid., pp. 317-327; see generally ibid).

In yet another embodiment, the therapeutic compound can be delivered in a controlled release system. For example, the polypeptide may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, J. Macromol. Sci. Rev. Macromol. Chem. 23:61 (1983); see also Levy et al., Science 228: 190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)). Preferably, a controlled release device is introduced into a subject in proximity of the site of inappropriate immune activation or a tumor. Other controlled release systems are discussed in the review by Langer (Science 249: 1527-1533 (1990)).

A subject in whom administration of an active component as set forth above is an effective therapeutic regimen for a condition or pathology associated with the central nervous system, including in certain instances, bacterial infection is preferably a human, but can be any animal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., i.e., for veterinary medical use.

In the therapeutic methods and compositions of the invention, a therapeutically effective dosage of the active component is provided. A therapeutically effective dosage can be determined by the ordinary skilled medical worker based on patient characteristics (age, weight, sex, condition, complications, other diseases, etc.), as is well known in the art. Furthermore, as further routine studies are conducted, more specific information will emerge regarding appropriate dosage levels for treatment of various conditions in various patients, and the ordinary skilled worker, considering the therapeutic context, age and general health of the recipient, is able to ascertain proper dosing. Generally, for intravenous injection or infusion, dosage may be lower than for intraperitoneal, intramuscular, or other route of administration. The dosing schedule may vary, depending on the circulation half-life, and the formulation used. The compositions are administered in a manner compatible with the dosage formulation in the therapeutically effective amount. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

Administration with other compounds. For treatment of a demyelinating condition, for instance multiple sclerosis, one may administer the present active component in conjunction with one or more pharmaceutical compositions used for treating multiple sclerosis, including but not limited to (1) anti-inflammatory agents, such as steroids; (2) Betaseron; (3) Copaxone; or 94) polyclonal IgM. Administration may be simultaneous (for example, administration of a mixture of the present active component and an antibiotic), or may be in seriatim.

Accordingly, in specific embodiment, the therapeutic compositions may further include an effective amount of the active component, and one or more of the following active ingredients: an antibiotic, a steroid, etc.

Also contemplated herein is pulmonary delivery of the present neuromodulatory agent or agents, which may be associated with an anti-inflanunatory. Reports of preparation of proteins for pulmonary delivery are found in the art [Adjei et al. *Pharmaceutical Research*, 7:565-569 (1990); Adjei et al., *International Journal of Pharmaceutics*, 63:135-144 (1990) (leuprolide acetate); Braquet et al., *Journal of Cardiovascular Pharmacology*, 13(suppl. 5):143-146 (1989) (endothelin-1); Hubbard et al., *Annals of Internal Medicine*, Vol. III, pp. 206-212 (1989) ($\alpha$1-antitrypsin); Smith et al., *J. Clin. Invest.* 84:1145-1146 (1989) ($\alpha$-1-proteinase); Oswein et al., "Aerosolization of Proteins", *Proceedings of Symposium on Respiratory Drug Delivery II*, Keystone, Colo., March, (1990) (recombinant human growth hormone); Debs et al., *J. Immunol.* 140:3482-3488 (1988) (interferon-$\gamma$ and tumor necrosis factor alpha); Platz et al., U.S. Pat. No. 5,284,656 (granulocyte colony stimulating factor)]. A method and composition for pulmonary delivery of drugs is described in U.S. Pat. No. 5,451,569, issued Sep. 19, 1995 to Wong et al.

All such devices require the use of formulations suitable for the dispensing of adhesin inhibitory agent (or derivative). Typically, each formulation is specific to the type of device employed and may involve the use of an appropriate propellant material, in addition to the usual diluents, adjuvant and/or carriers useful in therapy. Also, the use of liposomes, microcapsules or microspheres, inclusion complexes, or other types of carriers is contemplated. Chemically modified adhesin inhibitory agent may also be prepared in different formulations depending on the type of chemical modification or the type of device employed.

Formulations suitable for use with a nebulizer, either jet or ultrasonic, will typically comprise neuromodulatory agent (or derivative) dissolved in water at a concentration of about 0.1 to 25 mg of biologically active agent per ml of solution. The formulation may also include a buffer and a simple sugar (e.g., for neuromodulatory agent stabilization and regulation of osmotic pressure). The nebulizer formulation may also contain a surfactant, to reduce or prevent surface induced aggregation of the neuromodulatory agent caused by atomization of the solution in forming the aerosol. Formulations for use with a metered-dose inhaler device will generally comprise a finely divided powder containing the neuromodulatory agent (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

The liquid aerosol formulations contain neuromodulatory agent and a dispersing agent in a physiologically acceptable diluent. The dry powder aerosol formulations of the present invention consist of a finely divided solid form of neuromodulatory agent and a dispersing agent. With either the liquid or dry powder aerosol formulation, the formulation must be aerosolized. That is, it must be broken down into liquid or solid particles in order to ensure that the aerosolized dose actually reaches the mucous membranes of the nasal passages or the lung. The term "aerosol particle" is used herein to describe the liquid or solid particle suitable for nasal or pulmonary administration, i.e., that will reach the mucous membranes. Other considerations, such as construction of the delivery device, additional components in the formulation, and particle characteristics are important. These aspects of pulmonary administration of a drug are well known in the art, and manipulation of formulations, aerosolization means and construction of a delivery device require at most routine experimentation by one of ordinary skill in the art. In a particular embodiment, the mass median dynamic diameter will be 5 micrometers or less in order to ensure that the drug particles reach the lung alveoli [Wearley, L. L., *Crit. Rev. in Ther. Drug Carrier Systems* 8:333 (1991)].

The neuromodulatory agents of the invention may also be prepared for administration in the form of vaccines, which may comprise as the active, the herein recited autoantibodies, peptide analogs, or haptens, or possibly combinations thereof. Thus, the preparation of vaccines may proceed in accordance with known procedures, and monovalent as well as polyvalent vaccines are contemplated. Also, DNA sub unit vaccines, based upon the DNA molecules of the invention, may be prepared. All vaccines may be administered in accordance with standard practices of the physician or clinician, and such parameters are considered to be within the scope of the present invention.

Vectors containing e.g. a DNA-based vaccine in accordance with the invention can be introduced into the desired host by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963-967; Wu and Wu, 1988, J. Biol. Chem. 263:14621-14624; Hartmut et al., Canadian Patent Application No. 2,012,311, filed Mar. 15, 1990).

The vaccine can be administered via any parenteral route, including but not limited to intramuscular, intraperitoneal, intravenous, and the like. Preferably, since the desired result of vaccination is to elucidate an immune response to the antigen, and thereby to the pathogenic organism, administration directly, or by targeting or choice of a viral vector, indirectly, to lymphoid tissues, e.g., lymph nodes or spleen, is desirable. Since immune cells are continually replicating, they are ideal target for retroviral vector-based nucleic acid vaccines, since retroviruses require replicating cells.

Passive immunity can be conferred to an animal subject suspected of suffering an autoimmune-mediated demyelinating disease, e.g. multiple sclerosis, by administering antiserum, polyclonal antibodies, or a neutralizing monoclonal antibody to the patient. Preferably, the antibodies administered for passive immune therapy are autologous antibodies. For example, if the subject is a human, preferably the antibodies are of human origin or have been "humanized," in order to minimize the possibility of an immune response against the antibodies. The active or passive vaccines of the invention, or the administration of an adhesin, can be used to protect an animal subject from infection of a Gram positive bacteria, preferably streptococcus, and more preferably, pneumococcus.

Further, the present invention contemplates treatment by gene therapy, where the appropriate neuromodulatory agent is correspondingly introduced to target cells for treatment, to cause or increase expression of the corresponding agent. Thus, in one embodiment, the DNA or a gene encoding the neuromodulatory agent, autoantibody, antibody peptide, etc., or a protein or polypeptide domain fragment thereof is introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both.

Viral vectors commonly used for in vivo or ex vivo targeting and therapy procedures are DNA-based vectors and retroviral vectors. Methods for constructing and using viral vectors are known in the art [see, e.g., Miller and Rosman, BioTechniques 7:980-990 (1992)].

DNA viral vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, adipose tissue can be specifically targeted. Examples of particular vectors include, but are not limited to, a defective herpes virus 1 (HSV1) vector [Kaplitt et al., Molec. Cell. Neurosci. 2:320-330 (1991)], defective herpes virus vector lacking a glycoprotein L gene [Patent Publication RD 371005 A], or other defective herpes virus vectors [International Patent Publication No. WO 94/21807, published Sep. 29, 1994; International Patent Publication No. WO 92/05263, published Apr. 2, 1994]; an attenuated adenovirus vector, such as the vector described by Stratford-Perricaudet et al. [J. Clin. Invest. 90:626-630 (1992); see also La Salle et al., Science 259:988-990 (1993)]; and a defective adeno-associated virus vector [Samulski et al., J. Virol. 61:3096-3101 (1987); Samulski et al., J. Virol. 63:3822-3828 (1989); Lebkowski et al., Mol. Cell. Biol. 8:3988-3996 (1988)].

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors [see, e.g., Wilson, Nature Medicine (1995)]. In addition, it is advantageous to employ a viral vector that is engineered to express a minimal number of antigens.

In another embodiment the DNA or gene can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980,289; Markowitz et al., 1988, J. Virol. 62:1120; Temin et al., U.S. Pat. No. 5,124,263; International Patent Publication No. WO 95/07358, published Mar. 16, 1995, by Dougherty et al.; and Kuo et al., 1993, Blood 82:845. Retroviral vectors can be constructed to function as infections particles or to undergo a single round of transfection. In the former case, the virus is modified to retain all of its genes except for those responsible for oncogenic transformation properties, and to express the heterologous gene. Non-infectious viral vectors are prepared to destroy the viral packaging signal, but retain the structural genes required to package the co-introduced virus engineered to contain the heterologous gene and the packaging signals. Thus, the viral particles that are produced are not capable of producing additional virus.

Targeted gene delivery is described in International Patent Publication WO 95/28494, published October 1995.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Feigner, et. al., Proc. Natl. Acad. Sci. U.S.A. 84:7413-7417 (1987); see Mackey, et al., Proc. Natl. Acad. Sci. U.S.A. 85:8027-8031 (1988); Ulmer et al., Science 259:1745-1748 (1993)]. The use of cationic lipids may promote encapsulation of negatively charged nucleic acids, and also promote fusion with negatively charged cell membranes [Feigner and Ringold, Science 337:387-388 (1989)]. The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreas, liver, kidney, and the brain. Lipids may be chemically coupled to other molecules for the purpose of targeting [see Mackey, et. al., supra]. Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., *J. Biol. Chem.* 267:963-967 (1992); Wu and Wu, *J. Biol. Chem.* 263:14621-14624 (1988); Hartmut et al., Canadian Patent Application No. 2,012,311, filed Mar. 15, 1990; Williams et al., *Proc. Natl. Acad. Sci. USA* 88:2726-2730 (1991)]. Receptor-mediated DNA delivery approaches can also be used [Curiel et al., *Hum. Gene Ther.* 3:147-154 (1992); Wu and Wu, *J. Biol. Chem.* 262: 4429-4432 (1987)].

In a preferred embodiment of the present invention, a gene therapy vector as described above employs a transcription control sequence that comprises the DNA consensus sequence recognized by e.g. an autoantibody of the invention, i.e., an antibody binding site, operably associated with a therapeutic heterologous gene inserted in the vector. That is, a specific expression vector of the invention can be used in gene therapy.

The present invention will be better understood from a consideration of the following non-limiting examples, which describe the preparation of materials, compounds and compositions and the development and practice of methods illustrative of the present invention. It will be apparent to those skilled in the art that many modifications, both of materials and methods, may be practiced without departing from the purpose and intent of this disclosure. The following examples are presented in order to more fully illustrate the preferred embodiments of the invention and serve also in fulfillment of applicants' duty to present the best mode known for the practice of the invention, and should in no way be construed as limiting the broad scope thereof.

EXAMPLES

Example 1

Monoclonal Antibody Production, Screening and Purification Animals

Spleens of two SJL/J mice (Jackson Laboratories, Bar Harbor, Me.) that had been injected twice with spinal cord homogenate (SCH) in incomplete Freund's adjuvant were used as the source of B cells for fusion and hybridoma production. Splenocytes were fused with NS-1 myeloma cells using polyethylene glycol, and viable cell fusions were selected with hypoxanthine-aminopterin-thymidine (HAT) media and cloned by limiting dilution as described (Katzmann, J. A. et al., Proc. Nat. Acad. Sci. USA, 78:162-166 (1981)).

ELISAs

Hybridoma supernatants from viable Ig-producing clones were screened for binding to SCH by an enzyme-linked immunosorbant assay (ELISA). The following antigens were used for screening mAbs: SCH—(10 µg) reconstituted in carbonate-bicarbonate buffer (pH 8.53), MBP—(1 µg) dissolved in PBS, GC (1 µg) dissolved in absolute alcohol, PLP (1 µg) dissolved in water. PLP was provided by Dr. W. Macklin (UCLS) who has published a solid phase immunoassay for PLP. For SCH, MBP or GC ELISA, Immuno II plates were coated with prepared antigen (100 µl/well) which was incubated overnight at 4° C. The following day well were washed in PBS and blocked with PBS+1% serum for 1 hour at room temperature. Plates were washed again in PBS and serial dilutions of primary Ab diluted in PBS/0.1% BSA were added and incubated at room temperature for 2 hours. Plates were washed in PBS/0.05% Tween and appropriate secondary Ab conjugated to alkaline phosphatase (1:1000 in PBS 0.1% BSA) was added. Plates were incubated at 37° C. for 2 hours, washed in PBS 0.05% Tween, and the substrate (Sigma 104 Phosphatase Substrate Tablet in 5 ml diethanolamine buffer) was added for 30 min. The reaction was terminated with 50 µl of 1 N NaOH. The plates were read on a Dynatech ELISA plate reader.

Ascites Production

The hybridomas chosen for treatment experiments were injected into pristane-treated BALB/c mice for ascites production. Hybridomas were also grown in RPM1-1640 media supplemented with 10% fetal bovine serum for IgM production. IgM mAbs were purified by either ammonium sulfate precipitation and gel filtration on a Sephacryl S-400 HR (Sigma) column for the initial transfer experiments, or by affinity chromatography using goat anti-mouse IgM (µ-chain specific; Jackson Immunoresearch, West Grove, Pa.) coupled to Reacti-Gel 6× matrix (Pierce, Rockford, Ill.) for later transfer experiments.

Example 2

In Vitro Testing of Monoclonal Antibodies

Selection of mAbs that Promote Glial Cell Proliferation

The ability of the mAbs to promote proliferation of glial cells in vitro was tested. Glial cells isolated from rat brain or optic nerves were seeded in Falcon Microtest II plates at a concentration of $2 \times 10_4$ cells per well in 0.1 ml of DME. Whole serum (SCH, IFA, MBP, GC, MBP/GC, PBS or PLP), purified Ig or mAb, was serially diluted and 0.1 ml aliquot was added to cells and assayed in triplicate. Three days later $^3$H-thymidine was added (1 µCi/ml) and cells were harvested after 17 hours with an automated cell harvester (Mash II Harvester). To document identity of cells proliferating (i.e., astrocytes, progenitor glial cells, macrophages), selected cultures after exposure to $^3$H-thymidine, were incubated with appropriate Ab specific for cell type followed by ABC immunoperoxidase technique. After reaction of Hanker-Yates reagent, the slides were immersed in Ilford K2 nuclear emulsions, exposed for 4 days at 4° C. and developed.

mAb 94.03 and 94.32 Induce Proliferation of Mixed Rat Optic Nerve Brain Cultures One- to two-day-old rats were killed with ether. Through careful dissection, optic nerves were removed from the optic nerve chiasm to the eye. Nerves were transferred to centrifuge tubes containing 2 mls of DMEM. An equal volume of 0.25% trypsin was added and incubated to 37° C. in a water bath for 45 min. 0.2 ml of FCS was added to terminate trypsinization. Nerves were passed through a sterile needle and syringe (gauge no. 21) and then centrifuged at 1400 rpm for 10 minutes. The cell count was adjusted to provide concentration of $5 \times 10^5$ cells/100 µl of media in 24-well trays in DMEM+ 0.5% FCS. After 12 to 16 hours, appropriate antibodies or growth media were added as per experimental protocols.

Brains of 1-2 day old rats were removed and placed in Hank's Balanced Salt Solution with 10 mM HEPES buffer (HBSS/H), approximately 1-2 ml per brain. The brain stem, cerebellum, nd midbrain was discarded whereas the forebrain was minced with a bent syringe. The tissue was further disrupted by repeated passage through a 10 ml pipet and transferred to a 50 ml conical tube. The tissue suspension was shaken on a rotary shaker (75 rpm) for 30 min at 37° C. Trypsin was added to a final concentration of 0.125% and the suspension was shaken for an additional 60 minutes. Trypsin digestion was stopped by adding FCS (10%). The cell suspension was passed sequentially through 120 and 54 μm Nytex, centrifuged, resuspended in serum-free medium with 10% FCS, and filtered again through 54 μm Nytex. Serum-free media was DMEM with 3.7 g/l sodium bicarbonate, 6.0 g/l glucose, 2 mM L-glutamine, 0.1 nM nonessential amino acids, 5 μg/ml insulin, 5 μg/ml streptomycin. The cells were counted, plated onto uncoated tissue culture flasks or plates at $5 \times 10_4$ cells/$cm_2$ and cultured at 37° C. in 5% $CO_2$. The media was changed after 72 hours, and every 48 hours thereafter. On day 8 after culture initiation, the media was aspirated and replaced by SFM with various supplements (for example, antibody). For most experiments, the cells were grown for an additional 48 hours before harvesting. Cells were pulsed with [$^3$H]thymidine (5 μCi/ml) for the final 1824 hours of culture.

Western Blot Procedure

Antigens were denatured and solubilized by heating at 100° C. in sodium dodecyl sulfate (SDS) sample buffer. Samples were electrophoresed on stacking and separating gels containing 4.75% and 12.0% acrylamide at 200 volts. After electrophoresis, gels and nitrocellulose membranes were equilibrated for 30 minutes in transfer buffer (25 mM Tris, 192 mM glycine, 20% methanol, pH 8.1-8.3). All steps were done at room temperature. Gels were electroblotted for either 1 hour at 100V or overnight at 30V using the Bio-Rad Mini Trans-blot apparatus. The nitrocellulose membrane was cut into strips and washed, 3×TBS (100 mM NaCl, 50 nil Trig, pH 7.6) with 0.03% Tween 20. Nitrocellulose strips were blocked (TBS with 3% non-fat milk and 0.03% Tween 20) for 2-4 hours, washed 3×, and incubated with primary Ab or antisera (diluted in blocking buffer) for 4 hours or overnight. After primary Ab incubation, strips were washed 3×, incubated with either biotin- or alkaline phosphate-labeled secondary Ab (diluted in blocking buffer) for 2 hours, washed 3×, and incubated with alkaline-phosphatase labeled-streptavidin (diluted in blocking buffer) for 2 hours if the biotin system is used. Nitrocellulose strips were washed 4× (final wash in TBS without Tween 20) and incubated with substrate solution (0.165 mg/ml BCIP and 0.33 mg/ml NBT in 100 mM sodium chloride, 100 mM Tris, 5 mM MgGl2, pH 9.5) until sufficient color developed (approximately 10-15 min). The reaction was stopped by adding PBS with 5 mM EDTA.

Cell lines or mixed brain cultures were lysed in 1×SDS reducing sample buffer (2.3% SDS, 10% 2-ME, 0.125 M Tris, 20% glycerol) and heated to 85° C. for 15 minutes. Nucleic acids were sheared by repeated passage of lysate through 21-27-gauge needles. Lysate proteins were separated on a 12% acrylamide reducing gel, transferred to nitrocellulose membranes, and blotted with various antibodies as previously described.

Example 3

Promotion of CNS Remyelination Using a Monoclonal Antibody

Virus

The DA strain of TMEV was obtained from Drs. J. Lehrich and B. Arnason after eight passages in BHK cells. The virus was passaged an additional four times at a multiplicity of infection of 0.1 plaque forming units (PFU) per cell. Cell-associated virus was released by Freeze-thawing the cultures followed by sonication. The lysate was clarified by centrifugation and stored in aliquots at −70° C. All subsequent experiments will use passage 12 virus. This virus isolate causes white matter pathology without destruction of anterior horn cells.

In Vitro TMEV Neutralization Assay

Viral plaque assays were done as previously described (Patick, A. K., et al., J. Neuropath. Exp. Neurol., 50:523-537 (1991)). To assess neutralization, aliquots of TMEV (200 PFU/ml) were incubated with various concentrations of Ab for 1 hour t room temperature prior to plating onto confluent L2 cells. As a positive control, serum from susceptible mice chronically infected with TMEV was used. Under the assay conditions described above, a serum dilution of 1:34,000 gave 50% neutralization, which corresponded to an estimated 20 ng/ml of TMEV-specific Abs, assuming a total serum Ig concentration of 15 mg/ml, and a TMEV-specific fraction of 5%.

Demyelination Protocol

Demyelination was induced in female SJL/J mice, ages four to six weeks, from the Jackson Laboratory, Bar Harbor, Me. Mice were inoculated intracerebrally with $2 \times 10^5$ plaque-forming units of DA virus in a volume of 10 l. Mice infected chronically with TMEV (4 to 6 months following infection) were assigned randomly to groups of treatment.

Treatment Protocol and Clinical Disease Assessment

Chronically infected mice were given either intraperitoneal (ip) or intravenous (iv) injections of mAb twice weekly for 4-5 weeks. At each treatment injection, mice were assessed clinically by three criteria: appearance, activity, and paralysis. A score for each criterion was given ranging from 0 (no disease) to 3 (severe disease). For appearance, 1 indicated minimal change in coat, 2 indicated a severe change (incontinence and stained coat). For activity, 1 indicated decreased spontaneous movements (minimal ataxia), 2 indicated moderate slowing (minimal spontaneous movements), and 3 indicated severe slowing (no spontaneous movement). For paralysis, 0.5 indicated a spastic extremity, 1 indicated a paralyzed extremity, 1.5 indicated two or more spastic extremities, 2 indicated two paralyzed extremities (unable to walk), 2.5 indicated no righting response, and 3 indicated three or four paralyzed extremities (moribund). The total score for each mouse was the cumulative total from each criterion (maximum of 9). As the clinical score was an ordinal, but not a cardinal scale, the change in clinical score to assess clinical disease was used. The clinical assessment data were not disclosed until after the morphological assessment of remyelination was completed.

Light and Electron Micrograph Preparation and Assessment of Remyelination

Preparation of light and electron microscopy sections and morphological assessment of remyelination were done. Briefly, treated mice were anesthetized with pentobarbital (0.2 mg ip), exsanguinated by cardiac puncture, and filled by intracardiac perfusing with Trump's fixative (100 mM phosphate buffer, pH 7.2, with 4% formaldehyde and 1.5% glutaraldehyde). The entire spinal cord was removed carefully from the spinal canal, and sectioned into 1 mm transverse blocks. Every third block was post-fixed in 1% osmium tetroxide and embedded in Araldite (Polysciences, Warrington, Pa.). One micron sections from each block were cut and stained with p-phenylenediamine. On each section, remyelination was quantitated using a Zeiss interactive digital analysis system (ZIDAS) and camera lucida attached to a Zeiss photomicroscope (Carl Zeiss Inc., Thornwood, N.Y.). Abnormally thin myelin sheaths relative to axonal diameter was used as the criterion for CNS remyelination. Ten spinal cord sections from each mouse were examined; this corresponded to 8-9 $mm^2$ of white matter examined per mouse. To avoid bias, slides were coded and quantitation was done without knowledge of the treatment groups.

Myelin Thickness and Axonal Diameter Measurements and Quantitation of Myelination Axons Electron micrographs of normal and remyelinated axons from plastic-embedded spinal cord sections were imaged with a Hamamatsu video camera, digitized, and analyzed using an IBAS 2000 Image Analysis System (Kontron, Munich, Germany). The Axonal cross-sectional area with and without the myelin sheath was measured, and equivalent circle calculations were used to determine the axonal diameter and myelin sheath thickness. For myelinated axon quantitation, the number of myelinated axons in lesions from plastic-embedded spinal cord sections were counted using the analysis system described above attached to an Axiophot microscope (Carl Zeiss, Inc.). 17 remyelinated and 15 demyelinated lesions in spinal cord sections from animals treated with mAb SCH94.03, control IgM, or buffer only were analyzed. This corresponded to 0.6 $mm^2$ of remyelinated area and 0.8 $mm^2$ of demyelinated area. The criterion for selection of a lesion as demyelinated was the presence of substantial demyelination with minimal repair, whereas remyelinated lesions were chosen based upon the presence of almost complete remyelination throughout the lesion.

Immunostaining

Rat 5.5B8 glial cells were grown on poly-D/L-lysine-coated chamber slides in Dulbecco's modified Eagle's medium (DMED) supplemented with 1.5 g/L D-glucose, 30 nM $SeO_2$, 15 nM triiodothyronine, 10 ng/ml biotin, 100 μM $ZnCl_2$ 50 μg/ml gentamicin, and 10% fetal bovine serum. All staining steps were done at room temperature. For surface staining, slides were briefly rinsed with PBS, and cells were lightly fixed with 1% formaldehyde in PBS for 10 minutes to prevent cell detachment during subsequent staining steps. For cytoplasmic staining, slides were rinsed twice in PBS and either air dried for 1 hour or incubated with 0.1% Triton X-100 in PBS for 10 minutes. Cells were blocked in 2% BSA for 30 min, washed, incubated with control IgM or mAb SCH94.03 (10 μg/ml in 1% BSA) for 1 hour, and washed extensively with PBS. After fixation with 4% paraformaldehyde for 15 min, slides were incubated with fluorescein-labeled goat anti-mouse IgM (Jackson Immunoresearch) for 1 hour, washed with PBS, coverslipped with 10% MOWIOL® (Hoechst) in 100 mM Tris, 25% glycerol, pH 8.5 with 25 μg/ml 1,4-diazobicyclo-[2.2.2]-octane (DABCO) to prevent fading, and allowed to set overnight in the dark. For frozen tissue sections, fresh neonatal rat, adult mouse, or autopsied human cortical brain tissue was quick frozen in isopentane chilled in liquid nitrogen prior to liquid nitrogen storage. Frozen sections (10 μm) were transferred onto gelatinized glass microscope slides, air dried for 4-8 hours, and stored at −70° C. Prior to immunostaining, slides were placed at room temperature overnight. The immunoperoxidase staining protocol was similar that described above, using the ABC immunoperoxidase reagent (Vector Laboratories, Burlingame, Calif.), developed with 1.5 mg/ml Hanker-Yates reagent (p-phenylene diamine-procatechol) in 50 mM Tris, pH 7.6 with 0.034% H202, counterstained with Mayer's hematoxylin, and mounted with Permount (Fischer Scientific, Pittsburgh, Pa.).

Data Analysis

A modified cumulative rank sum test (O'Brien, P. C., Biometrics, 40:1079-1087 (1984)) was used to compare remyelination between treatment groups. This statistical test takes into account several numerically unrelated parameters of therapeutic effectiveness, and is used routinely for clinical trial efficacy assessment. Parallel analyses using a standard unpaired Student's t-test to compare individual parameters of remyelination gave equivalent results. Comparisons of disease severity and correlation significance were determined by a one-way analysis of variance (ANOVA). Statistical analyses were done with either the SigmaStat (Jandel Scientific, San Rafael, Calif.) or EXCEL (Microsoft Corporation, Redmond, Wash.) software programs. Calculated values were considered significant when p was <0.05.

Example 4

1. Hybridoma Culture and Determination of Ig Isotype

A2B5, HNK-1, and XXMEN-OE5 (anti-bacterial lipopolysaccharide) hybridomas were purchased from American Type Culture Collection (Rockville, Md.). O1 and O4 hybridomas were the gift of Dr. S. E. Pfeiffer (University of Connecticut, Farmington, Conn.). Hybridomas were cultured in RPMI 1640 containing 10% fetal calf serum (HyClone, Logan, Utah) and $2 \times 10^{-2}$ mM β-mercaptoethanol. IgM concentrations of the supernatants were determined by a β-chain-specific capture ELISA With purified MOPC104E (Sigma, St. Louis, Mo.) as the standard. To determine the IgM isotype of mAbs O1, O4, and A2B5, Mouse Monoclonal Antibody Isotyping Kit (Gibco, Grand Island, N.Y.) was used.

2. mRNA Isolation and Cloning of Ig Variable Region

Poly(A) RNA was isolated from hybridoma cells by oligo (Dt)-cellulose chromatography using the Micro-Fast Track kit (Invitrogen, San Diego, Calif.). Ig heavy and light chain variable region cDNAs were cloned by the 5'-rapid amplification of cDNA ends (RACE) method using the 5'-AmpliFINDER™ RACE kit (Clontech, Palo Alto, Calif.). Briefly, first strand cDNA was synthesized using an oligo Dt primer. An anchor oligonucleotide was ligated to the 3' end of the first strand cDNA, and variable region cDNAs were amplified by polymerase chain reaction using primers corresponding to the anchor sequence and constant region-specific primers for the μ (Cμ) or $_x$ ($C_x$) chains described previously [Miller et al., J. Immunol., 154 (1995), 2460-2469].

3. Sequencing and Analysis

Amplified cDNA products were purified from agarose gel after electrophoresis and directly subcloned into pCRII using the TA cloning kit (Invitrogen). Both strands of the insert were sequenced using automated DNA sequencer (Applied Biosystems model 373A, Mayo Molecular Biology Core Facility). For nucleotide sequence homology searches, the FastA program (GCG program, version 8) was used [Devereux, J. et al., Nucleic Acids Res., 12 (1984), 387-395].

4. Direct ELISA to Determine Polyreactivity

HNK-1 was shown previously to be polyreactive by Western blots [McGarry et al., supra]. Therefore, the polyreactivity of O1, O4 and A2B5 was tested by direct ELISA. Human RBC spectrin, bovine myosin (heavy chain), mouse albumin, mouse hemoglobin, mouse transferrin, hen egg lysozyme, rabbit actin, rabbit myelin basic protein, and keyhole limpet hemocyanin (KLH) were purchased from Sigma. Proteins were tested for purity by SDS-polyacrylamide gel electrophoresis. The chemical hapten trinitrophenyl (TNP) was coupled to bovine serum albumin (BSA) [Miller et al., 1995, supra]. Protein antigens were used at 5 μg/ml, and hapten was used at 2 μM. The proteins and hapten-BSA antigens were coated onto polystyrene or polyvinylchloride microtiter plates in 0.1 M carbonate buffer, pH 9.5, for 18 hours at 4° C. Coated plates were blocked with PBS containing 5% nonfat dry mild and 0.05% Tween 20 for 2 hours at room temperature, and incubated with mAbs diluted in blocking buffer (2 μg/ml) for 4 hours at room temperature. TEPC183 (Sigma) and XXMEN-0E5 IgM mAbs were used as control antibodies. Bound IgM was detected with biotinylated goat anti-mouse IgM (μ chain specific; Jackson Immunoresearch, West Grove, Pa.) followed by alkaline phosphatase conjugated to streptavidin, with p-n itrophenylphosphate as the chromogenic substrate. Absorbance was determined at 405 nm.

Results

Nucleotide sequences of variable region cDNA including leader peptide were compared with published sequences of germline genes, mouse myeloma and natural autoantibodies.

1. Heavy Chain Variable Region cDNA Sequences

Figure 12:
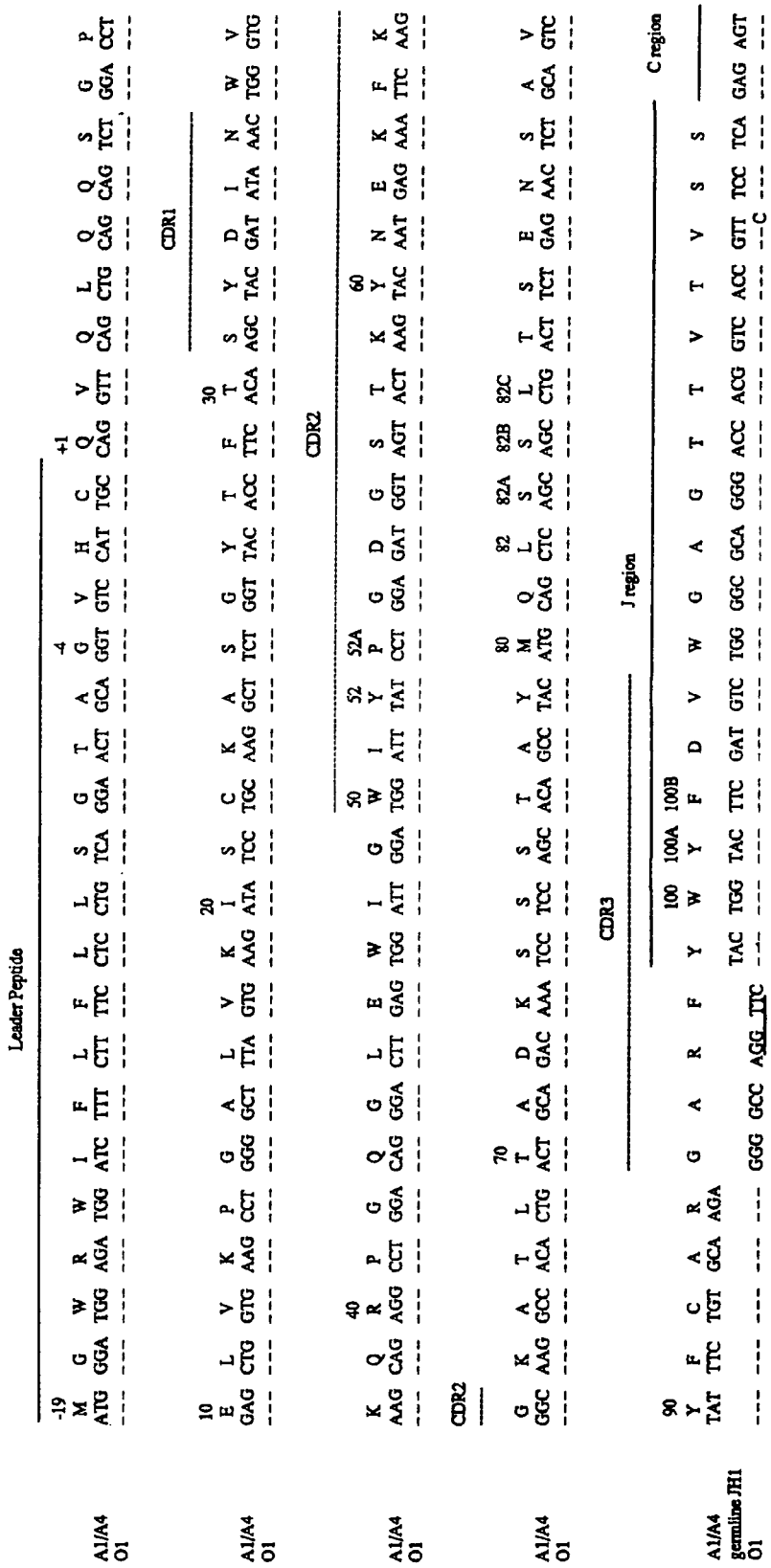
FIG. 12 shows the nucleotide and deduced amino acid sequences of $V_H$, D and $J_H$ regions encoding O1, compared with the unrearranged $V_H$ segment transcript A1 and A4, and the JH germline gene (SEQ. ID NO: 1, 67). Dashed lines indicate identity with unrearranged $V_H$ segment transcript A1 and A4. Underline indicates identity with germline AP2 gene family (DSP2.3, 2.4, 2.6). Amino acids are represented by the single-letter code. CDR represents the complementarity determining region. This sequence has been assigned the GenBank TM/EMBL Data Bank Accession number L41877.

O1 $V_H$ was identical with unrearranged $V_H$ segment transcripts A1 and A4 [Yancopoulos et al. Cell, 40 (1985), 271-281], which belong to $V_H558$ family (FIG. 12). The O1 D segment was relatively short and contained four nucleotides derived from germline SP2 gene family (common sequence to DSP2.3, 2.4 and 2.6) [Kurosawa et al., J. Exp. Med., 155 (1982), 201-218]. The D segment for O1 was dG and dC rich in the 5' end, probably representing non-coded (N) nucleotides inserted by terminal deoxynucleotide transferase (TdT) during V-D-J recombination. O1 displayed sequence identity with germline $J_H1$ [Sakano et al., Nature, 286 (1980), 676-683], except for one nucleotide (GTC for GTT in the germline), which did not result in an amino acid substitution.

Figure 13:
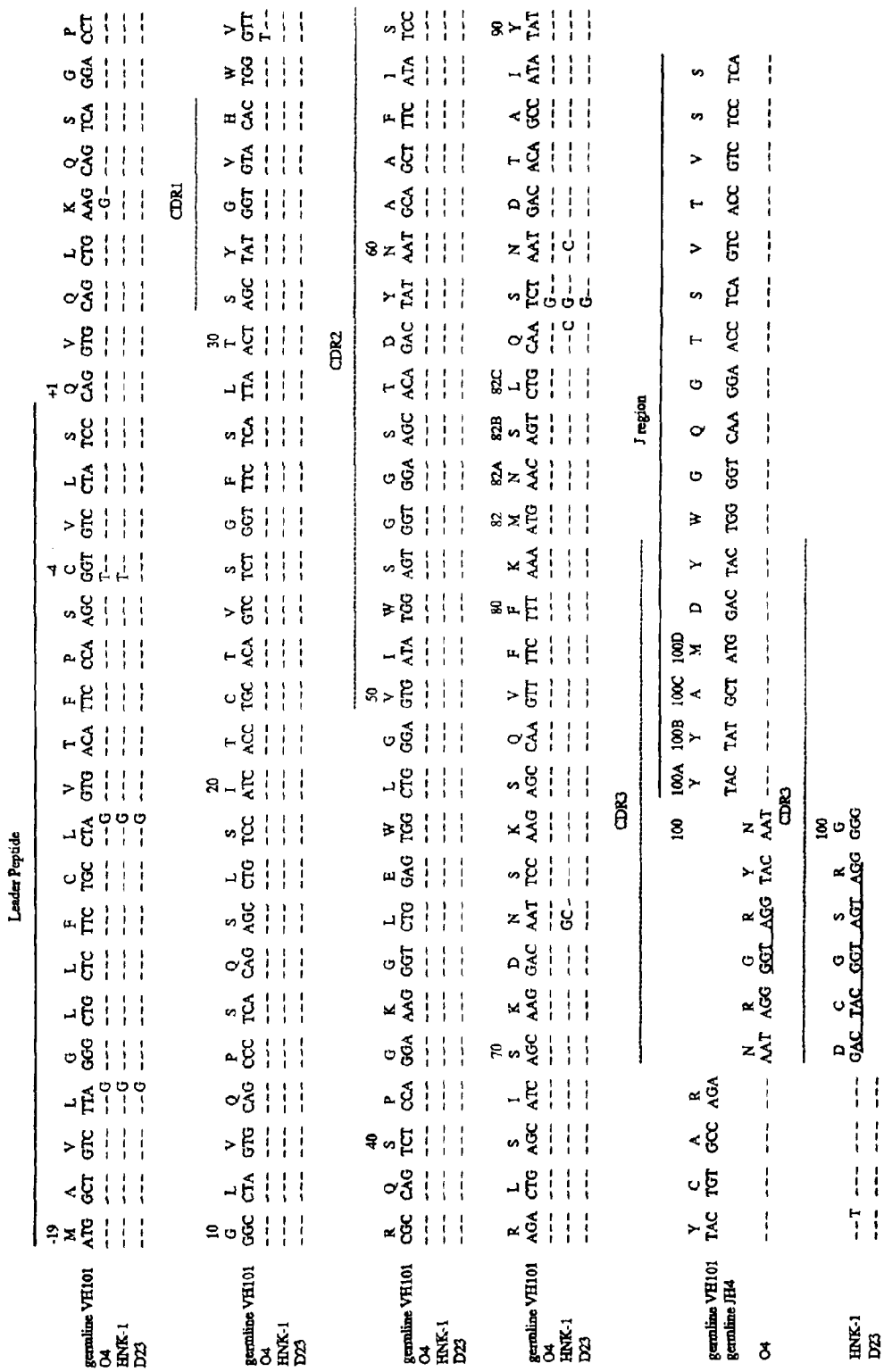
FIG. 13 shows the nucleotide and deduced amino acid sequences of $V_H$, D and $J_H$ regions encoding O4 and HNK-1 (SEQ. ID NO: 2, 68), compared with those reported for germline gene $V_H101$ and JH, and for natural autoantibody D23. Dashed lines indicate identity with $V_H101$ and $J_H4$. Underline indicates identity with germline DFL16.1. Amino acids are represented by the single-letter code. CDR represents the complementarity determining region. These sequences have been assigned the GenBank TM/EMBL Data Bank Accession Numbers L41878 (O4) and L41876 (HNK-a).

Compared with the germline BALB/c $V_H101$ [Kataoka et al., J. Biol. Chem., 257 (1982), 277-285], O4 $V_H$ showed three nucleotide differences in the $V_H$ coding region (FIG. 13), all of which resulted in amino acid substitutions. Compared to natural autoantibody D23 [Baccala et al., Proc. Natl. Acad. Sci. USA, 86 (1989), 4624-4628], which is encoded by germline $V_H101$, O4, $V_H$ showed two nucleotide differences with amino acid substitutions in the $V_H$ coding region. Compared with germline $V_H101$, HNK-1 $V_H$ showed six nucleotide differences and four amino acid differences in the $V_H$ coding region (FIG. 13). Compared to natural autoantibody D23, HNK-1 $V_H$ showed five nucleotide differences and three amino acid differences in the $V_H$ coding region. D23 had three nucleotide differences when compared with germline $V_H101$; all differences were also seen in the O4 and FINK-1 $V_H$. The O4 D segment contained five nucleotides and the HNK-1 D segment contained 13 nucleotides derived from germline DFL16.1 gene [Kurosawa et al., J. Exp. Med., 155 (1982), 201-218]. The HNK-1 D segment had one dG residue in the 5' end and four dG residues in the 3' end, which probably represent N nucleotides inserted by TdT during V-D-J recombination. The heavy chain joining region of O4 corresponded to germline $J_H4$ [Sakano et al., supra]. The heavy chain joining region of FINK-1 corresponded to germline $J_H4$ beginning with the fifth codon.

Figure 14:
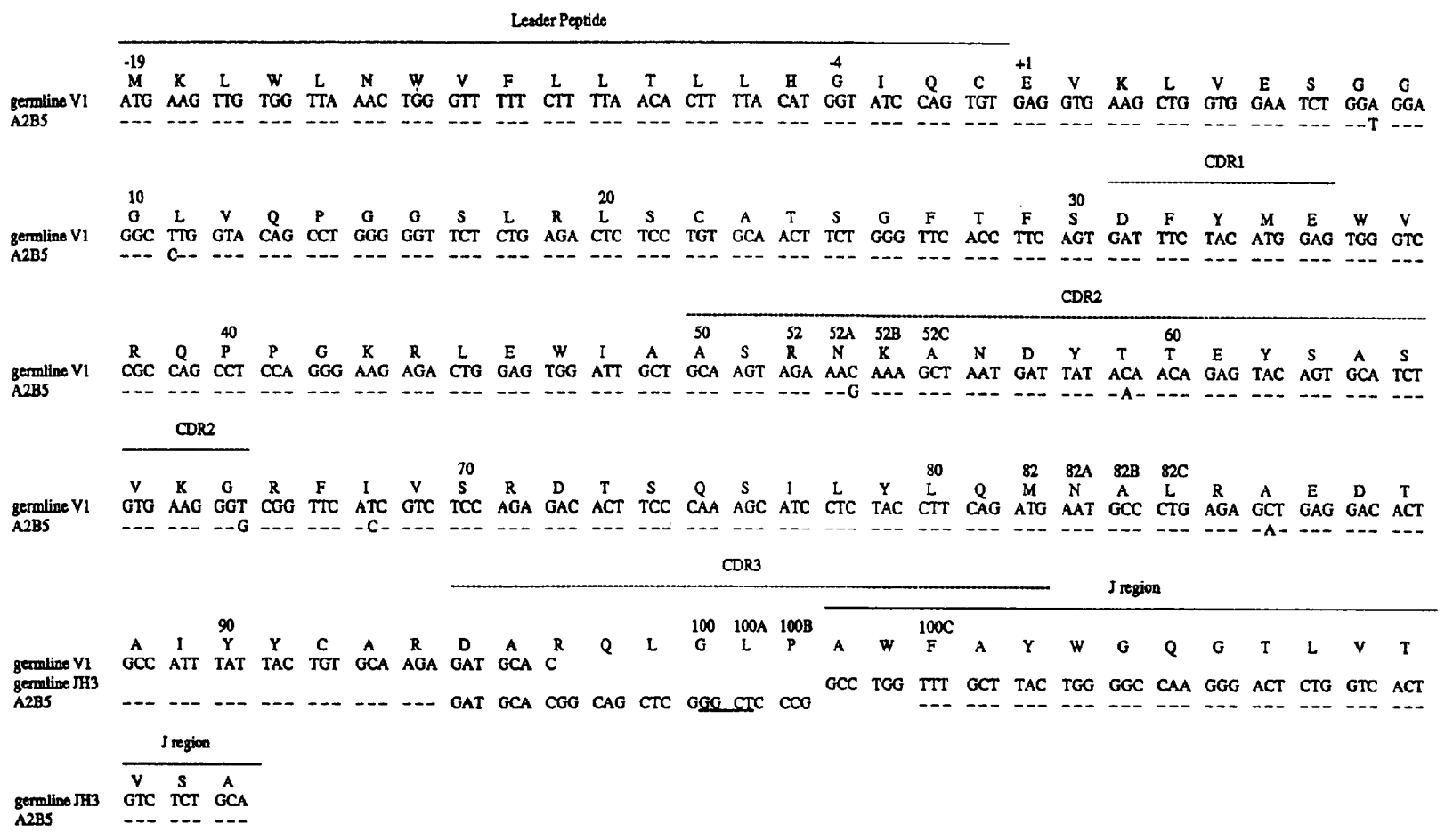

The A2B5 $V_H$ showed seven nucleotide and four amino acid differences in its coding region in comparison with the germline V1 (also called T15 and S107) [Crews et al., Cell, 25 (1981), 59-66; Siu et al., J. Immunol., 138 (1987), 4466-4471] (FIG. 14). The heavy chain joining region of A1B5 corresponded to germline beginning with the third codon [Sakano et al., supra].

2. Light Chain Variable Region cDNA Sequences

Figure 15:
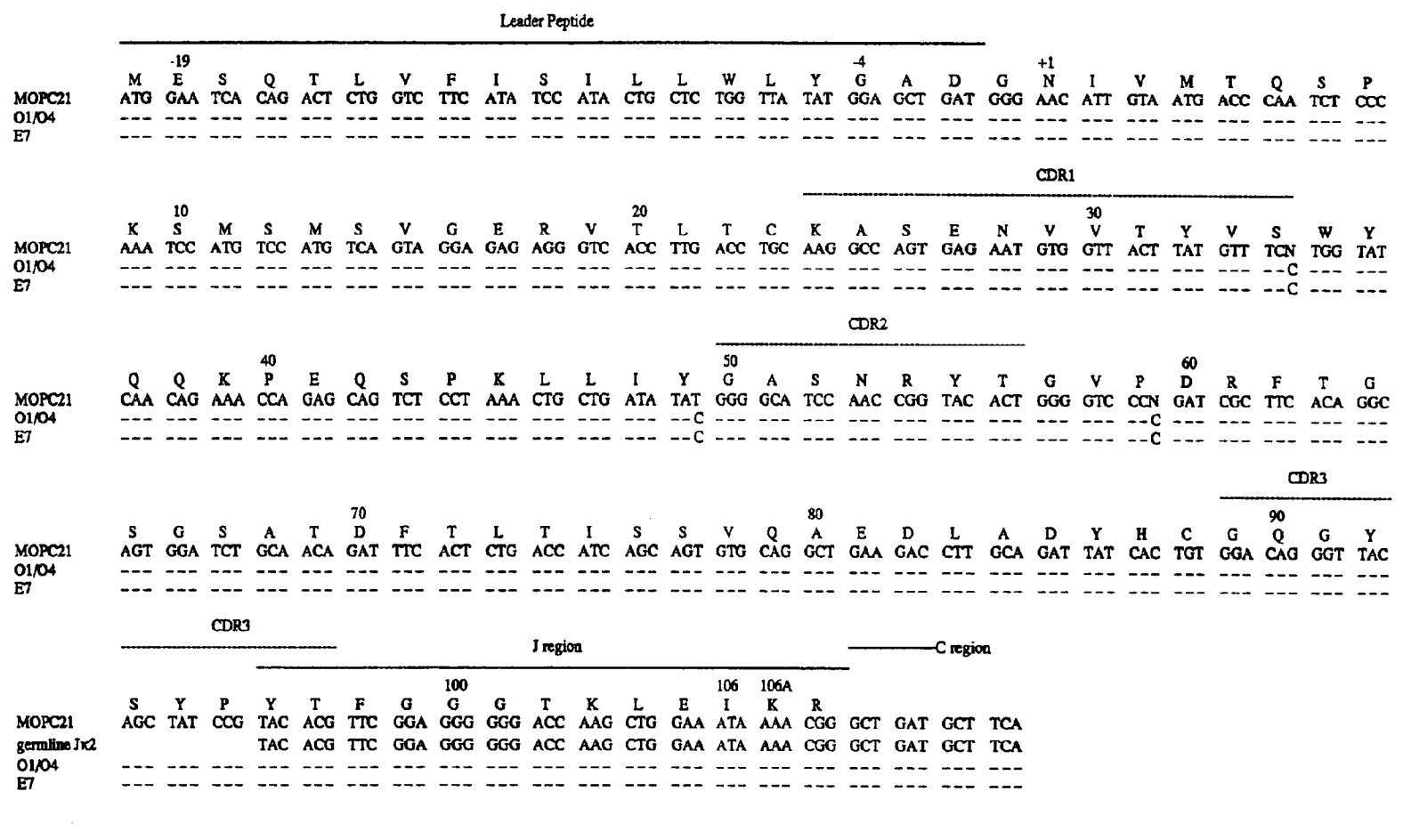

Since all the hybridomas produced $IgM_x$ antibodies as determined by isotyping assay, a $C_x$ primer was used for polymerase chain reaction. O1 and O4 light chain variable region cDNA sequences were identical (FIG. 15). The $V_x$ segments of O1 and O4 were identical with natural autoantibody E7 [Baccala et al., supra], and showed only one silent nucleotide difference when compared with myeloma MOPC21 [Hamlyn et al., Nucleic Acids Res., 9 (1981), 4485-4494]. The $J_x$ segment of HNK-1 showed sequence identity with $J_x2$.

The genomic germline gene which encodes the $V_x$ segment of A2B5 (FIG. 17) is unknown, but belongs to the $V_x19$ group [Potter et al., Mol. Immunol., 19 (1982), 1619-1630]. The $V_x$ segment of A2B5 was identical with the $V_x$ segment from hybridomas H220-11, H230-2, H230-5 and H250-6 [Caton et al., J. Immunol., 147 (1991), 1675-1686] except for two nucleotide changes, one of which resulted in an amino acid substitution (data not shown). The $V_x$ segments of H220-11, H230-2, H230-5 and H250-6 are identical to each other. The $J_x$ segment of A2B5 was identical with $J_x5$ [Max et al., J. Biol. Chem., 256 (1981), 5116-5120; Sakano et al., supra] except for one nucleotide which resulted in an amino acid substitution.

3. Direct ELISA

Figure 18:
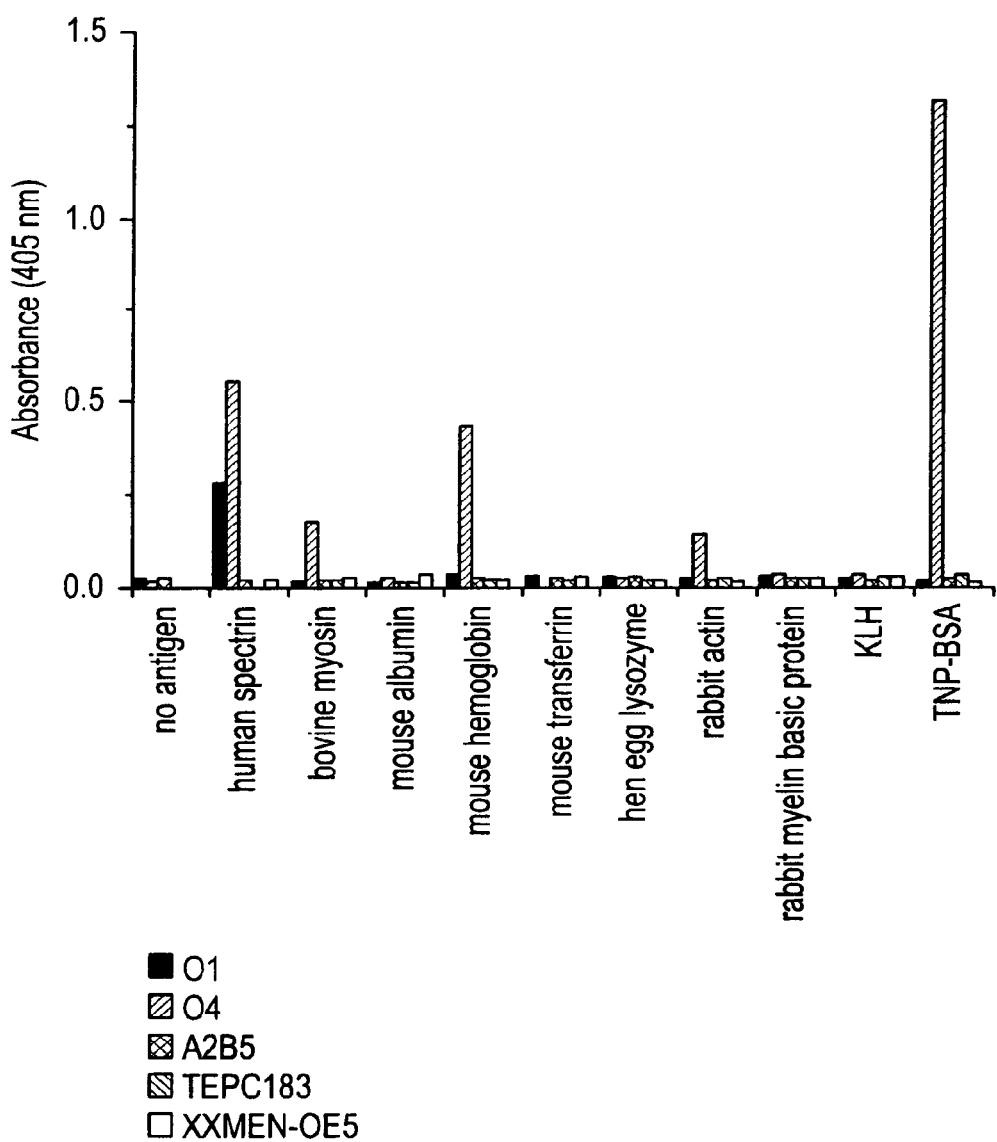
FIG. 18 is a graph showing the reactivity of O1, O4, A2B5 and control (TEPC183 and XXMEN-OES)IgMxmAbs by direct ELISA.

To assess the polyreactivity of the O1, O4, and A2B5, binding of mAbs to a panel of defined antigens was determined by ELISA (FIG. 18). O1 reacted with human RBC spectrin. O4 reacted with human RBC spectrin, bovine myosin, mouse hemoglobin, rabbit actin, and TNP-BSA. A2B5 and the two control $IgM_x$ mAbs did not react with this panel of antigens.

4. Utility

The enormous diversity in the Ig variable region is due primarily to combinations of multiple germline coding gene segments. Different primary structures are produced by recombination of V,D,J (heavy chain) or V,J (light chain) gene segments. Assuming the random association of heavy and light chains to form a complete antibody molecule, the number of different molecules is estimated to be $1.6 \times 10^7$ [Max et al., Fundamental Immunology, Raven Press, N Y, 1993, pp. 315-382]. Somatic mutation during the process of antigen challenge provides even further diversity and specificity. In contrast to the majority of Igs produced following antigen challenge, natural autoantibodies are encoded directly by germline genes with no or few to several mutations. Natural autoantibodies are present in sera of healthy humans and rodents [Dighiero et al., J. Immunol., 131 (1983), 2267-2272; Guilbert et al., J. Immunol., 128 (1982), 2279-2287; Hartman et al., Mol. Immunol., 26 (1989), 359-370]. These natural autoantibodies are polyreactive, capable of binding to a variety of structurally unrelated antigens [Avrameas et al., Mol. Immunol., 30 (1993), 1133-1142]. The physiologic function of natural autoantibodies is unknown. However, by interacting with many self constituents, these natural autoantibodies and their targets are believed to establish a vast network whereby the immune system can participate in general homeostasis.

These results provide evidence based on Ig variable region cDNA sequences that three of the four OL-reactive $IgM_x$ mAbs (O1, O4 and HNK-1) have characteristics of natural autoantibodies. The $J_H$ segments of O4 and HNK-1, and the $J_x$ segments of O1, O4 and HNK-1 are encoded by unmutated germline Ig genes. The $J_x$ segment of O1 has only one silent nucleotide change. O1 $V_H$ is identical with unrearranged VH segment transcripts A1 and A4, which belong to the $V_H558$ family [Yancopoulos et al., supra]. Because the germline genes corresponding to the $V_x$ genes of myeloma MOPC21 $V_x19$ gene family [Potter et al., supra] are unknown, direct evaluation of the somatic mutations of the light chains was not possible. However, O1 and O4 light chain variable regions are identical with the sequence reported for natural autoantibody E7 [Baccala et al., supra], and are identical with myeloma MOPC21 $V_x$ segment [Hamlyn et al., supra], except for one silent nucleotide change. This provides strong evidence that O1 and O4 $V_x$ segments are directly encoded by germline Ig genes. Though O4 and HNK-1 V had minor differences from germline $V_H 101$ [Katsoka et al, J. Biol. Chem., 257 (1982) 277-285], their sequences are very close to D23 $V_H$ sequence, a well-characterized natural autoantibody [Baccala et al., supra]. In addition, HNK-1 $V_x$ showed identity with myeloma MOPC41 [Seidman et al., Nature, 280 (1979), 370-375] and germline $V_x 41$ [Seidman et al., supra], except for two silent nucleotide changes. Our results were not able to determine whether A2B5 $V_x$ segment is encoded by germline Ig gene. However, the A2B5 $V_x$ is encoded by an unidentified germline Ig gene rather than by extensive somatic mutation of a germline Ig gene.

The results also showed that O1 and O4 react to multiple different antigens as demonstrated by ELISA. This is consistent with the immunocytochemistry [Eisenbarth et al., supra; Sommer et al., supra] demonstrating the reactivity of these mAbs to intracellular antigens in many cells. HNK-1 was shown previously to be polyreactive by Western blots using the lysates of chick embryo spinal cord neuron-enriched cultures and rat brain [McGarry et al., supra].

The Ig cDNA sequences and polyreactivity to multiple antigens are consistent with the hypothesis that O1, O4 and HNK-1 are natural autoantibodies. In contrast, A2B5 does not show polyreactivity by ELISA and the Ig cDNA sequence similarity to the germline is undetermined. Characterization of O1, O4 and HNK-1 as natural autoantibodies raises the possibility that they exist normally in serum and have physiologic function during development or in CNS diseases. In support of a physiologic function for these mAbs is the report that O4 stimulates the differentiation of OLs in vitro [Bansal et al., supra]. Since Schwann cells share with OLs the antigens recognized by O1, O4 and HNK-1, this suggests that these mAbs may have a function not only in the CNS but also in the peripheral nervous system. Direct proof of this hypothesis awaits experiments with these mAbs in vivo during development and in animal models of CNS diseases.

Examples 5-25

The Examples that follow, present the preparation and testing of human polyclonal and monoclonal antibodies that correspond to the antibodies that correspond to the antibodies previously set forth herein. In particular, human polyclonal IgM antibodies were prepared, and tested whereby their ability to bind e.g. oligodendrocytes, with a high specificity for neural tissue, and concomitant ability to enhance remyelination and to promote neurite outgrowth and regeneration, was demonstrated. As presented hereinbelow remyelination was verified in a Theiler's virus, and neurite outgrowth and regeneration have been validated in the results of experiments with the well-established lysolecithin-induced demyelination model. Further details follow below.

Introduction

Enhancement of remyelination is an important therapeutic goal in inflammatory demyelinating disorders of the CNS such as multiple sclerosis (MS). The identification of extensively remyelinated CNS lesions in some patients dying from acute MS, and in the applicants' recent data from cerebral biopsies suggests that full repair may be possible in the early stages of disease. However, as the disease progresses, remyelination is limited and occurs primarily at the periphery of the lesion. A number of reasons have been proposed for the failure to achieve complete remyelination in MS lesions. Two important considerations include the depletion of cells capable of remyelination, and depletion of factors, which sustain their growth and differentiation. Thus early intervention to stimulate reparative cells or to remove inhibitory factors preventing myelin repair may be key to a therapeutic strategy.

A number of approaches have been tested as therapeutic strategies to promote remyelination in experimental animals. Transplantation of oligodendrocytes or progenitor glial cells into previously demyelinated lesions can result in remyelination of CNS axons, and to a smaller extent migration of myelinating precursor cells. It has been shown that central remyelination restores conduction. An alternative strategy proposed by the applicants is to enhance endogenous remyelination. This approach implies that the cells capable of remyelination and the factors which sustain their growth or differentiation are present in demyelinated lesions, but that there are mechanisms which inhibit this response and thus prevent full remyelination.

One of the first descriptions of enhancement of endogenous CNS remyelination came from the experimental autoimmune encephalomyelitis (EAE) model. Using incomplete Freund's adjuvant (IFA) as a vehicle and myelin components as the antigen, immunization after disease induction promoted structural and functional recovery in guinea pigs with EAE. Based on the promotion of endogenous remyelination in EAE, similar experiments were conducted in mice chronically infected with Theiler's murine encephalomyelitis virus (TMEV). TMEV infection of susceptible strains of mice results in chronic inflammatory demyelination in the context of virus persistence which serves as an excellent model of MS. Chronically infected mice treated with spinal cord homogenate (SCH) in IFA showed substantial CNS remyelination compared to control animals given adjuvant alone. This observation was followed by experiments demonstrating that passive transfer of either antiserum or purified 1 g from uninfected syngeneic animals immunized with SCH/IFA promotes remyelination in mice chronically infected with TMEV. These experiments were novel and contrasted the classical view that the humoral immune response plays a pathogenic role in CNS demyelinating disease. These experiments were the first to demonstrate that Igs, in particular autoantibodies, could play a beneficial role in promoting CNS remyelination.

Based on these observations, the generation was begun of mAbs which promoted CNS remyelination in the Theiler's model of demyelination. Spleens from SJL mice that had been injected with SCH/IFA were used as the source of B cells for fusion hybridoma production. Serum from these mice had been shown previously to promote remyelination in chronically demyelinated mice. Hybridomas were generated and screened by ELISA using SCH as the antigen. After initial fusion, two of 95 viable hybridomas secreted antibodies that bound significantly to SCH. Hybridoma cells from these wells (designated SCH79 and SCH94) were subcloned and screened for SCH immunoreactivity. In the SCH79 series, 14 of 49 clones were positive, and for the SCH94 series 17 of 32 were positive. The monoclonal antibodies produced by these hybridomas were then tested in vivo for their ability to promote remyelination in the Theiler's model system. Six to eight month chronically infected SJL mice were given either intraperitoneal or intravenous injection of mAbs twice weekly for 4 to 5 weeks for a total dose of 0.5 mg to 5.0 mg. Two mAbs, SCH94.03 and SCH94.32, showed the greatest enhancement of CNS remyelination. Sequence of variable heavy and light chains proved these two antibodies to be identical, thus later designated as SCH94.03.

SCH94.03 treatment of SJL mice with chronic TMEV-induced demyelination generally results in 20-30% remyelination of total demyelinated area, as compared to less than 5% in PBS treated control animals. This represents a 4-6 fold increase in remyelination over controls and it is estimated from axonal counts that this represents an average of 100,000 remyelinated axons in SCH94.03 treated animals. Electron microscopic analysis of fully remyelinated lesions reveals no remaining unremyelinated axons suggesting that the remyelination of available axons in these lesions is close to 100%.

SCH94.03 belongs to the IgM subclass and is highly polyreactive against known and unknown protein antigens including cytoskeletal proteins. Of interest, it is encoded by unmutated Ig germline genes confirming that SCH94.03 is a natural autoantibody. Of importance, SCH94.03 recognizes an unidentified surface antigen on oligodendrocytes, providing a potential target for the mechanisms of action of this antibody.

Central to this hypothesis are the differences in the biology between SCH94.03 and CH12. At the time of the identification of the Ig gene sequence of SCH94.03, it was discovered that there was another mouse, IgMk antibody with an identical germline sequence and gene combination. This IgM antibody, designated CH12, is from a CD5+ B cell lymphoma and has apparent specificity to phosphatidyl choline. SCH94.03 and CH12 have 99.1% amino acid identity in the $V_L$ region and have identical $V_H$ sequences. The only differences between SCH94.03 and CH12 are in the CDR3 region, due to N-region insertions. CH12 does not label the surface of oligodendrocytes and does not promote remyelination in the Theiler's model system, thus establishing that the only molecular difference to account for the mechanism of promotion of remyelination lies within the CDR3 region. This conclusion supports the hypothesis that binding of these mAbs to specific antigens, likely within the demyelinated lesion, is important for the induction of remyelination. To date, six different mouse monoclonal antibodies have been identified which promote remyelination in the TMEV model for demyelinating disease. All six antibodies are of the IgM isotype and retain germline sequences that are reminiscent of autoantibodies. Each displays a broad antigen binding specificity but most importantly, each binds to antigens expressed on the surfaces of oligodendrocytes. IgM antibodies which do not bind oligodendrocytes do not promote remyelination. The prototypic member of this group, mAb SCH94.03, has been shown to promote remyelination in several mouse models for demyelinating disease. In mice with chronic virus-induced (TMEV) demyelination, treatment with SCH94.03 results in a 4-6 fold increase in remyelination. SCH94.03 treatment has also been shown to significantly increase the rate of spontaneous remyelination that occurs after chemically-induced demyelination following lysolecithin injection.

Given the success with the isolation and characterization of remyelination promoting mouse antibodies, the identification of human counterparts to the mouse monoclonals was begun using an antigen-independent strategy. The rationale was to identify human antibodies that react with mouse spinal cord homogenate by ELISA assay, and which bind with high affinity to structures and cells within the CNS. These antibodies were then tested in the mouse demyelination models for their ability to promote myelin repair. Pooled human IgM and IgG, sera from patients from the Mayo Hematology clinic, and monoclonal antibodies from EBV-immortalized human B cells (from various sources as described in the results) were characterized and tested in the mouse models. The results of these experiments are presented below.

Results

Human Polyclonal IgM, but not IgG, Binds to Rat Brain Slices and Oligodendrocytes in Culture.

Figure 19:
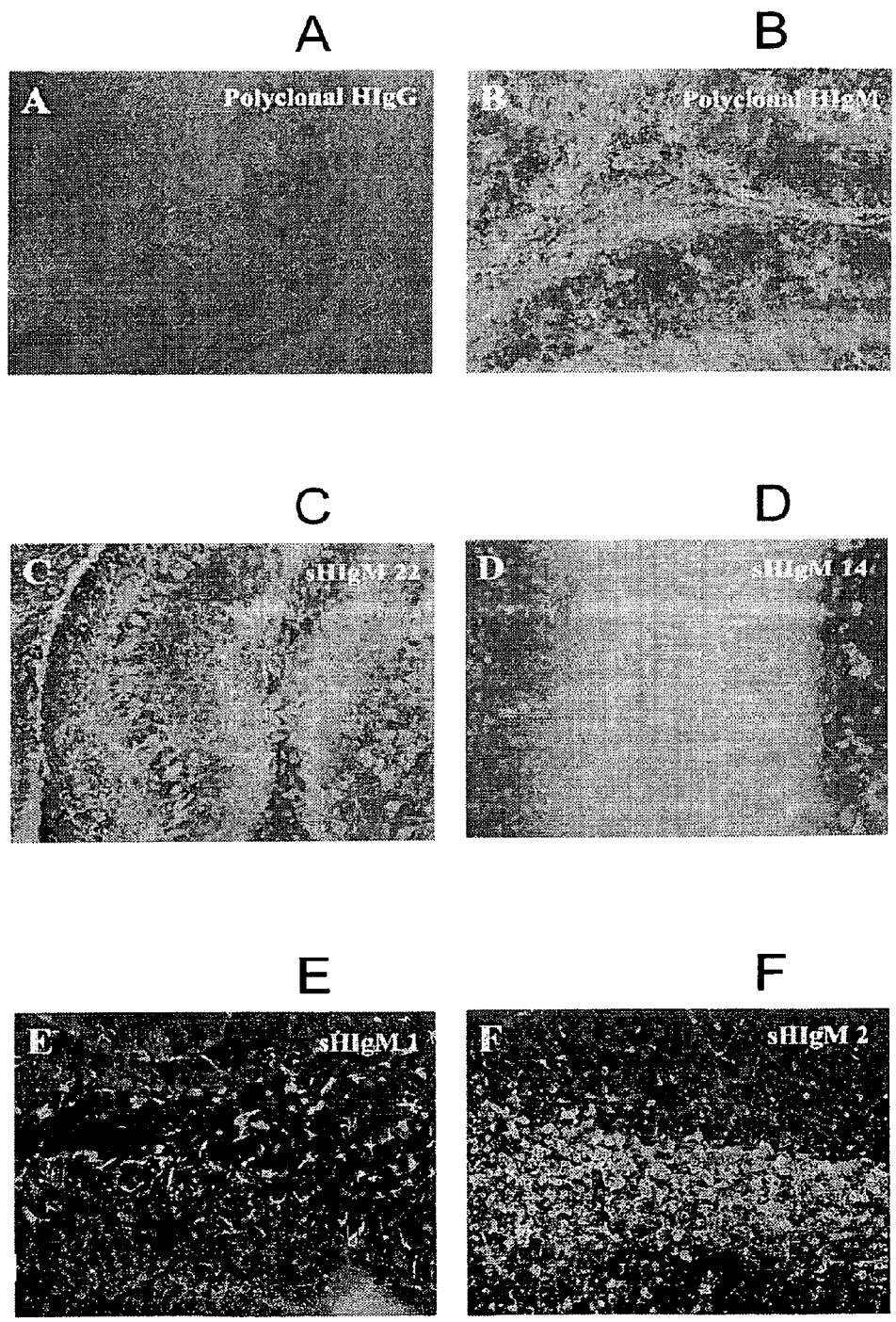
FIG. 19A-19F comprises photographs showing that polyclonal human antibodies and serum-derived human monoclonal IgM antibodies (sHIgMs) bind with high specificity to surface antigens on cells in slices of cerebellum. Indirect immunofluorescent labeling of unfixed slices of postnatal rat cerebellum. sHIgMs demonstrate a variety of specificities to cell populations and structures within an unfixed brain slice. This property was used as one of the criteria to select candidate antibodies to test in vivo for the ability to promote remyelination (see Table 7 and FIG. 12). Polyclonal human IgG binds very weakly to many structures within the cerebellum, including white matter and Purkinje cells (A), while polyclonal human IgM strongly binds to myelin and presumptive oligodendrocytes within the central white matter of the folia, Purkinje cell bodies and many small cells within the granular and molecular layer (B). sHIgM22 (C) binds well to the cytoskeleton of damaged astrocytes overlying the central white matter of the folia, Purkinje cells and their dendritic arborizations, and to small round cells in the molecular layer. sHIgM22 weakly, but uniformly, labels the surface of granule cells. sHIgM 14 (D) binds well to cells of the granular layer and Purkinje cells located at the surface of the slice, while the central white matter of the folia is largely devoid of label. sHIgM 1 (E) labels the cytoskeleton of astrocytes overlying the central white matter of the folia. All other structures are identified just above background levels. sHIgM 2 (F) binds to cells of the granular layer and to fibers traversing the central white matter of the folia. Magnification x.
Figure 24:
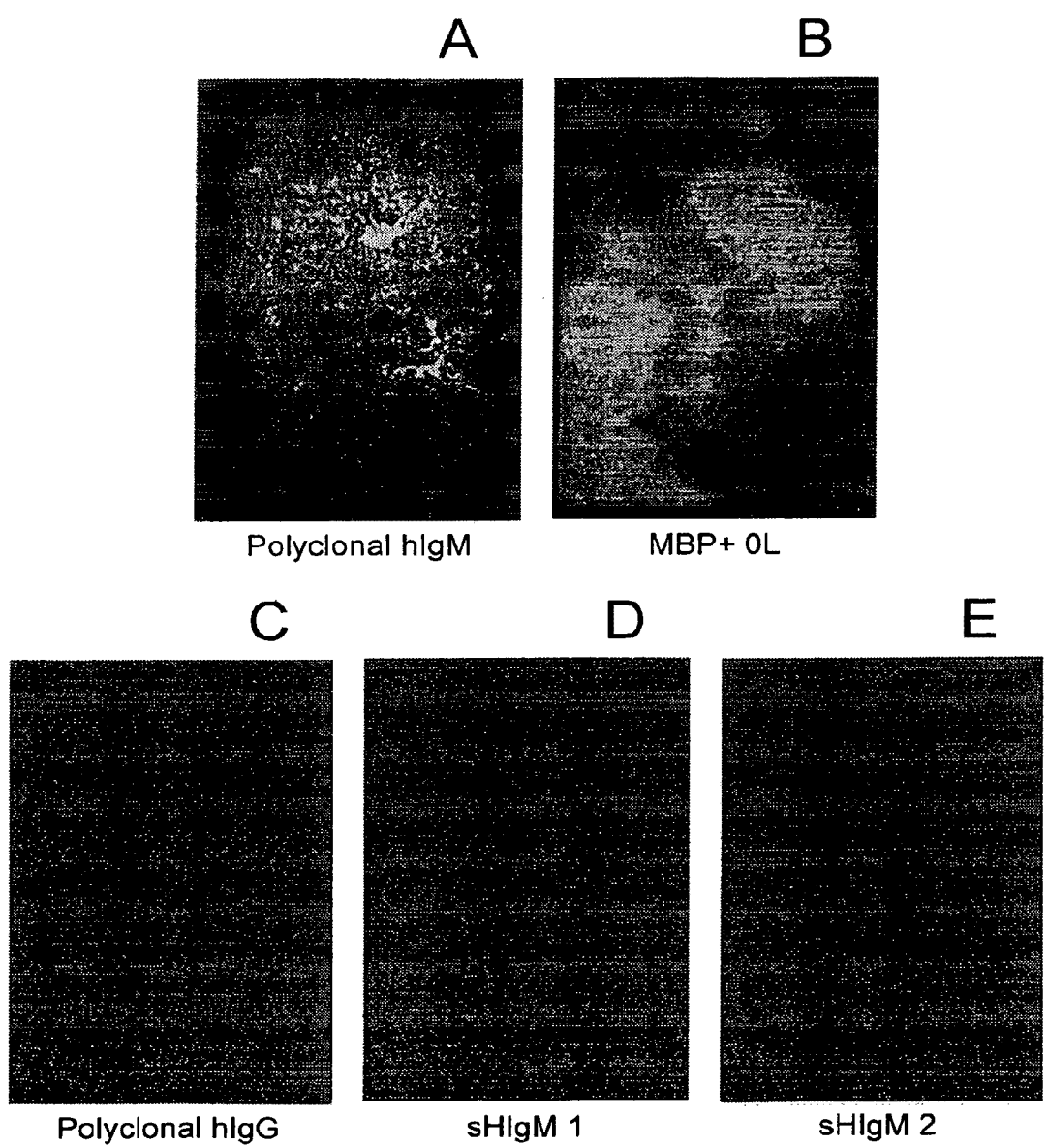
FIG. 24A-24E shows that polyclonal human IgM binds to oligodendrocytes in culture. By immunocytochemistry, polyclonal human IgM stains the surface of a subpopulation of oligodendrocytes. No reactivity to oligodendrocyte surface antigens was observed with polyclonal human IgG, or sera from sHIgM 1 or SHIgM 2. Immunocytochemistry with pooled human IgM or IgG in fixed and permeabilized cells showed minimal staining of intracellular structures.

By immunocytochemistry, polyclonal human IgM stains the surface of a subpopulation of oligodendrocytes (FIG. 24) and is highly reactive to structures and cells in a slice of rat brain (FIG. 19B). No reactivity to oligodendrocyte surface antigens (FIG. 24A) or slices of rat brain (FIG. 19A) was observed with polyclonal human IgG. Immunocytochemistry utilizing polyclonal human IgM or IgG on fixed and permeabilized mixed glial cells demonstrated minimal staining of intracellular structures (data not shown).

The specificity of polyclonal human IgM to CNS structures and cells and the binding to oligodendrocytes may drive the pronounced remyelinating potential. In contrast, polyclonal human IgG, while promoting remyelination over control levels (See Table 7), does not bind to CNS, and may function by a different mechanism than polyclonal human IgM.

Human Polyclonal IgG and IgM Promote CNS Remyelination in TMEV Infected Mice.

Even though the cause of MS is unknown, epidemiologic studies suggest that the disease may be triggered by an infectious agent (11), although to date no conclusive evidence proves this theory. Most recently, herpes virus type 6 has received attention as a possible etiologic agent in a subset of patients (12). Of the multiple epidemiological factors studied to correlate with exacerbations, only recent virus infection has been associated consistently (13). In addition, the major established treatment for MS, IFN-β, is a cytokine central for control of virus replication (14).

One important murine model for the study of MS is Theiler's murine encephalomyelitis virus (TMEV). This positive-stranded picornavirus has a number of advantages: (1) The virus is a natural pathogen of mice, a species for which there is vast known regarding immunology and genetics; (2) Primary demyelination (destruction of myelin sheaths) is the main physical manifestation of chronic infection (15); (3) Host genetics play a critical role in determining susceptibility or resistance to chronic viral persistence, demyelination and neurologic disease (16-18); (4) As in MS, pathology is immune-mediated (19-22); (5) There is complete information regarding the molecular virology, including details of virus replication and virus assembly {5476,62,4100,116}. (6) The majority of susceptible mice harboring chronic TMEV infection develop neurologic disease similar to MS—weakness of the extremities, spasticity, incontinence, decreased spontaneous activity and eventually paralysis (23,24).

Similar to MS, TMEV-infected mice demonstrate a wide spectrum of disease phenotypes (defined as both demyelination and neurologic deficits) (2). At one extreme are animals in which virus replicates rapidly in CNS neurons, is not cleared by the immune system, and results in severe encephalitis and death (25). This pattern of pathology is observed in neonatal mice or mice with severe immunodeficiency. This fulminant disease contrasts with mice that mount a protective immune response, primarily mediated by class I-restricted T cells which clear virus from CNS. These animals develop acute encephalitis, after which virus is cleared from the CNS without subsequent demyelination (26-28). In between these extremes are animals which develop and resolve acute disease, but enter a chronic phase characterized by progressive demyelination, and virus persistence in oligodendrocytes, astrocytes, and microglia (29,30). Although these mice mount an immune response which prevents death and overwhelming encephalitis, failure to clear virus from white matter results in chronic, persistent inflammation and immune-mediated demyelination. To avoid anti-human immune responses, chronically infected mice (5 to 6 months after TMEV infection) were treated with a single bolus injection of 1 mg of Ig intraperitoneally. The total dose of Ig was approximately 0.05 g/kg body weight, which corresponds to one eighth the total dose used for human IVIg treatment. There was no significant differences in the areas of myelin pathology between the treatment groups (Table 7). However, mice treated with polyclonal human IgM demonstrated prominent remyelination. Approximately one quarter of the total area of myelin pathology was repaired in mice treated with polyclonal human IgM. The extent of remyelination was significantly higher than the spontaneous remyelination observed in the PBS-treated control groups ($p<0.01$), but also higher than that observed in mice treated with polyclonal human IgG ($p=0.05$). Mice treated with polyclonal human IgG demonstrated more remyelination than mice treated with PBS. Individual lesions which were remyelinated showed almost complete repair with few inflammatory cells or macrophages (FIG. 30A,B). Frequently 500 to 1000 remyelinated axons were observed in each of lesion of this type. In contrast, most lesions in mice treated with PBS had few remyelinated axons and the lesions contained many inflammatory cells and macrophages, signs of active myelin destruction.

Polyclonal Human IgM Enhances Remyelination in Lysolecithin-Induced Demyelination.

Lysolecithin injection into the spinal cord is a well established method for chemically induced spinal cord injury and demyelination. Injection results in reproducible demyelinated lesions which undergo complete spontaneous remyelination by 5-6 weeks. Previous work by the present applicants has shown that treatment with remyelination promoting antibodies increases the rate of endogenous remyelination such that lesions are substantially repaired by 3 weeks. The monophasic nature of lysolecithin lesions, their rapid spontaneous repair, and the lack of clinical deficits in lesioned animals, are in contrast to chronic TMEV induced demyelination and may model aspects of spinal cord injury better than MS.

Animals with lysolecithin-induced spinal cord lesions were treated with polyclonal human IgM and IgG. Photomicrgraphs of the lesion areas showed the animals that received polyclonal human IgM contained many remyelinated axons, while the animals treated with polyclonal human IgG or PBS contained few remyelinated axons (data not shown). In an effort to quantitate the number of remyelinated axons per area of lesion, remyelinated axons were counted under high magnification from lesions of the 3 treatment groups. There were significantly more myelinated axons in lysolecithin lesions treated with polyclonal human IgM than animals treated with polyclonal human IgG ($p<0.05$).

Polyclonal Human Immunoglobulins React with Multiple Self Antigens and Chemical Haptens.

Antigen specificities of Igs used in this study were studied by ELISA. Previous studies have indicated the antibodies which promote remyelination show wide reactivity to multiple protein and hapten antigens (Miller et al., 1995). Both polyclonal human IgG and IgM bound multiple protein antigens and chemical haptens (FIGS. 33 & 34).

Polyclonal Human IgG and IgM does not React with TMEV Antigens.

To exclude the possibility that enhanced remyelination by pooled human IgM was the result of specificity for TMEV antigens. Western blotting using purified TMEV was performed. None of the Abs used in this study reacted with any of the known TMEV capsid proteins (data not shown). In contrast, rabbit polyclonal antibody raised against TMEV showed strong reactivity to the VP1, VP2, VP3 capsid antigens of the virus.

CNS-Reactive Monoclonal Antibodies can be Identified from Human Serum.

Since natural autoantibodies exist in the normal human population it should be possible to identify human natural monoclonal autoantibodies by screening a large number of human monoclonal IgM clones. An initial screen was designed for polyreactivity of serum-derived human monoclonal antibodies utilizing an unfixed brain slice binding assay system. Positive clones are those samples that bound to specific brain structures or anatomical layers or cell populations significantly above the background level of a fluorescently-conjugated secondary antibody alone.

Fifty two samples of human IgM, purified from the sera of patients obtained from the hematology department Mayo Clinic, under the direction of Dr. Robert A Kyle, were tested for CNS specificity ina brain slice binding assay. Thirty two antibodies were determined to bind above background. A variety of the reactivities are presented in FIGS. 19 and 20. Fifty human serum-derived IgGs were also tested for CNS specificity in a brain slice binding assay and no distinct binding patterns above background were identified (data not shown). Thus, immediately, a major difference between human monoclonal IgMs and IgGs was identified.

Figure 28:
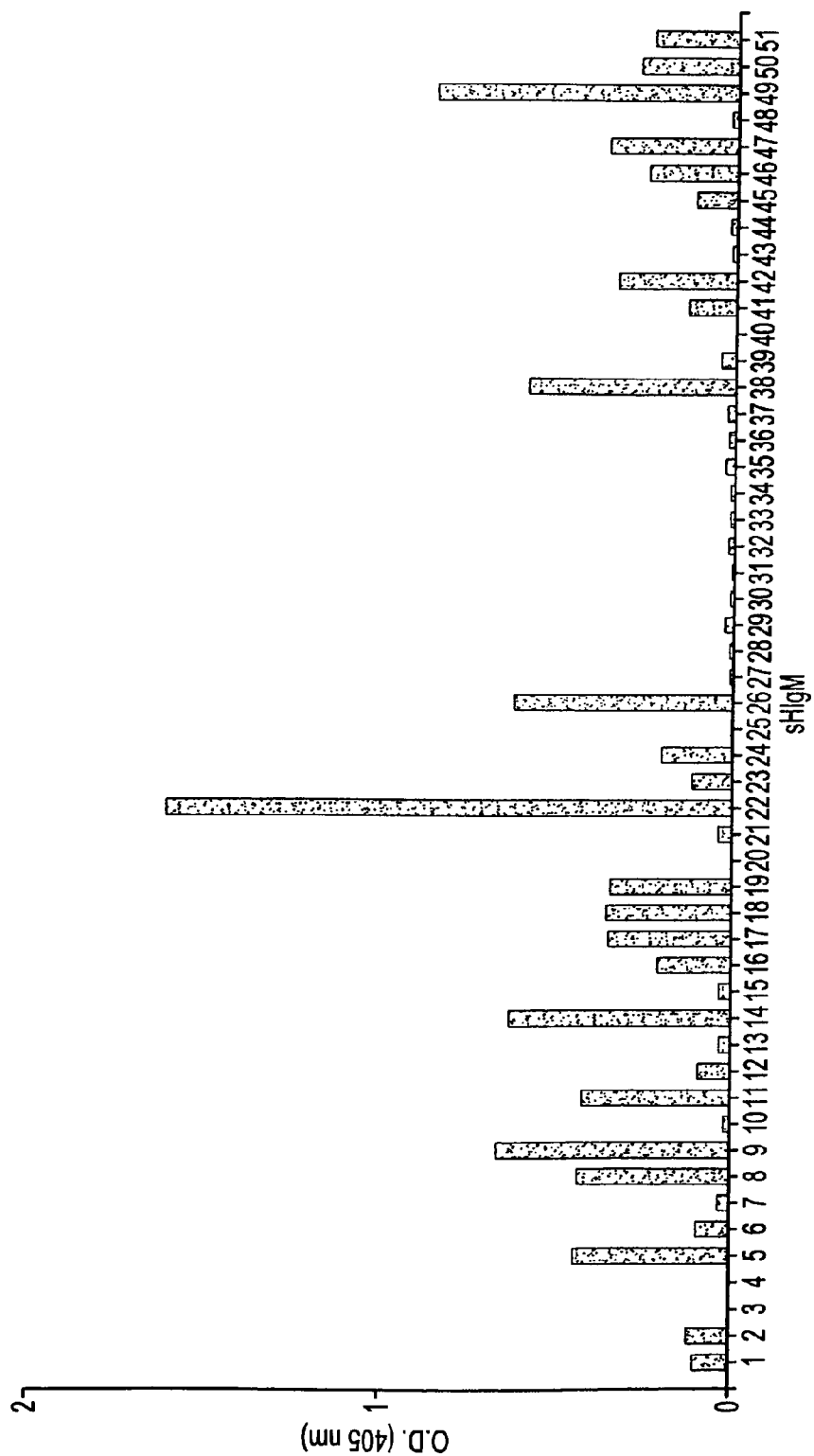
FIG. 28 presents the results of screening sHIgMs for binding to CNS antigens found in spinal cord homogenate. sHIgMs were screened for their binding to spinal cord homogenate bound to polystyrene plates. Most of antigens that bind to the plate are lipids and proteins from the white matter of the spinal cord. Thus, strong antibody binding to SCH homogenate may be interpreted as binding to white matter components. Only 1 sHIgM binds to SCH with an OD greater than 1, sHIgM22. This antibody also binds well to brain slices, oligodendrocytes in culture and has been tested for the ability to promote remyeliation in vivo (see Table 7). This simple assay has proven to be a powerful tool in predicting the capacity of an antibody to promote remyelination in vivo. Other sHIgMs that bind well to SCH (such as 38 and 49) are under study.
Figure 29:
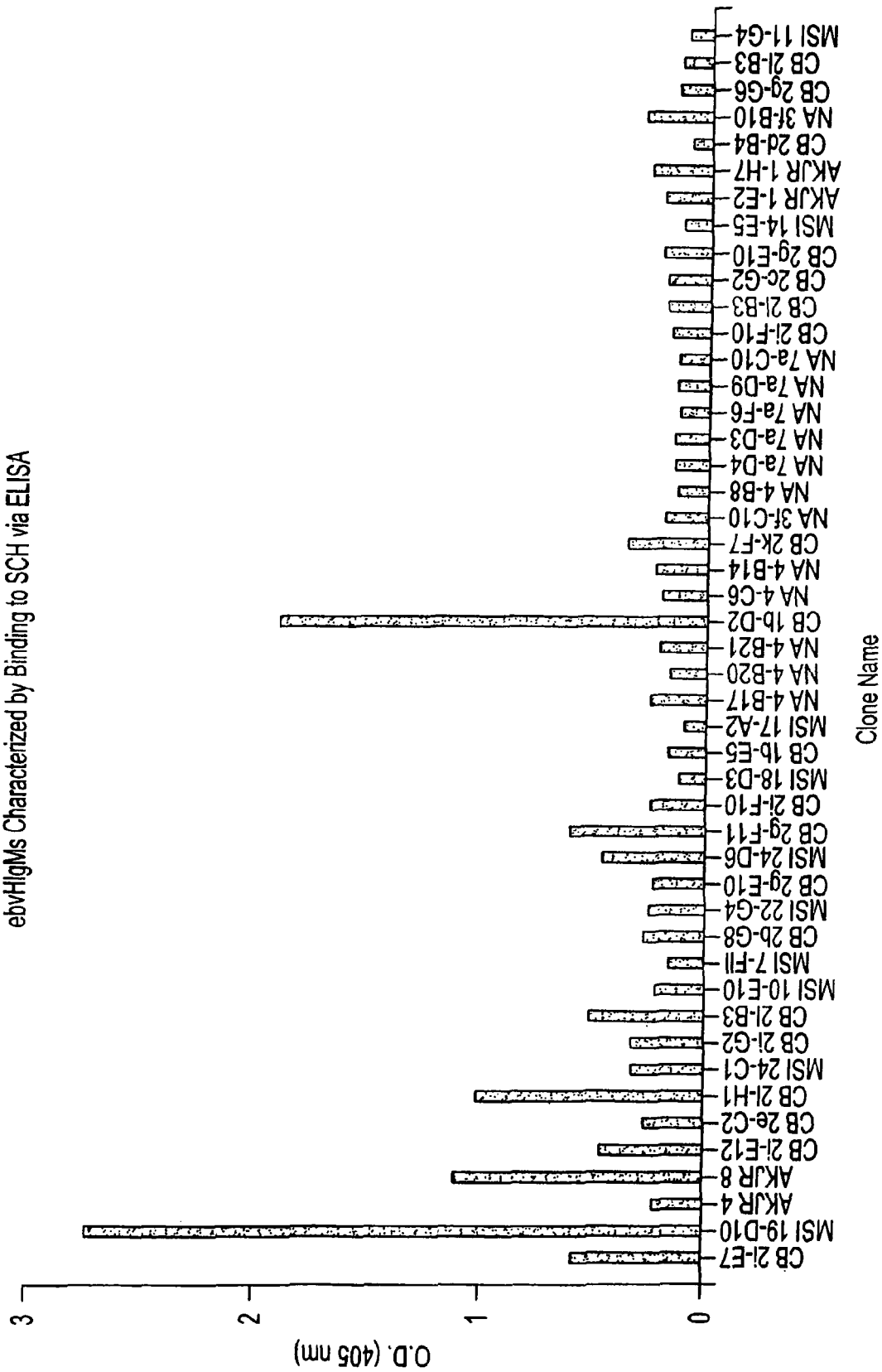
FIG. 29 shows the results of screening ebvHIgMs for binding CNS antigens found in spinal cord homogenate. ebvHIgMs were screened for their binding to spinal cord homogenate bound to polystyrene. Four ebvHIgMs bound to SCH homogenate with a OD greater than 1. One of these, MSI19D10 has been tested for the ability to promote remyelination in vivo. (see Table 7). A low binding antibody, AKJR4 has also been tested in vivo (see Table 7). One other strong binding antibody, AKJR8 is under study. The clones CB2iH1 and CB1bD2, produce very little antibody in culture. Again, this simple assay has proven to be a very powerful tool for screening antibodies, and predicting which antibodies are capable of promoting remyelination in vivo.

The 32 positive antibodies were further tested for binding via a spinal cord homogenate ELISA system (FIG. 28) and for binding to both live and fixed rat mixed primary glial cell cultures (FIG. 25). A tabulation of the reactivities of those antibodies (sHIgM # antibodies) is shown in TABLE 8. The criteria for testing an antibody for biological activity in vivo was CNS specificity, binding to unfixed oligodendrocytes in culture and a significant reactivity to SCH via ELISA. Thus, sHIgM22 was identified as promoting remyelination. Several other sHIgM candidates remain to be carefully studied. The ability of tested sHIgM antibodies to bind oligodendrocytes is shown in TABLE 9.

CNS-Reactive Monoclonal Antibodies were Identified from the Supernatant of EBV-Immortalized Human B-Cell Clones.

Figure 23:
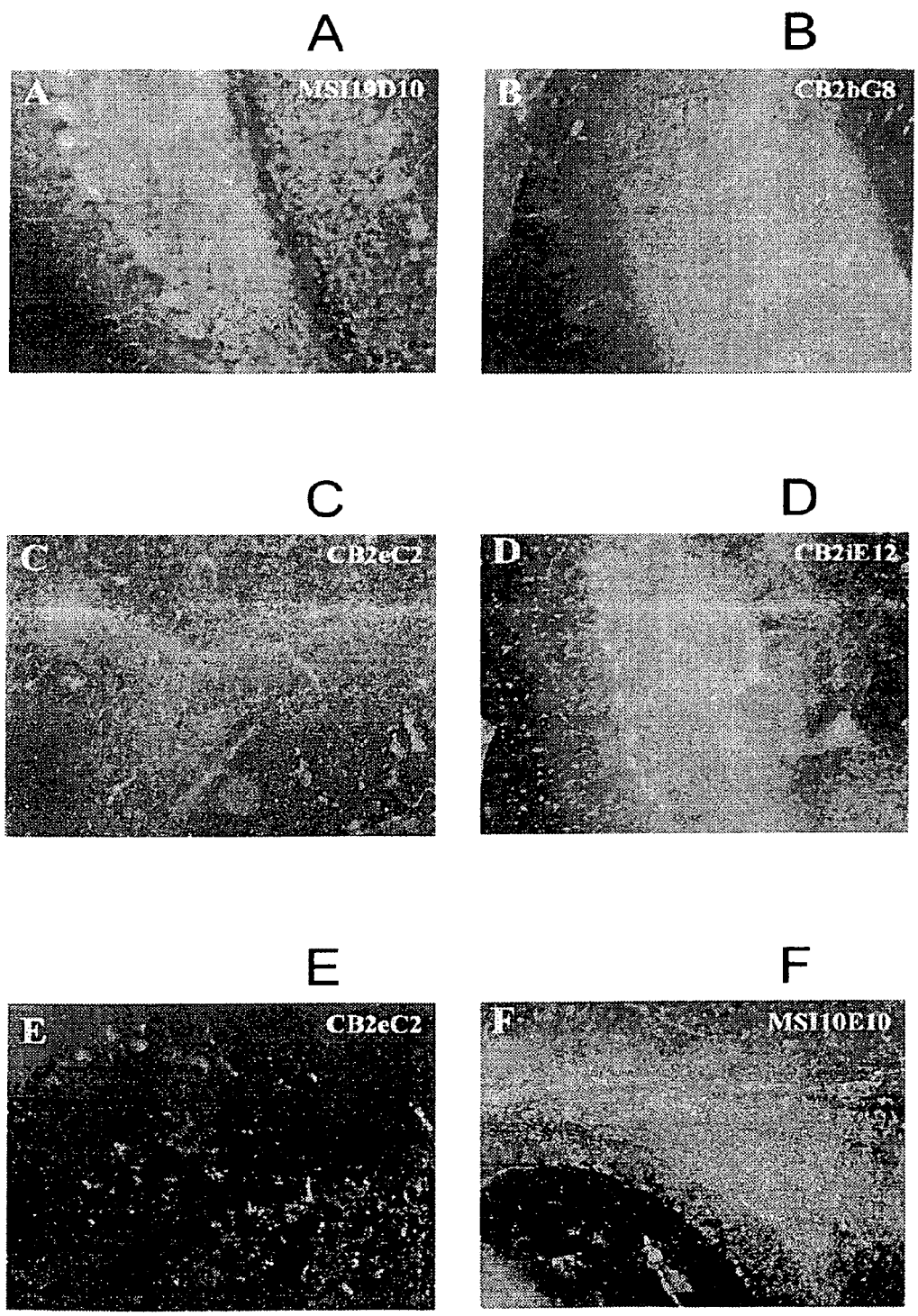
FIG. 23A-23F shows that additional ebvHIgMs that bind with high specificity to surface antigens on cells in slices of cerebellum. Indirect immunofluorescent labeling of unfixed slices of postnatal rat cerebellum. ebvHIgMs demonstrate a variety of specificities to cell populations and structures within an unfixed brain slice. Each panel shows the terminal end of a single cerebellar folia, including the central white matter, and the granular, Purkinje and molecular layers. Supernatants containing ebvHIgMs were incubated 1:1 with buffered media on slices of brain. Many ebvHIgMs bind to white matter, Purkinje cell bodies, and small cells within the molecular layer, but with varying affinities. ebvHIgM MSI19D10 (A) binds strongly to cells of the granular layer and to Purkinje cells and their dendritic arbors, in addition to weakly identifying white matter and astrocytes. ebvHIgM MSI19D10 was tested for the ability to promote remyelination in vivo (see Table 7 and FIG. 13). Other brain-binding ebvHIgMs, CB2bG8(B), CB2eC2 (C), CB2iE12 (D), and MSI10E10 (F) have been isolated and warrant further study, but have not been tested in vivo. CB2eC2 (E) is the typical intensity of a non-reactive Supernatants. Magnification x.

Supernatants from cell clones that had a total IgM concentration over 3 ug/ml were tested in a brain slice assay system for their ability to bind to CNS structures. One hundred forty clone supernatants were tested for brain slice binding. Fifteen antibodies were determined to bind above background. A tabulation of the reactivities of these antibodies (MSI #) are shown in Table 8. A representation of ebvHIgM reactivities are presented in FIGS. 22 and 23. The ability of certain of these antibodies to bind oligodendrocytes was tested. These results are tabulated in Table 9.

sHIgMs Bind to Human Cortical White Matter.

Figure 3:
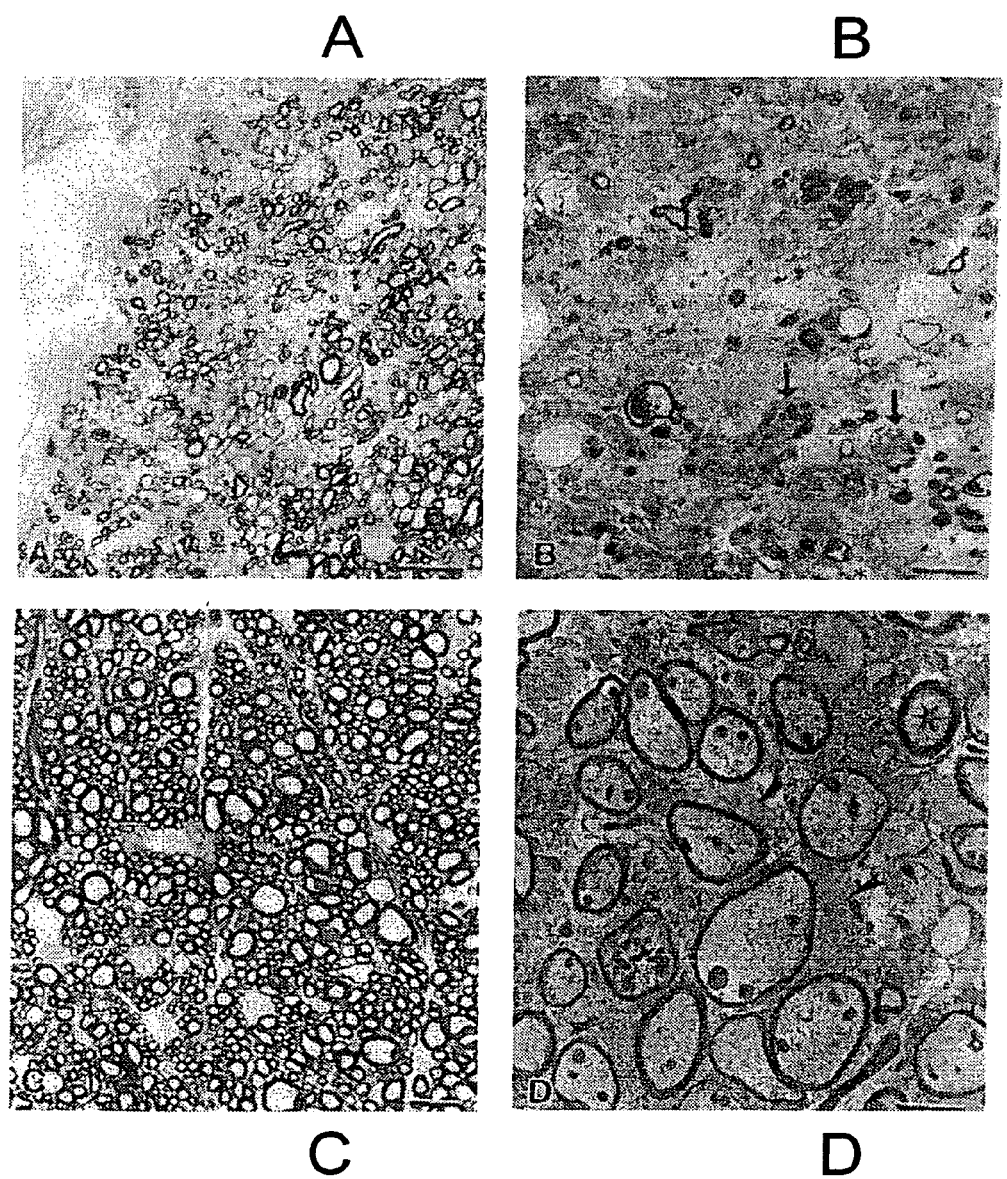
FIG. 3A-3D shows light and electron micrographs of CNS remyelination promoted by mAb SCH94.03. (A) Light micrograph of spinal cord section from a chronically infected SJL/J mouse treated with SCH94.03 showing CNS remyelination. (B) Light micrograph of spinal cord section from a chronically infected SJL/J muse treated with a control IgM showing extensive demyelination, and the relative absence of remyelination. Inflammatory cells, including macrophages with ingested myelin debris are indicated by arrows. The asterisk indicates a representative naked axon. (C) Light micrograph of spinal cord section with normal myelin. (D) Electron micrograph of spinal cord section from an animal treated with SCH94.03 showing multiple axons with abnormally thin myelin sheaths relative to axon diameter. The star in the upper right-hand corner indicates an axon with normal myelin sheath thickness. Arrowheads point to astrocytic processes, which are intimately associated with remyelinated axons. Scale bars represent 13 µm in A-C, and 2 µm in D.
Figure 21:
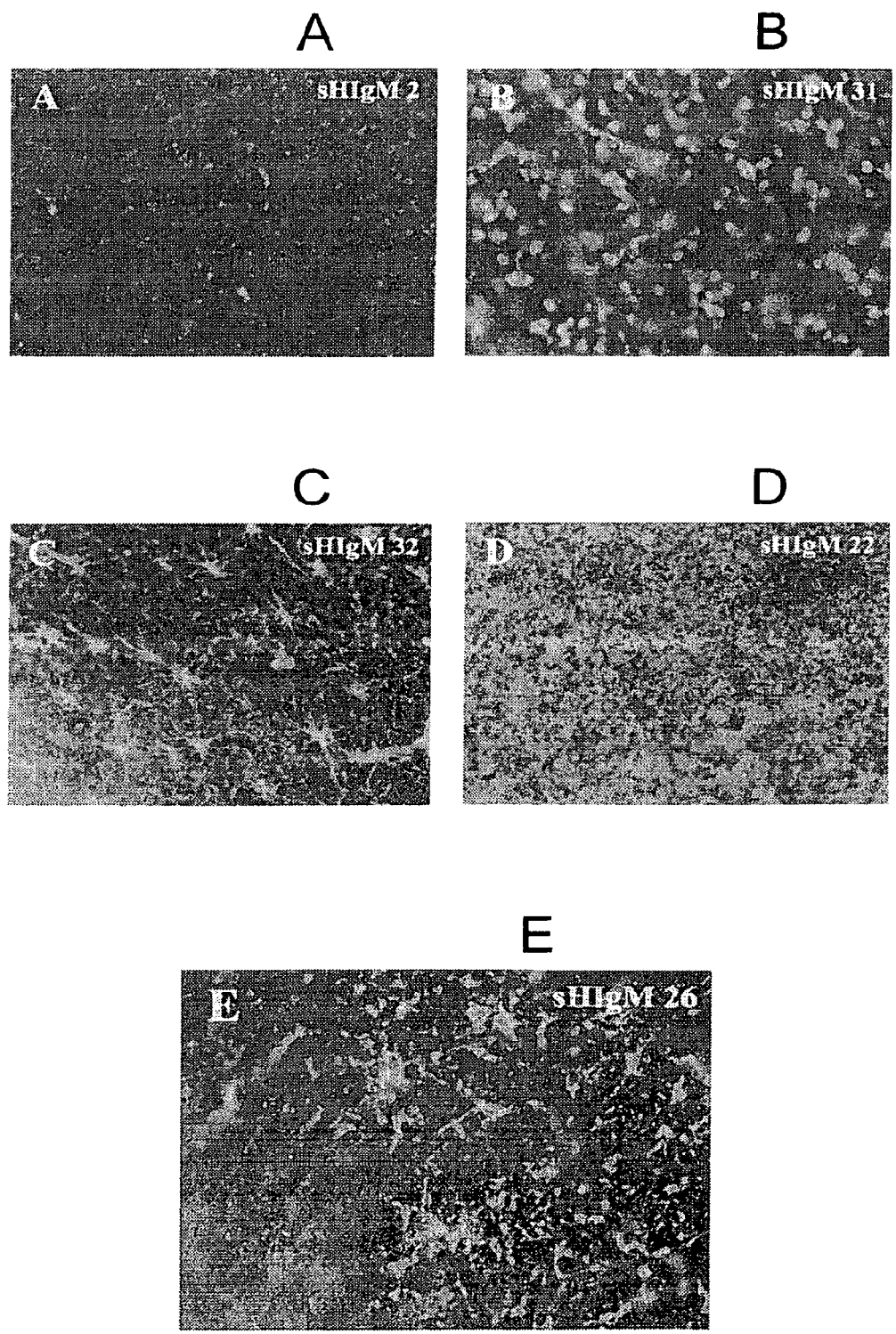
FIG. 21A-21E comprise photographs that show that sHIgMs bind with high specificity to unfixed slices of adult human cortical white matter. Indirect immunofluorescent labeling of unfixed slices of adult human cortical white matter. Cortical human white matter was obtained at autopsy from an individual with no CNS infection or trauma. The cause of death was other than CNS-related. Tissue was obtained on ice and maintained cold throughout the antibody labeling procedure. sHIgM 2 (A) binds to only a few cells within the field of view. In contrast, others sHIgMs bind human white matter quite well and with a high degree of specificity. sHIgM 32 binds to type 2 astrocyte-appearing cells (C), while sHIgM 31 binds to many unidentified round cell bodies (B). sHIgM 26 binds to oligodendrocyte-appearing cells and fibrous white matter (E). sHIgM22 binds to human cortical white matter in a manner that is suggestive of an extracellular matrix bound molecule (D). Magnification x.

To confirm that sHIgMs bind to human CNS, human cortical white matter was immune-labeled in system analogous to the rat brain slce assay. FIG. 3 presents several of the CNS specificities of sHIgMs. Four antibodies bind well to human CNS (FIG. 21B,C,D,E) while FIG. 21A shows a SHIgM that binds slightly above background level.

Human Monoclonal Antibodies Bind to Surface Antigens on Cells in Mixed Primary Glial Cultures.

Several of the sHIgMs bind to cells in rat primary mixed glial cell cultures. sHIgM 12 binds to presumptive oligodendrocyte progenitor clusters (FIG. 25A) in a field of O4 positive oligodendrocytes. Four other sHIgMs (FIG. 25B,C,D,F) bind to morphologically mature oligodendrocytes. sHIgM 30, binds to most cells (oligodendrocytes, asrocytes, microglial) in the culture (FIG. 25E).

sHIgMs and ebvHIgMs Promote CNS Remyelination in TMEV Infected Mice.

Figure 30:
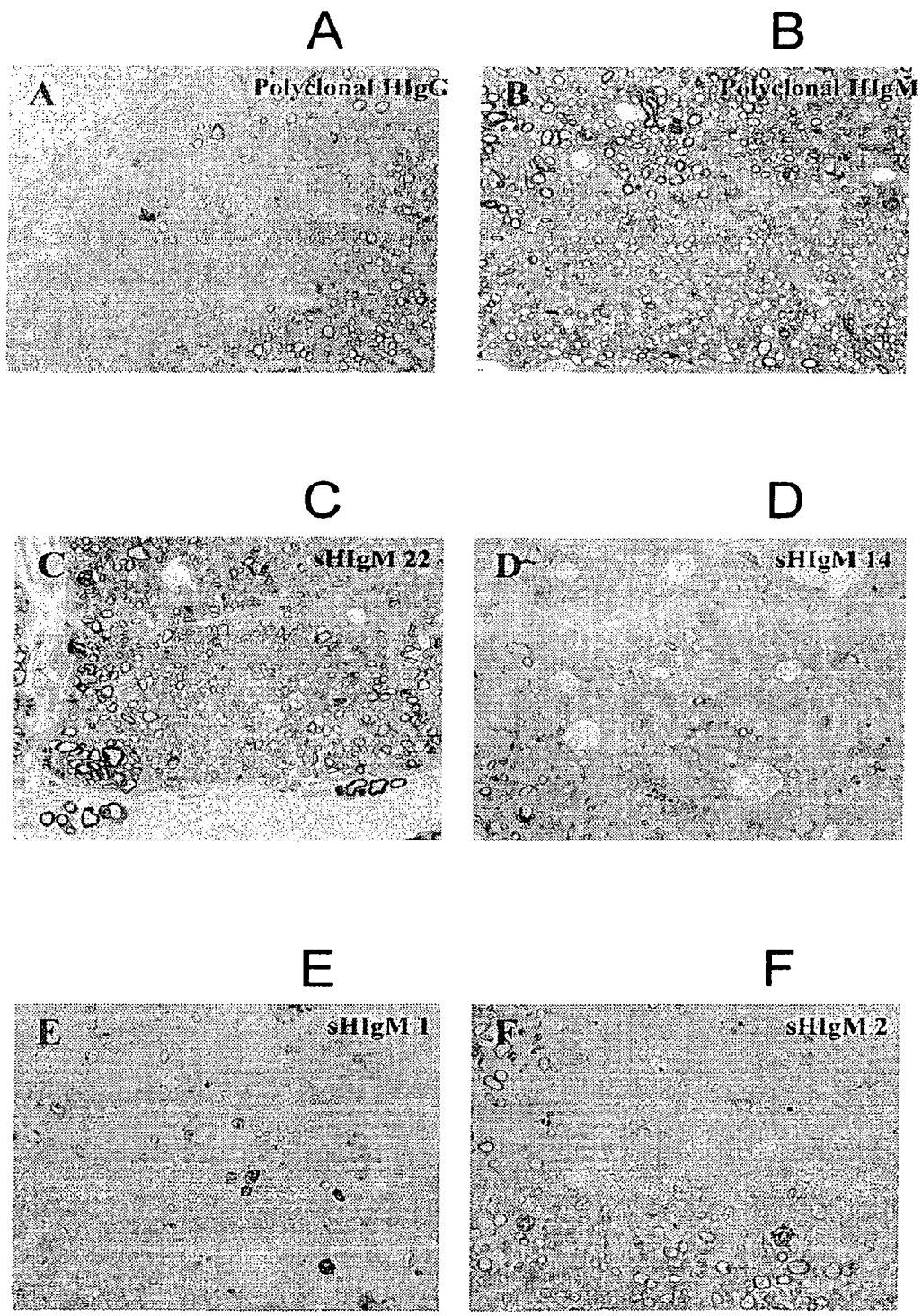
FIG. 30A-30F demonstrates that polyclonal human antibodies and a sHIgM promote remyelination in TMEV infected mice. Light photomicrographs of regions of myelin pathology in the spinal cords of SJL/J mice chronically infected with TMEV. Extensive CNS remyelination, characterized by thin myelin sheaths in relation to axon diameter. is observed in mice after treatment with polyclonal human IgG (A), polyclonal human IgM (B), and sHIgM22(C). Demyelination without significant remyelination was observed in mice treated with sHIgM 14 (D), sHIgM 1(E) and sHIgM 2. Araldite embedded sections were stained with 1% p-phenylenediamine. Magnification x. Polyclonal human IgM proved to be superior in the ability to promote remyelination in vivo than polyclonal human IgG (Table 7). Strong CNS specificity appears to be one of the requirements for an antibody to promote remyelination in vivo, but alone is not sufficient to predict an antibody's capacity to promote remyelination.
Figure 32:
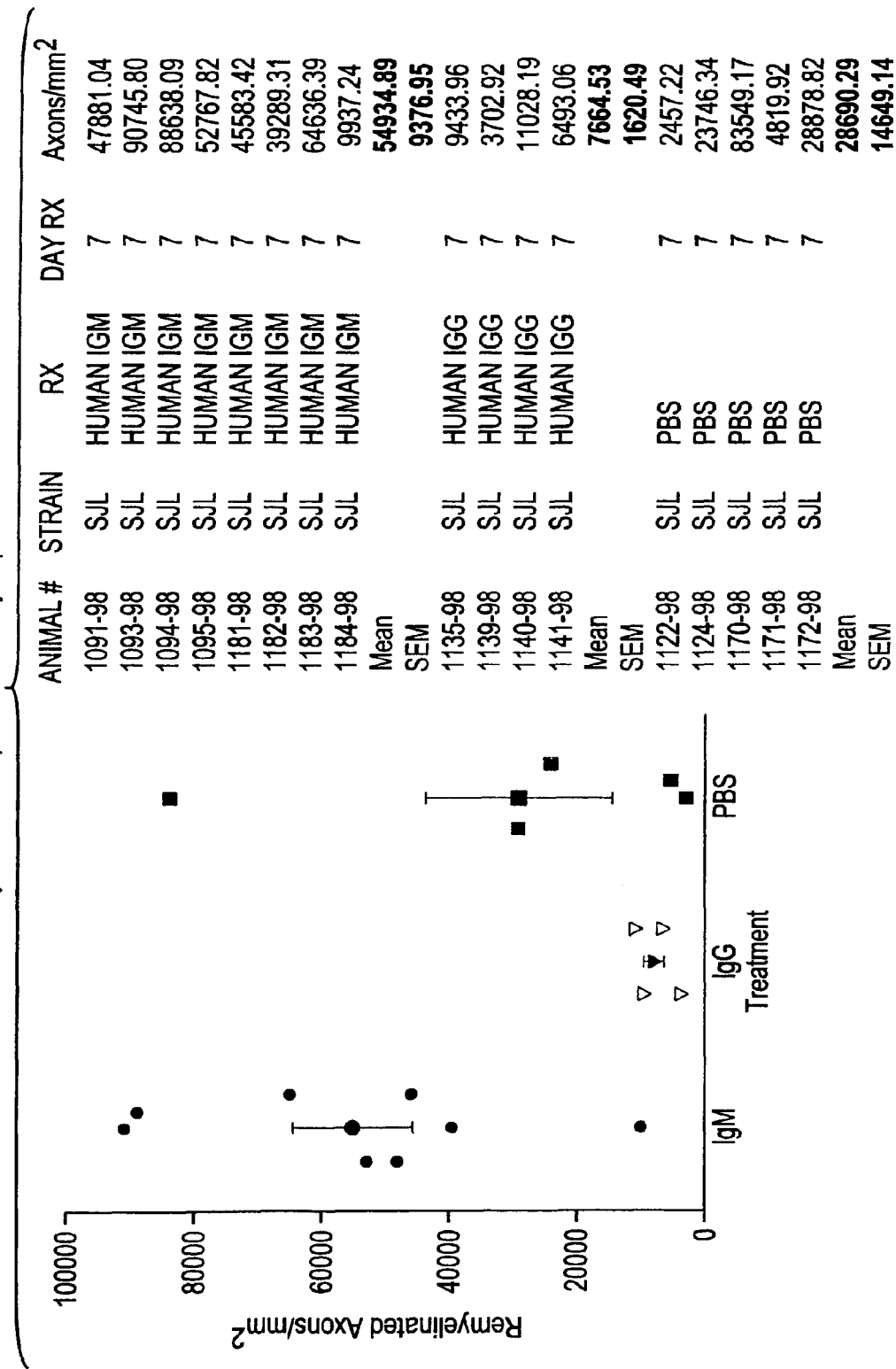
FIG. 32 presents the quantitation of myelinated axons in lysolecithin lesions treated with human polyclonal IgM. Remyelinated axons/mm2 in treated vs untreated lysolecithin lesions. There are significantly more myelinated axons in lysolecithin lesions treated with polyclonal human IgM than animals treated with polyclonal human IgG ($p<0.05$). One animal in the PBS control group spontaneously remyelinated and thus the difference between the human antibody treated groups and the control group is not statistically significant ($p>0.05$).

To avoid anti-human immune responses, chronically infected mice (5 to 6 months after TMEV infection) were treated with a single intraperitoneal bolus injection of 0.5 mg of human monoclonal antibody. Of the human monoclonal antibodies tested in vivo to date, sHIgM22 and ebvHIgM MSI19D10 significantly promoted remyelination over other tested human monoclonal IgMs (sHIgMs 1,2, and 14). There are no differences in the areas of myelin pathology between the treatment groups (Table 7). Mice treated with sHIgM22 demonstrated prominent remyelination. Approximately one fifth of the total area of myelin pathology was repaired in mice treated with sHIgM22 (Table 7). The extent of remyelination was significantly higher than the spontaneous remyelination observed in PBS-treated control groups (p<0.05, Table 7). Individual remyelinated lesions showed almost complete repair with few inflammatory cells or macrophages (FIG. 30). Frequently 500 to 1000 remyelinated axons were observed in each of lesion of this type. In contrast, most lesions in mice treated with PBS had few remyelinated axons and the lesions contained many inflammatory cells and macrophages, signs of active myelin destruction. Consistent with previous work demonstrating that oligodendrocyte-reactive mouse monoclonal antibodies can promote remyelination in vivo (Asukara et al., 1998); oligodendrocyte-reactive human antibodies with similar reactivities to the mouse counterparts can promote remyelination in vivo as well.

TABLE 7

CNS Remyelination by Human Antibodies

| Treatment | No. of Mice | Area of White Matter (mm2) | Area of Myelin Pathology (mm2) | Area of CNS-Type Remyelination (mm2) | Area of CNS-Type Remyelination (%) |
|---|---|---|---|---|---|
| Polyclonal Human IgG | 10 | 8.6 ± 0.52 | 0.86 ± 0.10 | 0.13 ± 0.02 | 14.15 ± 2.38* |
| Polyclonal Human IgM | 13 | 9.70 ± 0.43 | 1.21 ± 0.21 | 0.24 ± 0.04 | 23.2 ± 3.26** |
| sHIgM 1 | 4 | 9.34 ± 1.93 | 0.68 ± 0.07 | 0.03 ± 0.01 | 8.35 ± 3.73 |
| sHIgM 2 | 4 | 8.78 ± 0.70 | 0.87 ± 0.12 | 0.09 ± 0.01 | 11.37 ± 1.30 |
| sHIgM 14 | 7 | 10.68 ± 0.24 | 0.98 ± 0.09 | 0.08 ± 0.03 | 8.57 ± 2.51 |
| sHIgM22 | 8 | 10.55 ± 0.41 | 1.16 ± 0.22 | 0.19 ± 0.05 | 17.06 ± 3.42* |
| sHIgM 46 | 5 | 9.44 ± 0.36 | 0.66 ± 0.06 | 0.18 ± 0.04 | 27.12 ± 4.01 |
| ebvHIgM MSI19D10 | 3 | 8.24 ± 0.40 | 0.90 ± 0.14 | 0.26 ± 0.07 | 26.47 ± 3.71*** |
| ebvHIgM AKJR4 | 4 | 8.70 ± 0.84 | 1.10 ± 0.15 | 0.05 ± 0.03 | 4.15 ± 1.98 |
| PBS | 7 | 9.78 ± 0.60 | 1.20 ± 0.22 | 0.06 ± 0.02 | 6.74 ± 1.80 |

Values represent the mean ± SEM.
One way ANOVA and t-test were used to compare the percent area of CNS-type remyelination in mice treated with human antibodies to mice treated with PBS. Such analysis revealed *$p < 0.05$; †$p < 0.01$, ‡$p < 0.001$.
Comparison of mice treated with polyclonal human IgG to other treatments revealed; polyclonal human IgM p = 0.05, sHIgM 46 P < 0.05. All other comparisons were not statistically significant. There was no difference in the CNS-type remyelination between polyclonal human IgM, sHIgM22 and sHIgM 46.
Area of PNS-type Schwann cell remyelination ranged from) to 0.08 mm². This corresponded to 0.0 to 6.92 percent area of PNS-type Schwann cell remyelination as a function of myelin pathology.
There was no statistical difference in the area of myelin pathology in the various treatment groups or compared to PBS or in the PNS-type Schwann cell remyelination between groups.

TABLE 8

| CLONE NAME* | DESCRIPTION OF IMMUNOFLUORESCENT STAINING OF NEONATAL RAT CEREBELLUM |
|---|---|
| CB2b-G8 | Identified large neuronal cell bodies in granular layer; small round cell bodies in the molecular layer; fibrous astrocytes in the central white matter. |
| CB2e-C2 | Weak label of Purkinje cell bodies; small processed cells, of oligodendrocyte and microglial morphology, and astrocytes in central white matter and granular layer. |
| CB2i-E12 | Strong label of Purkinje cell bodies, dendritic arbors and small round cells in molecular layer; nearly confluent label of granular layer; fibrous astrocytes in central white matter. |
| CB2i-E7 | labels Purkinje cells; cells in granular layer; central white matter in the folia; oligodendrocytes; astrocyte cytoskeleton and microglial cells |
| CB2i-G2 | Strong fibrous astrocyte label in central white matter tracts; identifies Purkinje cell bodies; punctate label over granular layer; small cell bodies in molecular layer. |
| CB2L-H1 | Strong label of glial cell bodies in central white matter and Purkinje cell bodies; weaker label of dendritic arbors; very pronounced small cel bodies in molecular layer. |
| MSI 10-E10 | Strong label of fibrous central white matter tracts, similar to that observed using anti-glycolipid or anti-microglial antibodies. |
| MSI 16-E6 | Strong label of Purkinje cell bodies; weaker dendritic arbors; nearly confluent label of small cells in granular layer; central white matter nearly unlabeled. |
| MSI 17-A2 | Strong label of small round cells in molecular layer and Purkinje cell bodies; diffuse label of granular layer; unlabeled central white matter. |
| MSI 19-C11 | Fibrous appearance to central white matter with many cells of oligodendrocyte morphology; punctate surface label over most of tissue, but concentrated over presumptive cell bodies. |
| MSI 19-E5 | Extra cellular matrix-like label of molecular layer; strong fibrous label of central white matter, identifying many individual glial cells. |
| AKJR4 | Identifies all neuronal cell bodies in granular layer; small round cell bodies in central white matter and molecular layer. |
| MSI 19D10 | Binds strongly to cells of the granular layer and to Purkinje cells and their dendritic arbors, in addition to weakly identifying white matter and astrocytes. |
| MSI 20H10 | Binds to central white matter, the granular and molecular layer and Purkinje cells with varying degrees of intensity. |

TABLE 8-continued

| CLONE NAME* | DESCRIPTION OF IMMUNOFLUORESCENT STAINING OF NEONATAL RAT CEREBELLUM |
|---|---|
| MSI 17E11 | Binds in a punctate manner to only a few glial-appearing cells at the surface of the brain slice. |
| sHIgM1 | Binds the cytoskeleton of astrocytes overlying the central white matter of the folia. |
| sHIgM2 | Binds to cells of the granular layer and to fibers traversing the central white matter of the folia. |
| sHIgM12 | Binds to lend a spongy appearance to the central white matter of the folia, and a uniform label over the molecular layer, reminiscent of an extracellular matrix molecule. |
| sHIgM14 | Binds well to cells of the granular layer and Purkinje cells located at the surface of the slice, while the central white matter of the folia is largely devoid of label. |
| sHIgM22 | Binds well to the cytoskeleton of damaged astrocytes overlying the central white matter of the folia, Purkinje cells and their dendritic arborizations. and to small round cells in the molecular layer, weakly labels surface of granular cells. |
| sHIgM26 | Binds to oligodendrocyte-appearing cells and fibrous white matter. |
| sHIgM29 | Binds weakly to many structures in the cerebellum with intensity just above background except for a small population of neurons in the granular and molecular layer. Axon extensions over 100 µm are clearly delineated. |
| sHIgM30 | No binding to unfixed cerebellum |
| sHIgM31 | Binds predominantly to the granular layer, with little binding to the white matter, Purkinje cells or astrocytes. |
| sHIgM32 | Binds to type 2 astrocyte-appearing cells. |
| sHIgM42 | Binds in a fibrous pattern to the entire folia, molecular and granular layers and white matter. |
| sHIgM46 | Binds in a fibrous pattern to the granular layer and white matter. The Purkinje cells are well defined. |
| sHIgM50 | Binds predominantly to the granular layer with little binding to the white matter, Purkinje cells or astrocytes. |
| sHIgM51 | Binds to small cells similar to microglia in molecular and granular layers. |

Of the 96 human EBV B-cell clones generated, 60 produced IgM antibody t a concentration of 2 µg/ml or greater. Of these, 11 were found to strongly bind to murine cerebellum on a consistent basis. Another 10 bound to murine cerebellum weakly or inconsistently, while 39 did not bind at all. Pictures of the immunofluorescent staining of the consistently strongly staining antibodies listed above as well as four representative negative clones (CB2g-E10, CB2g-F11, CB2I-F10, MSI24-D6) are included.
*CB: clones generated from human umbilical cord blood; MSI: clones generated from the peripheral blood of multiple sclerosis patients; AKJR: clones generated from the peripheral blood of rheumatoid arthritis patients.

TABLE 9

Oligodendrocyte Binding

| Antibody | Binding to Oligodendrocyte |
|---|---|
| MSI 17 A.2 | negative |
| MSI 19C11 | negative |
| MSI 19E5 | labels oligodendrocyte of mature morphology |
| AKJR 4 | negative |
| MSI 19O10 | labels some oligodendrocyte of mature morphology |
| MSI 20H10 | not tested |
| MSI 17E11 | not tested |
| sHIgM 1 | no reactivity to surface antigens |
| SHIGM 2 | no reactivity to surface antigens |
| SHIGM 12 | presumptive oligodendrocyte progenitors prior to sulfortide expression |
| SHIGM 14 | label of mature multi-processed oligodendrocyte |
| SHIGM 22 | labels mature stages of oligodendrocyte and process extensions |
| SHIGM 26 | no reactivity to surface antigens |
| SHIGM 29 | no reactivity to surface antigens |
| SHIGM 30 | no reactivity to surface antigens |
| poly hIgG | negative on surface |
| poly hIgm | subset of mature oligodendrocyte |
| CB2b G8 | labels oligodendrocytes (human) of mature morphology |
| CB2e C2 | negative |
| CB2i E7 | labels oligodendrocytes of mature morphology |
| CB2i E12 | negative |
| CB2i G2 | negative |
| CB2L H1 | negative |
| MSI 10E10 | negative |
| MSI 16E6 | negative |
| sHIgM31 | No binding to Oligodendrocyte |
| sHIgM32 | No binding to Oligodendrocyte |
| sHIgM42 | Binds to mature stages of oligodendrocyte and faintly to underlying astrocytes. |
| sHIgM46 | Strongly binds to both mature and immature stages of oligodendrocytes with punctate label. |
| sHIgM50 | Weak punctate label of subset of mature stages of oligodendrocyte |
| sHIgM51 | Binds to mature stages of oligodendrocytes and faintly to underlying astrocytes. |

Monoclonal Antibodies that Promote Remyelination Cause $Ca^{2+}$ Flux in Glial Cells in Culture.

Figure 39:
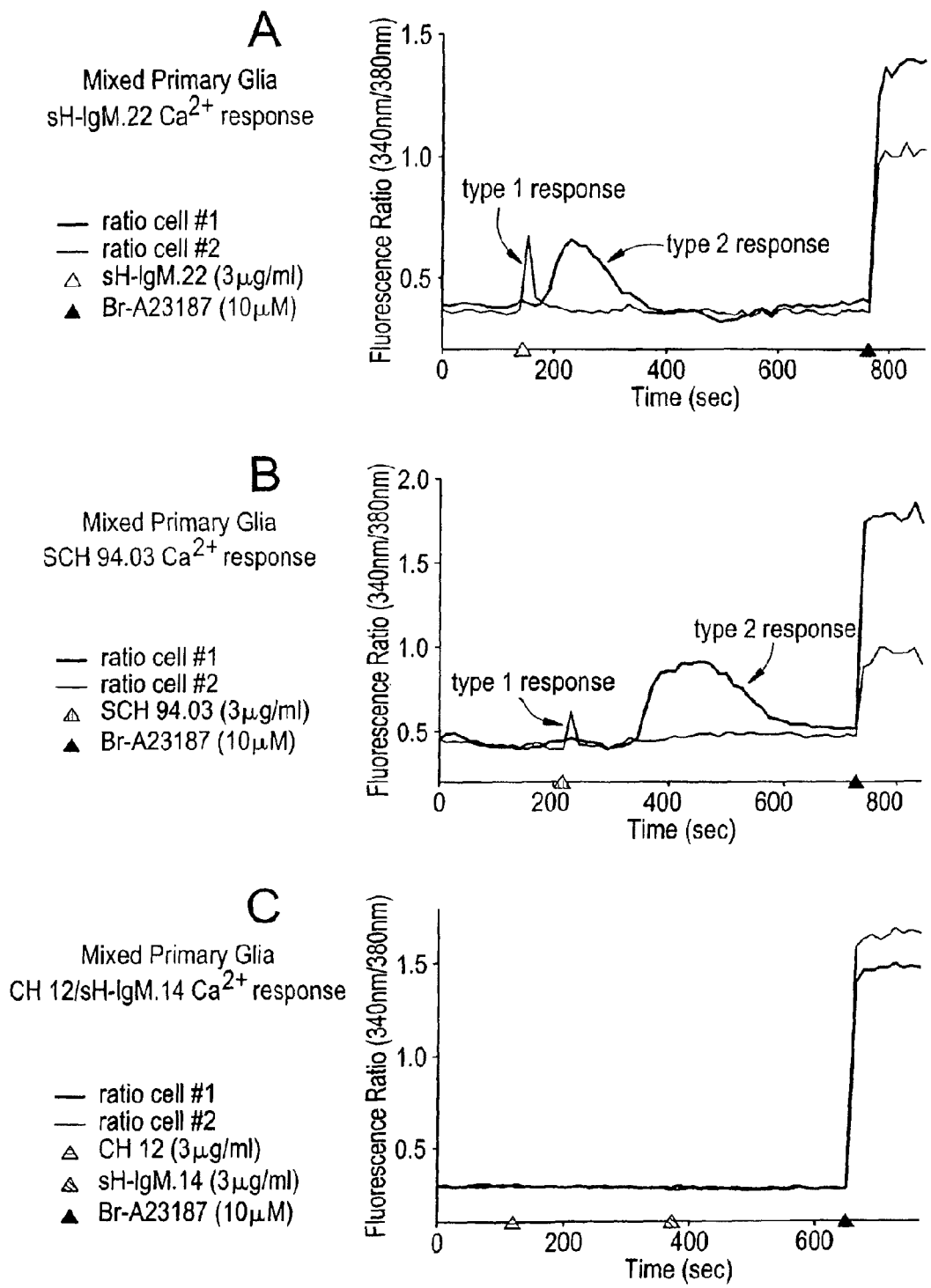
FIG. 39A-39C demonstrates that monoclonal antibodies that promote remyelination cause $Ca^{2+}$ flux in glial cells in culture. The three panels demonstrate glial $Ca^{2+}$ responses to four different antibodies: two which promote remyelination in vivo, sHIgM22 (A) and SCH94.03 (B), and two which do not promote remyelination, sHIgM 14 (panel C) and CH12 (C). Cells which responded exhibited one of two different types of calcium spikes, either a fast spike immediately upon addition of antibody (A & B, red traces), or a broader spike which appears with a short delay after addition of antibody (A & B, black traces). The small colored triangles on the time axis represent the moment antibody (or ionophore) were added. Antibodies sHIgM22 and SCH94.03 elicited both types of responses but from different subsets of glial cells (panels A & B). Antibodies sHIgM14 and CH12, which do not promote remyelination in vivo, were not observed to cause calcium flux in cultured glia (panel C). At the end of each experiment the calcium ionophore Br-A23187 was added to each culture as a control for cellular integrity. Addition of ionophore to viable cells causes a large $Ca^{2+}$ influx which is apparent in each of the experiments that are depicted.
Figure 41:
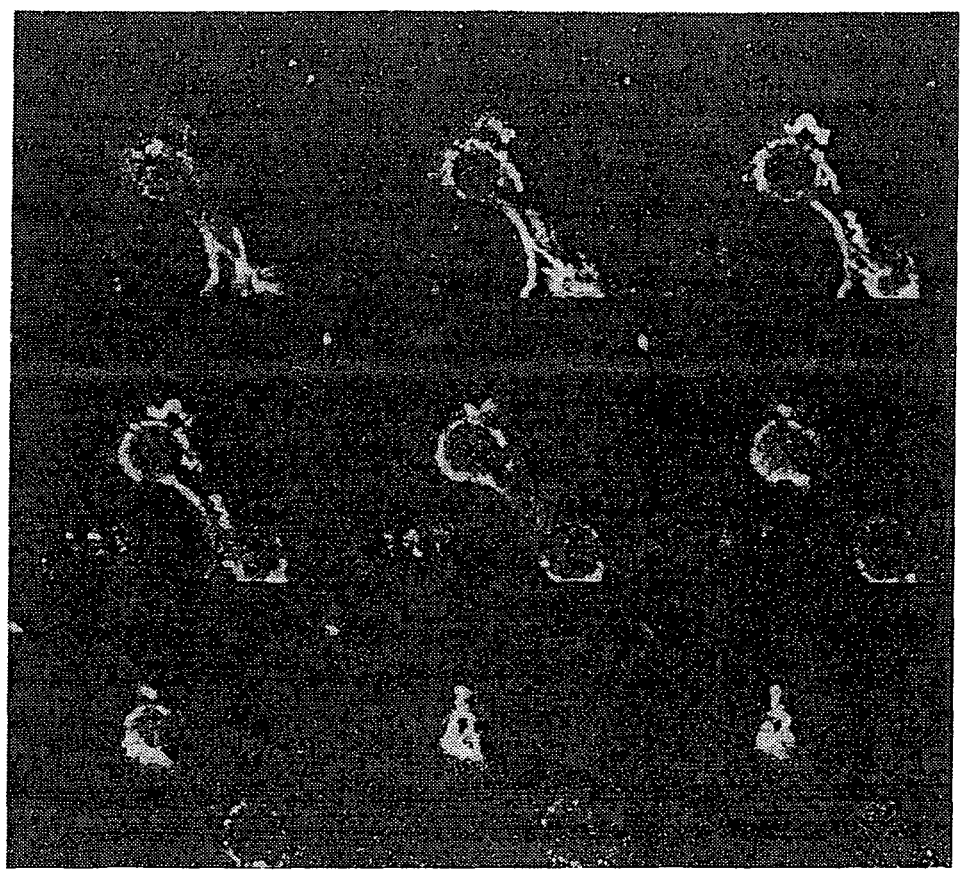
FIG. 41 demonstrates that mouse monoclonal antibody SCH94.03 binds to the surface of granule cells in culture. Indirect immunofluorescent labeling and confocal serial imaging demonstrates that the mouse monoclonal antibody SCH94.03 binds only to the surface in granule cell neurons in culture. The series of images were taken 1 um apart and clearly show the concentric circular rings expected of an externally labeled spherical cell body with process extensions.

The response of cultured glial cells to physiological concentrations of remyelination promoting antibodies suggests that these antibodies may have direct effects on the biochemistry of glial cells through the regulation of cellular calcium flux. This effect may represent an important aspect of the molecular mechanism of antibody induced remyelination. FIG. 39 demonstrates glial $Ca^{2+}$ responses to four different antibodies. Two of these antibodies, sHIgM22 and SCH94.03, promote remyelination in vivo, and two, sHIgM 14 and CH12, do not promote remyelination. Cells which responded to antibody, exhibited one of two different types of calcium spikes. Some cells responded with a rapid onset spike of short duration (fast response) as shown by the red traces in panels A and B. A separate subset of cells responded with a slower onset, longer duration spike (slow response) as demonstrated by the black traces in Panels A and B. The antibodies sHIgM22 and SCH94.03 each elicited both types of responses but always from different individual glial cells. These qualitatively different responses clearly suggest two distinct molecular modes of action on distinct subsets of cells. A response to antibody (either the fast or the slow response) was observed in 30 of 251 cells after treatment with sHMab22 and in 36 of 251 cells treated with SCH 94.03. Antibodies which do not promote remyelination in vivo (sHIgM 14 & CH12) were not observed to cause calcium flux in cultured glia (panel C). A total of 203 cells were examined for each of these antibodies.

Human Monoclonal Antibodies Bind to Primary Neurons.

Many of the sHIgMs and ebvHIgMs bind to neuronal populations in brain slices. However, many of the neurons bound are at the surface of the slice, presenting the likelihood that the antibodies may bind internal epitopes inside damaged neurons. Positive binding HIgMs were tested for binding to live rat granule cells in culture. FIG. 40 demonstrates the binding of two sHIgMs to live neurons. sHIgM 12 binds to both axonal and dendritic extensions of the neurons (FIG. 40A), while ebvHIgm CB2iE12 binds exclusively to the exterior of the granule cells membrane and proximal axon extensions (FIG. 40B). These reactivities were verified by double label immunocytochemistry by c-labeling human antibodies positive neurons with anti-neurofilament and anti-microtublue associated protein 2 antibodies (data not shown).

Of particular interest to our laboratory is the possibility that demyelination predisposes axons to immune-mediated injury and corresponding neurologic deficits. In our recent analysis of β2 microglobulin deficient mice (β2 m –/–), we demonstrated that in the absence of class I MHC, TMEV infected mice develop large demyelinating lesions but fail to develop clinical deficits. The mice demonstrated a relative preservation of axons with increased sodium channel densities and remyelination of spinal cord white matter. Axonal preservation appears to be essential for the maintenance of neurologic function. The observation that human antibodies can bind specifically to neurons presents another potential avenue for antibodies mediate repair of the CNS. Certain antibodies may be able to potentiate remyelination through action on the neuron. The repair of CNS lesions may be potentiated by monoclonal antibodies by many possible scenerios. 1) increasing the adhesive bonds between neurons and oligodendrocytes. 2) direct cell stimulation of neuron to upregulate trophic factors and attract oligodendrocyte progenitors the area of bare axons. 3) neuroprotection of axons by antibody blockade of leaky ion channels on bare axons. 4) protection of bare axons from recognition by activated and destructive immune cells.

Materials and Methods

A. Monoclonal Antibody Production, Characterization, Screening and Purification:
Sources of Abs and Ab Purification.

Normal human IgM was purified from pooled plasma of over 2,500 healthy donors by modified Deutsch-Kistler-Nitschmann's ethanol fractionation procedure followed by octanoic acid precipitation and two successive ion-exchange chromatography steps as previously described (Hurez et al., 1997). The purity of IgM was over 90% as confirmed by ELISA and SDS-polyacrylamide gel electrophoresis (PAGE). Pooled human IgG from healthy donors used clinically as IVIg was purchased from Miles Inc. (Elkhart, Ind.). Samples were obtained from the dysproteinase clinic under the direction of Dr. Robert A. Kyle, Mayo Clinic. The samples of sera came from patients with a wide variety of conditions characterized by a monoclonal IgG or IgM spike in the serum, including Waldenstrom's macroglobulinemia, multiple myeloma, lymphoma, benign monoclonal gammopathy.

Generation of Epstein-Barr Virus (EBV) Immortalized B Cell Lines

The B95-8 marmoset cell line was obtained from ATCC (#CRL 1612) for the growth and isolation of EBV. Cells are seeded at $1\times10^6$ cells/ml in complete RPMI-10 medium followed by 3 days of incubation in a humidified, 37° C., 5% $CO_2$ incubator. The cells are harvested and the supernatant is cleared by centrifugation for 10 minutes at 300×g and 4° C. The EBV-containing supernatant is passed through a 0.45 mm filter and the flow through is collected and stored at −130° C. (liquid nitrogen). This EBV-supernatant generally contains $10^2$-$10^3$ transforming units/ml.

Peripheral B cells for immortalization were collected from the blood of normal adults (NA), adults with rheumatiod arthritis (AKJR), adults with multiple sclerosis (MS), and from fetal cord blood (CB). Heparinized blood (15 ml) is diluted 1:2 in phosphate buffered saline (PBS) and 12 ml of this dilution is underlayered with 12 ml of Ficoll-Hypaque in a 50 ml centrifuge tube. The tube is centrifuged for 8 minutes at 1500×g, at room temperature, and the buffy coat interface is removed and transferred to a new 50 ml centrifuge tube. The cells are washed by centrifugation (15 minutes, 300×g, room temperature), once in PBS and then twice in Hank's balanced saline solution (HBSS). The cells are then resuspended in 2-5 ml of complete RPMI-10 medium and counted.

The cells are diluted to $4\times10^6$ cells/ml in complete RPMI-10 medium, 2.5 ml ($1\times10^7$ cells) are transferred to a 50 ml centrifuge tube and 2.5 ml of EBV-supernatant is added. The tube is incubated for two hours in a 37° C. water bath followed by the addition of 5 ml of complete RPMI-10 medium containing 1 µg/ml cyclosporin A. The 10 ml of cell suspension is then transferred to a 25 $cm^2$ tissue culture flask and cultured for 3 weeks in a humidified, 37° C., 5% $CO_2$ incubator. After 3 weeks, an aliquot of the culture is cryopreserved and the remainder is expanded and clonal cell lines are isolated by limiting dilution.

Purification of IgM Antibodies—

Human serum samples used for study were chosen solely by the presence of a high IgM peak in the Ig chromatogram. Samples were obtained from the dysproteinase clinic under the direction of Dr. Robert A. Kyle, Mayo Clinic. The samples of sera came from patients with a wide variety of conditions characterized by a monoclonal IgG or IgM spike in the serum, including Waldenstrom's macroglobulinemia, multiple myeloma, lymphoma, benign monoclonal gammopathy. Patients sera were dialyzed against deionized water during three days. Euglobulinic precipitates were collected by centrifugation (14000 rpm/30 min.) and dissolved in PBS. Solutions were cleared by centrifugation (14000 rpm/30 min.) and chromatographed on Superose 6 column (Pharmacia, Upsalla) equilibrated with PBS. Fractions corresponding to IgM were pooled and analyzed by reducing SDS PAGE (12% gel). IgM concentrations were determined by staining the SDS gels with Cypro Orange (Molecular Probes, Eugene) and subsequent scanning on Storm 840 (Molecular Dynamics). Monoclonal IgM (Sigma, St Louis) were used as a standard for concentration measuring. IgM solutions were sterilized by filtration through 0.22 filters.

Characterization of Antigen Binding Specificity

ELISA against mouse spinal cord homogenate (SCH) was used as an assay for the preliminary screening of antibodies prior to in vivo testing for ability to promote remyelination. To further characterize the polyreactivity and antigenic specificity of selected antibodies, an ELISA against a standard panel of protein and chemical antigens is used, as well as analysis of the antibody staining patterns in sectioned neural tissues and on cultured oligodendrocytes.

ELISA Assay

Antibodies were screened for their reactivity to mouse spinal cord homogenate (SCH). SCH at 0.01 mg/ml coated onto polystyrene microtiter plates in 0.1 M carbonate buffer, pH 9.5, for 18 hours at 4° C., and then washed 3× with PBS. Coated plates were blocked with phosphate buffered saline (PBS) containing 1% BSA for 1 hour at room temperature, and then incubated with antibody diluted to 10 µg/ml in blocking buffer for 2-24 hours at room temperature. Plates are washed three times with PBS/0.05% Tween 20 and bound antibody is then detected with biotinylated goat anti-IgM or IgG followed by alkaline phosphatase conjugated to streptavidin, with p-nitrophenylphosphate as chromogenic substrate. Absorbance of the reaction is measured at 405 nm.

Antibodies are also tested for their reactivity to a panel of protein antigens (human erythrocyte spectrin, bovine myosin heavy chain, mouse hemoglobin, bovine transferrin, bovine vimentin, chicken egg lysozyme, rabbit actin, rabbit myelin basic protein, keyhole limpet hemocyanin) and bovine serum albumin (BSA)-coupled chemical haptens (4-hydroxy-3-nitrophenyl acetyl (NP), phenyloxazolone (PhoX), axophenyl-trimethylammonium (TMA), fluorescein (FL), azophenylphosphoryl-choline (PC), azophenylarsonate (Ars), trinitrophenyl acetyl (TNP)). Proteins are used at 5 µg/ml and BSA-coupled haptens are used at 2 µM hapten concentration. Antigens are coated onto polystyrene microtiter plates, reacted with antibody, and the bound antibodies are detected as described for SCH ELISA.

Tissue Section Staining

Rat pup cerebellum is used as a source of neural tissue for the comparison of antibody staining patterns. Fresh, unfixed, tissue is embedded in 2% low melting point agarose and cut into 300 µM saggital sections on a McIlwain Tissue Chopper. Sections are not fixed and are kept at 4° C. or on ice throughout the rest of the procedure. Slices are transferred into 48-well tissue culture plates in HEPES buffered Earles balanced salts (E/H) and blocked for 30 minutes in E/H with 5% BSA. Sections are stained with primary antibody at 10 µg/ml in E/H with 1% BSA for 2-12 hours at 4° C. Sections are washed 3× in E/H and incubated with an appropriate fluorescent secondary antibody in E/H with 1% BSA for 2 hours. Sections are washed 3× in E/H, 1× in PBS and then post-fixed with 4% paraformaldehyde for 30 minutes. Sections are washed 3× with PBS and mounted in 90% glycerin with 2.5% 1,4-diazabicyclo[2.2.2]octane to prevent photobleaching.

Cultured Oligodendrocyte Staining

Cerebral hemispheres are dissected from P0-P3 Sprague-Dawley rats and the meninges and blood vessels are removed. The tissue is minced and transferred to a 0.25% trypsin solution in calcium and magnesium free HEPES buffered Earles salts (E/H), 10 ml final volume per brain. The tissue is shaken at low rpm at 37° C. for 30 minutes and then heat inactivated fetal calf serum is then added to final a final concentration of 10% to inactivate trypsin. $MgSO_4$ and DNAse I are added (to 0.1% and 20 µg/ml respectively) and the tissue is shaken for an additional 5 minutes. The cells are washed by centrfugation and resuspended in E/H with DNase I and dissociated by trituration through a glass pipette. Large debris is allowed to settle and the overlying cellular supernatant is washed by centrifugation through a 4% BSA cushion in E/H. The cell pellet is resuspended in culture medium and the cells are plated at $2.5 \times 10^5$ cells per $cm^2$ on poly-D-lysine culture plates. Plates are shaken to isolate for oligodendrocyte progenitors at day 9-12. A complete phenotypic spread of oligodendrocytes is present in the culture at this time with progenitors present as a top layer in clusters of recently divided cells. Oligodendrocyte progenitors are isolated by gently shaking the cultures, replated on poly-lysine coated cover slips and stimulated to differentiate by removal of growth factors from the culture medium.

Live surface staining is performed at 4° C. for 15 minutes on unfixed cells after blocking with PBS and 5% BSA. Intracellular staining is performed after fixation with 4% paraformaldehyde and permeabilization with 0.1% Triton X-100. Primary antibodies are detected with fluorescein-conjugated second antibodies. Coverslips are mounted in 90% glycerin with 2.5% 1,4-diazabicyclo[2.2.2]octane to prevent photobleaching and viewed on an epifluorescent microscope.

Western Blotting

Purified TMEV (Njenga et al., 1996) was separated by SDS-PAGE on 15% acrylamide gels. Proteins were transferred to a nitrocellulose membrane by electroblotting. The membrane was blocked with Tris buffered saline containing 5% non-fat dry milk and 0.05% Tween 20 for 2 hours at room temperature. The membrane was incubated with pooled human IgM, pooled human IgG, IgMs from two patients with Waldenstrom's macroglobulinemia, and rabbit polyclonal anti-TMEV Ab (1:2000) (Njenga et al., 1996) for 4 hours at room temperature. All human Igs were used at the same concentration (10 ug/ml). Bound Igs were detected with biotinylated goat anti-human abs or biotinylated goat anti-rabbit abs (both from Jackson ImmunoResearch Laboratories, Inc., West Grove, Pa.) and alkaline phosphatase-conjugated streptavidin using 5-bromo-4-chloro-3-indolyl phosphate and nitro blue tetrazorium (BCIP/NBT).

B. Promotion of Remyelination Using Human Monoclonal Antibodies:

TMEV Induced Demyelination—For the production of TMEV induced demyelination, intracerebral virus injection is performed on 4-6 week old animals that are lightly anesthetized with metofane. Virus is injected using a 27 gauge needle with a Hamilton syringe that delivers a 10 µl volume which contains $2 \times 10^5$ PFU of the Daniel's strain of TMEV. Intracerebral injection results in greater than 98% incidence of chronic viral infection with demyelination. Chronically infected animals for remyelination experiments are generally 6-8 months post-infection.

Antibody Treatment Protocol

Animals with chronic demyelination receive intraperitoneal (IP) injections of purified antibodies in phosphate buffered saline. For TMEV infected animals the injection schedule consists of twice weekly injections of 50 µg in 100 ml. The duration of antibody treatment is five weeks (500 µg total dose). Animals are then sacrificed and spinal cord tissue is processed for morphological evaluation as described below. For each different antibody treatment, nine chronically infected, female SJL/J mice are injected with antibody. At the end of the treatment period, six of the animals are perfused and processed for morphometric quantitation of demyelination/remyelination and three are sacrificed for frozen tissue that is used for assessment of axonal integrity. Three separate treatment trials, with reproducible and consistent results, are required for any given antibody before the data is considered significant. PBS and isotype control groups are included as negative controls for each new antibody treatment experiment.

Morphological Evaluation of Demyelination/Remyelination

At the end of each experiment the spinal cord of each animal will be assessed histologically. Mice are anesthetized with pentobarbital and perfused by intracardiac administration of fixative (phosphate buffered 4% formaldehyde with 1% glutaraldehyde, pH 7.4). Spinal cords are removed and sectioned coronally into 1 mm blocks, postfixed with osmium, and embedded in araldite. One micron-thick cross-sections are cut from each block and stained with 4% paraphenyldiamine. This technique is reproducible and allows consistent visualization of myelin sheaths in spinal cord white matter.

Demyelination and remyelination are quantified using a Zeiss digital analysis system (ZIDAS) and camera lucida (Miller and Rodriguez, 1995; Miller et al, 1994). For each mouse, ten spinal cord cross sections are examined which span the entire cord from the cervical to the proximal coccygeal spinal column regions. Total area of white matter, area of demyelination, and area of remyelination are determined for each section, and the areas from all ten sections analyzed for a specific mouse are added to provide total areas for each mouse. Areas of demyelination are characterized by large amounts of myelin debris, macrophages engulfing debris, cellular infiltration and naked axons. Oligodendrocyte remyelination is is characterized by areas of axons with abnormally thin myelin sheaths and the absence of Schwann cells. Statistical comparison of the extent of demyelination and remyelination is performed using the Student's t test.

Lysolecithin Induced Demyelination

For these experiments, 12 weeks old SJL/J mice are anesthetized with sodium pentobarbitol and a dorsal laminectomy is performed in the upper thoracic region of the spinal cord. A 34 gauge needle attached to a Hamilton syringe is used to inject 1 µml of a 1% solution of lysolecithin directly into the dorsolateral aspect of the cord. Animals are killed on day 21 post injection and the injected region of the spinal cord is removed and processed for morphological evaluation.

As a second model of demyelination, intraspinal injection of lysolecithin was used. Twelve-week-old SJL/J mice were anesthetized by intraperitoneal injection of sodium pentobarbitol (0.08 mg/g). Dorsal laminectomies were performed on the upper thoracic region of the spinal cord and lysolecithin (L-a-lysophosphatidylcholine) (Sigma, St. Louis, Mo.) was injected as described previously (Pavelko et al., 1998). Briefly, a 34 gauge needle attached to a Hamilton syringe mounted on a stereotactic micromanipulator was used to inject 1% solution of lysolecithin in sterile PBS (pH 7.4) with Evan's blue added as a marker. The needle was inserted into the dorsolateral part of the spinal cord, 1 ul of lysolecithin solution was injected, and then the needle was slowly withdrawn. The wound was sutured in two layers, and mice were allowed to recover. The day of lysolecithin injection was designated day 0.

Seven days after lysolecithin injection, mice were treated with bolus intraperitoneal injection of human IgM or human IgG (1 mg/injection each). Control mice were treated with bolus intraperitoneal injection of PBS. Three weeks and five weeks after the lysolecithin injection, mice were sacrificed and one (m thick sections were prepared as described in the previous section. The araldite block showing the largest lysolecithin-induced demyelination lesion was used for quantitative analysis. The total area of the lesion was quantitated using a Zeiss interactive digital analysis system. The total number of remyelinated fibers was quantitated using a Nikon microscope/computer analysis system. The data was expressed as number of remyelinated axons/mm$^2$ of lesion.

Lysolecithin treated mice are given 50 μg IP injections of antibody on days 0, 3, 7, 10, 14, and 17 after lysolecithin injection. Animals are killed on day 21 after lysolecithin injection. We routinely find statistically significant treatment effects with experimental treatment groups of ten animals. PBS and isotype control groups serve as negative controls.

C. Mechanism of Action of Remyelination Promoting Human Monoclonal Antibodies:

Ca2+ Ratiometric Fluorescent Analysis

Mixed primary glial cultures, from day 2-4 postnatal rat pups, are seeded onto poly-D-lysine coated coverslips and cultured for 5-7 days prior to analysis. Fura-2-AM and Plutonic F-127 are mixed 1:1 and added to DMEM (serum free) to yield 4 mM Fura-2 in solution (Fura-2 loading media).

Coverslips with cells are washed once with DMEM and then incubated in Fura-2 loading media for 60 minutes at 37° C. The cells are then washed 4 times in DMEM. The coverslip is mounted in a recording chamber on an inverted fluorescence microscope connected to a computer controlled data acquisition system which captures digital images of 510 nm fluorescence emission at two different wavelengths of excitation: 340 nm and 380 nm. For each recording, digital images are captured from an individual cell, at 10 second intervals over 600-800 seconds. Relative internal Ca$^{2+}$ concentration is calculated as the ratio of 340 nm/380 nm fluorescence. All recordings are made at 37° C. in 1 ml DMEM.

Test antibody is introduced by adding 50 ml of concentrated (60 mg/ml in PBS) antibody stock solution to the recording chamber to yield a final concentration of 3 mg/ml. After recording the effects of the addition of test antibodies, 50 ml of of a calcium ionophore stock (200 mM Br-A23187 in PBS) is added to the recording chamber to yield a final concentration of 10 mM.

Discussion

Normal human immunoglobulin (Ig), especially IgG, administered intravenously (IVIg) has been shown to be effective in treating various autoimmune neurological diseases including Guillain-Barré syndrome (van der Mech et al., 1992), chronic idiopathic demyelinating neuropathies (van Doom et al., 1991), multifocal motor neuropathy (Chaudhry et al., 1993), polymyositis (Cherin et al., 1991), and myasthenia gravis (Edan and Landgraf, 1994). The mechanisms by which administered Ig acts is unclear. Some investigators have also suggested that this therapy may be effective in T cell-mediated autoimmune CNS diseases such as multiple sclerosis (MS)(van Engelen et al., 1992; Achiron et al., 1992; Fazekas et al., 1997: Achiron et al., 1998; Sorensen et al., 1998).

Theiler's murine encephalomyelitis virus (TMEV)-induced demyelination has been used as a model to develop novel treatments for MS. When this picornavirus is inoculated intracerebrally in susceptible strains of mice, TMEV induces immune-mediated progressive CNS demyelination which is clinically and pathologically similar to MS. We showed previously that multiple mouse IgMκ monoclonal antibodies (mAbs) directed against normal CNS antigens promote CNS remyelination following TMEV-induced demyelination (Miller et al., 1994; Asakura et al., 1998). The prototypic antibody, designated SCH94.03, was also shown to enhance the rate of spontaneous CNS remyelination following lysolecithin-induced demyelination (Pavelko, et al., 1980) and decrease the severity and frequency of relapses in a relapsing model of experimental autoimmune encephalomyelitis (EAE) (31). The common features of these remyelinating-promoting IgMκ mAbs are that they react to surface antigens on oligodendrocytes and have phenotypic and genotypic features of natural autoantibodies (Miller and Rodriguez, 1995; Asakura et al., 1998). Natural autoantibodies have wide spectrum of reactivities with self and non-self antigens. These antibodies represent a major fraction of the normal circulating IgM repertoire. Though their physiological function is unknown, the beneficial effects of natural autoantibodies have been reported in various autoimmune disease models including myasthenia gravis, systemic lupus erythmatosus, and non-obese diabetes (Sundblad et al., 1989; Hentati et al., 1994; Andersson et al., 1991, 1994).

IVIg is purified from human plasma pools of 3000 to 10000 healthy donors and contains more than 95% IgG and a negligible amounts of IgM (Dalakas, 1997). Based on our previous observations we hypothesized that human IgM from healthy donors, which is enriched in natural autoantibodies, would be a more effective treatment for demyelinating disease than conventional IVIg. To test this hypothesis we treated chronically TMEV-infected mice with pooled human IgM obtained from over 2,500 healthy donors and examined for CNS remyelination.

In this study we demonstrated that treatment with pooled human IgM from healthy donors resulted in significantly enhanced remyelination by oligodendrocytes in TMEV-infected mice as compared to the treatment with pooled human IgG, or PBS. We confirmed by ELISA and immunocytochemistry that pooled human IgM contains a population of polyreactive natural autoantibodies to proteins and haptens. This is the first demonstration that polyclonal human IgM promotes CNS remyelination in models of demyelinating disease, thus raising the possibility that IgM from healthy donors may be more effective to treat human inflammatory demyelinating diseases than conventional pooled human IgG.

To our knowledge pooled human IgM has never been tested in MS, even though it has been shown to be safe and effective in severe infections and immunodeficiency.

Natural autoantibodies are a major fraction of the IgM repertoire. In mice natural autoantibodies are exclusively IgM, whereas in humans natural autoantibodies are also of the IgG isotypes although with much less frequency. To date, the only mAbs which have been shown to enhance remyelination have been oligodendrocyte-reactive IgMκ mAbs, which have genotypic and phenotypic features of natural autoantibodies, (Asakura et al. 1998).

In conclusion, we have demonstrated that a logical screening technique can be used to identify human monoclonal antibodies that have the potential to promote remyelination in model systems of demyelination. Properties of the antibody, such as CNS specificity, the ability to recognize antigens present on oligodendrocytes and a strong binding to spinal cord homogenate, combined, can predict which antibodies are the best candidates to test for remyelination in vivo. Many of these monoclonal antibodies bind well to human CNS, giving reason to hope that some may be useful as a therapy to successfully treat human disease.

The following is an alphabetical list of the references referred to in this Example.

Asakura, K., D. J. Miller, K. Murray, R. Bansal, S. E. Pfeiffer, and M. Rodriguez. 1996. Monoclonal autoantibody SCH94.03, which promotes central nervous system remyelination, recognizes an antigen on the surface of oligodendrocytes. *J Neurosci Res* 43:273-281.

Asakura, K., D. J. Miller, L. R. Pease, and M. Rodriguez. 1998. Targeting of IgMkappa antibodies to oligodendrocytes promotes CNS remyelination. *Journal of Neuroscience* 18:7700-7708.

Asakura, K., D. J. Miller, R. J. Pogulis, L. R. Pease, and M. Rodriguez. 1996. Oligodendrocyte-reactive O1, O4, and HNK1 monoclonal antibodies are encoded by germline immunoglobulin genes. *Mol. Brain Res*. 34:282-293.

Blakemore, W. F., R. A. Eames, K. J. Smith, and W. I. McDonald. 1977. Remyelination in the spinal cord of the cat following intraspinal injections of lysolecithin. *J. Neurol. Sci*. 33:31-43.

Crang, A. J. and W. F. Blakemore. 1991. Remyelination of demyelinated rat axons by transplanted mouse oligodendrocytes. *GLIA*. 4:305-313.

Dubois-Dalcq, M. and R. Armstrong. 1990. The cellular and molecular events of central nervous system remyelination. *Bioessays* 12:569-576.

Franklin, R. J., A. J. Crang, and W. F. Blakemore. 1991. Transplanted type-1 astrocytes facilitate repair of demyelinating lesions by host oligodendrocytes in adult rat spinal cord. *J. Neurocytol*. 20:420-430.

Groves, A. K., S. C. Barnett, R. J. Franklin, A. J. Crang, M. Mayer, W. F. Blakemore, and M. Noble. 1993. Repair of demyelinated lesions by transplantation of purified O-2A progenitor cells *Nature*. 362:453-455.

Jeffery, N. D. and W. F. Blakemore. 1995. Remyelination of mouse spinal cord axons demyelinated by local injection of lysolecithin. *Journal of Neurocytology* 24:775-781.

Lang, W., M. Rodriguez, V. A. Lennon, and P. W. Lampert. 1984. Demyelination and remyelination in murine viral encephalomyelitis. *Ann. N.Y. Acad. Sci*. 436:98-102.

Ludwin, S. K. 1981. Pathology of demyelination and remyelination. *Adv. Neurol*. 31:123-168.

Ludwin, S. K. 1987. Remyelination in demyelinating diseases of the central nervous system. *Crit. Rev. Neurobiol*. 3:1-28.

Ludwin, S. K. 1989. Evolving concepts and issues in remyelination. *Dev. Neurosci*. 11:140-148.

Miller, D. J. and M. Rodriguez. 1995. Spontaneous and induced remyelination in multiple sclerosis and the Theiler's virus model of central nervous system demyelination. [Review] [119 refs]. *Microscopy Research & Technique* 32:230-245.

Miller, D. J., K. Asakura, and M. Rodriguez. 1995. Experimental strategies to promote central nervous system remyelination in multiple sclerosis: insights gained from the Theiler's virus model system. *J Neurosci Res*. 41:291-296.

Miller, D. J., K. S. Sanborn, J. A. Katzmann, and M. Rodriguez. 1994. Monoclonal autoantibodies promote central nervous system repair in an animal model of multiple sclerosis. *J Neurosci* 14:6230-6238.

Miller, D. J. and M. Rodriguez. 1995. A monoclonal autoantibody that promotes central nervous system remyelination in a model of multiple sclerosis is a natural autoantibody encoded by germline immunoglobulin genes. *J Immunol* 154:2460-2469.

Miller, D. J., C. Rivera-Quinones, M. K. Njenga, J. Leibowitz, and M. Rodriguez. 1995. Spontaneous CNS remyelination in beta(2) microglobulin-deficient mice following virus-induced demyelination. *J Neurosci* 1545:8345-8352.

Miller, D. J., J. J. Bright, S. Sriram, and M. Rodriguez. 1997. Successful treatment of established relapsing experimental autoimmune encephalomyelitis in mice with a monclonal natural autoantibody. *Journal of Neuroimmunology* 75:204-209.

Prineas, J. W. and F. Connell. 1979. Remyelination in multiple sclerosis. *Ann. Neurol*. 5:22-31.

Prineas, J. W., R. O. Barnard, E. E. Kwon, L. R. Sharer, and E. S. Cho. 1993. Multiple sclerosis: remyelination of nascent lesions. *Ann Neurol* 33:137-151.

Raine, C. S. and E. Wu. 1993. Multiple sclerosis: remyelination in acute lesions. *J. Neuropathol. Exp. Neurol*. 52:199-204.

Rivera-Quinones, C., D. B. McGavern, J. D. Schmelzer, S. F. Hunter, P. A. Low, and M. Rodriguez. 1998. Absence of neurological deficits following extensive demyelination in a class I-deficient murine model of multiple sclerosis. *Nature Med* 4:187-193.

Rodriguez, M. and B. Scheithauer. 1994. Ultrastructure of multiple sclerosis. *Ultrastruct Pathol* 18:3-13.

Rodriguez, M., E. Oleszak, and J. Leibowitz. 1987. Theiler's murine encephalomyelitis: a model of demyelination and persistence of virus. *Crit. Rev. Immunol*. 7:325-365.

Rodriguez, M., V. A. Lennon, E. N. Benveniste, and J. E. Merrill. 1987. Remyelination by oligodendrocytes stimulated by antiserum to spinal cord. *J. Neuropathol. Exp. Neural*. 46:84-95.

Rodriguez, M. and V. A. Lennon. 1990. Immunoglobulins promote remyelination in the central nervous system. *Ann. Neurol*. 27:12-17.

Rodriguez, M. 1991. Immunoglobulins stimulate central nervous system remyelination: electron microscopic and morphometric analysis of proliferating cells. *Lab Invest*. 64:358-370.

Smith, K. J., W. F. Blakemore, and W. I. McDonald. 1981. The restoration of conduction by central remyelination. *Brain*. 104:383-404.

Traugott, U., S. H. Stone, and C. S. Raine. 1982. Chronic relapsing experimental autoimmune encephalomyelitis. treatment with combinations of myelin components promotes clinical and structural recovery. *J. Neurol. Sci*. 56:65-73.

Example 6

Screening for Epitope Mimic Peptides with an Autoantibody

In this example, the identification and preparation of peptides which mimic the recognized antigens, or portions thereof, corresponding to the autoantibodies of the invention is described. As described earlier herein, such peptides could serve as vaccines to elicit enhanced immune response to conditions indicated to be favorably responsive to increased circulating levels of antibodies.

An exemplary strategy for the identification of peptide mimics would be to search for peptides specifically binding, for example to the HNK-1 antibody, a mouse autoantibody demonstrated to be capable of inducing remyelination. The HNK-1 epitope antigen is a carbohydrate. The HNK-1 epitope is expressed predominantly on glycolipids and glycoproteins from nervous tissue (McGarry et al., (1983) *Nature* 306:376-378; Ilyas et al., (1984) *Biochem. Biophys. Res. Comm.* 122:1206-1211; Kruse et al., (1984) *Nature* 31 1:153-155; Yuen et al., (1997) *J. Biol. Chem.* 272:8924-8931). The structure which reacts with HNK-1 antibody was first described by Chou and Jungalwala for the major antigenic glycolipid present in human peripheral nerve. The compostion, sugar linkage, configuration and position of the sulfate group, were characterised as sulfate-3 GlcA$\beta$ (1-3) Gal$\beta$ (1-4) GlcNAc$\beta$ (1-3) GalNAc$\beta$ (1-3) Gal$\beta$ (1-4) Glc$\beta$ (1-1)-ceramide for SGGL-1 and as sulfate-3 GlcA$\beta$ (1-3) Gal$\beta$ (1-4) GlcNAc$\beta$ (1-3) Gal$\beta$ (1-4) GlcNAc$\beta$ (1-3) Gal$\beta$ (1-4) Glc$\beta$ (1-1)-ceramide for SGGL-2. (Chou et al, 1986).

Screening phage-displayed random peptide libraries offers a rich source of molecular diversity and represents a powerful means of identifying peptide ligands that bind a receptor molecule of interest. Phage expressing binding peptides are selected by affinity purification with the target of interest. This system allows a large number of phage to be screened at one time. Since each infectious phage encodes a random sequence expressed on its surface, a particular phage, when recovered from an affinity matrix, can be amplified by another round of infection. Thus, selector molecules immobilized on a solid support can be used to select peptides that bind to them. This procedure reveals a number of peptides that bind to the selector and that often display a common consensus amino acid sequence. Biological amplification of selected ibrary members and sequencing allows the determination of the primary structure of the peptide(s).

Peptide ligand identified by phage display frequently interact with natural binding site(s) on the target molecule, and often resemble the target's natural ligand(s). Although this system has often been used to identify peptide epitopes recognized by antibodies, it has also been successfully used to find peptide mimics of carbohydrate molecules. Work directed towards using peptide mimics in place of carbohydrate antigens has been reviewed by Kieber-Emmons et al, 1998). The demonstrated ability of a peptide to mimic a carbohydrate determinant indicates that, although mimicry is accomplished using amino acids in place of sugars, the specificity pattern can be reproduced.

A first screening was done with the amplified starting library of 15 mer peptides. Several clones positive in binding to the HNK-1 antibody were found. In the initial screening with HNK-1, bound phage were eluted by pH shift, so that there was no differentiation between specifically and non-specifically bound phage. Therefore a screening was carried out wherein HNK-1 antibody is biotinylated with a coupling agent incorporating a disulfide bridge. The biotinylated antibody is pre-reacted with the streptavidin-coated tube, unbound antibody is washed off, and the immunotube is used for screening. Alternatively, phage are reacted with the biotinylated antibody in solution, and then the biotinylated complex is allowed to react with an immunotube coated with streptavidin. In either case, after washing away unbound phage, the bound phage are eluted by addition of dithiothrei-tol, which releases the antibody and the attached phage (Griffiths et al, 1994). Furthermore, these screenings were done in the presence of mouse serum (12.5%). This provides a large excess of mouse IgM over the HNK-1 antibody, so that non-specific binding to the HNK-1 antibody should be suppressed.

In some cases, when phage in solution were allowed to react with "pre-immobilized" antibody, a rise was obtained in the number of phage bound after the third or the fourth round of selection. The clones tested bound to total mouse IgM as well. In a final experiment various procedures were compared in parallel: Phage were allowed to bind either to HNK-1 coated immunotube or to biotinylated HNK-1 in solution, and in the presence or absence of mouse serum. An enrichment was observed using the pre-coated antibody, but the selected clones again bound to total mouse IgM, although they also bound I-INK-1. It is interesting to note that the selected phage were also reactive to L2-412 antibody, which recognizes the same carbohydrate as HNK-1, although HNK-1 requires a terminal sulfate group, while L2-412 antibody recognizes the carbohydrate with or without a sulfate group.

Materials and Methods

Materials

A 15-mer peptide library and *E. coli* K91 Kan cells may be used. The 15-mer library was constructed in the vector fUSE5, a derivative of the filamentous phage fd-tet (Scott et al, 1990). This vector carries a tetracycline resistance gene allowing for selection. The filamentous phage do not kill their host; thus the infected cells become tetracycline resistant, continue to grow and secrete progeny particles. The *E. coli* strain K91 Kan is a lambda$^-$ derivative of K38 (Lyons et al, 1972), has a chromosomal genotype thi and carries a kanamycin-resistance gene (mkh) (Smith et al, 1993; Yu et al, 1996). Peptides and peptide (10 mg) coupled to SPDP-activated BSA (60 mg) via C-terminal cysteine, may be obtained e.g. from ANAWA AG, 8602 Wangen, Switzerland. Tetracycline and Kanamycin may be purchased from Sigma. L2/HNK-1 glycolipids were purified from beef cauda equina by B. Becker in our laboratory. Sulfated sugars, $SO_3$-GlcA-Gal-allyl, were kindly provided by N. Nifant'ev, Zelinsky Institutre of Organic Chemistry, Russian Academy of Sciences, Moscow.

Antibodies

Characterization and purification of the monoclonal antibody (mAb L2-412), raised in rats and recognizing the HNK-1 carbohydrate has been described by Noronha, A. et al., *Brain Res.* 385, 237-244 (1986)). HNK-1 antibody is available as TIB200 from the American Type Culture Collection (ATCC). Polyclonal rat IgG and HRP-Streptavidin were obtained from Sigma (USA). HRP/anti-M13 polyclonal antibody was purchased from Pharmacia Biotech. Horseradish peroxidase (HRP)-conjugated secondary antibody directed against rat IgG was obtained from Jackson Immunoresearch.

Amplifying the Starting Library

The primary library encoding the 15mer peptides was amplified based on the Smith procedure (Smith et al, 1992) as follows:

The night before the cells were needed, 2 ml of LB medium (g/L Bacto-Tryptone, 5 g/L NAcl, 5 g/L yeast extract), containing 100 µg/ml kanamycin, were inoculated with K91Kan cells and shaken overnight at 37° C. A 1 L flask containing 100 ml of Terrific Broth was prepared (12 g Bacto-Tryptone, 24 g yeast extract, 5.04 g glycerol (4 ml) added to 900 ml of water and autoclaved in 90 ml portions; 10 ml of potassium phosphate buffer (0.17M $KH_2PO_4$, 0.72M $K_2HPO_4$, no pH adjustment required) were added to each 90 ml portion before use).

The 100 ml Terrific Broth were inoculated with 1 ml of the overnight culture of K91kan cells and shaken vigorously until the $OD_{600}$ of a 1:10 dilution reached 0.2. Shaking was then slowed down for 10 min to allow F-pili to regenerate and 10 µl of the starting library was added to the flask; slow shaking was continued to allow for adsorption. The culture was then transferred to 1 L of LB containing 0.22 µg/ml tetracycline and allowed to shake vigorously for 35 minutes at 37° C. The tetracycline concentration was adjusted to 20 µg/ml, and an aliquot was taken for determination of the titer. The phage were titered (recovered titer) by plating infected cells on tetracycline medium and counting the number of tetracycline resistant colonies. An infectious unit defined in this way is called a transforming unit (TU) and the infectivity is the ratio of number of TU's to number of physical particles. Typically, an aliquot of 50 µl of the culture was removed and diluted with LB containing 0.2 µg/ml tetracycline (dilution range was $10^3$-$10^5$). An aliquot of 200 µl of each dilution were spread on an agar-plate containing 40 µg/ml tetracycline and 100 µg/ml kanamycin, incubated overnight at 37° C. The colonies were counted on the next day. At this stage, the titer of tetracycline resistant colonies should be about $10^7$/ml. The remainder of the culture was shaken vigorously overnight.

The next morning the doubly cleared supernatant obtained after 2 steps of centrifugation (4000×g, 10 min, 4° C. and 10'500×g, GSA, 10 min, 4° C.) was precipitated overnight at 4° C. by adding 0.15 volume of PEG/NaCl solution (16.7% polyethylene glycol in 3.3 M NaCl solution). The precipitated phages collected after centrifugation (10'500×g, GSA, 40 min, 4° C.) were dissolved in 10 ml of TBS (50 mM Tris-HCl pH7.5, 150 mM NaCl) and a second precipitation was carried out by adding 0.15 volume of the PEG/NaCl solution to the phage suspension and incubating for 1 hr on ice. At this stage, a heavy precipitate should be evident.

The pellet obtained after centrifugation (14'500×g, SA600, 10 min, 4° C.) was redissolved in 10 ml TBS and transferred into a tared vessel containing 4.83 g CsCl. The vessel was retared and TBS was added to a net weight of 10.75 g. This should give 12 ml of a 31% w/v solution of CsCl (density 1.30 g/ml); the solution was centrifuged 48 hrs at 150'000×g at 5° C. in a SW41 rotor (Beckman). With the help of a strong visible light source, a faint bluish non-flocculent band (containing the amplified phages) was visible above a narrow flocculent opaque white band (probably deriving from PEG). The phage band was collected by first aspirating slowly the fluid overlying the phage band and then, using a pipette, the phage band was withdrawn avoiding as much as possible the flocculent band underneath. The phage band was then delivered to a 26 ml polycarbonate centrifuge bottle, which was filled to the shoulder with TBS and centrifuged in a Ti70 rotor (279'000×g, 4 h, 5° C.) and resuspended in 2 ml TBS per 1 L of culture. Phages can be stably stored in this form in a refrigerator.

The amplified library was then titered (final titer) as follows: several dilutions of phage were prepared in TBS/gelatine (0.1 g gelatin in 100 ml TBS) covering the dilution range from $10^7$ to $10^{10}$. Then 10 µl of each of these dilutions were used to infect 10 µl of K91kan cells prepared as described at the beginning of this section and each dilution mixture was incubated 15 min at room temperature (RT) to allow phage to infect the concentrated cells. One ml of LB containing 0.2 µg/ml tetracycline was added and incubated 30 min at 37° C. in a shaker-incubator. The infected cells were then spread (200 µl) on an agar plate containing 40 µg/ml tetracycline and 100 µg/ml kanamycin as described above (recovered titer).

Screening Procedure

A. Direct Binding

The phage library was panned using Immunotubes (Nunc., Maxisorb) coated with $mAbL_2$-412. The tubes were coated by incubating overnight at 4° C. with antibody L2-412 at 10 µg/ml protein in PBS (1 ml total volume) for the first round and 1 µg/ml for the second and third round of screening. After blocking 2 hours with Blotto (5% non-fat dry milk, 0.05%(v/v) Tween 20 in PBS) at 4° C., $10^{11}$ transforming units (in 250 µl volume) of the phage library per immunotube were allowed to bind 1 hour at 37° C. in a rotating chamber. For the second and third rounds, the phages were preincubated 1 hour with 100 µg/ml of rat IgG before being added to the immunotube, in order to decrease the number of non-specific binders. After recovery of the unbound phages (from which the negative control phage was chosen), the tubes were washed 10 times with PBS-0.05% (v/v) Tween 20 and eluted with 0.1 M Glycine pH 2.2 (0.5-1 ml total volume), 10 min. at 40 C. Eluted phages were neutralized with 1.5M Tris pH9 and then used to infect 0.5-1 ml of log phase *E. coli* K91 Kan cells 15 min at room temperature. The infected bacteria were transferred to 20 ml of LB containing 0.2 µg/ml tetracycline, and after removing an aliquot for determination of the titer (recovered titer), allowed to grow overnight as described in the previous section. The amplified eluate was then twice centrifuged (10 min, 3600×g and 10 min, 14'500×g, SA600) and the final supernatant was precipitated with 0.15 volume of PEG/NaCl overnight at 4° C. The phage was pelleted (15 min. 14'500×g, SA600) and dissolved in 1 ml PBS by pipetting and vortexing, microcentrifuged 1 min. to pellet insoluble matter, and PEG-precipitated again for at least 1 hr at 4° C. A heavy precipitate should be visible at this stage. The pellet obtained after 10 min. microcentrifugation was finally dissolved in 200 µl of PBS containing 0.02% azide. This amplified eluate can be stored and kept at 4° C. The library was subjected to three rounds of amplification and selection.

The same procedure was used for the HNK-1 screening with HNK-1 antibody, except that a 100-fold excess of mouse IgM was included to decrease non-specific binding.

The phage were titered (final titer) as described. The colonies were counted on the next day and the yield of the screening was calculated by dividing the recovered titer by the titer (input) of the previous round.

B. Screening with Biotinylated Antibody

Two procedures were used to accomplish this screening, both following protocols of G. Smith (unpublished protocols). The HNK-1 antibody was biotinylated as described below using NHS-SS-biotin. NHS-SS-Biotin links the biotin to the protein via a disulfide bridge, in order to allow the biotin group to be subsequently removed by incubation with dithiothreitol (DTT). The L2-412 antibody was similarly biotinylated as described below. In procedure A, the biotinylated antibody is first allowed to bind to a streptavidin coated immunotube, which is then subsequently used to pan the phage input. In procedure B, the biotinylated antibody is preincubated with the phage in solution, and the reaction mixture is allowed to bind (a few minutes) to the streptavidin-coated immunotube.

In procedure A, the immunotubes were coated with 10 µg/ml streptavidin in PBS, 1 ml total volume (wet the entire surface of the tube), overnight at 4° C. on a rotator. Streptavidin was discarded and the tube was filled with blocking solution, PBS containing 0.5% (w/v) BSA, for 2 hrs at 4° C. After washing 6 times with PBS-0.05% (v/v) Tween 20 (PBS-T), the biotinylated antibody was added. Typically, 3 µg of the biotinylated HNK-1, or 5 µg of the biotinylatedL2-412 antibody were added in 400 µl of the blocking solution. The antibody was allowed to bind for at least 2 hrs (or overnight)

at 4° C. on the rotator. After washing 6 times with PBS-T, $10^{10}$ phages from the 15-mer starting library, in 400 µl of blocking solution, were allowed to bind to the respective antibody-coated immunotube for 4 hr at 4° C. on the rotator. In procedure B, during coating of the immunotubes $10^{10}$ phage were preincubated overnight with 3 or 5 µg of the biotinylated FINK-1 or L2-412 antibody, respectively. The biotinylated antibody was then allowed to bind to the coated immunotube for 10 minutes at 4° C. on the rotator. In both procedures, the tubes were then washed 10 times, then phage-antibody complexes were eluted with 20 mM DTT (0.5 ml volume) in PBS 1-5 min. at room temperature. Amplification and titering were performed as described above. The library was subjected to four rounds of amplification and selection.

ELISA Screening

A. Direct Binding for Detection of Positive Clones

Individual colonies resistant to tetracycline and kanamycin were grown in LB containing 20 µg/ml tetracycline in 96-wells plates (Nunc) overnight at 37° C. (300 µl/well), then centrifuged 10 minutes at 3000 rpm in Jouan centrifuge and the supernatant (100 µl) was incubated for 2 hr in another 96-well plate previously coated with $mAb_{L2}$-412 (100 µl, µg/ml overnight at 4° C.) and blocked by incubation for 2 hours with PBS-0.5% (w/v) BSA. After washing 5 times, the binding of the phages was detected by incubation with HRP-conjugated anti-M13 antibody (Pharmacia, Biotech.) for 1 hour at a dilution of 1:2000. The peroxidase reaction was started by the addition of 100 µl developer containing 0.01% hydrogen peroxide and 0.1% (w/v) 2,2'-azino-bis(3-ethyl-benzthiazoline-6-sulfonic acid)-diammonium salt (ABTS, Boehringer Mannheim) in HRP buffer (0.1M sodium acetate, 0.05M $NaH_2PO_4$, pH adjusted to 4.2 with acetic acid). The absorbance of the colored reaction product was determined at 405 nm in a Multiscan TitertekPlus (Flow, Switzerland). In parallel, each clone was also tested on 96-well plates coated with rat IgG, (100 µg/ml in PBS and identically blocked for 2 hours). Bacteria producing the selected binding clones (named positive phage), that were positive binders for the $mAb_{L2}$-412 but did not bind to rat IgG were streaked on an agar plate containing LB medium with 40 µg/ml tetracycline and 100 µg/ml kanamycin. Two individual colonies were picked and re-assayed for positivity towards mAb L2-412. Positive single colonies were stored in 40% glycerol at –800 C.

B. Competition Binding

Microtiter plates (Nunc) were coated with the L2/HNK-1 glycolipids (50 µl, 1 µg/ml, dissolved in EtOH) and allowed to dry overnight. While blocking the wells for 2 hours with 0.5% (w/v) fatty-acid-free BSA in PBS, a limiting concentration of $_{L2}$-412, previously determined, was pre-incubated with successive 2-fold dilutions of the inhibitor, starting at a concentration of 2.2 mM for the free peptide, 5 mM for the $SO_3$ sugar and $10^{12}$ positive and negative phages (the negative phages were cloned from the unbound fraction of the first round of screening). The pre-incubated mixture was then added to the well in 100 µl and incubated for 1 hour at RT. After washing 5 times with PBS-0/05% (v/v) Tween 20, the binding of mAb L2-412 was detected by incubation with HRP-conjugated goat anti-rat IgG for 1 hour, followed by the color reaction described earlier. The percentage of inhibition of the binding of mAb L2-412 to the substrate in the presence of the inhibitor was calculated with reference to the control value obtained in the absence of inhibitor (0% of inhibition).

C. Inhibition of Binding

Microtiterplates were coated overnight at 4° C. with laminin (Gibco/BRL), (10 µg/ml, 100 µl), or $mAb_{L2}$-412 (1 µg/ml, 100 µl) in PBS. All the following reaction steps were carried out at room temperature. After blocking with PBS+0.5% (w/v) BSA, 50 µl of successive 2-fold dilutions of peptide coupled to BSA (ANAWA Ag, Switzerland) starting at a concentration of 30 µM was added for 1-2 hours at RT. Then a limiting number of phages bearing the peptide of interest, previously determined, was added and incubated for another hour. The bound phages were detected with HRP/anti-M13 antibody as described in the ELISA screening section. The analogous experiment was done with immobilized L2-412 instead of laminin, the peptide coupled to BSA competing with the binding of positive phages to the antibody L2-412.

D. Direct Binding to Laminin

Microtiter plates were coated with 100 µl of mAb L2-412 or laminin as described above and 100 µl of biotinylated peptide coupled to BSA was added starting at a concentration of 30 µM, incubated 2 hours at room temperature, and detected with HRP-streptavidin.

DNA Sequencing

Positive clones, toothpicked from frozen glycerol stocks, were grown overnight at 370 C in LB containing 20 µg/ml tetracycline. Single stranded DNA was purified as described by G. Smith (1992) using the double-spin method, sequenced with the Thermo Sequenase cycle sequencing kit (Amersham), and loaded on an automated sequencer (B10 Genetic Analyzer, Applied Biosystems Inc.).

Biotinylation

Biotinylation of the HNK-1 antibody, BSA and the peptide coupled to BSA was done using Sulfo-NHS-biotin (Pierce) according to the manufacturer's instructions. A molar ratio of 10 to 1 was used for the antibody and 5 to 1 for BSA or the peptides coupled to BSA. The biotinylated product was dialysed overnight against PBS at 4° C.

Neurite Outgrowth Experiments and Culture
Preparation of Motor Neurons

Cover slips were sterilized by baking them overnight at 160° C. and coated by an overnight incubation with polyornithine (Sigma, 1.5 µg/ml in water) at 4° C. The cover slips were then washed 3 times with water and further coated with test substances as follows: 1) The BSA-peptide conjugates were dissolved at 100 µg/ml in PBS, sonicated 1 min with a table sonicator and centrifuges in a microfuge for 20 min at maximum speed. The protein concentration of the supernatant was determined each time by the method of Bradford (Bradford et al, 1976). Then 120 µl complex was mixed with 280 µl of collagen solution (20 µg/ml collagen in PBS) and 100 µl were applied on each cover slip overnight at 4° C.; 2) As a negative control, untreated BSA was used in place of the peptide-BSA complex; 3) The glycolipids carrying the L2/HNK-1 carbohydrate were dissolved in ethanol at a concentration of 10 µg/ml, and 80 µl were added to 1 ml of the collagen solution described above. A volume of 100 µl was used for coating. Cover slips were placed in quadruplicate in a 24-well plate (NUNC), and finally washed 3 times before the cells were plated (the cover slips were never allowed to dry).

Motor neuronal cells were prepared as described by Arakawa (1990) from spinal cord of 6-day old chick embryos dissociated in 1 ml of ice cold solution containing 0.05% DNAse 1 (Sigma), 0.1% BSA in L-15 medium (Life Technologies). Cells were layered on 2 ml of 6.8% Metrizamide (Fluka) in L-15 and centrifuged 15 minutes at 500×g, 40 C. Cells collected from the Metrizamide/medium interface were diluted in 5 ml L-15 and loaded on a 4 ml cushion of BSA (4% BSA in L-15) and centrifuged 10 minutes at 300×g, 4° C. The pellet was resuspended in 0.5-1 ml of complete medium ((22 mM $NaHCO_3$, 22 mM glucose, 1% of penicillin and streptomycin (Gibco) in L-15 supplemented with 1% N2 supplement (Gibco) and 15 μg/ml chicken muscle extract (3.5 mg/ml). 30,000 cells were plated on poly-ornithine/collagen coated cover slips in the presence or absence of the peptide coupled to BSA and incubated in a humidified chamber at 37° C. and 5% $CO_2$. The length and number of neurites were measured and counted for isolated neurons that were not in contact with other cells and with at least one process that was as long as the diameter of the cell body after 24 hours of culture.

Preparation and Culture of Dorsal Root Ganglion Neurons

The cover slips were prepared identically as for the experiments with motor neurons. Dorsal root ganglia neurons were isolated from embryonic-day 11 chicken eggs. The ganglia were transferred into 1 ml of digestion solution (0.05% Trypsin, 0.01% DNAse 1 in HBSS medium) and incubated 15 min. at 37° C. with resuspending every 2-5 min. The ganglia were then dissociated in 1 ml of ice cold dissociation solution (0.05% DNAse 1, 0.1% BSA, in L15 medium), loaded on 3 ml of a 4% BSA cushion in a 15 ml Falcon tube and centrifuged at 4° C., 600×g for 20 min. The cells were resuspended in 0.5 ml of the complete medium described in the previous section. 20,000 cells were added to wells containing one cover slip, and allowed to grow for 18 hrs in a humidified chamber at 37° C. and 5% $CO_2$. Fixing and analysis of neurite outgrowth was performed as described in the preceding section.

Immunohistology and Immunocytology

Immunohistology

Cryosections of femoral nerve from a 4-month-old mouse were used to look for binding of peptide-BSA complex. The sections were treated for 1 hr with 1% $H_2O_2$, 0.5% bovine serum albumin (BSA), and 10% goat serum in PBS, in order to reduce the endogenous peroxidase activity. The sections were then incubated overnight at 4° C. with peptide-BSA complex or BSA (1 mg/ml in PBS, 150 μl/cover slips), and then washed 4 times with PBS-0.01% Tween 20. For detection, anti-BSA antibody (Sigma, 1:16 dilution, 150 μl/cover slips) was added and incubated overnight at 4° C. HRP-coupled goat anti rabbit serum was added (1:2000), for 1 hr in a volume of 150 μl per cover slip. The color reaction was developed using a 5% dilution of a 4 mg/ml stock solution of 9-amino-3-ethylcarbazol (AEC, Fluka) in N,N-dimethylformamide in 0.1 M sodium acetate buffer, pH 4.8, containing 0.1% $H_2O_2$.L2-412 antibody and HRP-coupled goat anti-rat antibody were used for the positive control. A similar experiment was performed using biotinylated BSA-peptide conjugate. A concentration of 50 μg/ml was used for the overnight incubation and HRP-coupled streptavidin (1:2000) was added for 1 hr. The color reaction was developed as described above.

Immunocytology

Cover slips were coated with polyornithine (1.5 μg/ml) then with collagen (20 μg/ml,) and 40,000 cells were allowed to grow for 40 hrs at 37° C. under 5% $CO_2$ as described above. The fixed cover slips were then blocked in 5% non-fat dry milk powder in PBS for 2 hrs. After extensive washing with PBS-0.05% Tween-20, biotinylated BSA-peptide conjugate was added at a concentration of 50 μg/ml for 4 hrs. After another six times wash steps, detection was done using HRP-coupled streptavidin, 1:500, for 1 hr. Color detection was as described above for immunohistology. The fixed neurons were photographed at 40× magnification. The images presented were processed for enhanced color rendition using Adobe Photoshop.

The following is an alphabetical list of the references referred to in this Example.

Chou, D., and Jungalwala, F. *J. Biol. Chem.* 268, 21727-21733 (1993).
Chou, D. K., et al., *J. Biol. Chem.* 261, 11717-25 (1986).
Griffiths, A. et al. (1994) *EMBO J.* 13:3245-3260.
Kieber-Emmons, T. *Immunologic Research* 17, 95-108 (1998).
Lyons, L. and Zinder, N. (1972) *Virology* 49:45-60.
Scott, J. K. and Smith, G. P. (1990) *Science* 249:386-390.
Smith G. P. and Smith, J. K. (1993) *Methods Enzymol.* 217: 228-257.
Yu, J. and Smith, G. (1996) *Methods Enzymol.* 267:3-27.

Example 7

Human Monoclonal Antibodies Reactive to Oligodendrocytes Promote Remyelination in a Model of Multiple Sclerosis Promoting remyelination, a major goal of an effective treatment for demyelinating diseases, has the potential to protect vulnerable axons, increase conduction velocity and improve neurologic deficits. Strategies to promote remyelination have focused on transplanting oligodendrocytes (OLs) or recruiting endogenous myelinating cells with trophic factors. Immunoglobulin (Ig) based therapies, routinely used to treat a variety of neurological and autoimmune diseases, underlies our approach to enhance remyelination. We isolated two human monoclonal antibodies (mAbs) directed against OL surface antigens that promoted significant remyelination in a virus-mediated model of multiple sclerosis (MS). Four additional OL-binding human mAbs did not promote remyelination. Both human mAbs were as effective as human intravenous immunoglobulin (IVIg), a treatment shown to have efficacy in MS, and bound to the surface of human OLs suggesting a direct effect of the mAbs on the cells responsible for myelination. Alternatively, targeting human mAbs to areas of central nervous system (CNS) pathology may facilitate the opsonization of myelin debris allowing repair to proceed. Human mAbs were isolated from the sera of individuals with a form of monoclonal gammopathy. These individuals carry a high level of monoclonal protein in their blood without detriment, lending support to the belief that administration of these mAbs as a therapy would be safe. Our results are 1) consistent with the hypothesis that CNS-reactive mAbs, part of the normal Ig repertoire in humans, may help repair and protect the CNS from pathogenic immune injury and 2) further challenge the premise that Abs that bind OLs are necessarily pathogenic.

Introduction

Enhancement of remyelination and protection from axonal injury are important therapeutic goals in the treatment of inflammatory demyelinating CNS disorders such as MS. Remyelination in MS plaques can occur, but is limited (1,2) even though OL progenitors are present in the adult (3,4). A number of therapeutic strategies to promote remyelination have been tested in experimental animals. Transplantation of OLs (5) or their progenitors (6) into demyelinated tissue produces new myelin. Transplanted OL progenitors can also remyelinate demyelinated lesions in the adult CNS (7) and migrate toward an area of damage when placed in close proximity to the lesion (8). Unresolved issues remain concerning the survival of transplanted OL progenitors in the intact adult CNS and their ability to target to areas of myelin pathology (9). However, if CNS lesions are surgically approachable and axons are still intact, transplantation of glial cells maybe a viable therapy for improving functional performance (10).

The in vitro administration of growth or trophic factors induces the expansion of OL progenitors (11,12) or promotes mature OLs to dedifferentiate and subsequently reinitiate a program of myelination (13,14). The in vivo administration of trophic factors via genetically engineered fibroblasts to the injured CNS promotes axonal sprouting and OL proliferation (15). Obstacles to in vivo trophic factor therapy remain, specifically determining the biologically relevant local factor concentration and the potential pleiotropic roles of most trophic factors administered in high concentrations.

As an alternative, our laboratory proposes to repair CNS pathology and enhance endogenous remyelination by using CNS-binding Igs (16), building on a natural reparative response that may already be upregulated following demyelination. Ig therapy can be rapidly adapted and tested as a treatment for human demyelinating disease (17, 18). The premise of our approach is that cells capable of remyelination—and the factors necessary to sustain their growth and differentiation—are present in the demyelinated CNS, but their capacity to produce myelin is limited. The emerging heterogeneity of pathology and OL sparing within the MS population (19) suggests that in practice, the treatment of human demyelinating disease may require combinations of several therapeutic approaches based on an individual's requirements.

We have used a virus-mediated model of demyelination to develop Ig-based therapy. When Theiler's murine encephalomyelitis virus (TMEV) is inoculated intracerebrally into susceptible strains of mice, TMEV induces immune-mediated progressive CNS demyelination clinically and pathologically similar to MS (20). The efficacy of therapies in human MS closely parallel those observed in the TMEV model (21) making this an important platform for the design of clinical trials. A mouse mAb raised against spinal cord homogenate, designated SCH94.03, enhances remyelination in the TMEV model (22). SCH94.03 is a polyreactive, mouse IgMk mAb that binds to the surface of OLs (23). SCH94.03 also enhances the rate of spontaneous CNS remyelination following lysolecithin-induced demyelination (24) and decreases relapse in experimental autoimmune encephalomyelitis (EAE) (25). Additional OL-binding mouse IgMk mAbs, several of which are routine markers for the OL lineage, also promote CNS remyelination (26).

Since mouse IgM mAbs promote remyelination, we hypothesized that polyclonal human IgM would be a more effective treatment of demyelinating disease than IVIg, an established therapy for immune-mediated disorders (27). Treatment of chronically TMEV-infected mice with polyclonal human IgM resulted in enhanced remyelination when compared to IVIg. Two human IgM mAbs were also identified, using an antigen-independent strategy, which promote remyelination to an equivalent or greater degree than polyclonal human IgM. We suggest that human remyelination-promoting mAbs may be an easily implemented, effective therapy for human demyelinating disease. Human mAbs are readily applicable to clinical trials, can be produced free of infectious agents and may alleviate the national shortage and high cost of IVIg. An effective human mAb that promotes remyelination may also simplify the investigation for the mechanism of action of immunomodulatory therapies.

Materials and Methods

Human Antibodies and Their Isolation

Normal human IgM purified from the pooled plasma of more than 2500 healthy donors was obtained from S. V. Kaveri (28). The purity of IgM was more than 90% as confirmed by SDS-PAGE. Pooled human IgG from healthy donors designated clinically as IVIg was from Miles Inc (Elkhart, Ind.).

Human serum samples were obtained from the dysproteinemia clinic under the direction of Dr. Robert A. Kyle, Mayo Clinic, and chosen solely by the presence of an Ig clonal peak of greater than 20 mg/ml. Sera were from 102 patients with a wide variety of conditions characterized by a monoclonal IgG or IgM spike in the serum, including Waldenstrom's macroglobulinemia, multiple myeloma, lymphoma, and monoclonal gammopathy of undetermined significance. Sera were dialyzed against water, the precipitates collected by centrifugation (14,000 rpm/30 min) and dissolved in PBS. Solutions were centrifuged and chromatographed on Superose-6 column (Pharmacia, Upsalla, Sweden). IgM fractions were pooled and analyzed by SDS PAGE. Concentrations were determined by gel staining with Sypro Orange (Molecular Probes, Eugene, Oreg.) densitometry. IgM solutions were sterile filtered and cryopreserved.

OL Cell Culture and Immunocytochemistry

Cerebral hemispheres from P0-P2 Holtzman Sprague-Dawley rats were prepared for mixed primary glial cell culture as described (29) and grown for 9 days in vitro. Rat OL progenitors were isolated as described (30). Adult human OLs were prepared from temporal lobe biopsies obtained from patients undergoing therapeutic resection for intractable epilepsy. Tissue did not contain the epileptic focus and was of normal cytoarchitecture when examined by the Department of Surgical Pathology. Adult glial cells isolated as described (31) and seeded onto poly-ornithine (Sigma) and laminin (Life Technologies) coated plastic multi-wells (Becton Dickenson) or glass coverslips (Fisher Scientific) in a defined media of DMEM/F12 supplemented with biotin (0.01 mg/ml), tri-iodotyronine (15 nM), 0.5% BSA (all from Sigma), N2, 1% pen/strep (both from Life Technologies) and recombinant human PDGF AA® & D Systems, Minneapolis, Minn.). Cell surface staining was done at 4oC for 12 min on unfixed cells after blocking with HEPES-buffered EBSS (E/H) with 5% BSA. All human Abs were used at 10 mg/ml. Intracellular staining for myelin basic protein using polyclonal mouse antisera (Boehringer Mannheim) was done at room temperature after fixation with 4% paraformaldehyde and permeabilization for 5 min with 0.05% saponin. Primary Abs were detected using fluorescently-conjugated secondary Abs (Jackson ImmunoResearch Laboratories, West Grove, Pa.). Cell monolayers were mounted in 90% glycerin/PBS with 2.5% 1,4-diazabicyclo[2.2.2]octane to prevent fading (37) and 0.1 µg/ml bisbenzimide (both from Sigma) and viewed with an Olympus Provis epifluorescent microscope equipped with a SPOT digital camera (Diagnostic Instruments Inc, Sterling Heights, Mich.).

Virus and Animals

The Daniel's strain of TMEV was used for these experiments and was prepared as described (32). Female SJL/J mice from the Jackson Laboratories were used after 1-week acclimation. Mice 4- to 6-weeks of age were injected intracerebrally with $2 \times 10^5$ plaque forming units of TMEV in 10 ml volume resulting in greater than 98% incidence of chronic viral infection. Animals used in this study were 5 to 8 months post-infection and received a single intraperitoneal injection of Ig or PBS. Dosages were 1.0 mg of IVIg or human polyclonal IgM or 0.5 mg of the human mAbs. Animals were killed 5 weeks following Ab treatment for morphologic assessment; chosen because studies in toxic models of demyelination indicate that CNS remyelination is almost complete by this time (33). Spinal cord sections embedded in plastic were cut by a centralized microscopy facility and returned to the laboratory marked with a numerical code. In this way slides are graded for remyelination in a blinded manner.

Western Blotting

Purified TMEV (34) was separated by SDS-PAGE and proteins transferred to nitrocellulose. After blocking with Tris buffered saline containing 5% non-fat dry milk and 0.05% Tween 20 for 2 hours at room temperature the membrane was incubated with human Igs (10 μg/ml) or rabbit polyclonal anti-TMEV Ab (1:2000) for 4 hours. Bound Igs were detected with biotinylated goat anti-human mAbs or biotinylated goat anti-rabbit mAbs (both from Jackson InununoResearch) and alkaline phosphatase-conjugated streptavidin using 5-bromo-4-chloro-3-indolylphosphate and nitro blue tetrazorium (BCIP/NBT, KPL, Gaithersburg, Md.).

Quantitation of Spinal Cord Demyelination/Remyelination

Figure 43:
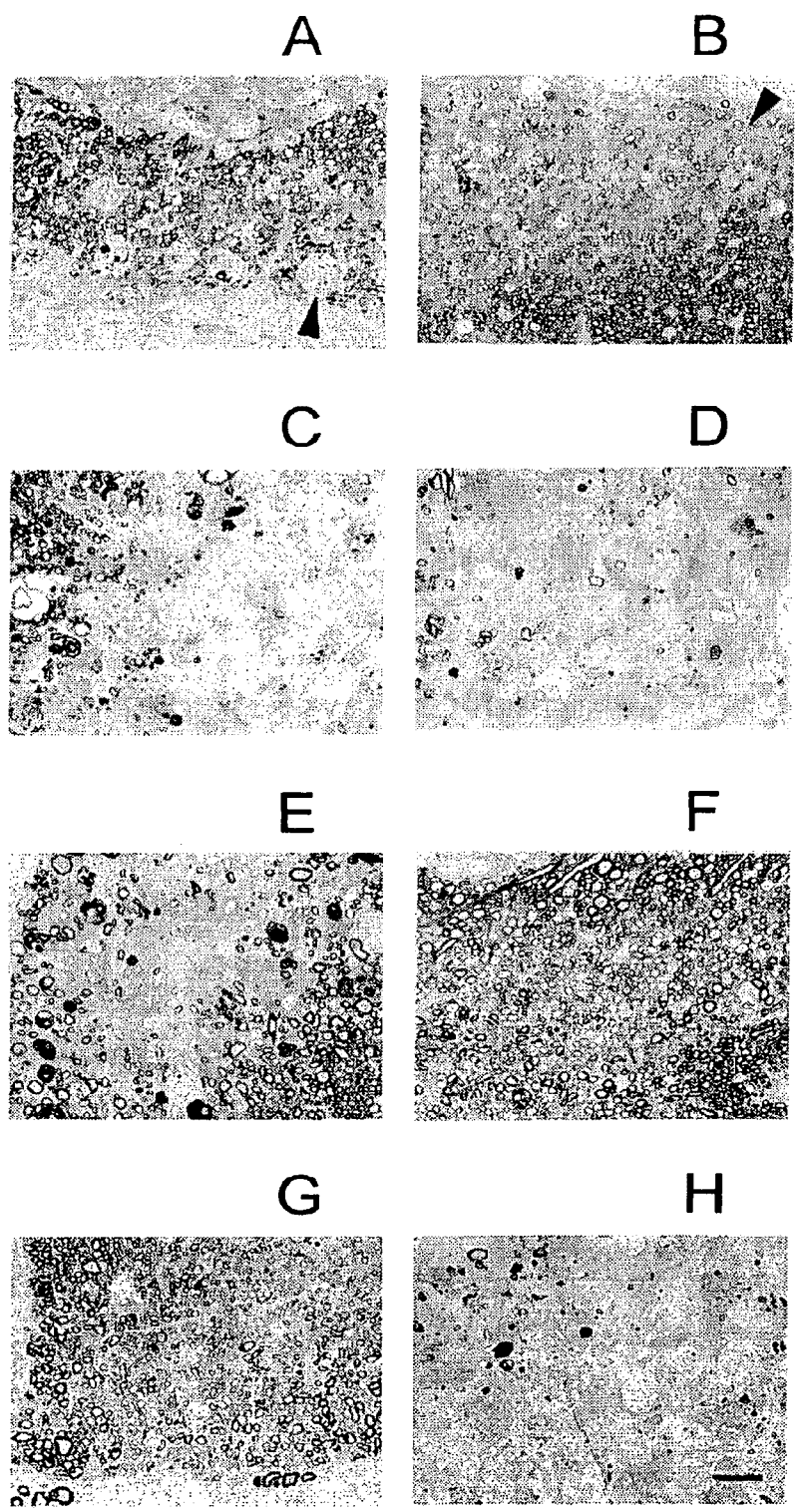
FIG. 43A-43H Following treatment with human Abs, chronically TMEV-infected mice demonstrate significant OL remyelination. Light photomicrographs of representative areas of spinal cord white matter pathology of different treatment groups. Treatment with IVIg resulted in significant OL remyelination (A). Almost complete OL remyelination, characterized by densely packed thin myelin sheaths in relation to axon diameter (B, arrowhead), was observed in sections from the spinal cords of mice following treatment with polyclonal human IgM (B) and human mAbs sHIgM22 (F) and sHIgM46 (G). In contrast, following treatment with human mAbs sHIgM1 (C), sHIgM2 (D), sHIgM14 (E) or PBS (H)

We have developed methods to quantify the amount of spinal cord demyelination, remyelination and atrophy in susceptible mice using plastic-embedded cross sections stained with 4% paraphenylenediamine (PPD) to visualize myelin (35, FIG. 42A). To obtain a representative sampling of the entire spinal cord, 1 mm thick cross sections were cut from every third serial 1 mm block, generating 10 to 12 cross sections that represent the whole spinal cord. From each cross section the area of white matter, white matter pathology, OL remyelination, and Schwann cell (SC) remyelination were calculated using a Zeiss interactive digital analysis system (ZIDAS) and camera lucida attached to a Zeiss photomicroscope (Carl Zeiss Inc., Thornwood, N.Y.). White matter was outlined at a magnification of 40×. The areas of white matter pathology, defined as regions of white matter with demyelination or remyelination, were then traced at a magnification of 100×. Regions of white matter pathology often contained macrophage infiltration, inflammation, and little or no PPD stain (FIGS. 43 C, D, H). The sum of the areas of pathology containing primary demyelination with or without remyelination was determined as a measure of total demyelination.

The areas of remyelination, either OL or SC, were traced at a magnification of 250×. OLs can remyelinate multiple axon fibers, and thus, OL remyelination results in densely packed, yet thin, myelin sheaths compared to spared normally myelinated axons. SCs can remyelinate only a single axon fiber, resulting in thicker myelin sheaths and increased space between axon fibers compared OL remyelination. SC bodies and nuclei can be observed adjacent to the axons they have remyelinated. Total areas were calculated for each mouse by summing all the areas traced from each of 10 to 12 spinal cord sections per mouse.

The percent area of spinal cord white matter pathology per mouse was obtained by dividing the total area of white matter pathology by the total area of white matter sampled. The percent area of remyelination per mouse was obtained by dividing the area of OL or SC remyelination by the total area of white matter pathology. Repeated measures of white matter pathology and extensive myelin repair revealed comparable values differing only by 1.5%. To determine the validity of using 10 cross sections as a representation of the remyelination throughout the spinal cord, a comparison was performed using 10 cross sections versus all 32 cross sections of a single chronically infected mouse. Assaying 10 cross sections resulted in a percent area remyelination value of 47.7%, whereas the data from all 32 cross sections resulted in a value of 40.0%. Either value would have indicated significant remyelination in our assay.

Results

Human IVIg and Polyclonal Human IgM Promote CNS Remyelination in TMEV-Infected Mice Clinical studies in MS indicate that IVIg may be partially effective in stabilizing the disease course (18,36,37). To determine if human IVIg could promote remyelination in the TMEV model of MS, chronically infected mice were treated with a single intraperitoneal injection of 1 mg of IVIg. A single dose was administered to avoid evoking an immune response to the foreign Ig. The total dose of human Ig was approximately 0.05 g/kg body weight, one-quarter the total dose used for human IVIg treatment (18). Additional mice were treated with a single 1 mg bolus of polyclonal human IgM. Upon examination of the spinal cords, the percent area of OL remyelination in mice receiving either IVIg or polyclonal human IgM (Table 10, 14.15% and 23.19%, respectively) was significantly higher than the spontaneous OL remyelination observed in the PBS-treated group (6.74%, $p<0.05$ for IgG, $p<0.01$ for IgM). There were no statistically significant differences in the areas of white matter or the areas of white matter pathology between either treatment group or the PBS control group. The data describes two independent experiments treating groups of 7 and 9 mice with IVIg and groups of 7 and 10 mice treated with polyclonal human IgM. The final values in Table 10 include only those animals that contained at least 5% white matter pathology.

TABLE 10

CNS remyelination in mice after treatment with human Abs

| Treatment | No. of Mice | Area of white matter, mm$^2$ | Area of myelin pathology, mm$^2$ | Area of CNS type remyelination, mm$^2$ | Area of CNS-type remyelination, % |
|---|---|---|---|---|---|
| IVIg | 10 | 8.60 ± 0.52 | 0.86 ± 0.10 | 0.13 ± 0.02 | 14.15 ± 2.38* |
| Human Igm | 14 | 9.70 ± 0.43 | 1.21 ± 0.21 | 0.24 ± 0.04 | 23.19 ± 3.26† |
| sHIgM 1 | 4 | 9.34 ± 1.93 | 0.68 ± 0.07 | 0.03 ± 0.01 | 8.35 ± 3.73 |
| sHIgM 2 | 4 | 8.78 ± 0.70 | 0.87 ± 0.12 | 0.10 ± 0.01 | 11.37 ± 1.30 |
| sHIgM 14 | 7 | 11.01 ± 0.60 | 1.13 ± 0.18 | 0.08 ± 0.03 | 8.41 ± 2.59 |
| sHIgM22 | 8 | 10.55 ± 0.41 | 1.16 ± 0.22 | 0.19 ± 0.05 | 17.06 ± 3.42* |

TABLE 10-continued

CNS remyelination in mice after treatment with human Abs

| Treatment | No. of Mice | Area of white matter, mm$^2$ | Area of myelin pathology, mm$^2$ | Area of CNS type remyelination, mm$^2$ | Area of CNS-type remyelination, % |
|---|---|---|---|---|---|
| sHIgM 46 | 5 | 9.44 ± 0.36 | 0.66 ± 0.06 | 0.18 ± 0.04 | 27.12 ± 4.01‡ |
| PBS | 7 | 9.78 ± 0.60 | 1.20 ± 0.22 | 0.06 ± 0.02 | 6.74 ± 1.80 |

Values represent the mean ± SEM.
One-way ANOVA and t test were used to compare the percent area of CNS-type remyelination in mice treated with human antibodies to mice treated with PBS. Such analysis revealed *P < 0.05; †P < 0.01, ‡P < 0.001.
Comparison of mice treated with other treatments revealed polyclonal human IgM P = 0.05, sHIgm 46 P < 0.05.
All other comparisons were not statistically significant. There was no difference in the CNS-type remyelination between polyclonal human IgM, sHIgM22, and sHIgM 46.
Area of peripheral nervous system-type SC remyelination ranged from 0 to 0.08 mm$^2$. This corresponded to 0.0 to 6.92 percent area of peripheral nervous system type SC remyelination as a function of myelin pathology.
There was no statistical difference in the area of myelin pathology in the various treatment groups or compared to PBS or in other peripheral nervous system-type SC remyelination between groups.

Treatment with polyclonal human IgM resulted in more OL remyelination than that observed in mice treated with IVIg (p=0.05, FIG. 43A, B). Approximately one quarter of the total area of myelin pathology was remyelinated in mice treated with polyclonal human IgM, representing thousands of ensheathed axons. On average, 1 mm2 within confluently remyelinated areas of pathology (FIG. 43B) corresponded to 46,000 to 125,000 remyelinated axons. Therefore, the CNS remyelination following human Ig treatment was extensive. Few inflammatory cells or macrophages were present. In contrast, in mice treated with PBS, areas of myelin pathology contained few remyelinated axons (FIG. 43H). Signs of active myelin destruction, such as myelin whirls, inflammatory cells and macrophages were present.

As an additional, faster, method to judge the effectiveness of a treatment to promote remyelination the 10 spinal cord sections representative of an animal were examined for the presence of areas of white matter pathology that demonstrated nearly complete repair. We defined complete repair as an area of white matter pathology with nearly confluent remyelinated axons and no inflammatory cells or macrophages present (as in FIG. 43 B, F, G), a very rare event in spontaneous remyelination. At least one area of complete repair was observed in four of ten animals treated with IVIg and in ten of fourteen animals treated with polyclonal human IgM. We concluded that both IVIg and polyclonal human IgM promote remyelination compared to PBS treatment and that polyclonal human IgM is superior to IVIg in the ability to promote CNS remyelination.

Human mAbs that Bind to OLs Promote CNS Remyelination in TMEV-Infected Mice

All of the previously identified mouse mAbs that promote CNS remyelination bind to OLs (23,26). To screen human mAbs for testing in the TMEV model, human mAbs were tested for the ability to bind to the surface of rat OLs in unfixed mixed primary glial culture. Primary cultures established from neonatal rat brain contain OLs at varying stages of differentiation at 9 days in vitro (38). Our sources of human mAbs were serum-derived human monoclonal IgMs (sHIgMs) and sera-derived human monoclonal IgGs (sHIgGs). None of 50 sHIgGs bound to unfixed rat OLs, but six of 52 sHIgMs bound to the surface of rat OLs co-labeled with the anti-sulfatide mAb, 04 (39).

The six OL-binding sHIgMs were used to treat TMEV-infected mice. Groups of five animals each received a single injection of 0.5 mg of human mAb. The average percent area of OL remyelination following treatment with sHIgM22 and sHIgM46 (FIG. 43 F, G) were both significantly above the background levels attributable to spontaneous remyelination.

The other four OL-binding sHIgMs promoted remyelination at levels comparable to or below the level observed following treatment with PBS. A second set of animals were treated with sHIgM22, sHIgM46 or PBS to confirm the initial observations. SHIgM14 was also repeated as an example of a human mAb that bound to OLs, but did not promote remyelination. The combined data are presented in Table 1. Only animals that contained at least 5% total white matter pathology were included in statistical analysis.

The highest percent area of OL remyelination was observed in animals treated with sHIgM46 (27.1%), followed by animals treated with sHIgM22 (17.1%). The percent area of remyelination following treatment with sHIgM14 (8.41%) was similar to that observed following treatment with PBS (6.74%). To test if any sHIgM, irrespective of antigen specificity, could promote remyelination we studied two mAbs in vivo which demonstrated no immunoreactivity to OLs in mixed primary culture, sHIgM1 and sHIgM2 (FIG. 43C, D). The percent area of remyelination following treatment with sHIgM1 (8.3%), sHIgM2 (11.4%) were not significantly different from the sHIgM14 or PBS treatment groups. In all groups the areas of white matter and areas of white matter pathology were not statistically different. Compared to the remyelination observed in the PBS-treated group, the percent area of remyelination following treatment with sHIgM46 or sHIgM22 resulted in p values of <0.001 and <0.05, respectively. The area of peripheral nervous system-type SC remyelination ranged within treatment groups from 0 to 0.08 mm2. This corresponded to values of 0.0 to 6.92 percent area of SC remyelination as a function of white matter pathology. There were no statistical differences in the percent area of SC remyelination between any treatment group.

Comparing the percent area of OL remyelination observed following treatment with either human polyclonal or monoclonal preparations revealed that sHIgM46 was statistically superior to IVIg (p<0.05), but not to polyclonal human IgM. The percent area of OL remyelination observed following treatment with sHIgM22 was no different than that following treatment with IVIg, polyclonal human IgM or sHIgM46.

When examined for areas of white matter pathology with complete repair at least one area was observed in four out of eight animals treated with sHIgM22 and in five out of five animals treated with sHIgM46. In contrast, none of the animals treated with sHIgM1, sHIgM2, sHIgM14 or PBS contained a single area of complete repair.

Human mAbs, but not Polyclonal Human Igs. Bind to Rat Human OLs

If human mAbs are to be a potential therapy to promote remyelination in humans, a reactivity to surface antigens on human OLs may prove important in targeting to areas of human CNS pathology. Therefore, we determined whether human remyelination-promoting mAbs could bind to OLs obtained from the adult human brain. Human glial cell cultures were established from adult temporal lobe biopsies and immune-labeled with the human mAbs at several time points in culture.

Figure 44:
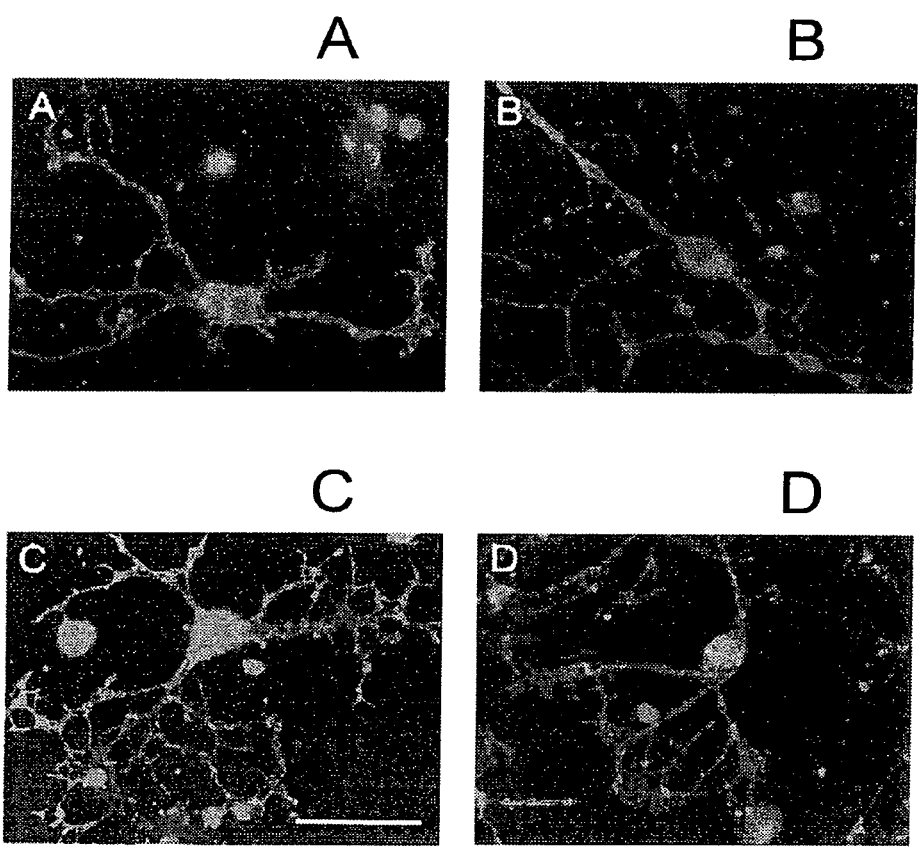

Three of the six sHIgMs that bound to the surface of OLs in our initial screen, also bound to human OLs. At one week in culture morphologically immature sulfatide positive human OLs labeled with sHIgM14 and sHIgM46, but not with sHIgM22. By 3 weeks in culture, morphologically complex sulfatide positive human OLs co-labeled with sHIgM14, sHIgM22 and sHIgM46 (FIG. 44A, B, C). By 4 weeks in culture, virtually all MBP-positive human OLs also bound sHIgM22 and sHIgM46, but the binding of sHIgM14 was greatly reduced (data not shown).

Neither IVIg nor polyclonal human IgM bound to the surface of human OLs in culture at any time tested. However, polyclonal human IgM bound strongly to white matter tracts and a variety of neuronal populations when incubated with fresh unfixed slices of rodent CNS. IVIg was completely negative in this binding assay (data not shown). SHIgM22 and sHIgM46, both of which promoted remyelination, and sHIgM14, which did not promote remyelination, also bound to the surface of purified myelin basic protein-positive rat OLs (data not shown).

We concluded that an affinity for OL antigens may be necessary, but is not sufficient for a human mAb to promote remyelination. The fact that both human mAbs that promote significant remyelination bind to mature differentiated human OLs underscores the possible requirement of mAbs to be directed against surviving adult OLs for in vivo function.

To exclude the possibility that human Igs or mAbs promoted remyelination by neutralizing virus, each preparation was tested for reactivity to purified TMEV antigens by Western blotting (34). None of the human Ab preparations reacted with TMEV proteins; however, rabbit polyclonal Ig raised against TMEV reacted strongly to four virus capsid proteins (data not shown).

Peripheral B-cells were obtained from the individual from which sHIgM22 was identified. The light and heavy chain variable domain sequences of sHIgM22 were determined. The sHIgM22 light chain variable region (GenBank accession AF212992) belongs to the λ subgroup I of the human light chain variable regions. The sHIgM22 heavy chain variable region (GenBank accession AF212993) belongs to subgroup III of the human heavy chain variable regions. There were significant differences between the sHIgM22 variable domains and the closest known human germline variable domain sequence (40).

Discussion

In this series of experiments we have demonstrated that human Abs can promote CNS remyelination. More extensive remyelination was observed in the spinal cords of TMEV-infected mice following treatment with polyclonal human IgM than treatment with human IVIg. In addition, we identified two human monoclonal IgMs that consistently enhanced remyelination. Both mAbs were isolated from the sera of patients with Waldenstrom's macroglobulinemia (WM), a class of lymphoma characterized by the malignant clonal expansion of a single B-cell at the late stage of maturation which floods the serum with a monoclonal IgM (41). The high level of these mAbs do not appear to be deleterious. In patients with WM the dominant IgM normally recognizes antigens that are recognized by the IgM repertoire present in healthy individuals (42). Our ability to readily identify and isolate OL antigen-binding, remyelination promoting mAbs from the human population lends support to the concept that these Abs are common among the B-cell repertoire and may function as modifiers in response to CNS injury.

Remyelination-Promoting mAbs May be Produced in the Sera of Individuals when Confronted with CNS Damage.

Although both IVIg and polyclonal human IgM promoted remyelination neither bound to rat or human OLs in culture. In contrast, both human mAbs that promoted remyelination bound to both rat and human OL surface antigens. The increased efficacy of human mAbs to promote remyelination may be due to the effective targeting to adult OLs in the area of damage. Stangel reported that IVIg had no affect on the differentiation, migration or proliferation of OL progenitors in culture; however, the binding of IVIg to OL progenitors was not assessed (43). The lack of affinity of IVIg to OLs likely explains the lack of any discernible affect on OL progenitors. Nevertheless, the fact that IVIg does not bind to OLs implies that the mechanism of action in promoting remyelination may be distinct from that of the human mAbs.

The very same preparation of polyclonal human IgM used in this study has been demonstrated to neutralize autoantibodies (28) and alter cytokine expression in EAE (44) and to be beneficial in a mouse model of myasthenia gravis (45). Polyclonal human IgM, but not IVIg, binds to myelinated tracts in unfixed slices of rodent brain. Neither polyclonal preparation bound to fresh human white matter. Polyclonal human IgM may promote significant remyelination in the mouse via a combination of general immunoregulation, binding to pathogenic antibodies and opsonization of myelin debris.

The mechanism by which Igs promote remyelination remains to be elucidated. Since many of the remyelination-promoting mAbs bind to OLs and/or myelin, it is reasonable to hypothesize a direct effect on the recognized cells. There are examples of mAbs binding to and altering the biology of OLs in culture (46-48). However, since the mAbs that promote remyelination have varying specificities (23, 26) it is unlikely that each mAb functions directly through a common antigen or receptor. A polyvalent molecule like an IgM could bring normally disparate signaling molecules into close proximity within the plasma membrane with subsequent activation (49). Since most of the remyelination-promoting mAbs appear to bind to lipids (26), the binding of these IgMs to the cell surface could reorganize the plasma membrane and facilitate a signaling pathway. When SCH94.03 is added to mixed primary glial cultures a 2-3 fold increase the uptake of tritiated thymidine is observed (Rodriguez, unpublished observations), but the exact identity of the proliferating cells remains to be determined.

Another potential mechanism by which remyelination-promoting mAbs may function is by targeting to myelin debris or damaged OLs. Binding to OLs or myelin may enhance the clearance of cellular debris from areas of damage, allowing the normal process of spontaneous CNS repair to progress. Perhaps the mechanism of action of polyclonal human Igs is primarily through immunomodulation-via an inhibition of B-cell differentiation or an alteration of cytokine expression and the anti-idiotypic network (27, 50)-whereas the action of the human mAbs is via a direct targeting to OL antigens and/or myelin. No characteristic was completely predictive of an Ab's ability to promote remyelination. In fact, one human mAb tested in chronically TMEV-infected mice appears to suppress remyelination below the level of spontaneous remyelination, suggesting that certain OL-binding human mAbs can inhibit remyelination in vivo or may exacerbate demyelination. This is consistent with the observation that specific mAbs reactive to OL antigens (i.e., myelin oligodendrocyte glycoprotein, 51) enhance demyelination in EAE (52). Ultimately, proof of an Ab's remyelinating potential and lack of pathogenicity requires in vivo testing.

Several double-blind, placebo-controlled trials with human IVIg have shown some efficacy in MS (18,36,37). Polyclonal human IgM, sHIgM22 and sHIgM46 all enhanced CNS remyelination in the TMEV model as well as IVIg, suggesting that these Abs may be as effective in MS. Human mAbs that bind to OLs may have the additional benefit of direct OL stimulation. Human mAbs can be produced free from potential pathogen infection and can be structurally altered to augment their effectiveness and immunogenicity. In contrast to mouse mAbs or "humanized" mouse mAbs, human mAbs should result in minimal immune response and are readily applicable to human trials. Given that human mAbs promoted remyelination in chronically paralyzed animals provides hope that successful therapies can be developed for patients with long-standing disabilities.

REFERENCES

1. Perier, O. & Gregoire, A. (1965) Brain 88, 937-952.
2. Prineas, J. W. & Connel, F. (1979) Ann. Neurol. 5, 22-31.
3. Wolswijk, G. & Nobel, M. (1989) Development 105, 387-400.
4. Armstrong, R. C., Dorn, H. H., Kufta, C. V., Friedman, E. & Dubois-Dalcq, M. E. (1992) J. Neurosci. 12, 1538-1547.
5. Gumpel, M., Baumann, N., Raoul, M. & Jaques, C. (1983) Neurosci. Lett. 37, 307-312.
6. Warrington, A. E., Barbarese, E. & Pfeiffer, S. E. (1993) J. Neurosci. Res. 34, 1-13.
7. Groves, A. K Barnett, S. C., Franklin, R. J., Crang, A. J., Mayer, M Blakemore, W. F. & Noble, M. (1993) Nature 362, 453-455.
8. Franklin, R. J. M., Bayley, S. A. & Blakemore, W. F. (1996) Exp. Neurol. 137, 263-276.
9. O'Leary, M. T. & Blakemore, W. F. (1997) J. Neurosci. Res. 48, 159-167.
10. Jeffery, N. D., Crang, A. J., O'Leary, M. T., Hodge, S. J. & Blakemore W F. (1999) Eur. J. Neurosci. 11, 1508-1514.
11. McKinnon, R. D., Matsui, T., Dubois-Dalcq, M., & Aaronson, S. A. (1990) Neuron 5, 603-614.
12. Bogler, O., Wren, D., Barnett, S. C., Land, H. & Noble, M. (1990) Proc Natl Acad Sci USA 87, 6368-6372.
13. Rosano, C., Felipe-Cuervo, E., & Wood, P. M. (1999) Glia 27, 189-202.
14. Bansal, R. & Pfeiffer, S. E. (1997) J. Neurosci. Res. 50, 215-228.
15. McTigue, D. M., Homer, P. J., Stokes, B. T. & Gage, F. H. (1998) J. Neurosci. 18, 5354-5365.
16. Miller, D. J., Asakura, K. & Rodriguez, M. (1995) J. Neurosci. Res. 41, 291-296.
17. Noseworthy, J. H., O'Brien, P. C., van Engelen, B. G. & Rodriguez, M. (1994) J. Neurol. Neurosurg. Psychiatry 57 Suppl: 11-14.
18. Fazekas, F., Deisenhammer, F., Strasser-Fuchs, S., Nahler, G. & Mamoli, B. (1997) Lancet 349, 589-593.
19. Lucchinetti, C. F., Bruck, W., Rodriguez, M. & Lassmann, H. (1996) Brain Pathol. 6, 259-274.
20. Dal Canto, M. C. & Lipton, H. L. (1997) Am. J. Pathol. 88, 497-500.
21. Drescher, K. M., Rivera-Quinones, C., Lucchinetti, C. & Rodriguez M. (1998) J. Neuroimmunol. 88, 111-119.
22. Miller, D. J., Sanborn, K. S., Katzmann, J. A. & Rodriguez, M. (1994) J. Neurosci. 14, 6230-6238.
23. Asakura, K., Miller, D. J., Murray, K., Bansal, R., Pfeiffer, S. E. & Rodriguez, M. (1996) J. Neurosci. Res. 43, 273-281.
24. Pavelko, K. D., van Engelen, B. G. & Rodriguez, M. (1998) J. Neurosci. 18, 2498-2505.
25. Miller, D. J Bright, J. J., Sriram, S. & Rodriguez, M. (1997) J. Neuroimmunol. 75, 204-209.
26. Asakura, K., Miller, D. J., Pease, L. R. & Rodriguez, M. (1998) J. Neurosci. 18, 7700-7708.
27. Dwyer, J. M. (1992) N. Engl. J. Med. 326, 107-116.
28. Hurez, V., Kazatchkine, M. D., Vassilev, T., Ramanathan, S., Pashov, A., Basuyaux, B., de Kozak, Y., Bellon, B. & Kaveri, S. V. (1997) Blood 90, 4004-4013.
29. Gard, A. L. & Pfeiffer, S. E. (1989) Development 106, 119-132.
30. Asakura, K., Hunter, S. F. & Rodriguez, M. (1997) J. Neurochem. 68, 2281-229035.
31. Hunter, S. F. & Bottenstein, J. E. (1991) J. Neurosci. Res. 28, 574-583.
32. Rodriguez, M., Leibowitz, J. L. & Lampet, P. W. (1983) Ann. Neurol. 13, 426-433.
33. Blakemore, W. F., Eames, R. A., Smith, K. J. & McDonald, W. I. (1977). J. Neurol. Sci. 33, 34. Njenga, M. K., Pavelko, K. D., Baisch, J., Lin, X., David, C., Leibowitz, J. & Rodriguez, M. (1996) J. Virol. 70, 1729-1737.
35. McGavern, D. B., Murray, P. D. & Rodriguez, M. (1999) J. Neurosci. Res. 58, 492-504.
36. Achiron, A., Pras, E., Gilad, R., Ziv, I., Mandel, M., Gordon, C. R., Noy, S., Sarova-Pinhas, I. & Melamed, E. (1992) Arch. Neurol. 49, 1233-1236.
37. Sorensen, P. S., Wanscher, B., Jensen, C. V., Schreiber, K., Blinkenberg, M., Ravnborg, M., Kirsmeier, H., Larsen, V. A. & Lee, M. L. (1998) Neurology 50, 1273-1281.
38. Pfeiffer, S. E. (1984) in Oligodendroglia, ed. Norton, W. T. (Plenum, N.Y.), pp. 233-298.
39. Sommer, I. & Schachner, M. (1981) Devel. Biol. 83, 311-327.
40. Kabat, E. A., Wu, T. T., Perry, H. M., Gottesman, K. S. & Foeller, C. (1991) Sequences of proteins of immunological interest, 5th ed. (NIH Publication, Bethesda, Md.).
41. Kyle, R. A. & Garton, J. P. (1987) Mayo Clin. Proc. 62, 719-731.
42. Lacroix-Desmazes, S., Mouthon, L., Pashov, A., Barreau, C., Kaveri, S. V. & Kazatchkine, M. D. (1997) Intl. Immunol. 8, 1175-1183.
43. Stangel, M., Compston, A. & Scolding, N.J. (1999) J. Neuroimmunol. 96, 228-233
44. Pashov, A., Bellon, B., Kaveri, S. V. & Kazatchkine, M. D. (1997) Mult. Scler. 3, 153-156.
45. Vassilev, T., Yamamoto, M., Aissaoui, A., Bonnin, E., Berrih-Aknin, S., Kazatchkine, M. D. & Kaveri, S. V. (1999) Eur. J. Immunol. 29, 2436-2442.
46. Bansal, R. & Pfeiffer, S. E. (1989) Proc. Natl. Acad. Sci. USA 86, 6181-6185.
47. Dyer, C. A. & Benjamins, J. A. (1990) J. Cell Biol. III, 625-633.
48. Cohen, J. A., Williams, W. V., Geller, H. M. & Greene, M. I. (1991) Proc. Natl. Acad. Sci. USA 88, 1266-1270.
49. Bansal, R., Winkler, S. & Bheddah, S. (1999) J. Neurosci. 19, 7913-7924.
50. Stangel, M. Toyka, K. V. & Godl, R. (1999) Arch. Neurol. 56, 661-663.
51. Lebar, R., Lubetzki, C., Vincent, C., Lombrail, P. & Boutry, J. M. (1986) Clin. Exp. Immunol. 66, 423-443.
52. Genain, CIP, Nguyen, M. H., Letvin, N. L., Pearl, R., Davis, R. L., Adelman, M., Lees, M. B., Linington, C. & Hauser, S. L. (1995) J. Clin. Invest. 6, 2966-2974.

Example 8

As described in the prior Examples, we have used two approaches to identify human monoclonal antibodies that induce a similar pattern of remyelination in the Theiler's virus model of demyelinating disease. The first approach was to transform human B cells with Epstein Barr Virus (EBV) to generate immunoglobulin secreting B cell clones. The resulting cell lines were screened to identify cultures that expressed high levels of antibody and the ability of the produced antibodies to bind CNS antigens, with particular emphasis on those that bound oligodendrocytes. The second approach was to perform a similar screen CNS-binding of serum from patients diagnosed with a monoclonalgammopathy such as MUGUS, lymphoma, or Waldenstrom's syndrome. In the case of the EBV transformed cells, the cells themselves might provide a source of antibody for generating sufficient quantities of GMP grade antibodies for clinical trials. In addition, antibodies identified from either source could be produced more optimally in an artificial antibody producing system using synthetic antibody genes encoding the antibodies of interest. We anticipate that hybridoma cell lines transfected with an antibody expression cassette encoding the antibody of interest will provide sufficient antibody of interest for in vivo analysis and clinical trials.

In the course of the screening studies, we have identified a set of human monoclonal IgM antibodies that induce statistically significant remyelination in our in vivo Theiler's virus model of demyelinating disease (TABLE 11). Each of these antibodies mimicked the remyelination response originally described with the prototypical murine monoclonal antibody SCH 94.03. Among these human antibodies are two derived from EBV-transformed B cell lines, designated MSI 19-D10- and CB2b-G8, and two antibodies, designated sHIgM22 and sHIgM 46, identified among a panel of antibodies from more than 50 patients expressing high levels of monoclonal IgM in their sera.

TABLE 11

Remyelination induced by human monoclonal antibodies in SJL/J mice chronically infected with Theiler's virus.

| Treatment | % Remyelination | Statistical Evaluation |
|---|---|---|
| Comparison 1 | | |
| PBS (n = 7) | 6.74 (+/−1.80) | |
| sHIgM22 (n = 8) | 17.6 (+/−3.42) | P < 0.05 |
| sHIgM 46 (n = 5) | 27.12 (+/−4.01) | P < 0.001 |
| Comparison 2 | | |
| PBS (n = 12) | 8.25 (+/−1.44) | |
| MSI 19-D10 (n + 13) | 24.38 (+/−2.91) | P < 0.001 |
| CB2b-G8 (n = 12) | 23.51 (+/−3.13) | P < 0.001 |

Animals were chronically infected with DA strain of Theiler's virus for greater than 9 months prior to treatment with a single ip injection of 0.5 mg IgM antibody isolated from patient serum (sHIgM22 and sHIgM 46) or EBV transformed cell lines (MSI 19-D10 or CB2b-G8). Five weeks later, the mice were perfused with fixative and spinal cords were isolated for histological analysis. Areas of demyelination and remyelination were assessed directly by microscopy. Percent area remyelination was determined by the formula area remyelinated/area demyelinated x 100. Treatment effects were evaluated by statistical comparison to groups of animals that received PBS injections instead of antibody.

The structures of the IgM heavy and light chains for both the antibodies derived from the EBV-transformants have been determined by analysis of cDNA generated from immunoglobulin mRNA isolated from the cells. The sequences of the heavy and light chain variable regions of MSI 19-D10 and sHIgM22 are provided in FIGS. 35-38 (SEQ ID NOS: 11, 12, 13, 14 and 7, 8, 9 and 10). The sequences of the heavy and light chain variable regions of CB2b-G8 are provided in FIGS. 45 and 46 (SEQ ID NOS: 15, 16, 17, 18). The sequences themselves are not remarkable other than they differ somewhat from known germline immunoglobulin sequences. Thus, they may be the products of somatic diversification during the course of immune responses against unidentified antigens. The value of the sequences is that they provide a blue print for the construction of expression vectors for the production of the immunoglobulin under controlled conditions.

Similarly, the structures of the heavy and light chains from the serum of one of the IgM-producing patients were determined by protein sequence analysis, followed by cloning and sequence analysis of cDNA from peripheral blood mononuclear cells isolated from the patient. Two closely related heavy and light chains were identified in the patient's serum, designated sHIgM22 (FIGS. 35 and 36) (SEQ ID NOS: 7, 8, 9, 10). The two heavy and two light chains were both present in the isolated cDNA populations at a ration of 60:40. Both antibodies share a common μ-VDJ rearrangement and λ-VJ rearrangement, indicting that they are derived from a common B cell precursor. They have subsequently diverged, as a result of the accumulation of mutations that have altered the structures of their variable regions. We conclude that both antibodies are expressed in the scrum of the patient because peptides from both antibodies were characterized from the protein isolated from the serum. However, the two distinct combinations of variable and light chains were not observed directly, leaving open the possibility that other combinations of the identified heavy and light chains may actually be present. Based on the positions of the observed amino acid substitutions, we suspect that the antibodies have very similar reactivity patterns.

Example 9

Development of a Transfection System for the Expression of Antibody Genes in Cell Culture In order to generate a renewable supply of high titer antibody from the human antibodies, we have developed a transfection-based expression system for generation of recombinant antibody. Hybridoma cells which have been selected for the loss of endogenous immunoglobulin mRNA production can be transfected with recombinant antibody genes to generate cells expressing the antibodies of interest.

We have explored the use of a series of genomic and cDNA based vector systems to express cloned antibody genes in cell culture. We have successfully expressed light chain protein using either genomic or cDNA-based genes. We have achieved heavy chain expression using a genomic-based heavy chain vector PAC 4026 (kindly provided by Dr. Sherie Morison at UCLA). However, the yield of antibody with this vector system is too low for practical use in vivo. Our focus has been to develop a new vector that will routinely yield transfected hybridoma clones that produce high titer antibody. Our current strategy is to assemble the vector from components that individually have been shown to work well in our hands.

Figure 47:
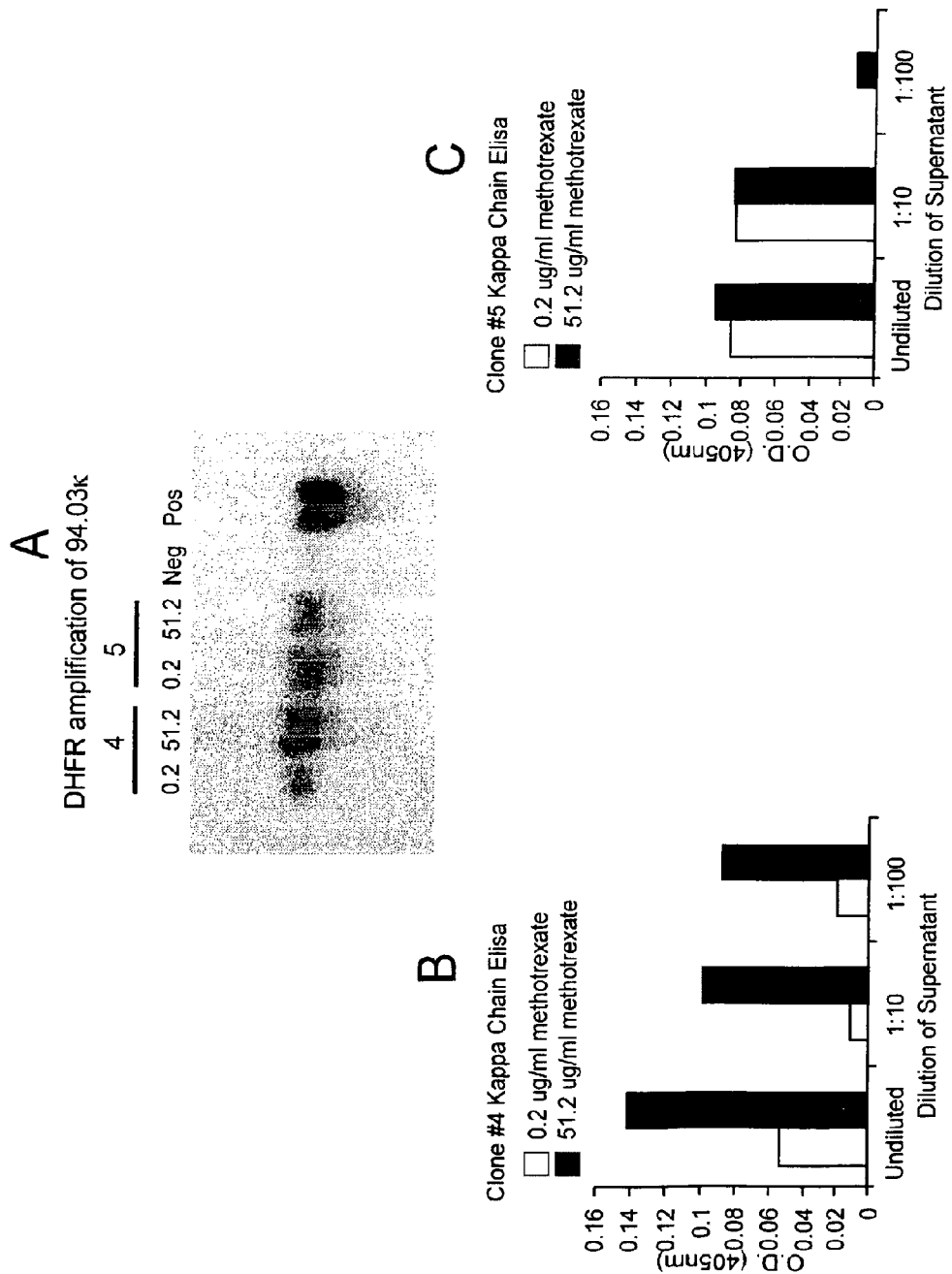

We have shown that a vector expressing dHfR and an immunoglobulin light chain cDNA under CMV-promoter control expresses light chain and that this expression can be amplified by growing the transfected immunoglobulin producing cells in increasing concentrations of methotrexate (FIG. 47). We then clone this functional unit, expressing immunoglobulin light chain and dHfR, into the vector expressing the genomic heavy chain gene encoding the complementing μ chain. The first vector we have created along this line encodes mouse/human chimeric 94.03 and is shown in the top panel of FIG. 48. The vector has been introduced into antibody-negative hybridoma cells and clones expressing small amounts of functional antibody have been isolated. The antibody stains CNS tissue in a manner identical to the native mouse antibody 94.03 (FIG. 49). These antibody-producing clones are now undergoing selection with increasing amounts of methotrexate to expand the amount of antibody being produced. Because we have identified two heavy and two light chains in the human serum sHIgM22, all four permutations of heavy and light chain need to be evaluated. Vectors expressing three of the four possible combinations of sHIgM22 identified in our sequence study have been prepared and are now being introduced into the immunoglobulin-negative hybridoma cells. The prototype vector is shown in the bottom panel of FIG. 48. Recombinant sHIgM22 (22BII) comprising Clone B heavy chain and Clone II light chain (as denoted in FIGS. 35 and 36) was generated based on the prototype vector. Recombinant 22BII is active and demonstrates cell binding similar to native LYM 22.

Methods

Construction of Expression Vectors for Expressing Mouse/Human Chimeric 94.03 (M1) and sHIgM 22 Antibody:

Assembly of Expression System for Mouse/Human Chimeric 94.03

The assembled vector consists of two units. The first encodes the heavy chain of the immunoglobulin which is encoded by a genomic DNA-derived immunoglobulin gene. The vector is in part a derivative of a backbone vector (PAG 4026) obtained from the laboratory of Dr. Sherrie Morrison from UCLA. The PAG 4026 vector encoded an IgM heavy chain expressing an irrelevant variable region. There were no convenient cloning sites available for the substitution of variable regions of interest. We therefore engineered sites by deletion of the irrelevant heavy chain sequences and reconstitution of the regions flanking the variable region with unique restriction sites (Rsr II at the 5' end and Pac I at the 3' end). As the sequence of the PAG vector was not known, we determined which restriction enzyme sites would be unique by trial and error using enzymes that recognize sequences infrequently present in mammalian DNA.

The heavy chain variable region of the mouse IgM monoclonal antibody 94.03 was isolated from cDNA by PCR using the RsrII primer ACTCCCAAGTCGGCTCGCTTTCTCT-TCAGTGACAAACACAGACATAGAACA TTCAC-CATGGGATGGAGCTGTATCACT (SEQ ID NO: 53) to introduce the RsrII site upstream of the leader sequence and the PacI primer ACTGACTCTCTTAATTAAGACTCACCT-GAGGAGACTGTGAGAGTGGT (SEQ ID NO: 54) to introduce the PacI site while maintaining the correct splice junction at the 3' end of the variable region coding block.

The second part of the expression vector is a derived from multiple plasmids. The finished construct contains EagI sites at both termini, the DHFR (dihydrofolate reductase) coding sequence under regulatory control of the SV40 promoter and a chimeric mouse/human kappa light chain cDNA coding block under regulatory control of the CMV promoter. This portion of the vector was assembled in a step wise fashion starting with three plasmids (pCIneo (Promega Corporation), pUC18 (New England Biolabs), and pFR400 (Simonsen and Levinson, Proc Natl Acad Sci USA 80:2495:1983)) that provided appropriate cloning sites, promoter regions, polyadenylation signals, and the DHFR coding block. After a series of modifications which included the introduction of synthetic linker regions and deletions of undesirable restriction endonuclease recognition sites, the methotrexate selectable light chain cassette was assembled. The cassette includes unique restriction endonuclease sites (Nhe I and Xho 1) that flank the cDNA coding block of the light chain gene.

The chimeric light chain gene was assembled from two cDNA sequences using the PCR splicing by overlap extension technique (Horton et al. Gene 77:61:1989). The primers flanking the fused regions of the chimeric cDNA (contained the enzyme recognition sequences for the endonuclease Xho I and Nhe I. The 5' primer used to amplify the fused gene product was TTGGCGCGCCAAAGACTCAGCCTGGA-CATGATGTCCTCTGCTCAGTTC (SEQ ID NO: 55); the 3' primer was ATAGTTTAGCGGCCGCATTCTTATCTAA-CACTCTCCCCTGTTG (SEQ ID NO: 56). The cDNA coding block was inserted into the light chain cassette vector using these sites.

Once assembled, the cassette was excised using the endonuclease Eag I and inserted into the unique Eag I site in the vector containing the heavy chain gene. The resulting construct contains the coding sequences for both the heavy and light chain components of the mouse/human chimeric antibody for "humanized" 94.03. The heavy chain is expressed by the human IgH promoter and the light chain is expressed by the CMV promoter. The dHFR gene provides an amplification marker and is expressed by the SV40 promoter. Each of these genes contains polyadenylation signals at the 3' ends. Other important features of the vector include a bacterial origin of replication and a gene expressed in bacteria encoding resistance to ampicillin. The heavy variable and light chain cDNA coding blocks are flanked by unique restriction endonuclease sites that can be use to substitute new immunoglobulin sequences isolated from mRNA of any antibody producing cell or synthetic immunoglobulin genes.

Insertion of sHIgM22 Sequences into the Expression Vector System

The cDNA of mRNA encoding the heavy and light chains of sHIgM22 were prepared by PCR amplification of peripheral blood RNA using 5' primers deduced from amino acid sequence information and sequences in the constant regions of the heavy and light chain respectively. The heavy chain variable region coding block, leader sequence and donor splice junction along with the flanking RsrII and Pac I sites were assembled by using PCR to add the 5' region GACTCG-GTCCGCCCAGCCACTGGAAGTCGCCGGT-GTTTCCATTCGGTGATC ATCACTGAACACAGAG-GACTCACCATGGAGTTTGGGCTGAGCTGGGTTTTC CTCGTTGCTCTTTTAAGAGGTGTCCAGT-GTCAGGTGCAGCTGGTGGAGTCT GG (SEQ ID NO: 57) and the 3' sequences CCTTAATTAAGACCTGGAGAG-GCCATTCTTACCTGAGGAGACGGTGACCAG GGTTC (SEQ ID NO: 58). The resulting DNA molecule was digested with Rsr II and Pac I and subsequently cloned into the expression vector, substituting the desired variable region sequence for the irrelevant sequence in the vector.

The light chain sequence was assembled in two steps. The lambda constant region was isolated from mRNA by RT-PCR using the 5' primer CTAGCTAGCGTCCTAGGTCAGC-CCAAGGCTGCCCCC (SEQ ID NO: 59) and 3' primer ATAGTTTAGCGGCCGCACCTATGAACATTCTGTAGG (SEQ ID NO: 60). This fragment was cloned using a unique AvrII site and a 3' Not I site into the pCIneo vector.

The variable region of sHIgM22 was generated by RT-PCR using the 5' primer CTAGCTAGCCCGAATTTCGGGA-CAATCTTCATCATGACCTGCTCCCCTCTCC TCCT-CACCCTTCTCATTCACTGCACAGGGTC-CTGGGCCCAGTCTGTGTTGAC GCAGCCG (SEQ ID NO: 61) in order to introduce the needed Nhe I site and leader sequence onto the cDNA. The 3' primer, GGGCAGCCT-TGGGCTGAGCTAGGACGGTCAGC (SEQ ID NO: 62), was used to introduce an AvrII site so that this fragment could be joined with the constant region piece. The resulting coding block containing a functional leader signal was flanked by the necessary NheI and Xho I sites for cloning into the dHFR/light chain cassette, which was subsequently assembled with the heavy chain plasmid to generate the final product containing both the heavy and light chain coding sequences and promoters needed for expression in mammalian cells.

Example 10

A 94.03 IgG Isotype Antibody

Figure 50:
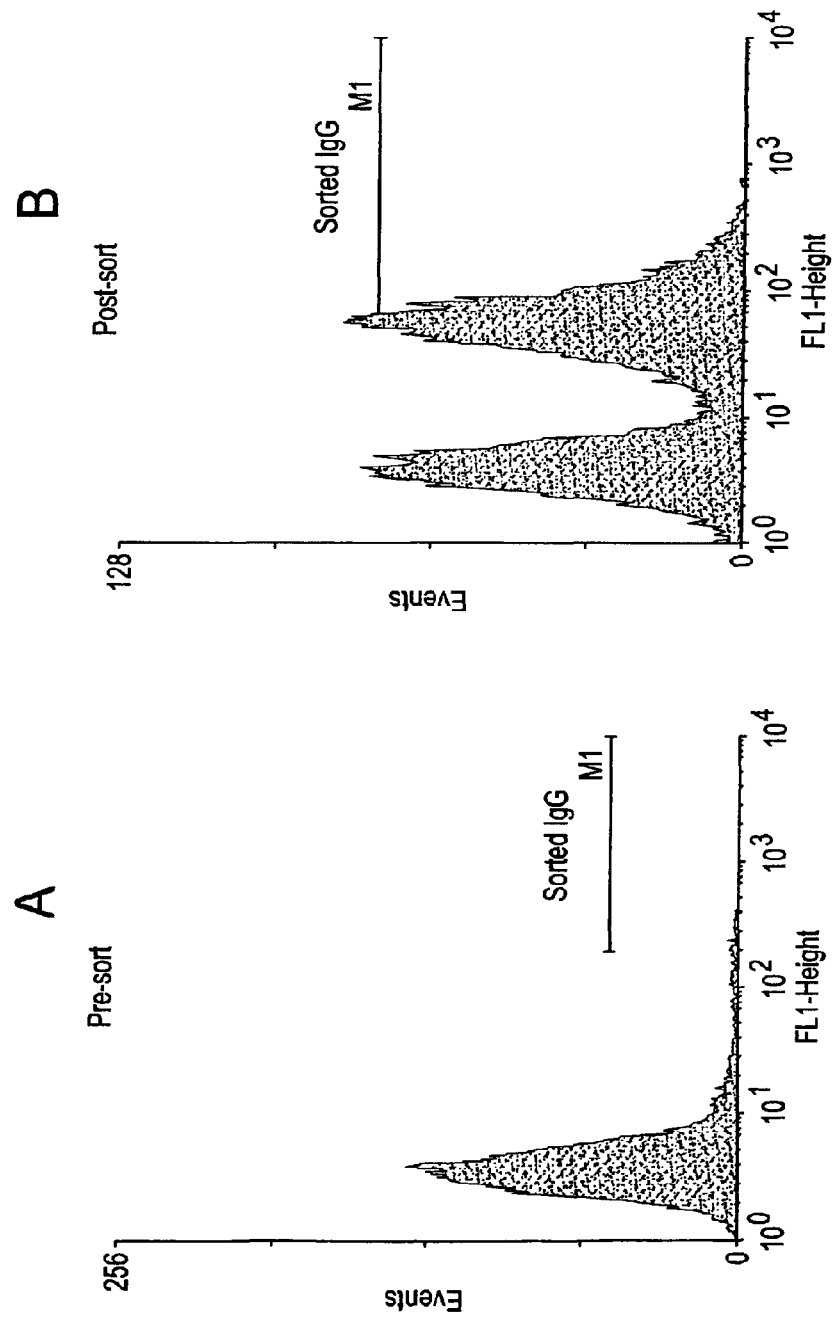

One strategy for determining the importance of isotype in the ability of the mouse antibody 94.03 to induce remyelination is to generate a recombinant antibody that expresses the variable region of 94.03 with an IgG isotype. As an alternative strategy, we sought to identify a natural isotype switch variant within the population of 94.03-producing cells in culture. Spontaneous switch variants have been known to appear upon occasion in cultures of this type. After successive FACS sorts of cells stained for cell surface IgG, we were able to isolate a clonal cell line secreting 94.03 bearing the $IgG_1$ isotype (FIG. 50). The structure of the antibody produced by these cells was confirmed by ELIZA, by characterization of the produced protein on SDS gels, and by cDNA cloning. Direct sequence analysis as outlined in FIG. 51 produced definitive data indicated that we have isolated an $IgG_1$ variant of the 94.03 antibody.

Example 11

$IgG_3$ Isotype Anti-Oligodendrocyte Mouse Antibody O9

The mouse O9 antibody was isolated as an anti-oligodendrocyte antibody and is of the $IgG_3$ subtype (Kuhlmann-Krieg, S., Sammer, I. and Shachner M. (1988) *Devel Brain Res* 39:269-280). The 09 antibody binds strongly and specifically to white matter in the CNS. We examined and demonstrated the ability of the O9 antibody to stimulate remyelination in the TMEV model. The O9 antibody heavy chain variable region sequence is provided in FIG. 52 (SEQ ID NOS: 19 and 20). The sequence of the kappa light chain 1 variable region of O9 is provided in FIG. 53 (SEQ ID NOS: 21 and 22). The sequence of the kappa light chain 2 variable region of O9 is provided in FIG. 54 (SEQ ID NOS: 23 and 24).

Example 12

IgM Monomers Induce Remyelination

Another approach to deciphering the importance of structural features of the IgM antibodies for the induction of remyelination is to fractionate the antibody biochemically and to evaluate the ability of the antibody fragments to induce remyelination in vivo. One possibility is that the identified antibodies have low affinity for CNS structures, and therefore, the decavalency of IgM may be critical for remyelinating activity because the multiple binding sites provide enough avidity for the antibodies to interact with the target structures in the CNS. To address this question, we have generated IgM monomers by reduction of the disulfied bonds that hold the pentameric immunoglobulin molecules together. The resulting monomers are divalent. The monomers fail to bind oligodendrocytes in vitro and do not stain brain sections in the pattern observed with the intact native antibody. However, the monomeric antibodies retain the ability to induce remyelination in vivo (TABLE 12 and TABLE 13). This is a notable result in light of the absence of observed staining in our in vitro assays. One possibility is that in vitro assays monitoring binding are not as sensitive as the bioassay for remyelination. Because there is such a strong correlation between binding and the induction of remyelination, we believe that the specificity of these antibodies for CNS structures is important despite our inability to observe binding with the monomers.

TABLE 12

Remyelination induced by monomeric fragments of murine IgM mAb 94.03.

| Treatment | % Remyelination | Statistical Evaluation |
|---|---|---|
| PBS (n = 7) | 6.74 (+/−1.80) | |
| Monomeric 94.03 (n = 8) | 17.32 (+/−2.67) | P < 0.01 |
| Pentameric 94.03 (N = 5) | 18.1 (+/−5.76) | P < 0.01 |

IgM antibodies were reduced in mild conditions and alkylated. This treatment disrupted the pentameric structure of the antibodies and allowed divalent monomers to be isolated by column chromatography. Chronically infected SJL/J mice received a total of 0.5 mg of antibody administered ip twice a week over the five week treatment period. After five weeks, the animals were perfused with fixative and their spinal cords removed for histological analysis. Percent remyelination was determined microscopically by comparing the area of remyelinated lesions to total demyelinated area as indicated in Table 1. Individual treatment groups were compared to animals which received PBS injections instead of antibody.

TABLE 13

CNS Remyelination by Mouse Monoclonal Antibodies

| Treatment | No. of Mice | Area of White Matter (mm2) | Area of Myelin Pathology (%) | Area of CNS-Type Remyelination (%) | Comparison of % Remyelination to PBS Group |
|---|---|---|---|---|---|
| Pentameric 94.03 | 5 | 9.7 ± 1.2 | 14.2 ± 3.6 | 18.1 ± 5.8 | P = 0.05 |
| Monomeric 94.03 Expt 1 & 2 | 8 | 9.3 ± 1.0 | 9.3 ± 1.2 | 17.3 ± 2.7 | P = 0.007 |
| Monomeric 94.03 Expt 1 | 5 | 9.8 ± 1.3 | 9.1 ± 1.1 | 19.1 ± 3.4 | P = 0.006 |
| Monomeric 94.03 Expt 2 | 3 | 8.4 ± 1.5 | 9.8 ± 2.9 | 14.4 ± 4.5 | P = 0.087 |
| PBS | 7 | 9.8 ± 0.6 | 11.9 ± 1.8 | 6.7 ± 1.8 | |

Values represent the mean ± standard error of the mean.

Statistics by t test of the percentage of area of CNS-type remyelination per area of white matter pathology in mice treated with monoclonal antibodies as compared to those treated with PBS. Only animals with area of white matter pathology ≥5% were included in statistical analysis.

We have further fractionated the antibody by generating (Fab')$_2$ Fab, and Fv fragments of the antibody. SJL mice chronically infected with Theiler's virus have been treated with these antibody fragments to determine whether divalent fragments missing the Fc portion of the antibody or monovalent antibody fragments comprised primarily of a single antigen binding site can induce remyelination.

A parallel analysis of the human monoclonal antibody sHIgM22 was performed to determine whether antibody fragments of this human IgM behave in a similar manner. Preliminary analysis indicates that the (Fab')$_2$ fragments of sHIgM22 induce remyelination. If it can be determined that a single small binding domain can induce remyelination, this information may prove important for determining the mechanism of repair as well as provide an avenue for the development of an pharmacological analogue.

Example 13 sHIgM 46 Antibody Induces Myelin Repair

Our initial studies suggests that the inductin of myelin repair by sHIgM 46 may be qualitatively superior to the repair observed with sHIgM22. Upon histological examination of sections of SJL mice that were chronically infected with TMEV, smaller areas of demyelination were observed following treatment with sHIgM 46 than with other monoclonal antibodies (TABLE 14). This observation was highly statistically significant. This result is notable because treatment with the antibody does not begin until demyelinated lesions are well established and have reached maximum size in chronically infected animals. Our interpretation of this result is that myelin repair is so complete in some areas of the spinal cord that they are not being distinguished from normal areas of the cord during our standard histological examination. The lesions in sHIgM 46 treated mice are examined by electron microscopy to confirm whether the repaired lesions contain higher numbers of myelin wraps than in other treatment groups.

TABLE 14

Qualitative differences in myelin repair by human antibody sHIgM 46

| Treatment | % White Matter Demyelinated | Statistical Evaluation |
| --- | --- | --- |
| sHIgM 46 (n = 15) | 4.07 (+/−2.52) | |
| All other antibodies (n = 70) | 10.41 (+/−6.26) | P < 0.001 |

SJL/J mice chronically infected with Theiler's virus for more than 9 months were divided into groups and individual groups received a single 0.5 mg ip injection of one of a battery of monoclonal antibodies. After five weeks animals were perfused with fixative and their spinal cords were isolated for histological analysis. The area of demyelination was determined by measuring the total area of the cord occupied by white matter and the area of demyelination visualized by light microscope using 25X optics. The data are comprised of mice from three independent experiments.
Antibodies used to treat animals in the pooled treatment group ("all other antibodies") were human monoclonal IgM sHIgM 12, 14, 22, 47, 50, AKJR8, MSI 10E10, 2B2GE7, NA8FE4, and mouse antibodies O6, O9, RIP, and MOG. The data set passed normality tests and were analyzed by ANOVA.

Example 14

The sequences of the heavy and light chain variable regions of human antibodies AKJR4, CB2iE12 and CB2iE7, and the light chain variable region of MSI19E5 were determined. The sequences of the heavy and light chain variable region of AKJR4 are shown in FIGS. 55 and 56, respectively (SEQ ID NOS: 25, 26 and 27, 28). The sequences of the heavy and light chain variable region of CB2iE12 are shown in FIGS. 57 and 58, respectively (SEQ ID NOS: 29, 30 and 31, 32). The sequences of the heavy and light chain variable region of CB2iE7 are shown in FIGS. 59 and 60, respectively (SEQ ID NOS: 33, 34 and 35, 36). The sequence of the light chain variable region of MSI19E5 is shown in FIG. 61, respectively (SEQ ID NOS: 37 and 38).

Example 15

A series of mouse and human antibodies were tested for their ability to induce or generate calcium flux in mixed primary glial cultures (composed of astrocytes and oligodendrocytes) using the method provided above in Example 5. The results (as a percentage of cells showing calcium flux) for these antibodies are tabulated in TABLE 15, along with remyelination and oligodendrocyte surface immunoreactivity for each antibody.

Antibodies demonstrating intracellular calcium changes are also noted as promoting remyelination.

TABLE 15

CNS Reactive Antibodies Mediate Intracellular Calcium Changes

| Treatment (10 µg/ml) | # of responding cells (mixed cell cultures) | Remyelination Promotion | Oligodendrocyte Surface Immunoreactivity |
| --- | --- | --- | --- |
| SCH 94.03 (3 µg/ml) | 36/251 (14%) * | + | + |
| SCH 79.08 | 25/137 (18%) * | + | − |
| sHIgM22 (3 µg/ml) | 33/272 (12%) * | + | + |
| sHIgM50 | 12/222 (5%) * | ? | + |
| O4 | 49/265 (18%) * | + | + |
| CB2BG8 | 43/269 (16%) * | + | + |
| AKJR8 | 49/244 (20%) * | +/−(p = .06) | − |
| 94.03 monomer | 3/310 (1%) * | + | − |
| CH12 | 0/203 (0%) | − | − |
| sHIgM12 | 0/247 (0%) | − | − |
| sHIgM14 | 0/203 (0%) | − | + |
| sHIgM47 | 0/177 (0%) | − | + |
| AKJR4 | 1/268 (0.4%) | − | − |

Example 16

Remyelination studies in TMEV-infected mice were performed with mouse antibody O9 versus monomeric and pentameric 94.03. The results of these studies are shown in TABLE 16.

Similarly, remyelination studies were performed with human antibodies AKJR4, AKJR8 and MSI10E10 and are shown in TABLE 17. Remyelination with MSI10E10 is significant.

TABLE 16

CNS Remyelination by Mouse Monoclonal Antibodies

| Treatment | No. of Mice | Area of White Matter (mm2) | Area of Myelin Pathology (mm2) | Area of CNS-Type Remyelination (mm2) | Area of CNS-Type Remyelination (%) |
|---|---|---|---|---|---|
| Pentameric 94.03 | 5 | 9.68 ± 1.27 | 1.47 ± 0.42 | 0.26 ± 0.11 | 18.1 ± 5.76 |
| Monomeric 94.03 | 8 | 9.30 ± 0.96 | 0.85 ± 0.12 | 0.13 ± 0.02 | 17.32 ± 2.67 |
| O9 | 5 | 8.44 ± 0.96 | 1.35 ± 0.33 | 0.36 ± 0.13 | 27.4 ± 6.33 |
| PBS | 7 | 9.78 ± 0.60 | 1.20 ± 0.22 | 0.06 ± 0.02 | 6.74 ± 1.80 |

Values represent the mean ± standard error of the mean.
Statistics by t test of the percentage of area of CNS-type remyelination per area of white matter pathology in mice treated with monoclonal antibodies as compared to those treated with PBS revealed, monomeric 94.03 p = 0.007, O9 p = 0.005. Only animals with areas of white matter pathology ≥5% were included in statistical analysis.

TABLE 17

CNS Remyelination in TMEV-Infected Mice Following Treatment with Human Monoclonal Antibodies (October 2000)

| Treatment | No. of Mice | Area of White Matter (mm2) | Area of Myelin Pathology (mm2) | Area of CNS-Type Remyelination (mm2) | Area of CNS-Type Remyelination (%) | p value compared to PBS |
|---|---|---|---|---|---|---|
| AKJR4 | 4 | 8.78 ± 0.8 | 1.1 ± 0.2 | 0.05 ± 0.03 | 4.2 ± 2.0 | 0.160 |
| AKJR8 | 6 | 10.0 ± 0.7 | 1.0 ± 0.1 | 0.12 ± 0.02 | 13.3 ± 2.2 | 0.066 |
| MSI10E10 | 5 | 9.3 ± 1.4 | 1.9 ± 0.6 | 0.18 ± 0.04 | 11.3 ± 3.7 | 0.360 |
| PBS | 12 | 9.9 ± 0.4 | 1.1 ± 0.1 | 0.07 ± 0.01 | 8.3 ± 1.4 | |

Values represent the mean ± standard error of the mean.
Statistics by t test of the percentage of area of CNS-type remyelination per area of white matter pathology in mice treated with human bodies as compared to those treated with PBS. Only animals with areas of white matter pathology ≥5% were included in statistical analysis.

Example 17

Antibodies Promote Glial Cell Proliferation

The ability of mouse and human antibodies to promote glial cell proliferation was assessed. Mixed primary cultures of rat glia were grown to 8 days in culture in a minimal media of DMEM, insulin and amino acids. Antibodies were added to the media at the indicated concentrations for 24 hrs. Cultures were then pulsed with tritiated thymidine for 24 hrs. Cell monolayers were dislodged with trypsin and counted. PDGF and FGF are the positive control. The upper panel of FIG. 63 shows that 94.03 promoted glial cell proliferation over media alone and equal to that observed with the PDGF/FGF combination. In the lower panel of FIG. 63 it is shown that sHIgM22 and RsHIgM22 both promote glial proliferation over media alone.

FIG. 64 depicts the analysis of promotion of glial cell proliferation by human antibodies native LYM 22, 22BII (recombinant sHIgM22 composed of heavy chain Clone B and light chain Clone II), AKJR4 and AKJR8. Both native LYM 22 and recombinant 22BII promote glial cell proliferation.

Mouse antibody O9 induces glial cell proliferation at 1 µg/ml and 0.10 µg/ml, as shown in FIG. 65.

Example 18

Recombinant sHIgM22 (22BII) is Specific for White Matter

Figure 66:
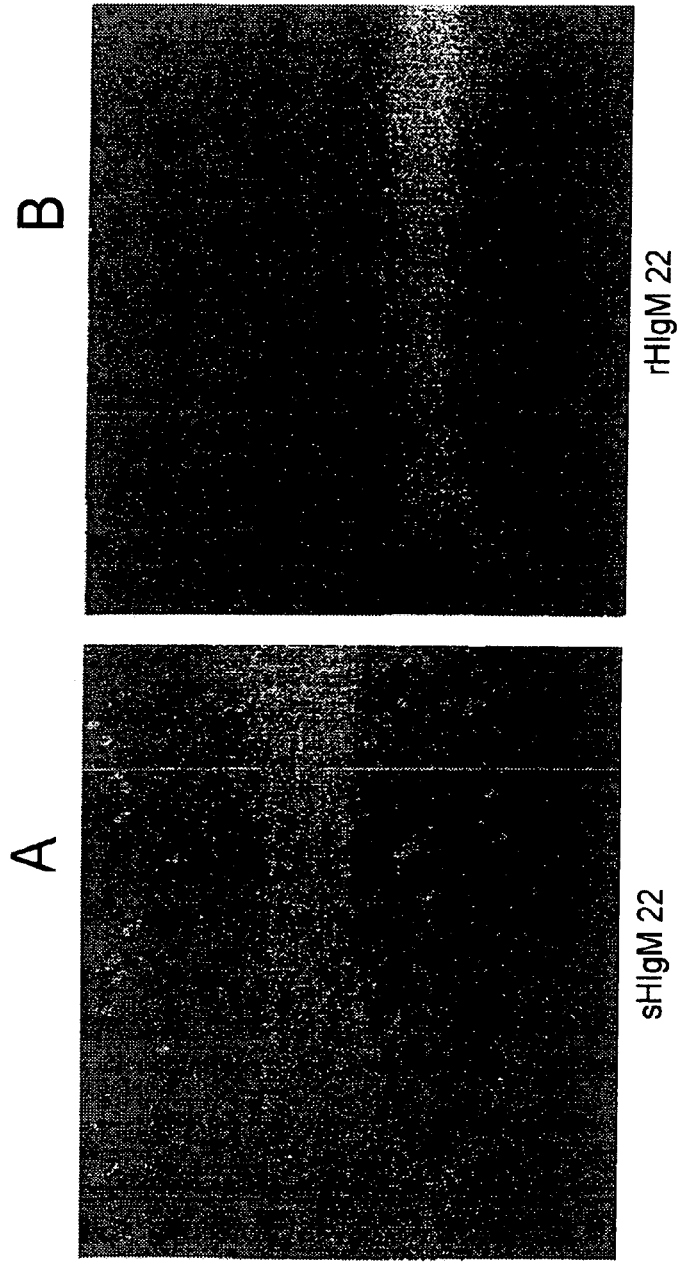

To assess the cell binding characteristics of recombinant LYM 22 (22BII), as compared to native LYM 22, slices of fixed postnatal rat cerebellum were incubated with serum derived human antibody 22 (sHIgM22) or the recombinant version (RsHIgM22) (22BII). As previously described, sHIgM22 binds to white matter tracts and to cells within the external granular and molecular layers. In contrast, RsHIgM22 is very specific for only white matter. It is likely that polyclonal human IgMs present in sHIgM22 account for the weak binding to other epitopes. The results are shown in FIG. 66.

Example 19

Mouse IgM Antibody Sequences

Upon examination of the cells for other purposes, we noted that the DNA sequences originally identified for certain mouse remyelinating antibodies, and published, were incorrect (Asakura et al. (1995) Mol. Brain Res. 34:283-293). Specifically, kappa chain sequences originally identified for the O1, O4, O9, A2B5 and HNK-1 antibodies were not correct. Each of the antibody producing cells were reanalyzed and the new antibody sequences were cross-checked using sequence specific oligonucleotide probes in a Northern Blot study to confirm the identify of the cells making the antibodies of interest. These correct sequences are appropriate and should be utilized in humanized recombinant antibodies.

O9 Kappa Chain Sequence:

O9 hybridoma produces two light chains. One of them (noted above and in FIG. 53 (SEQ ID NOS: 21 and 22) as "O9 kappa light chain 1") is ubiquitous for all O-series hybridomas and originates from MOPC21 fusion partner. This light chain does not appear to be important for the antibody activity of interest. The sequence of the O9-characteristic kappa chain (noted as "O9 kappa light chain 2" and provided in FIG. 54

(SEQ ID NOS: 23 and 24)) remains unchanged and is the correct O9 kappa chain sequence.

O4 Kappa Chain Sequence:

The correct and complete O4 kappa chain sequence is shown in FIG. 67 (SEQ ID NOS: 41 and 42).

O1 Kappa Chain Sequence:

This sequence, provided in FIG. 68 (SEQ ID NOS: 43 and 44) is completely new. The previously reported O1 kappa chain was the shared MOPC21 kappa chain which is also produced by the O1 hybridoma.

HNK-1 Kappa Chain Sequence:

The published HNK-1 sequence and the newly obtained sequence differ in two nucleotides: 174 (G-C) and 281 (C-T, this changes the amino acid from S to F). The changes are highlighted on the sequence provided in FIG. 69 (SEQ ID NOS: 45 and 46).

A2B5 Kappa Chain Sequence:

This sequence of A2B5 kappa chain shown in FIG. 70 (SEQ ID NOS: 47 and 48) is completely new. The previously reported A2B5 kappa chain sequence is in fact the O4 kappa chain sequence.

Example 20

Sequence of sHIgM46 (Lym46) Antibody and Recombinant Expression of Lym22 and Lym46

The sequence of LYM46 was determined. The amino acid sequence (SEQ ID NO: 49) and nucleic acid sequence (SEQ ID NO: 50) of the LYM46 heavy chain are depicted in FIG. 71. The amino acid sequence (SEQ ID NO: 51) and nucleic acid sequence (SEQ ID NO: 52) of the LYM46 heavy chain are depicted in FIG. 72.

Various vectors have been generated and are being utilized in generating recombinant LYM46 and recombinant LYM22 and are depicted in FIG. 48B and FIGS. 73 through 79. Recombinant LYM 46 was generated using vector pUD46M (depicted in FIG. 75). Recombinant LYM46 protein was tested using isotype specific antibodies to confirm its kappa type. Recombinant LYM46 stains equivalently to the isolated sHIgM46 from the patient on immunostaining.

The vectors and recombinant antibody expression constructs were generated as follows:

Construction of pUD22BIIM (FIG. 74)

The plasmid puD22BIIM is related to pADM22 (also called pAGDF22—FIG. 48B). All the functional elements (IgM heavy chain, lambda light chain, and dHfR gene cassette) are identical. The backbone plasmid of pAD was exchanged for the traditional pUC18 plasmid backbone. This manipulation was intended to simply and shorten the plasmid backbone of the vector. This vector has been used successfully to express small quantities of LYM 22 (approximately 0.5 ug antibody/ml supernatant).

Construction of pUD46M (FIG. 75)

The plasmid pUD46M is closely related to the plasmid pUD22BIIM. The variable region of the LYM22 heavy chain gene was removed as a cassette and replaced with the variable region sequence of the LYM46 sequence. The LYM22 lambda light chain sequence was replaced with the LYM46 kappa light chain sequence.

The Lym 46 heavy chain variable region sequence was synthesized using overlapping oligonucleotides and cloned into pUDM. The oligonucleotides used were: 5' act ccc aag tc ggtccgc ttt (SEQ. ID NO: 73)

```
                                                         (SEQ ID NO: 74)
5' act ccc aag tcg gtc cgc ttt
Template A-- act ccc aag tcg gtc cgc ttt ctc
ttc agt gac aaa cac aga cat aga aca ttc acc
ATG GAG TTT GGG CTG ACC TGG CTT TCT CTT GTT GCT ATT TTA GAA
GGT GTC CAG TGT GAG GTG CAG CTG GTG GAG TCT GGG GGA GGC TTG
GTC CAG CCT GGG GGG TCC CTG AGA CTC TCC TGT GCA GCC TCT GGA
TTC ACC TTT AGT AGC TAT TGG ATG ACC TGG GTC CGC CAG GCT CCA
GGG AAG GGG CTG GAG TGG GTG GCC AAC ATA AAG (SEQ ID NO: 75)
Template B -- CTG GAG TGG GTG GCC AAC ATA AAG AAA GAT GGA AGT
GAG AAA TCC TAT GTG GAC TCT GTG AAG GGC CGA TTC ACC ACC TCC
AGA GAC AAC GCC AAG AAC TCA CTG TAT CTG CAA ATG AAC AGC CTG
AGA GCC GAG GAC ACG GCT GTG TAT TAC TGT GCG AGA CCC AAT TGT
GGT GGT GAC TGC TAT TTA CCA TGG TAC TTC GAT CTC TGG GGC CGT
GGC ACC CTG GTC ACT GTC TCC TCA ggt gag tct taa tta aga gag tca gt (SEQ ID NO: 76)
3' primer -- act gac tct ctt aat tag
```

The kappa light chain variable region was isolated as cDNA from patient peripheral blood mRNA using primers derived from the amino acid sequences from the predicted leader sequence of the light chain protein. The cDNA variable region sequence was fused to the kappa chain constant region cDNA sequence using a unique internal restriction endonuclease site Bsu36I. The oligonucleotide primers used to generate the variable sequence cDNA were as follows:

```
                                                         (SEQ ID NO: 77)
5' primer containing the leader sequence CTA GCT AGC TCA AGA
CTC AGC CTG GAC ATG GTG TTG CAG ACC CAG GTC TTC ATT TCT CTG
TTG CTC TGG ATC TCT GGT GCC TAC GGG GAC ATC GTG ATG ACC CAG (SEQ ID NO: 78)
3' primer GAA CGC CTG AGG AGT ATT AT
```

The variable and constant region sequences were joined by ligation at their common Bsu36I endonuclease cleavage site.

The assembled LYM 46 kappa light chain gene contained XhoI and NheI sites introduced in the flanking 5' and 3' ends during assembly. The entire gene was cut out using these enzymes and then was ligated into the pUDM vector to make the assembled pUDM46 vector system.

Assembly of pAD46M (FIG. 73)

The heavy and light chain sequences were subsequently used to assemble pADM46 in a fashion identical to that described for LYM 22.

Assembly of pUD22G1 and pUD22G2 vectors (FIGS. 76 and 77)

cDNA sequences encoding the heavy chain regions of the IgG1 and IgG2 isotypes were isolated from normal peripheral blood mRNA using the oligonucleotide primers:

```
                                          (SEQ ID NO: 79)
5 ' Primer for all human IgG subclasses
with Bam HI site:
CTG ATG CTA CGA TGG ATC C GC CTC CAC CAA GGG
CCC ATC (SEQ ID NO: 780)
3' Primer for gamma 1. and 2 with Sal 1 site:
GCA TGA GTC TGA CAG CTG TTT ACC CGG AGA CAG
GGA GAG GCT
```

These sequences were modified at their 5' and 3' ends by adding AscI and BsiWI restriction endonuclease sites. They were cloned into the pUD vector series by substituting the genomic IgM constant region exons with the cDNA sequences encoding the IgG1 or IgG2 constant region cDNA sequences. A polyadenylation site was introduced 3' to the coding sequences. The resulting vectors were designated pUD22G1 and pUD22G2 respectively These vectors produced small quantities of LYM 22 antibodies of the IgG 1 or IgG 2 isotypes (<1 ug/ml of culture supernatant.)

Example 21

Expression of an Igg G1 and G2 Form of Lym22 and Lym46

Vectors to generate recombinant LYM22 and LYM46 IgG subtype G1 and G2 have been generated and are depicted in FIGS. 76-79. LYM22 sequences were inserted into vectors pAD22G1 and pAD22G2 (FIG. 76) at the RsrII/PacI and Xho/NheI sites, similarly as described above (Example 9). Recombinant G1 subtype antibody was recovered from pAD22G1 and recombinant G2 subtype antibody was recovered from pAD22G2.

Example 22

Lym46 Promotes Demyelination Early after TMEV Infection

Figure 80:
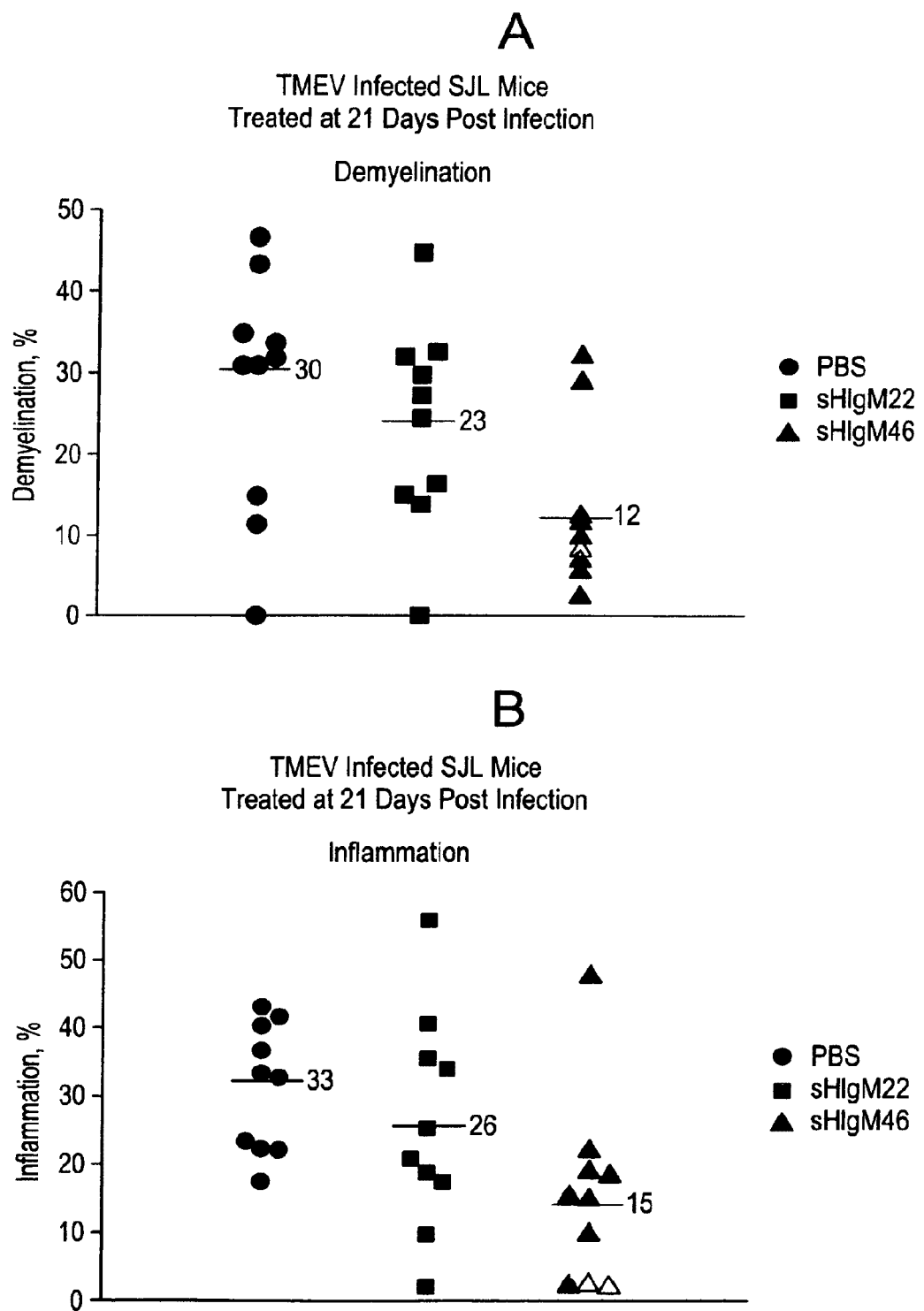

As previously described above, including in Example 13, smaller areas of demyelination were observed with LYM46 versus with other antibodies. To further assess and evaluate this, SJL mice were infected with TMEV as previously described and were examined early (21 days) after infection instead of evaluating mice longer after infection (6 months), or on chronic infection. FIG. 80 depicts evaluation of percent demyelination and percent inflammation 21 days post infection on treatment of mice with PBS, sHIgM22 and sHIgM46. The sHIgM46 treated group is different from the sHIgM22 or PBS treated group and shows significantly less demyelination and less inflammation. These results indicate that sHIgM46 is blocking demyelination from occurring in the TMEV model.

Example 23

Remyelination by Lym22 Fragments and Monomers

Lym22 Fv, F(ab) and F(ab)'$_2$ fragments and monomers were generated by enzymatic digestion or reduction and assessed for remyelination capacity in a TMEV model.

Fv, F(ab) and F(ab)'$_2$ fragments and monomers were generated using the following materials and methods:

Fv Fragments Production

For Fv production isolated IgM in 20 mM acetate buffer, 150 mM NaCl, pH 4.0 was digested with pepsin (Worthington, Lakewood, N.J.) in a IgM:pepsin ratio of 20:1 at 4° C. After 24 h the same (as initial) amount of pepsin was added and proteolysis was continued for one more day and then the solution was clarified by centrifugation (at 4° C.). Pepsin digestion was stopped by bringing pH up to 8.0 with 2 M Tris, pH 8.0, buffer and the solution was concentrated in a centrifugal filter device (Millipore, 5 kD cutoff) to the volume suitable for application on gel-filtration column (approx. 2 mL for bigger size column) and again clarified by centrifugation at 14000 rpm. The Fv fragments were isolated from the mixture by chromatography on a Superdex-75 column (Pharmacia, Upsalla, Sweden) equilibrated with PBS. Analysis of the Fv fragments was performed at 15% SDS-PAGE. Generally 2 and sometimes up to 4 closely spaced bands can be seen in the range from 10 to 15 kD. For Fv fragments the upper band observed was VH while the lower one was VL.

F(ab')$_2$ and Fab Production

For F(ab')$_2$ and Fab production, isolated IgM in 100 mM acetate buffer, 150 mM NaCl, pH 4.5 was digested with pepsin (Worthington, Lakewood, N.J.) in a IgM:pepsin ratio of 40:1 at 4° C. After 3 h, digestion was stopped by increasing pH to 8.0 with 2 M Tris buffer, pH 8.0, clarified by centrifugation and the solution was concentrated in a centrifugal filter device (Millipore, 10 kD cutoff) to the volume suitable for application on gel-filtration column (approx. 2 mL for bigger size column) and again clarified by centrifugation at 14000 rpm. F(ab')$_2$ and Fab fragments were isolated by size-exclusion chromatography on a Superdex-75 column (Pharmacia, Upsalla, Sweden) equilibrated with PBS.

Alternatively digestion with trypsin can be used as follows: IgM in 75 mM Tris, 150 mM NaCl, 12 mM CaCl2, pH 8.2 and IgM:trypsin (Worthington, Lakewood, N.J.) at ratio 20:1 was digested 4 h at 55° C. Before adding CaCl$_2$ IgM solution should be free of phosphates (i.e. from PBS) since Ca-phosphate which will form and precipitate thus changing the composition of the buffer. After cooling the proteolitic mixture on room temperature, trypsin-inhibitor (from soybean; Worthington, Lakewood, N.J.) and phosphate buffer, pH 7.0, to 50 mM final concentration were added. Phosphate buffer was added only to precipitate Ca$^{+2}$ and prevent its precipitation later in the column during the gel-filtration. The solution was cleared by centrifugation, concentrated and chromatographed over a Superdex-75 column. Identity of isolated fragments was confirmed by SDS-PAGE in reducing and nonreducing conditions and ELISA with anti-human lambda chain MAb.

In the case that yield of Fab is low and that F(ab')2 is primary product, an additional amount of Fab' (which is basically the same thing as Fab) can be generated by reducing and alkylating F(ab')$_2$ according to the protocol for production of monomeric IgM written below.

Production of Monomeric IgM

Monomeric IgM was produced in 200 mM Tris, 150 mM NaCl, 1 mM EDTA, pH 8.0, by reduction with 5 mM dithiothreitol (DTT) (Sigma), 2 h at room temperature in the dark and with occasional swirling. Subsequent alkylation was performed 1 h on ice by adding iodacetamide (IAA) to a final concentration of 12 mM. Both DTT and IAA stock solution should be freshly prepared. IgM-monomers were isolated by size-exclusion chromatography on a Superdex-200 column equilibrated with PBS, and characterized by reducing and nonreducing 12% SDS-PAGE.

The results of assessment of remyelination by Lym22 versus monomers and fragments in a TMEV model are shown below in TABLE 18.

TABLE 18

Remyelination promoted by Lym22 fragments[#]

| Treatment | No. of quadrants | Quadrants with lesions (%) | Quadrants with remyelination (%) | |
|---|---|---|---|---|
| PBS | n = 10 | 371 | 42.6 | 31.0 |
| Lym22 | n = 12 | 412 | 39.3 | 48.8  p = 0.002* |
| Monomer | n = 12 | 418 | 46.2 | 45.1  p = 0.01 |
| F(ab')2 | n = 12 | 404 | 41.6 | 57.1  p < 0.001 |
| Fab | n = 12 | 397 | 41.3 | 37.2  p > 0.05 |
| Fv | n = 5 | 184 | 28.3 | 34.6  p > 0.05 |
| Recombinant Lym22 | n = 6 | 197 | 37.0 | 59.7  p < 0.001 |

[#]Results presented in the table are summarized from two independent experiments performed from independent preps of Lym22 and its fragments.
*Statistics was done by chi-square test.

Example 24

Antibody Induced $Ca^{45}$ Internalization

Various autoantibodies were tested for their ability to induce calcium influx oligodendrocytes using labeled calcium $Ca^{45}$. While the earlier above described calcium flux assay is a dynamic representation on a cell by cell basis of the presence or absence of calcium flux, this $Ca^{45}$ internalization assay sums up the calcium influx over the assessment time and provides an influx signal. This influx can be used to measure the amount of calcium flowing in based on the number of cells and the amount of calcium flux. The results of assessment of antibodies LYM22, LYM2, 94.03 IgM, 94.03 IgG, and LYM46 are depicted in FIGS. 83 and 84. To assess calcium internalization, 10 ug/mL of each of the indicated antibodies was applied to adherent CG4 cells for 15 min at 37 C in the presence of $Ca^{45}$. Following calcium influx for this period of time, cells were chilled and washed extensively with $LaCl_3$ to chelate and remove any free calcium. Following washing, cells were lysed in 0.2 N NaOH and the lysates were assayed for cpm. The graph represents percent increase in measured $Ca^{45}$ above background influx occurring in untreated cells (i.e. cells only exposed to $Ca^{45}$ for 15 min in the absence of antibody). The ionophore represents a maximal calcium influx response induced pharmacologically (i.e. all cells will flux calcium in response to the ionophore). Error bars are standard error of the mean of four separate measurements.

As is evident from FIGS. 83 and 84, 94.03 IgM, LYM22 and LYM46 demonstrate $Ca^{45}$ influx that is significant versus untreated cells.

Example 25

Antibody-Induced Protection from Apoptosis

Antibody-induced protection from $H_2O_2$-mediated apoptosis or cell death was examined. 10 ug/mL of antibody was applied to adherent CG4 cells in the presence of varying concentrations of hydrogen peroxide (which induces a well-characterized apoptotic cell death) for 1 hr at 37° C. Following this incubation, cells were washed, fresh media was added, and an MTT assay was performed to measure cell viability and cell number. FIG. 85 indicates the relative number of cells surviving the $H_2O_2$-mediated insult in the presence of LYM22 versus the absence of LYM22. At all concentrations of $H_2O_2$, LYM22 induced a small but significant increase in cell survival (FIG. 85). Similarly, antibody 94.03 protected cells from $H_2O_2$ induced apoptosis (FIG. 86). The percentage of cells protected from apoptosis-induced cell death correlates with the percentage of cells which show antibody surface binding by immunostaining in each case of LYM22 and 94.03 at the antibody concentration used in the MTT assay.

The MTT assay was performed as follows:
1. Prepare 10×MTT stock as 250 mg MTT in 50 mL PBS. Sterile filter and store at 4° C.
2. Prepare lysis buffer (SDS-DMF):
100 g SDS
250 mL N,N-dimethylformamide
250 mL ddH2O
3. Photograph wells prior to manipulation.
4. Replace media in wells with 2 mL binding buffer (phenol red-free).
5. Add 200 uL stock MTT and incubate for 1 hr at 37° C.
6. Remove media from wells by aspiration (take care not to dislodge loosely adherent cells).
7. If possible, wash well 1× with ice-cold PBS.
8. Lyse cells in 1 mL SDS-DMF and incubate for 15 min at RT shaking vigorously.
9. Triturate lysate and transfer to microfuge tube. Centrifuge 2 min at 16000 g to clear S/N.
10. Read absorbance at 570 nm.
Reagents:
MTT: Sigma #M2128, 250 mg
3-[4,5-dimethylthiazol-2-yl]-2,5-diphenyltetrazolium bromide
DMF: Sigma #D4254, 250 mL
N,N-dimethylformamide The above described MTT assay measures viable cells after peroxide-induced apoptosis. The number of apoptosing cells can also be measured using known protocols or methods including the TUNEL assay (available from Roche Molecular Biochemicals Inc., catalog number 1684809) or other reported and known apoptosis assays (Gavrieli Y. et at J Cell Biol. 1992 November; 119(3):493-501; Gorczyca W. et al Cancer Res. 1993 Apr. 15; 53(8):1945-51; Gold R. et at Lab Invest. 1994 August; 71(2):219-25).

The disclosure of the listed references provided in this section of Examples as well as other publications, patent disclosures or documents recited herein, are all incorporated herein by reference in their entireties.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein. Those skilled in the art will recognize, or be able to ascertain, using no more than routine experimentation, many equivalents to the specific embodiments of the invention described herein. Such equivalents are intended to be encompassed by the following claims.

The invention claimed is:

1. A method of stimulating remyelination of central nervous system axons in a mammal, which method comprises:
   exogenously administering to said mammal an effective amount of a pharmaceutical composition comprising a recombinant antibody capable of binding oligodendrocytes and capable of inducing remyelination, having a heavy chain sequence comprising the heavy chain variable region CDR1, CDR2 and CDR3 sequences as set out in FIG. 71 and SEQ ID NO:49 and a light chain sequence comprising the light chain variable region CDR1, CDR2 and CDR3 sequences as set out in FIG. 72 and SEQ ID NO:51, or a monomer or an active fragment thereof wherein the monomer or active fragment comprises the heavy chain variable region CDR1, CDR2 and CDR3 sequences as set out in FIG. 71 and SEQ ID NO:49 and the light chain variable region CDR1, CDR2 and CDR3 sequences as set out in FIG. 72 and SEQ ID NO:51, and a pharmaceutically acceptable carrier, vehicle, or diluent.

2. The method of claim 1 comprising administering monomers, Fab fragments, Fab' fragments, F(ab)$_2$ fragments or F(v) fragments of a recombinant antibody having a heavy chain sequence comprising the heavy chain variable region CDR1, CDR2 and CDR3 sequences as set out in FIG. 71 and SEQ ID NO:49 and a light chain sequence comprising the light chain variable region CDR1, CDR2 and CDR3 sequences as set out in FIG. 72 and SEQ ID NO:51.

3. The method of claim 1 wherein said recombinant antibody comprises a heavy chain sequence comprising the heavy chain variable region sequence of SEQ ID NO: 49 and a light chain sequence comprising the light chain variable region sequence of SEQ ID NO: 51.

4. The method of claim 1 wherein the mammal is suffering from a demyelinating disease or viral disease of the central nervous system.

5. The method of claim 1 wherein the demyelinating disease or viral disease is multiple sclerosis (MS) or post-infectious encephalomyelitis.

6. A method of stimulating the proliferation of central nervous system glial cells in a mammal, which comprises:

exogenously administering to said mammal an effective amount of a pharmaceutical composition comprising a recombinant antibody capable of binding oligodendrocytes and capable of inducing remyelination, having a heavy chain sequence comprising the heavy chain variable region CDR1, CDR2 and CDR3 sequences as set out in FIG. 71 and SEQ ID NO:49 and a light chain sequence comprising the light chain variable region CDR1, CDR2 and CDR3 sequences as set out in FIG. 72 and SEQ ID NO:51, or a monomer or an active fragment thereof wherein the monomer or active fragment comprises the heavy chain variable region CDR1, CDR2 and CDR3 sequences as set out in FIG. 71 and SEQ ID NO:49 and the light chain variable region CDR1, CDR2 and CDR3 sequences as set out in FIG. 72 and SEQ ID NO:51, and a pharmaceutically acceptable carrier, vehicle, or diluent.

7. The method of claim 6 comprising administering monomers, Fab fragments, Fab' fragments, F(ab)$_2$ fragments or F(v) fragments of a recombinant antibody having a heavy chain sequence comprising the heavy chain variable region CDR1, CDR2 and CDR3 sequences as set out in FIG. 71 and SEQ ID NO:49 and a light chain sequence comprising the light chain variable region CDR1, CDR2 and CDR3 sequences as set out in FIG. 72 and SEQ ID NO:51.

8. The method of claim 6 wherein said recombinant antibody comprises a heavy chain sequence comprising the heavy chain variable region sequence of SEQ ID NO: 49 and a light chain sequence comprising the light chain variable region sequence of SEQ ID NO: 51.

9. A pharmaceutical composition comprising a recombinant antibody having a heavy chain sequence comprising the heavy chain variable region CDR1, CDR2 and CDR3 sequences as set out in FIG. 71 and SEQ ID NO:49 and having an amino acid substitution to change a heavy chain variable region amino acid in SEQ ID NO: 49, and a light chain sequence comprising the light chain variable region CDR1, CDR2 and CDR3 sequences as set out in FIG. 72 and SEQ ID NO:51 and having an amino acid substitution to change a light chain variable region amino acid in SEQ ID NO: 51, or a monomer or active fragment thereof, wherein the antibody, monomer, or fragment is capable of binding oligodendrocytes and capable of inducing remyelination, and a pharmaceutically acceptable carrier, vehicle, or diluent.

10. The pharmaceutical composition of claim 9 wherein the antibody is a monoclonal human antibody.

11. The pharmaceutical composition of claim 9 wherein the antibody is an IgM antibody or a monomer thereof.

12. The pharmaceutical composition of claim 9 wherein the fragment is an Fab, Fab', F(ab)$_2$ or F(v) fragment capable of binding oligodendrocytes and capable of inducing remyelination.

13. A method of stimulating remyelination of central nervous system axons or stimulating proliferation of central nervous system glial cells in a mammal, which method comprises exogenously administering to said mammal an effective amount of the pharmaceutical composition of claim 9.

14. The method of claim 13 wherein the mammal is suffering from a demyelinating disease or viral disease of the central nervous system.

15. The method of claim 13 wherein the demyelinating disease or viral disease is multiple sclerosis (MS) or post-infectious encephalomyelitis.

16. A method of stimulating remyelination of central nervous system axons or stimulating proliferation of central nervous system glial cells in a mammal, which method comprises exogenously administering to said mammal an effective amount of a monomer or active fragment of a recombinant antibody having a heavy chain sequence comprising the heavy chain variable region CDR1, CDR2 and CDR3 sequences as set out in FIG. 71 and SEQ ID NO:49, and a light chain sequence comprising the light chain variable region CDR1, CDR2 and CDR3 sequences as set out in FIG. 72 and SEQ ID NO:51, wherein the monomer or active fragment is capable of binding oligodendrocytes and capable of inducing remyelination.

17. The method of claim 16 wherein the mammal is suffering from a demyelinating disease or viral disease of the central nervous system.

18. The method of claim 16 wherein the demyelinating disease or viral disease is multiple sclerosis (MS) or post-infectious encephalomyelitis.

19. A labeled or tagged antibody capable of binding oligodendrocytes and capable of inducing remyelination having a heavy chain sequence comprising the heavy chain variable region CDR1, CDR2 and CDR3 sequences as set out in FIG. 71 and SEQ ID NO:49, and a light chain sequence comprising the light chain variable region CDR1, CDR2 and CDR3 sequences as set out in FIG. 72 and SEQ ID NO:51.

20. The labeled or tagged antibody of claim 19 wherein the label or tag is an enzyme, fluorophore, chromophore, radioisotope, dye, colloidal gold, latex particle, chemiluminescent agent, magnetic resonance shift reagent, radio-opaque reagent, or an immunofluorescent, radioactive or other diagnostically suitable tag.

21. A method of stimulating remyelination of central nervous system axons or stimulating proliferation of central nervous system glial cells in a mammal, which method comprises exogenously administering to said mammal an effective amount of the labeled or tagged antibody of claim 19.

22. The method of claim 21 wherein the mammal is suffering from a demyelinating disease or viral disease of the central nervous system.

23. The method of claim 21 wherein the demyelinating disease or viral disease is multiple sclerosis (MS) or post-infectious encephalomyelitis.

\* \* \* \* \*